US011066400B2

(12) United States Patent
Metzger et al.

(10) Patent No.: US 11,066,400 B2
(45) Date of Patent: Jul. 20, 2021

(54) COMPOUNDS FOR THE TREATMENT OF CANCER

(71) Applicant: Hoffmann-La Roche Inc., Little Falls, NJ (US)

(72) Inventors: Friedrich Metzger, Freiburg (DE); Hasane Ratni, Habsheim (FR)

(73) Assignee: Hoffmann-La Roche Inc., Little Falls, NJ (US)

( * ) Notice: Subject to any disclaimer, the term of this patent is extended or adjusted under 35 U.S.C. 154(b) by 321 days.

(21) Appl. No.: 15/851,188

(22) Filed: Dec. 21, 2017

(65) Prior Publication Data

US 2018/0170923 A1 Jun. 21, 2018

Related U.S. Application Data

(62) Division of application No. 15/019,135, filed on Feb. 9, 2016, now abandoned.

(30) Foreign Application Priority Data

Feb. 9, 2015 (EP) ..................................... 15154342
Feb. 16, 2015 (EP) ..................................... 15155286

(51) Int. Cl.

| C07D 417/14 | (2006.01) |
| A61K 31/433 | (2006.01) |
| A61K 31/435 | (2006.01) |
| A61K 31/4353 | (2006.01) |
| A61K 31/437 | (2006.01) |
| A61K 31/438 | (2006.01) |
| A61K 31/4436 | (2006.01) |
| A61K 31/454 | (2006.01) |
| A61K 31/4545 | (2006.01) |
| A61K 31/4709 | (2006.01) |
| A61K 31/501 | (2006.01) |
| A61K 31/502 | (2006.01) |
| A61K 31/506 | (2006.01) |
| A61K 31/5377 | (2006.01) |
| A61K 31/551 | (2006.01) |
| A61K 45/06 | (2006.01) |
| C07D 401/12 | (2006.01) |
| C07D 401/14 | (2006.01) |
| A61P 35/00 | (2006.01) |

(52) U.S. Cl.
CPC .......... *C07D 417/14* (2013.01); *A61K 31/433* (2013.01); *A61K 31/435* (2013.01); *A61K 31/437* (2013.01); *A61K 31/438* (2013.01); *A61K 31/4353* (2013.01); *A61K 31/4436* (2013.01); *A61K 31/454* (2013.01); *A61K 31/4545* (2013.01); *A61K 31/4709* (2013.01); *A61K 31/501* (2013.01); *A61K 31/502* (2013.01); *A61K 31/506* (2013.01); *A61K 31/5377* (2013.01); *A61K 31/551* (2013.01); *A61K 45/06* (2013.01); *A61P 35/00* (2018.01); *C07D 401/12* (2013.01); *C07D 401/14* (2013.01)

(58) Field of Classification Search
CPC .................................................. C07D 417/14
See application file for complete search history.

(56) References Cited

FOREIGN PATENT DOCUMENTS

| CN | 103 965 169 A | 8/2014 |
| EP | 2 014 656 A2 | 1/2009 |
| EP | 2 298 896 A1 | 3/2011 |
| WO | 03/074500 A2 | 9/2003 |
| WO | 2006/009575 A1 | 1/2006 |
| WO | 2007/003604 A2 | 1/2007 |
| WO | 2007/133561 A2 | 11/2007 |
| WO | 2007/137968 A1 | 12/2007 |
| WO | 2008/145681 A2 | 12/2008 |
| WO | 2008/154126 A1 | 12/2008 |
| WO | 2011/082732 A1 | 7/2011 |
| WO | 2011/127297 A1 | 10/2011 |
| WO | 2014/028459 A1 | 2/2014 |
| WO | 2014/110163 A2 | 7/2014 |
| WO | 2014/110163 A3 | 7/2014 |
| WO | 2014/116845 A1 | 7/2014 |
| WO | 2015/017589 A1 | 2/2015 |

OTHER PUBLICATIONS

Cahn et al., "Specification of Molecular Chirality" Angew. Chem. internat. Edit. 5(4):385-415 ( 1966).
Eliel et al. Stereochemistry of Organic Compounds (Table of Contents (in 11 pages)), New York:John Wiley & Sons, Inc., ( 1994).

(Continued)

*Primary Examiner* — Kortney L. Klinkel
*Assistant Examiner* — Tori Strong
(74) *Attorney, Agent, or Firm* — Zong-Qiang Bill Tian

(57) ABSTRACT

The present invention relates to a FoxM1 gene splicing modifier selected from a compound of formula (I) or of formula (VI)

wherein A and B are as defined herein, or a pharmaceutically acceptable salt thereof, for use in the treatment, prevention and/or delay of progression of cancer.

20 Claims, 5 Drawing Sheets

Specification includes a Sequence Listing.

(56) References Cited

OTHER PUBLICATIONS

Green et al. Molecular Cloning: A Laboratory Manual (Table of Contents & Preface (in 34 pages)), Fourth edition, Cold Spring Harbor, New York:Cold Spring Harbor Laboratory Press, ( 2012).

Harlow et al. Antibodies: A Laboratory Manual (Table of Contents (in 9 pages)), Cold Spring Harbor, New York:Cold Spring Harbor Laboratory, ( 1988).

International Search Report issued in International Application No. PCT/EP2016/052597, dated May 6, 2016, in 8 pages.

Korver et al., "The winged-helix transcription factor Trident is expressed in cycling cells", Nucleic Acids Research 25(9):1715-1719 ( 1997).

Liu et al., "FoxM1B is Overexpressed in Human Glioblastomas and Critically Regulates the Tumorigenicity of Glioma Cells" Cancer Res 66(7):3593-3602 ( 2006).

McNaught et al. International Union of Pure and Applied Chemistry: Compendium of Chemical Terminology (Table of Contents (in 3 pages)), 2nd edition, Oxford:Blackwell Science Ltd, ( 1997).

Nakamura et al., "Genome-wide cDNA microarray analysis of gene expression profiles in pancreatic cancers using populations of tumor cells and normal ductal epithelial cells selected for purity by laser microdissection" Oncogene 23(13):2385-2400 ( 2004).

Pilarsky et al., "Identification and Validation of Commonly Overexpressed Genes in Solid Tumors by Comparison of Microarray Data" Neoplasia 6(6):744-750 ( 2004).

Teh et al., "FOXM1 is a Downstream Target of Gli1 in Basal Cell Carcinomas" Cancer Res 62(16):4773-4780 ( 2002).

Wang et al., "The Forkhead Box m1b transcription factor is essential for hepatocyte DNA replication and mitosis during mouse liver regeneration" Proc Natl Acad Sci USA 99(26):16881-16886 ( 2002).

Written Opinion of International Searching Authority issued in International Application No. PCT/EP2016/052597, dated May 6, 2016, in 9 pages.

Ye et al., "Hepatocyte Nuclear Factor 3/fork head Homolog 11 is Expressed in Proliferating Epithelial and Mesenchymal Cells of Embryonic and Adult Tissues" Molecular and Cellular Biology 17(3):1626-1641 ( 1997).

SEQUENCE LISTING

```
<160> NUMBER OF SEQ ID NOS: 6

<210> SEQ ID NO 1
<211> LENGTH: 801
<212> TYPE: PRT
<213> ORGANISM: Homo sapiens

<400> SEQUENCE: 1

Met Lys Thr Ser Pro Arg Arg Pro Leu Ile Leu Lys Arg Arg Arg Leu
1               5                   10                  15

Pro Leu Pro Val Gln Asn Ala Pro Ser Glu Thr Ser Glu Glu Glu Pro
                20                  25                  30

Lys Arg Ser Pro Ala Gln Gln Glu Ser Asn Gln Ala Glu Ala Ser Lys
            35                  40                  45

Glu Val Ala Glu Ser Asn Ser Cys Lys Phe Pro Ala Gly Ile Lys Ile
        50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                85                  90                  95
```

-continued

```
Glu Ser Gly Ser Ser Gly Pro Asn Lys Phe Ile Leu Ile Ser Cys Gly
                100                 105                 110

Gly Ala Pro Thr Gln Pro Gly Leu Arg Pro Gln Thr Gln Thr Ser
        115                 120                 125

Tyr Asp Ala Lys Arg Thr Glu Val Thr Leu Glu Thr Leu Gly Pro Lys
    130                 135                 140

Pro Ala Ala Arg Asp Val Asn Leu Pro Arg Pro Pro Gly Ala Leu Cys
145                 150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
            180                 185                 190

Asp Gly Leu Gly Ser Arg Ser Ile Lys Gln Glu Met Glu Glu Lys Glu
        195                 200                 205

Asn Cys His Leu Glu Gln Arg Gln Val Lys Val Glu Glu Pro Ser Arg
    210                 215                 220

Pro Ser Ala Ser Trp Gln Asn Ser Val Ser Glu Arg Pro Pro Tyr Ser
225                 230                 235                 240

Tyr Met Ala Met Ile Gln Phe Ala Ile Asn Ser Thr Glu Arg Lys Arg
                245                 250                 255

Met Thr Leu Lys Asp Ile Tyr Thr Trp Ile Glu Asp His Phe Pro Tyr
            260                 265                 270

Phe Lys His Ile Ala Lys Pro Gly Trp Lys Asn Ser Ile Arg His Asn
        275                 280                 285

Leu Ser Leu His Asp Met Phe Val Arg Glu Thr Ser Ala Asn Gly Lys
    290                 295                 300

Val Ser Phe Trp Thr Ile His Pro Ser Ala Asn Arg Tyr Leu Thr Leu
305                 310                 315                 320

Asp Gln Val Phe Lys Pro Leu Asp Pro Gly Ser Pro Gln Leu Pro Glu
                325                 330                 335

His Leu Glu Ser Gln Gln Lys Arg Pro Asn Pro Glu Leu Arg Arg Asn
            340                 345                 350

Met Thr Ile Lys Thr Glu Leu Pro Leu Gly Ala Arg Arg Lys Met Lys
        355                 360                 365

Pro Leu Leu Pro Arg Val Ser Ser Tyr Leu Val Pro Ile Gln Phe Pro
    370                 375                 380

Val Asn Gln Ser Leu Val Leu Gln Pro Ser Val Lys Val Pro Leu Pro
385                 390                 395                 400

Leu Ala Ala Ser Leu Met Ser Ser Glu Leu Ala Arg His Ser Lys Arg
                405                 410                 415

Val Arg Ile Ala Pro Lys Val Phe Gly Glu Gln Val Val Phe Gly Tyr
            420                 425                 430

Met Ser Lys Phe Phe Ser Gly Asp Leu Arg Asp Phe Gly Thr Pro Ile
        435                 440                 445

Thr Ser Leu Phe Asn Phe Ile Phe Leu Cys Leu Ser Val Leu Leu Ala
    450                 455                 460

Glu Glu Gly Ile Ala Pro Leu Ser Ser Ala Gly Pro Gly Lys Glu Glu
465                 470                 475                 480

Lys Leu Leu Phe Gly Glu Gly Phe Ser Pro Leu Leu Pro Val Gln Thr
                485                 490                 495

Ile Lys Glu Glu Glu Ile Gln Pro Gly Glu Glu Met Pro His Leu Ala
            500                 505                 510

Arg Pro Ile Lys Val Glu Ser Pro Pro Leu Glu Glu Trp Pro Ser Pro
```

```
            515                 520                 525
Ala Pro Ser Phe Lys Glu Glu Ser His Ser Trp Glu Asp Ser Ser
    530                 535                 540

Gln Ser Pro Thr Pro Arg Pro Lys Lys Ser Tyr Ser Gly Leu Arg Ser
545                 550                 555                 560

Pro Thr Arg Cys Val Ser Glu Met Leu Val Ile Gln His Arg Glu Arg
                565                 570                 575

Arg Glu Arg Ser Arg Ser Arg Arg Lys Gln His Leu Leu Pro Pro Cys
            580                 585                 590

Val Asp Glu Pro Glu Leu Leu Phe Ser Glu Gly Pro Ser Thr Ser Arg
        595                 600                 605

Trp Ala Ala Glu Leu Pro Phe Pro Ala Asp Ser Ser Asp Pro Ala Ser
    610                 615                 620

Gln Leu Ser Tyr Ser Gln Glu Val Gly Gly Pro Phe Lys Thr Pro Ile
625                 630                 635                 640

Lys Glu Thr Leu Pro Ile Ser Ser Thr Pro Ser Lys Ser Val Leu Pro
                645                 650                 655

Arg Thr Pro Glu Ser Trp Arg Leu Thr Pro Pro Ala Lys Val Gly Gly
            660                 665                 670

Leu Asp Phe Ser Pro Val Gln Thr Ser Gln Gly Ala Ser Asp Pro Leu
        675                 680                 685

Pro Asp Pro Leu Gly Leu Met Asp Leu Ser Thr Thr Pro Leu Gln Ser
    690                 695                 700

Ala Pro Pro Leu Glu Ser Pro Gln Arg Leu Leu Ser Ser Glu Pro Leu
705                 710                 715                 720

Asp Leu Ile Ser Val Pro Phe Gly Asn Ser Ser Pro Ser Asp Ile Asp
                725                 730                 735

Val Pro Lys Pro Gly Ser Pro Glu Pro Gln Val Ser Gly Leu Ala Ala
            740                 745                 750

Asn Arg Ser Leu Thr Glu Gly Leu Val Leu Asp Thr Met Asn Asp Ser
        755                 760                 765

Leu Ser Lys Ile Leu Leu Asp Ile Ser Phe Pro Gly Leu Asp Glu Asp
    770                 775                 780

Pro Leu Gly Pro Asp Asn Ile Asn Trp Ser Gln Phe Ile Pro Glu Leu
785                 790                 795                 800

Gln

<210> SEQ ID NO 2
<211> LENGTH: 748
<212> TYPE: PRT
<213> ORGANISM: Homo sapiens

<400> SEQUENCE: 2

Met Lys Thr Ser Pro Arg Arg Pro Leu Ile Leu Lys Arg Arg Arg Leu
1               5                   10                  15

Pro Leu Pro Val Gln Asn Ala Pro Ser Glu Thr Ser Glu Glu Glu Pro
            20                  25                  30

Lys Arg Ser Pro Ala Gln Gln Glu Ser Asn Gln Ala Glu Ala Ser Lys
        35                  40                  45

Glu Val Ala Glu Ser Asn Ser Cys Lys Phe Pro Ala Gly Ile Lys Ile
    50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
```

```
                    85                  90                  95
Glu Ser Gly Ser Ser Gly Pro Asn Lys Phe Ile Leu Ile Ser Cys Gly
                100                 105                 110
Gly Ala Pro Thr Gln Pro Pro Gly Leu Arg Pro Gln Thr Gln Thr Ser
            115                 120                 125
Tyr Asp Ala Lys Arg Thr Glu Val Thr Leu Glu Thr Leu Gly Pro Lys
        130                 135                 140
Pro Ala Ala Arg Asp Val Asn Leu Pro Arg Pro Pro Gly Ala Leu Cys
145                 150                 155                 160
Glu Gln Lys Arg Glu Thr Cys Asp Gly Glu Ala Ala Gly Cys Thr Ile
                165                 170                 175
Asn Asn Ser Leu Ser Asn Ile Gln Trp Leu Arg Lys Met Ser Ser Asp
            180                 185                 190
Gly Leu Gly Ser Arg Ser Ile Lys Gln Glu Met Glu Glu Lys Glu Asn
        195                 200                 205
Cys His Leu Glu Gln Arg Gln Val Lys Val Glu Glu Pro Ser Arg Pro
    210                 215                 220
Ser Ala Ser Trp Gln Asn Ser Val Ser Glu Arg Pro Pro Tyr Ser Tyr
225                 230                 235                 240
Met Ala Met Ile Gln Phe Ala Ile Asn Ser Thr Glu Arg Lys Arg Met
                245                 250                 255
Thr Leu Lys Asp Ile Tyr Thr Trp Ile Glu Asp His Phe Pro Tyr Phe
            260                 265                 270
Lys His Ile Ala Lys Pro Gly Trp Lys Asn Ser Ile Arg His Asn Leu
        275                 280                 285
Ser Leu His Asp Met Phe Val Arg Glu Thr Ser Ala Asn Gly Lys Val
    290                 295                 300
Ser Phe Trp Thr Ile His Pro Ser Ala Asn Arg Tyr Leu Thr Leu Asp
305                 310                 315                 320
Gln Val Phe Lys Gln Gln Lys Arg Pro Asn Pro Glu Leu Arg Arg
                325                 330                 335
Asn Met Thr Ile Lys Thr Glu Leu Pro Leu Gly Ala Arg Arg Lys Met
            340                 345                 350
Lys Pro Leu Leu Pro Arg Val Ser Ser Tyr Leu Val Pro Ile Gln Phe
        355                 360                 365
Pro Val Asn Gln Ser Leu Val Leu Gln Pro Ser Val Lys Val Pro Leu
    370                 375                 380
Pro Leu Ala Ala Ser Leu Met Ser Ser Glu Leu Ala Arg His Ser Lys
385                 390                 395                 400
Arg Val Arg Ile Ala Pro Lys Val Leu Leu Ala Glu Glu Gly Ile Ala
                405                 410                 415
Pro Leu Ser Ser Ala Gly Pro Gly Lys Glu Glu Lys Leu Leu Phe Gly
            420                 425                 430
Glu Gly Phe Ser Pro Leu Leu Pro Val Gln Thr Ile Lys Glu Glu Glu
        435                 440                 445
Ile Gln Pro Gly Glu Glu Met Pro His Leu Ala Arg Pro Ile Lys Val
    450                 455                 460
Glu Ser Pro Pro Leu Glu Glu Trp Pro Ser Pro Ala Pro Ser Phe Lys
465                 470                 475                 480
Glu Glu Ser Ser His Ser Trp Glu Asp Ser Ser Gln Ser Pro Thr Pro
                485                 490                 495
Arg Pro Lys Lys Ser Tyr Ser Gly Leu Arg Ser Pro Thr Arg Cys Val
            500                 505                 510
```

Ser Glu Met Leu Val Ile Gln His Arg Glu Arg Glu Ser Arg
                515                 520                 525

Ser Arg Arg Lys Gln His Leu Leu Pro Pro Cys Val Asp Glu Pro Glu
    530                 535                 540

Leu Leu Phe Ser Glu Gly Pro Ser Thr Ser Arg Trp Ala Ala Glu Leu
545                 550                 555                 560

Pro Phe Pro Ala Asp Ser Ser Asp Pro Ala Ser Gln Leu Ser Tyr Ser
                565                 570                 575

Gln Glu Val Gly Gly Pro Phe Lys Thr Pro Ile Lys Glu Thr Leu Pro
            580                 585                 590

Ile Ser Ser Thr Pro Ser Lys Ser Val Leu Pro Arg Thr Pro Glu Ser
            595                 600                 605

Trp Arg Leu Thr Pro Pro Ala Lys Val Gly Gly Leu Asp Phe Ser Pro
    610                 615                 620

Val Gln Thr Ser Gln Gly Ala Ser Asp Pro Leu Pro Asp Pro Leu Gly
625                 630                 635                 640

Leu Met Asp Leu Ser Thr Thr Pro Leu Gln Ser Ala Pro Pro Leu Glu
                645                 650                 655

Ser Pro Gln Arg Leu Leu Ser Ser Glu Pro Leu Asp Leu Ile Ser Val
            660                 665                 670

Pro Phe Gly Asn Ser Ser Pro Ser Asp Ile Asp Val Pro Lys Pro Gly
            675                 680                 685

Ser Pro Glu Pro Gln Val Ser Gly Leu Ala Ala Asn Arg Ser Leu Thr
    690                 695                 700

Glu Gly Leu Val Leu Asp Thr Met Asn Asp Ser Leu Ser Lys Ile Leu
705                 710                 715                 720

Leu Asp Ile Ser Phe Pro Gly Leu Asp Glu Asp Pro Leu Gly Pro Asp
                725                 730                 735

Asn Ile Asn Trp Ser Gln Phe Ile Pro Glu Leu Gln
            740                 745

<210> SEQ ID NO 3
<211> LENGTH: 763
<212> TYPE: PRT
<213> ORGANISM: Homo sapiens

<400> SEQUENCE: 3

Met Lys Thr Ser Pro Arg Arg Pro Leu Ile Leu Lys Arg Arg Arg Leu
1               5                   10                  15

Pro Leu Pro Val Gln Asn Ala Pro Ser Glu Thr Ser Glu Glu Glu Pro
                20                  25                  30

Lys Arg Ser Pro Ala Gln Gln Glu Ser Asn Gln Ala Glu Ala Ser Lys
            35                  40                  45

Glu Val Ala Glu Ser Asn Ser Cys Lys Phe Pro Ala Gly Ile Lys Ile
    50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
            100                 105                 110

Gly Ala Pro Thr Gln Pro Pro Gly Leu Arg Pro Gln Thr Gln Thr Ser
            115                 120                 125

Tyr Asp Ala Lys Arg Thr Glu Val Thr Leu Glu Thr Leu Gly Pro Lys

-continued

```
                130                 135                 140
Pro Ala Ala Arg Asp Val Asn Leu Pro Arg Pro Pro Gly Ala Leu Cys
145                 150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
                180                 185                 190

Asp Gly Leu Gly Ser Arg Ser Ile Lys Gln Glu Met Glu Glu Lys Glu
                195                 200                 205

Asn Cys His Leu Glu Gln Arg Gln Val Lys Val Glu Glu Pro Ser Arg
                210                 215                 220

Pro Ser Ala Ser Trp Gln Asn Ser Val Ser Glu Arg Pro Pro Tyr Ser
225                 230                 235                 240

Tyr Met Ala Met Ile Gln Phe Ala Ile Asn Ser Thr Glu Arg Lys Arg
                245                 250                 255

Met Thr Leu Lys Asp Ile Tyr Thr Trp Ile Glu Asp His Phe Pro Tyr
                260                 265                 270

Phe Lys His Ile Ala Lys Pro Gly Trp Lys Asn Ser Ile Arg His Asn
                275                 280                 285

Leu Ser Leu His Asp Met Phe Val Arg Glu Thr Ser Ala Asn Gly Lys
                290                 295                 300

Val Ser Phe Trp Thr Ile His Pro Ser Ala Asn Arg Tyr Leu Thr Leu
305                 310                 315                 320

Asp Gln Val Phe Lys Pro Leu Asp Pro Gly Ser Pro Gln Leu Pro Glu
                325                 330                 335

His Leu Glu Ser Gln Gln Lys Arg Pro Asn Pro Glu Leu Arg Arg Asn
                340                 345                 350

Met Thr Ile Lys Thr Glu Leu Pro Leu Gly Ala Arg Arg Lys Met Lys
                355                 360                 365

Pro Leu Leu Pro Arg Val Ser Ser Tyr Leu Val Pro Ile Gln Phe Pro
                370                 375                 380

Val Asn Gln Ser Leu Val Leu Gln Pro Ser Val Lys Val Pro Leu Pro
385                 390                 395                 400

Leu Ala Ala Ser Leu Met Ser Ser Glu Leu Ala Arg His Ser Lys Arg
                405                 410                 415

Val Arg Ile Ala Pro Lys Val Leu Leu Ala Glu Glu Gly Ile Ala Pro
                420                 425                 430

Leu Ser Ser Ala Gly Pro Gly Lys Glu Glu Lys Leu Leu Phe Gly Glu
                435                 440                 445

Gly Phe Ser Pro Leu Leu Pro Val Gln Thr Ile Lys Glu Glu Glu Ile
                450                 455                 460

Gln Pro Gly Glu Glu Met Pro His Leu Ala Arg Pro Ile Lys Val Glu
465                 470                 475                 480

Ser Pro Pro Leu Glu Glu Trp Pro Ser Pro Ala Pro Ser Phe Lys Glu
                485                 490                 495

Glu Ser Ser His Ser Trp Glu Asp Ser Ser Gln Ser Pro Thr Pro Arg
                500                 505                 510

Pro Lys Lys Ser Tyr Ser Gly Leu Arg Ser Pro Thr Arg Cys Val Ser
                515                 520                 525

Glu Met Leu Val Ile Gln His Arg Glu Arg Glu Arg Ser Arg Ser
                530                 535                 540

Arg Arg Lys Gln His Leu Leu Pro Pro Cys Val Asp Glu Pro Glu Leu
545                 550                 555                 560
```

```
Leu Phe Ser Glu Gly Pro Ser Thr Ser Arg Trp Ala Ala Glu Leu Pro
                565                 570                 575

Phe Pro Ala Asp Ser Ser Asp Pro Ala Ser Gln Leu Ser Tyr Ser Gln
            580                 585                 590

Glu Val Gly Gly Pro Phe Lys Thr Pro Ile Lys Glu Thr Leu Pro Ile
        595                 600                 605

Ser Ser Thr Pro Ser Lys Ser Val Leu Pro Arg Thr Pro Glu Ser Trp
    610                 615                 620

Arg Leu Thr Pro Pro Ala Lys Val Gly Gly Leu Asp Phe Ser Pro Val
625                 630                 635                 640

Gln Thr Ser Gln Gly Ala Ser Asp Pro Leu Pro Asp Pro Leu Gly Leu
                645                 650                 655

Met Asp Leu Ser Thr Thr Pro Leu Gln Ser Ala Pro Pro Leu Glu Ser
            660                 665                 670

Pro Gln Arg Leu Leu Ser Ser Glu Pro Leu Asp Leu Ile Ser Val Pro
        675                 680                 685

Phe Gly Asn Ser Ser Pro Ser Asp Ile Asp Val Pro Lys Pro Gly Ser
    690                 695                 700

Pro Glu Pro Gln Val Ser Gly Leu Ala Ala Asn Arg Ser Leu Thr Glu
705                 710                 715                 720

Gly Leu Val Leu Asp Thr Met Asn Asp Ser Leu Ser Lys Ile Leu Leu
                725                 730                 735

Asp Ile Ser Phe Pro Gly Leu Asp Glu Asp Pro Leu Gly Pro Asp Asn
            740                 745                 750

Ile Asn Trp Ser Gln Phe Ile Pro Glu Leu Gln
            755                 760

<210> SEQ ID NO 4
<211> LENGTH: 3665
<212> TYPE: DNA
<213> ORGANISM: Homo sapiens
<220> FEATURE:
<221> NAME/KEY: CDS
<222> LOCATION: (284)..(2689)

<400> SEQUENCE: 4
tttcaaacag cggaacaaac tgaaagctcc ggtgccagac cccaccccg gccccggccc      60 gggacccct cccctccgg gatccccgg ggttcccacc ccgccgcac cgccgggac         120 ccggccggtc cggcgcgagc ccccgtccgg ggccctggct cggccccag gttggaggag     180 cccgagccc gccttcggag ctacggccta acggcggcgg cgactgcagt ctggagggtc    240
cacacttgtg attctcaatg gagagtgaaa acgcagattc ata atg aaa act agc     295
                                                Met Lys Thr Ser
                                                  1 ccc cgt cgg cca ctg att ctc aaa aga cgg agg ctg ccc ctt cct gtt     343
Pro Arg Arg Pro Leu Ile Leu Lys Arg Arg Arg Leu Pro Leu Pro Val
  5              10                  15                  20 caa aat gcc cca agt gaa aca tca gag gag gaa cct aag aga tcc cct     391
Gln Asn Ala Pro Ser Glu Thr Ser Glu Glu Glu Pro Lys Arg Ser Pro
              25                  30                  35 gcc caa cag gag tct aat caa gca gag gcc tcc aag gaa gtg gca gag     439
Ala Gln Gln Glu Ser Asn Gln Ala Glu Ala Ser Lys Glu Val Ala Glu
         40                  45                  50 tcc aac tct tgc aag ttt cca gct ggg atc aag att att aac cac ccc     487
Ser Asn Ser Cys Lys Phe Pro Ala Gly Ile Lys Ile Ile Asn His Pro
     55                  60                  65
```

-continued

| | |
|---|---|
| acc atg ccc aac acg caa gta gtg gcc atc ccc aac aat gct aat att<br>Thr Met Pro Asn Thr Gln Val Val Ala Ile Pro Asn Asn Ala Asn Ile<br>70                      75                        80 | 535 |
| cac agc atc atc aca gca ctg act gcc aag gga aaa gag agt ggc agt<br>His Ser Ile Ile Thr Ala Leu Thr Ala Lys Gly Lys Glu Ser Gly Ser<br>85                      90                      95                  100 | 583 |
| agt ggg ccc aac aaa ttc atc ctc atc agc tgt ggg gga gcc cca act<br>Ser Gly Pro Asn Lys Phe Ile Leu Ile Ser Cys Gly Gly Ala Pro Thr<br>                  105                      110                      115 | 631 |
| cag cct cca gga ctc cgg cct caa acc caa acc agc tat gat gcc aaa<br>Gln Pro Pro Gly Leu Arg Pro Gln Thr Gln Thr Ser Tyr Asp Ala Lys<br>                  120                      125                      130 | 679 |
| agg aca gaa gtg acc ctg gag acc ttg gga cca aaa cct gca gct agg<br>Arg Thr Glu Val Thr Leu Glu Thr Leu Gly Pro Lys Pro Ala Ala Arg<br>135                      140                      145 | 727 |
| gat gtg aat ctt cct aga cca cct gga gcc ctt tgc gag cag aaa cgg<br>Asp Val Asn Leu Pro Arg Pro Pro Gly Ala Leu Cys Glu Gln Lys Arg<br>150                      155                      160 | 775 |
| gag acc tgt gca gat ggt gag gca gca ggc tgc act atc aac aat agc<br>Glu Thr Cys Ala Asp Gly Glu Ala Ala Gly Cys Thr Ile Asn Asn Ser<br>165                      170                      175                      180 | 823 |
| cta tcc aac atc cag tgg ctt cga aag atg agt tct gat gga ctg ggc<br>Leu Ser Asn Ile Gln Trp Leu Arg Lys Met Ser Ser Asp Gly Leu Gly<br>                  185                      190                      195 | 871 |
| tcc cgc agc atc aag caa gag atg gag gaa aag gag aat tgt cac ctg<br>Ser Arg Ser Ile Lys Gln Glu Met Glu Glu Lys Glu Asn Cys His Leu<br>                  200                      205                      210 | 919 |
| gag cag cga cag gtt aag gtt gag gag cct tcg aga cca tca gcg tcc<br>Glu Gln Arg Gln Val Lys Val Glu Glu Pro Ser Arg Pro Ser Ala Ser<br>                  215                      220                      225 | 967 |
| tgg cag aac tct gtg tct gag cgg cca ccc tac tct tac atg gcc atg<br>Trp Gln Asn Ser Val Ser Glu Arg Pro Pro Tyr Ser Tyr Met Ala Met<br>230                      235                      240 | 1015 |
| ata caa ttc gcc atc aac agc act gag agg aag cgc atg act ttg aaa<br>Ile Gln Phe Ala Ile Asn Ser Thr Glu Arg Lys Arg Met Thr Leu Lys<br>245                      250                      255                      260 | 1063 |
| gac atc tat acg tgg att gag gac cac ttt ccc tac ttt aag cac att<br>Asp Ile Tyr Thr Trp Ile Glu Asp His Phe Pro Tyr Phe Lys His Ile<br>                  265                      270                      275 | 1111 |
| gcc aag cca ggc tgg aag aac tcc atc cgc cac aac ctt tcc ctg cac<br>Ala Lys Pro Gly Trp Lys Asn Ser Ile Arg His Asn Leu Ser Leu His<br>                  280                      285                      290 | 1159 |
| gac atg ttt gtc cgg gag acg tct gcc aat ggc aag gtc tcc ttc tgg<br>Asp Met Phe Val Arg Glu Thr Ser Ala Asn Gly Lys Val Ser Phe Trp<br>                  295                      300                      305 | 1207 |
| acc att cac ccc agt gcc aac cgc tac ttg aca ttg gac cag gtg ttt<br>Thr Ile His Pro Ser Ala Asn Arg Tyr Leu Thr Leu Asp Gln Val Phe<br>310                      315                      320 | 1255 |
| aag cca ctg gac cca ggg tct cca caa ttg ccc gag cac ttg gaa tca<br>Lys Pro Leu Asp Pro Gly Ser Pro Gln Leu Pro Glu His Leu Glu Ser<br>325                      330                      335                      340 | 1303 |
| cag cag aaa cga ccg aat cca gag ctc cgc cgg aac atg acc atc aaa<br>Gln Gln Lys Arg Pro Asn Pro Glu Leu Arg Arg Asn Met Thr Ile Lys<br>                  345                      350                      355 | 1351 |
| acc gaa ctc ccc ctg ggc gca cgg cgg aag atg aag cca cta cca<br>Thr Glu Leu Pro Leu Gly Ala Arg Arg Lys Met Lys Pro Leu Leu Pro<br>                  360                      365                      370 | 1399 |
| cgg gtc agc tca tac ctg gta cct atc cag ttc ccg gtg aac cag tca<br>Arg Val Ser Ser Tyr Leu Val Pro Ile Gln Phe Pro Val Asn Gln Ser<br>                  375                      380                      385 | 1447 |

-continued

| | |
|---|---|
| ctg gtg ttg cag ccc tcg gtg aag gtg cca ttg ccc ctg gcg gct tcc<br>Leu Val Leu Gln Pro Ser Val Lys Val Pro Leu Pro Leu Ala Ala Ser<br>390                   395                   400 | 1495 |
| ctc atg agc tca gag ctt gcc cgc cat agc aag cga gtc cgc att gcc<br>Leu Met Ser Ser Glu Leu Ala Arg His Ser Lys Arg Val Arg Ile Ala<br>405                 410                   415                   420 | 1543 |
| ccc aag gtt ttt ggg gaa cag gtg gtg ttt ggt tac atg agt aag ttc<br>Pro Lys Val Phe Gly Glu Gln Val Val Phe Gly Tyr Met Ser Lys Phe<br>                        425                   430                   435 | 1591 |
| ttt agt ggc gat ctg cga gat ttt ggt aca ccc atc acc agc ttg ttt<br>Phe Ser Gly Asp Leu Arg Asp Phe Gly Thr Pro Ile Thr Ser Leu Phe<br>            440                        445                   450 | 1639 |
| aat ttt atc ttt ctt tgt tta tca gtg ctg cta gct gag gag ggg ata<br>Asn Phe Ile Phe Leu Cys Leu Ser Val Leu Leu Ala Glu Glu Gly Ile<br>455                   460                   465 | 1687 |
| gct cct ctt tct tct gca gga cca ggg aaa gag gag aaa ctc ctg ttt<br>Ala Pro Leu Ser Ser Ala Gly Pro Gly Lys Glu Glu Lys Leu Leu Phe<br>470                   475                   480 | 1735 |
| gga gaa ggg ttt tct cct ttg ctt cca gtt cag act atc aag gag gaa<br>Gly Glu Gly Phe Ser Pro Leu Leu Pro Val Gln Thr Ile Lys Glu Glu<br>485                   490                   495                   500 | 1783 |
| gaa atc cag cct ggg gag gaa atg cca cac tta gcg aga ccc atc aaa<br>Glu Ile Gln Pro Gly Glu Glu Met Pro His Leu Ala Arg Pro Ile Lys<br>                        505                   510                   515 | 1831 |
| gtg gag agc cct ccc ttg gaa gag tgg ccc tcc ccg gcc cca tct ttc<br>Val Glu Ser Pro Pro Leu Glu Glu Trp Pro Ser Pro Ala Pro Ser Phe<br>520                   525                   530 | 1879 |
| aaa gag gaa tca tct cac tcc tgg gag gat tcg tcc caa tct ccc acc<br>Lys Glu Glu Ser Ser His Ser Trp Glu Asp Ser Ser Gln Ser Pro Thr<br>535                   540                   545 | 1927 |
| cca aga ccc aag aag tcc tac agt ggg ctt agg tcc cca acc cgg tgt<br>Pro Arg Pro Lys Lys Ser Tyr Ser Gly Leu Arg Ser Pro Thr Arg Cys<br>550                   555                   560 | 1975 |
| gtc tcg gaa atg ctt gtg att caa cac agg gag agg agg gag agg agc<br>Val Ser Glu Met Leu Val Ile Gln His Arg Glu Arg Arg Glu Arg Ser<br>565                 570                   575                   580 | 2023 |
| cgg tct cgg agg aaa cag cat cta ctg cct ccc tgt gtg gat gag ccg<br>Arg Ser Arg Arg Lys Gln His Leu Leu Pro Pro Cys Val Asp Glu Pro<br>                        585                   590                   595 | 2071 |
| gag ctg ctc ttc tca gag ggg ccc agt act tcc cgc tgg gcc gca gag<br>Glu Leu Leu Phe Ser Glu Gly Pro Ser Thr Ser Arg Trp Ala Ala Glu<br>            600                        605                   610 | 2119 |
| ctc ccg ttc cca gca gac tcc tct gac cct gcc tcc cag ctc agc tac<br>Leu Pro Phe Pro Ala Asp Ser Ser Asp Pro Ala Ser Gln Leu Ser Tyr<br>615                   620                   625 | 2167 |
| tcc cag gaa gtg gga gga cct ttt aag aca ccc att aag gaa acg ctg<br>Ser Gln Glu Val Gly Gly Pro Phe Lys Thr Pro Ile Lys Glu Thr Leu<br>630                   635                   640 | 2215 |
| ccc atc tcc tcc acc ccg agc aaa tct gtc ctc ccc aga acc cct gaa<br>Pro Ile Ser Ser Thr Pro Ser Lys Ser Val Leu Pro Arg Thr Pro Glu<br>645                   650                   655                   660 | 2263 |
| tcc tgg agg ctc acg ccc cca gcc aaa gta ggg gga ctg gat ttc agc<br>Ser Trp Arg Leu Thr Pro Pro Ala Lys Val Gly Gly Leu Asp Phe Ser<br>                        665                   670                   675 | 2311 |
| cca gta caa acc tcc cag ggt gcc tct gac ccc ttg cct gac ccc ctg<br>Pro Val Gln Thr Ser Gln Gly Ala Ser Asp Pro Leu Pro Asp Pro Leu<br>680                   685                   690 | 2359 |
| ggg ctg atg gat ctc agc acc act ccc ttg caa agt gct ccc ccc ctt<br>Gly Leu Met Asp Leu Ser Thr Thr Pro Leu Gln Ser Ala Pro Pro Leu | 2407 |

```
                695                 700                 705
gaa tca ccg caa agg ctc ctc agt tca gaa ccc tta gac ctc atc tcc      2455
Glu Ser Pro Gln Arg Leu Leu Ser Ser Glu Pro Leu Asp Leu Ile Ser
    710                 715                 720 gtc ccc ttt ggc aac tct tct ccc tca gat ata gac gtc ccc aag cca      2503
Val Pro Phe Gly Asn Ser Ser Pro Ser Asp Ile Asp Val Pro Lys Pro
725                 730                 735                 740 ggc tcc ccg gag cca cag gtt tct ggc ctt gca gcc aat cgt tct ctg      2551
Gly Ser Pro Glu Pro Gln Val Ser Gly Leu Ala Ala Asn Arg Ser Leu
                745                 750                 755 aca gaa ggc ctg gtc ctg gac aca atg aat gac agc ctc agc aag atc      2599
Thr Glu Gly Leu Val Leu Asp Thr Met Asn Asp Ser Leu Ser Lys Ile
            760                 765                 770 ctg ctg gac atc agc ttt cct ggc ctg gac gag gac cca ctg ggc cct      2647
Leu Leu Asp Ile Ser Phe Pro Gly Leu Asp Glu Asp Pro Leu Gly Pro
        775                 780                 785 gac aac atc aac tgg tcc cag ttt att cct gag cta cag tag              2689
Asp Asn Ile Asn Trp Ser Gln Phe Ile Pro Glu Leu Gln
    790                 795                 800 agccctgccc ttgcccctgt gctcaagctg tccaccatcc cgggcactcc aaggctcagt    2749
gcaccccaag cctctgagtg aggacagcag gcagggactt ttctgctcct catagctccc    2809
tgctgcctga ttatgcaaaa gtagcagtca caccctagcc actgctggga ccttgtgttc    2869
cccaagagta tctgattcct ctgctgtccc tgccaggagc tgaagggtgg aacaacaaa     2929
ggcaatggtg aaaagagatt aggaaccccc cagcctgttt ccattctctg cccagcagtc    2989
tcttaccttc cctgatcttt gcagggtggt ccgtgtaaat agtataaatt ctccaaatta    3049
tcctctaatt ataaatgtaa gcttatttcc ttagatcatt atccagagac tgccagaagg    3109
tgggtaggat gacctggggt ttcaattgac ttctgttcct tgcttttagt tttgatagaa    3169
gggaagacct gcagtgcacg gtttcttcca ggctgaggta cctggatctt gggttcttca    3229
ctgcagggac ccagacaagt ggatctgctt gccagagtcc tttttgcccc tccctgccac    3289
ctccccgtgt ttccaagtca gctttcctgc aagaagaaat cctggttaaa aaagtctttt    3349
gtattgggtc aggagttgaa tttggggtgg gaggatggat gcaactgaag cagagtgtgg    3409
gtgcccagat gtgcgctatt agatgtttct ctgataatgt ccccaatcat accagggaga    3469
ctggcattga cgagaactca ggtggaggct tgagaaggcc gaaagggccc ctgacctgcc    3529
tggcttcctt agcttgcccc tcagctttgc aaagagccac cctaggcccc agctgaccgc    3589
atgggtgtga gccagcttga gaacactaac tactcaataa agcgaaggt ggacatgaaa    3649
aaaaaaaaaa aaaaaa                                                    3665

<210> SEQ ID NO 5
<211> LENGTH: 801
<212> TYPE: PRT
<213> ORGANISM: Homo sapiens

<400> SEQUENCE: 5

Met Lys Thr Ser Pro Arg Arg Pro Leu Ile Leu Lys Arg Arg Arg Leu
1               5                   10                  15

Pro Leu Pro Val Gln Asn Ala Pro Ser Glu Thr Ser Glu Glu Glu Pro
            20                  25                  30

Lys Arg Ser Pro Ala Gln Gln Glu Ser Asn Gln Ala Glu Ala Ser Lys
        35                  40                  45

Glu Val Ala Glu Ser Asn Ser Cys Lys Phe Pro Ala Gly Ile Lys Ile
    50                  55                  60
```

-continued

```
Ile Asn His Pro Thr Met Pro Asn Thr Gln Val Val Ala Ile Pro Asn
 65                  70                  75                  80

Asn Ala Asn Ile His Ser Ile Ile Thr Ala Leu Thr Ala Lys Gly Lys
                 85                  90                  95

Glu Ser Gly Ser Ser Gly Pro Asn Lys Phe Ile Leu Ile Ser Cys Gly
            100                 105                 110

Gly Ala Pro Thr Gln Pro Pro Gly Leu Arg Pro Gln Thr Gln Thr Ser
            115                 120                 125

Tyr Asp Ala Lys Arg Thr Glu Val Thr Leu Glu Thr Leu Gly Pro Lys
        130                 135                 140

Pro Ala Ala Arg Asp Val Asn Leu Pro Arg Pro Pro Gly Ala Leu Cys
145                 150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
            180                 185                 190

Asp Gly Leu Gly Ser Arg Ser Ile Lys Gln Glu Met Glu Glu Lys Glu
        195                 200                 205

Asn Cys His Leu Glu Gln Arg Gln Val Lys Val Glu Glu Pro Ser Arg
210                 215                 220

Pro Ser Ala Ser Trp Gln Asn Ser Val Ser Glu Arg Pro Pro Tyr Ser
225                 230                 235                 240

Tyr Met Ala Met Ile Gln Phe Ala Ile Asn Ser Thr Glu Arg Lys Arg
                245                 250                 255

Met Thr Leu Lys Asp Ile Tyr Thr Trp Ile Glu Asp His Phe Pro Tyr
            260                 265                 270

Phe Lys His Ile Ala Lys Pro Gly Trp Lys Asn Ser Ile Arg His Asn
        275                 280                 285

Leu Ser Leu His Asp Met Phe Val Arg Glu Thr Ser Ala Asn Gly Lys
        290                 295                 300

Val Ser Phe Trp Thr Ile His Pro Ser Ala Asn Arg Tyr Leu Thr Leu
305                 310                 315                 320

Asp Gln Val Phe Lys Pro Leu Asp Pro Gly Ser Pro Gln Leu Pro Glu
                325                 330                 335

His Leu Glu Ser Gln Gln Lys Arg Pro Asn Pro Glu Leu Arg Arg Asn
            340                 345                 350

Met Thr Ile Lys Thr Glu Leu Pro Leu Gly Ala Arg Arg Lys Met Lys
        355                 360                 365

Pro Leu Leu Pro Arg Val Ser Ser Tyr Leu Val Pro Ile Gln Phe Pro
        370                 375                 380

Val Asn Gln Ser Leu Val Leu Gln Pro Ser Val Lys Val Pro Leu Pro
385                 390                 395                 400

Leu Ala Ala Ser Leu Met Ser Ser Glu Leu Ala Arg His Ser Lys Arg
                405                 410                 415

Val Arg Ile Ala Pro Lys Val Phe Gly Glu Gln Val Val Phe Gly Tyr
            420                 425                 430

Met Ser Lys Phe Phe Ser Gly Asp Leu Arg Asp Phe Gly Thr Pro Ile
        435                 440                 445

Thr Ser Leu Phe Asn Phe Ile Phe Leu Cys Leu Ser Val Leu Leu Ala
        450                 455                 460

Glu Glu Gly Ile Ala Pro Leu Ser Ser Ala Gly Pro Gly Lys Glu Glu
465                 470                 475                 480
```

-continued

Lys Leu Leu Phe Gly Glu Gly Phe Ser Pro Leu Pro Val Gln Thr
                    485                 490                 495

Ile Lys Glu Glu Glu Ile Gln Pro Gly Glu Glu Met Pro His Leu Ala
            500                 505                 510

Arg Pro Ile Lys Val Glu Ser Pro Leu Glu Glu Trp Pro Ser Pro
            515                 520                 525

Ala Pro Ser Phe Lys Glu Glu Ser Ser His Ser Trp Glu Asp Ser Ser
        530                 535                 540

Gln Ser Pro Thr Pro Arg Pro Lys Lys Ser Tyr Ser Gly Leu Arg Ser
545                 550                 555                 560

Pro Thr Arg Cys Val Ser Glu Met Leu Val Ile Gln His Arg Glu Arg
                565                 570                 575

Arg Glu Arg Ser Arg Ser Arg Arg Lys Gln His Leu Leu Pro Pro Cys
            580                 585                 590

Val Asp Glu Pro Glu Leu Leu Phe Ser Glu Gly Pro Ser Thr Ser Arg
        595                 600                 605

Trp Ala Ala Glu Leu Pro Phe Pro Ala Asp Ser Ser Asp Pro Ala Ser
610                 615                 620

Gln Leu Ser Tyr Ser Gln Glu Val Gly Gly Pro Phe Lys Thr Pro Ile
625                 630                 635                 640

Lys Glu Thr Leu Pro Ile Ser Ser Thr Pro Ser Lys Ser Val Leu Pro
                645                 650                 655

Arg Thr Pro Glu Ser Trp Arg Leu Thr Pro Pro Ala Lys Val Gly Gly
            660                 665                 670

Leu Asp Phe Ser Pro Val Gln Thr Ser Gln Gly Ala Ser Asp Pro Leu
        675                 680                 685

Pro Asp Pro Leu Gly Leu Met Asp Leu Ser Thr Thr Pro Leu Gln Ser
690                 695                 700

Ala Pro Pro Leu Glu Ser Pro Gln Arg Leu Leu Ser Ser Glu Pro Leu
705                 710                 715                 720

Asp Leu Ile Ser Val Pro Phe Gly Asn Ser Ser Pro Ser Asp Ile Asp
                725                 730                 735

Val Pro Lys Pro Gly Ser Pro Glu Pro Gln Val Ser Gly Leu Ala Ala
            740                 745                 750

Asn Arg Ser Leu Thr Glu Gly Leu Val Leu Asp Thr Met Asn Asp Ser
        755                 760                 765

Leu Ser Lys Ile Leu Leu Asp Ile Ser Phe Pro Gly Leu Asp Glu Asp
770                 775                 780

Pro Leu Gly Pro Asp Asn Ile Asn Trp Ser Gln Phe Ile Pro Glu Leu
785                 790                 795                 800

Gln

<210> SEQ ID NO 6
<211> LENGTH: 3506
<212> TYPE: DNA
<213> ORGANISM: Homo sapiens
<220> FEATURE:
<221> NAME/KEY: CDS
<222> LOCATION: (284)..(2530)

<400> SEQUENCE: 6
tttcaaacag cggaacaaac tgaaagctcc ggtgccagac cccaccccg gccccggccc    60 gggacccct cccctcccgg gatccccgg ggttcccacc ccgccgcac cgccgggac    120 ccggccggtc cggcgcgagc cccgtccgg ggccctggct cggccccag gttggaggag    180

-continued

| | |
|---|---|
| cccggagccc gccttcggag ctacggccta acggcggcgg cgactgcagt ctggagggtc | 240 |

| | | | | | | | | | | | | | | | | |
|---|---|---|---|---|---|---|---|---|---|---|---|---|---|---|---|---|
| cacacttgtg attctcaatg gagagtgaaa acgcagattc ata | atg<br>Met<br>1 | aaa<br>Lys | act<br>Thr | agc<br>Ser | | | | | | | | | | | | 295 |
| ccc<br>Pro<br>5 | cgt<br>Arg | cgg<br>Arg | cca<br>Pro | ctg<br>Leu | att<br>Ile<br>10 | ctc<br>Leu | aaa<br>Lys | aga<br>Arg | cgg<br>Arg | agg<br>Arg<br>15 | ctg<br>Leu | ccc<br>Pro | ctt<br>Leu | cct<br>Pro | gtt<br>Val<br>20 | 343 |
| caa<br>Gln | aat<br>Asn | gcc<br>Ala | cca<br>Pro | agt<br>Ser<br>25 | gaa<br>Glu | aca<br>Thr | tca<br>Ser | gag<br>Glu | gag<br>Glu<br>30 | gaa<br>Glu | cct<br>Pro | aag<br>Lys | aga<br>Arg | tcc<br>Ser<br>35 | cct<br>Pro | 391 |
| gcc<br>Ala | caa<br>Gln | cag<br>Gln | gag<br>Glu<br>40 | tct<br>Ser | aat<br>Asn | caa<br>Gln | gca<br>Ala | gag<br>Glu<br>45 | gcc<br>Ala | tcc<br>Ser | aag<br>Lys | gaa<br>Glu | gtg<br>Val<br>50 | gca<br>Ala | gag<br>Glu | 439 |
| tcc<br>Ser | aac<br>Asn | tct<br>Ser<br>55 | tgc<br>Cys | aag<br>Lys | ttt<br>Phe | cca<br>Pro | gct<br>Ala<br>60 | ggg<br>Gly | atc<br>Ile | aag<br>Lys | att<br>Ile | att<br>Ile<br>65 | aac<br>Asn | cac<br>His | ccc<br>Pro | 487 |
| acc<br>Thr | atg<br>Met<br>70 | ccc<br>Pro | aac<br>Asn | acg<br>Thr | caa<br>Gln | gta<br>Val<br>75 | gtg<br>Val | gcc<br>Ala | atc<br>Ile | ccc<br>Pro | aac<br>Asn<br>80 | aat<br>Asn | gct<br>Ala | aat<br>Asn | att<br>Ile | 535 |
| cac<br>His<br>85 | agc<br>Ser | atc<br>Ile | atc<br>Ile | aca<br>Thr<br>90 | gca<br>Ala | ctg<br>Leu | act<br>Thr | gcc<br>Ala | aag<br>Lys<br>95 | gga<br>Gly | aaa<br>Lys | gag<br>Glu | agt<br>Ser | ggc<br>Gly<br>100 | agt<br>Ser | 583 |
| agt<br>Ser | ggg<br>Gly | ccc<br>Pro | aac<br>Asn | aaa<br>Lys<br>105 | ttc<br>Phe | atc<br>Ile | ctc<br>Leu | atc<br>Ile | agc<br>Ser<br>110 | tgt<br>Cys | ggg<br>Gly | gga<br>Gly | gcc<br>Ala | cca<br>Pro<br>115 | act<br>Thr | 631 |
| cag<br>Gln | cct<br>Pro | cca<br>Pro | gga<br>Gly<br>120 | ctc<br>Leu | cgg<br>Arg | cct<br>Pro | caa<br>Gln | acc<br>Thr<br>125 | caa<br>Gln | acc<br>Thr | agc<br>Ser | tat<br>Tyr | gat<br>Asp<br>130 | gcc<br>Ala | aaa<br>Lys | 679 |
| agg<br>Arg | aca<br>Thr | gaa<br>Glu<br>135 | gtg<br>Val | acc<br>Thr | ctg<br>Leu | gag<br>Glu | acc<br>Thr<br>140 | ttg<br>Leu | gga<br>Gly | cca<br>Pro | aaa<br>Lys | cct<br>Pro<br>145 | gca<br>Ala | gct<br>Ala | agg<br>Arg | 727 |
| gat<br>Asp | gtg<br>Val<br>150 | aat<br>Asn | ctt<br>Leu | cct<br>Pro | aga<br>Arg | cca<br>Pro<br>155 | cct<br>Pro | gga<br>Gly | gcc<br>Ala | ctt<br>Leu | tgc<br>Cys<br>160 | gag<br>Glu | cag<br>Gln | aaa<br>Lys | cgg<br>Arg | 775 |
| gag<br>Glu<br>165 | acc<br>Thr | tgt<br>Cys | gca<br>Ala | gat<br>Asp<br>170 | ggt<br>Gly | gag<br>Glu | gca<br>Ala | gca<br>Ala | ggc<br>Gly<br>175 | tgc<br>Cys | act<br>Thr | atc<br>Ile | aac<br>Asn | aat<br>Asn<br>180 | agc<br>Ser | 823 |
| cta<br>Leu | tcc<br>Ser | aac<br>Asn | atc<br>Ile | cag<br>Gln<br>185 | tgg<br>Trp | ctt<br>Leu | cga<br>Arg | aag<br>Lys | atg<br>Met<br>190 | agt<br>Ser | tct<br>Ser | gat<br>Asp | gga<br>Gly | ctg<br>Leu<br>195 | ggc<br>Gly | 871 |
| tcc<br>Ser | cgc<br>Arg | agc<br>Ser | atc<br>Ile<br>200 | aag<br>Lys | caa<br>Gln | gag<br>Glu | atg<br>Met | gag<br>Glu<br>205 | gaa<br>Glu | aag<br>Lys | gag<br>Glu | aat<br>Asn | tgt<br>Cys<br>210 | cac<br>His | ctg<br>Leu | 919 |
| gag<br>Glu | cag<br>Gln | cga<br>Arg<br>215 | cag<br>Gln | gtt<br>Val | aag<br>Lys | gtt<br>Val<br>220 | gag<br>Glu | gag<br>Glu | cct<br>Pro | tcg<br>Ser | aga<br>Arg<br>225 | cca<br>Pro | tca<br>Ser | gcg<br>Ala | tcc<br>Ser | 967 |
| tgg<br>Trp | cag<br>Gln<br>230 | aac<br>Asn | tct<br>Ser | gtg<br>Val | tct<br>Ser | gag<br>Glu<br>235 | cgg<br>Arg | cca<br>Pro | ccc<br>Pro | tac<br>Tyr | tct<br>Ser<br>240 | tac<br>Tyr | atg<br>Met | gcc<br>Ala | atg<br>Met | 1015 |
| ata<br>Ile<br>245 | caa<br>Gln | ttc<br>Phe | gcc<br>Ala | atc<br>Ile<br>250 | aac<br>Asn | agc<br>Ser | act<br>Thr | gag<br>Glu | agg<br>Arg<br>255 | aag<br>Lys | cgc<br>Arg | atg<br>Met | act<br>Thr | ttg<br>Leu<br>260 | aaa<br>Lys | 1063 |
| gac<br>Asp | atc<br>Ile | tat<br>Tyr | acg<br>Thr<br>265 | tgg<br>Trp | att<br>Ile | gag<br>Glu | gac<br>Asp | cac<br>His<br>270 | ttt<br>Phe | ccc<br>Pro | tac<br>Tyr | ttt<br>Phe | aag<br>Lys<br>275 | cac<br>His | att<br>Ile | 1111 |
| gcc<br>Ala | aag<br>Lys | cca<br>Pro<br>280 | ggc<br>Gly | tgg<br>Trp | aag<br>Lys | aac<br>Asn | tcc<br>Ser<br>285 | atc<br>Ile | cgc<br>Arg | cac<br>His | aac<br>Asn | ctt<br>Leu<br>290 | tcc<br>Ser | ctg<br>Leu | cac<br>His | 1159 |
| gac<br>Asp | atg<br>Met | ttt<br>Phe | gtc<br>Val | cgg<br>Arg | gag<br>Glu | acg<br>Thr | tct<br>Ser | gcc<br>Ala | aat<br>Asn | ggc<br>Gly | aag<br>Lys | gtc<br>Val | tcc<br>Ser | ttc<br>Phe | tgg<br>Trp | 1207 |

-continued

```
                Asp Met Phe Val Arg Glu Thr Ser Ala Asn Gly Lys Val Ser Phe Trp
                            295                 300                 305 acc att cac ccc agt gcc aac cgc tac ttg aca ttg gac cag gtg ttt        1255
Thr Ile His Pro Ser Ala Asn Arg Tyr Leu Thr Leu Asp Gln Val Phe
310                 315                 320 aag cag cag aaa cga ccg aat cca gag ctc cgc cgg aac atg acc atc        1303
Lys Gln Gln Lys Arg Pro Asn Pro Glu Leu Arg Arg Asn Met Thr Ile
325                 330                 335                 340 aaa acc gaa ctc ccc ctg ggc gca cgg cgg aag atg aag cca ctg cta        1351
Lys Thr Glu Leu Pro Leu Gly Ala Arg Arg Lys Met Lys Pro Leu Leu
                345                 350                 355 cca cgg gtc agc tca tac ctg gta cct atc cag ttc ccg gtg aac cag        1399
Pro Arg Val Ser Ser Tyr Leu Val Pro Ile Gln Phe Pro Val Asn Gln
                360                 365                 370 tca ctg gtg ttg cag ccc tcg gtg aag gtg cca ttg ccc ctg gcg gct        1447
Ser Leu Val Leu Gln Pro Ser Val Lys Val Pro Leu Pro Leu Ala Ala
                375                 380                 385 tcc ctc atg agc tca gag ctt gcc cgc cat agc aag cga gtc cgc att        1495
Ser Leu Met Ser Ser Glu Leu Ala Arg His Ser Lys Arg Val Arg Ile
            390                 395                 400 gcc ccc aag gtg ctg cta gct gag gag ggg ata gct cct ctt tct tct        1543
Ala Pro Lys Val Leu Leu Ala Glu Glu Gly Ile Ala Pro Leu Ser Ser
405                 410                 415                 420 gca gga cca ggg aaa gag gag aaa ctc ctg ttt gga gaa ggg ttt tct        1591
Ala Gly Pro Gly Lys Glu Glu Lys Leu Leu Phe Gly Glu Gly Phe Ser
                425                 430                 435 cct ttg ctt cca gtt cag act atc aag gag gaa gaa atc cag cct ggg        1639
Pro Leu Leu Pro Val Gln Thr Ile Lys Glu Glu Glu Ile Gln Pro Gly
                440                 445                 450 gag gaa atg cca cac tta gcg aga ccc atc aaa gtg gag agc cct ccc        1687
Glu Glu Met Pro His Leu Ala Arg Pro Ile Lys Val Glu Ser Pro Pro
                455                 460                 465 ttg gaa gag tgg ccc tcc ccg gcc cca tct ttc aaa gag gaa tca tct        1735
Leu Glu Glu Trp Pro Ser Pro Ala Pro Ser Phe Lys Glu Glu Ser Ser
            470                 475                 480 cac tcc tgg gag gat tcg tcc caa tct ccc acc cca aga ccc aag aag        1783
His Ser Trp Glu Asp Ser Ser Gln Ser Pro Thr Pro Arg Pro Lys Lys
485                 490                 495                 500 tcc tac agt ggg ctt agg tcc cca acc cgg tgt gtc tcg gaa atg ctt        1831
Ser Tyr Ser Gly Leu Arg Ser Pro Thr Arg Cys Val Ser Glu Met Leu
                505                 510                 515 gtg att caa cac agg gag agg agg gag agg agc cgg tct cgg agg aaa        1879
Val Ile Gln His Arg Glu Arg Arg Glu Arg Ser Arg Ser Arg Arg Lys
                520                 525                 530 cag cat cta ctg cct ccc tgt gtg gat gag ccg gag ctg ctc ttc tca        1927
Gln His Leu Leu Pro Pro Cys Val Asp Glu Pro Glu Leu Leu Phe Ser
                535                 540                 545 gag ggg ccc agt act tcc cgc tgg gcc gca gag ctc ccg ttc cca gca        1975
Glu Gly Pro Ser Thr Ser Arg Trp Ala Ala Glu Leu Pro Phe Pro Ala
550                 555                 560 gac tcc tct gac cct gcc tcc cag ctc agc tac tcc cag gaa gtg gga        2023
Asp Ser Ser Asp Pro Ala Ser Gln Leu Ser Tyr Ser Gln Glu Val Gly
565                 570                 575                 580 gga cct ttt aag aca ccc att aag gaa acg ctg ccc atc tcc tcc acc        2071
Gly Pro Phe Lys Thr Pro Ile Lys Glu Thr Leu Pro Ile Ser Ser Thr
                585                 590                 595 ccg agc aaa tct gtc ctc ccc aga acc cct gaa tcc tgg agg ctc acg        2119
Pro Ser Lys Ser Val Leu Pro Arg Thr Pro Glu Ser Trp Arg Leu Thr
                600                 605                 610
```

| | | |
|---|---|---|
| ccc cca gcc aaa gta ggg gga ctg gat ttc agc cca gta caa acc tcc<br>Pro Pro Ala Lys Val Gly Gly Leu Asp Phe Ser Pro Val Gln Thr Ser<br>615                    620                    625 | | 2167 |
| cag ggt gcc tct gac ccc ttg cct gac ccc ctg ggg ctg atg gat ctc<br>Gln Gly Ala Ser Asp Pro Leu Pro Asp Pro Leu Gly Leu Met Asp Leu<br>    630                    635                    640 | | 2215 |
| agc acc act ccc ttg caa agt gct ccc ccc ctt gaa tca ccg caa agg<br>Ser Thr Thr Pro Leu Gln Ser Ala Pro Pro Leu Glu Ser Pro Gln Arg<br>645                    650                    655                    660 | | 2263 |
| ctc ctc agt tca gaa ccc tta gac ctc atc tcc gtc ccc ttt ggc aac<br>Leu Leu Ser Ser Glu Pro Leu Asp Leu Ile Ser Val Pro Phe Gly Asn<br>                665                    670                    675 | | 2311 |
| tct tct ccc tca gat ata gac gtc ccc aag cca ggc tcc ccg gag cca<br>Ser Ser Pro Ser Asp Ile Asp Val Pro Lys Pro Gly Ser Pro Glu Pro<br>            680                    685                    690 | | 2359 |
| cag gtt tct ggc ctt gca gcc aat cgt tct ctg aca gaa ggc ctg gtc<br>Gln Val Ser Gly Leu Ala Ala Asn Arg Ser Leu Thr Glu Gly Leu Val<br>695                    700                    705 | | 2407 |
| ctg gac aca atg aat gac agc ctc agc aag atc ctg ctg gac atc agc<br>Leu Asp Thr Met Asn Asp Ser Leu Ser Lys Ile Leu Leu Asp Ile Ser<br>    710                    715                    720 | | 2455 |
| ttt cct ggc ctg gac gag gac cca ctg ggc cct gac aac atc aac tgg<br>Phe Pro Gly Leu Asp Glu Asp Pro Leu Gly Pro Asp Asn Ile Asn Trp<br>725                    730                    735                    740 | | 2503 |
| tcc cag ttt att cct gag cta cag tag agccctgccc ttgccctgt<br>Ser Gln Phe Ile Pro Glu Leu Gln<br>                    745 | | 2550 |
| gctcaagctg tccaccatcc cgggcactcc aaggctcagt gcaccccaag cctctgagtg | | 2610 |
| aggacagcag gcagggactg ttctgctcct catagctccc tgctgcctga ttatgcaaaa | | 2670 |
| gtagcagtca caccctagcc actgctggga ccttgtgttc cccaagagta tctgattcct | | 2730 |
| ctgctgtccc tgccaggagc tgaagggtgg gaacaacaaa ggcaatggtg aaaagagatt | | 2790 |
| aggaaccccc cagcctgttt ccattctctg cccagcagtc tcttaccttc cctgatcttt | | 2850 |
| gcagggtggt ccgtgtaaat agtataaatt ctccaaatta tcctctaatt ataaatgtaa | | 2910 |
| gcttatttcc ttagatcatt atccagagac tgccagaagg tgggtaggat gacctggggt | | 2970 |
| ttcaattgac ttctgttcct tgcttttagt tttgatagaa gggaagacct gcagtgcacg | | 3030 |
| gtttcttcca ggctgaggta cctggatctt gggttcttca ctgcagggac ccagacaagt | | 3090 |
| ggatctgctt gccagagtcc tttttgcccc tccctgccac ctccccgtgt ttccaagtca | | 3150 |
| gctttcctgc aagaagaaat cctggttaaa aaagtctttt gtattgggtc aggagttgaa | | 3210 |
| tttggggtgg gaggatggat gcaactgaag cagagtgtgg gtgcccagat gtgcgctatt | | 3270 |
| agatgtttct ctgataatgt ccccaatcat accagggaga ctggcattga cgagaactca | | 3330 |
| ggtggaggct tgagaaggcc gaaagggccc ctgacctgcc tggcttcctt agcttgcccc | | 3390 |
| tcagctttgc aaagagccac cctaggcccc agctgaccgc atgggtgtga gccagcttga | | 3450 |
| gaacactaac tactcaataa aagcgaaggt ggacatgaaa aaaaaaaaa aaaaaa | | 3506 |

COMPOUNDS FOR THE TREATMENT OF CANCER

CROSS REFERENCE TO RELATED APPLICATIONS

This application is a divisional application of U.S. application Ser. No. 15/019,135, filed on Feb. 9, 2016, which claims priority to European Patent Application Nos. EP 15154342.8, filed Feb. 9, 2015 and EP 15155286.6 filed Feb. 16, 2015, the disclosures of which are incorporated herein by reference in their entirety.

SEQUENCE LISTING

The present application contains a Sequence Listing which has been submitted electronically as a text file in ASCII format and is hereby incorporated by reference in its entirety. Said text file, created on Dec. 21, 2017 is named P32500_US_1_SEQ_Listing.txt and is 53,263 bytes in size.

FIELD OF THE INVENTION

The present invention relates to a FoxM1 gene splicing modifier selected from a compound of formula (I) or of formula (VI)

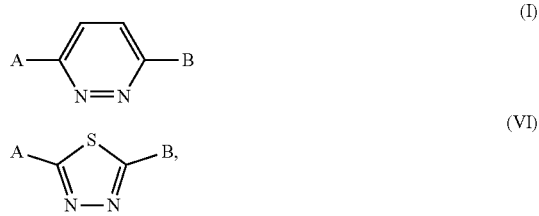

wherein A and B are as defined herein, or a pharmaceutically acceptable salt thereof, for use in the treatment, prevention and/or delay of progression of cancer.

BACKGROUND

FoxM1 is a transcription factor of the Forkhead family. It is also known in the literature as Trident (in mouse), HFH-11 (in human), WIN or INS-1 (in rat), MPP-2 (partial human cDNA) or FKHL-16. The Forkhead family comprises a large number of transcription factors defined by a conserved DNA binding domain called Forkhead or winged-helix domain. The FoxM1 gene was cloned by screening cDNA libraries with degenerate primers for homologues with a conserved Forkhead DNAbinding domain (W. Korver, J. Roose, H. Clevers, Nucleic Acids Res. 25 (1997) 1715-1719). The FoxM1 gene was revealed to encode a Forkhead transcription factor family member that exhibits 45% identity in the DNA-binding domain with five of its closest related Forkhead members, namely FoxA3 (HNF-3γ, FoxC1 (fkh-1), FoxF2 (FREAC-2), FoxK1 (ILF) and FoxN2 (HTLF). The FoxM1 C-terminal region was found to have homology (76% identity) with a human partial cDNA encoding an open reading-frame of 221 amino acids, termed MPP-2. MPP-2 stands for MPM-2-reactive phosphoprotein-2 and was identified after screening a lymphoblast-derived cDNA library with the MPM-2 monoclonal antibody, which binds specifically to epitopes on mitotic proteins that are phosphorylated in a phosphoserine-proline dependent manner. FoxM1 binds DNA in vitro through the consensus site TAAACA. This motif shares the core sequence recognized by other members of the forkhead family. In particular, repeats of these motifs, in alternating orientation, were often characterized within the selected binding sequences for FoxM1.

The human FoxM1 gene is a 10-exon structure spanning approximately 25 kb on the 12p13-3 chromosomal band (telomeric position) (W. Korver, J. Roose, H. Clevers, Nucleic Acids Res. 25 (1997) 1715-1719). Two exons, named exons Va and VIIa, also referred to as exon A1 (or rat exon 6) and A2 respectively, are alternatively spliced (H. Ye, T. F. Kelly, U. Samadani, L. Lim, S. Rubio, D. G. Overdier, K. A. Roebuck, R. H. Costa, Mol. Cell Biol. 17 (1997) 1626-1641). Exon Va encodes a 15 amino-acidinsertion within the C-terminal part of the DNA binding-domain, and is not seen in any of the other Forkhead transcription factor family members. Exon VIIa represents a 38 amino-acid insertion within the C-terminus of the protein. Differential splicing of exons Va and VIIa in human FoxM1, gives rise to three classes of transcripts, class A containing both alternative exons, class B containing none of the alternative exons, and class C in which exon Va only is retained (H. Ye, T. F. Kelly, U. Samadani, L. Lim, S. Rubio, D. G. Overdier, K. A. Roebuck, R. H. Costa, Mol. Cell Biol. 17 (1997) 1626-1641). Both FoxM1B and FoxM1C are transcriptionally active, whereas FoxM1A is transcriptionally inactive, due to the insertion of exon VIIa in the C-terminal transactivation domain. This disruption of the transactivation domain in FoxM1A not only leads to transcriptional inactivation, it might also cause this variant to act as a dominant-negative variant as it has retained normal DNA binding activity in the absence of a functional transactivation domain (H. Ye, T. F. Kelly, U. Samadani, L. Lim, S. Rubio, D. G. Overdier, K. A. Roebuck, R. H. Costa, Mol. Cell Biol. 17 (1997) 1626-1641).

FoxM1 is overexpressed in a broad range of tumor types, including those of neural, gastrointestinal, and reproductive origin (see Bektas et al., supra; Nakamura et al., 2004, Oncogene 23: 2385-400; Pilarsky et al., 2004, Neoplasia .Q: 744-50; Liu et al., 2006, Cancer Res 66: 3593-602). This expression pattern of FoxM1 is attributed to the ability of FoxM1 to transactivate genes required for cell cycle progression (Wang et al., 2002, Proc Nat. Acad Sci US A 99:16881-6). Increased nuclear staining of FoxM1B found in human basal cell carcinomas suggests that FoxM1 is required for cellular proliferation in human cancers (Teh et al., 2002, Cancer Res. 62: 4773-80). The detailed role of FoxM1 in establishing or facilitating tumor progression and disease management has not been fully elucidated, however.

EP 2 298 896 (A1) discloses siRNA molecules inhibiting expression of FoxM1B protein and the use of the siRNA molecules for inhibiting tumor growth.

WO 2011/127297 (A1) discloses a composition comprising a siRNA FoxM1 inhibitor and Herceptin for the treatment of breast cancer.

WO 2014/028459 (A1) discloses 1,4-disubstituted pyridazine analogs and methods for treating SMN-deficiency related conditions.

WO 2014/116845 (A1) discloses thiadiazole analogs and methods for treating SMN-deficiency related conditions.

WO 2015/017589 (A1) discloses 1,4-disubstituted pyridazine analogs and methods for treating SMN-deficiency related conditions.

The problem to be solved by the present invention was to provide new compounds suitable for modifying splicing of the FoxM1 gene for use in the treatment of cancer.

BRIEF DESCRIPTION OF THE FIGURES

FIG. 1A Compound 1; FIG. 1B Compound 2; FIG. 1C Compound 3; FIG. 1D Compound 4; FIG. 1E Compound 6; FIG. 1F Compound 7; FIG. 1G Compound 8; FIG. 1H Compound 9; FIG. 1I Compound 11. Data represent means±standard error of the mean (SEM) of 3-9 independent observations. Data was generated as described in Example 1.

DETAILED DESCRIPTION OF THE INVENTION

Figure 1A:
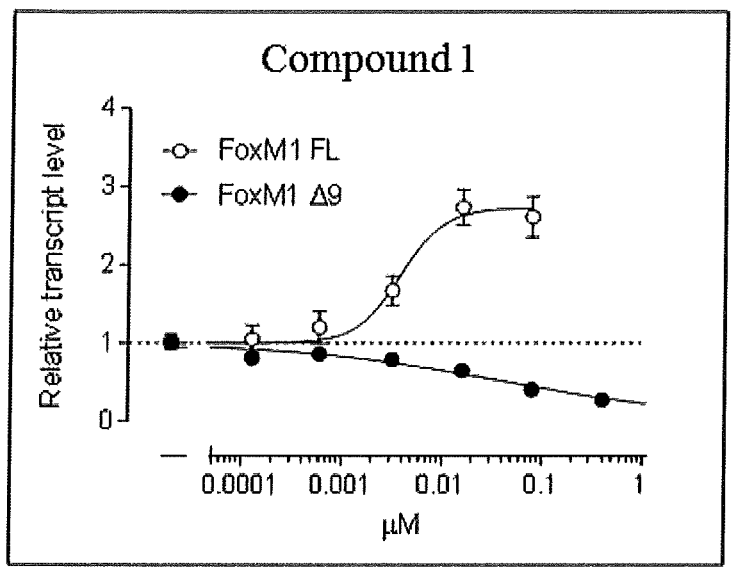
FIG. 1A, FIG. 1B, FIG. 1C, FIG. 1D, FIG. 1E, FIG. 1F, FIG. 1G, FIG. 1H and FIG. 1I: Induction of alternative splicing of FoxM1 towards full-length FoxM1 in fibroblasts. Human fibroblasts were incubated with compounds of present invention at different concentrations for 24 hours, and changes in FoxM1_FL (containing exon VIIa) and FoxM1_ΔVIIa (lacking exon VIIa) mRNA expression were assessed by RT-qPCR.
Figure 1B:
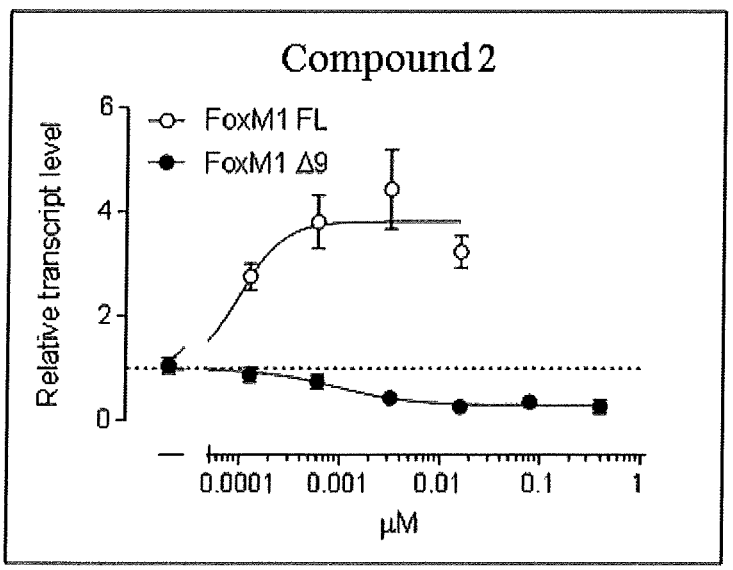
Figure 1C:
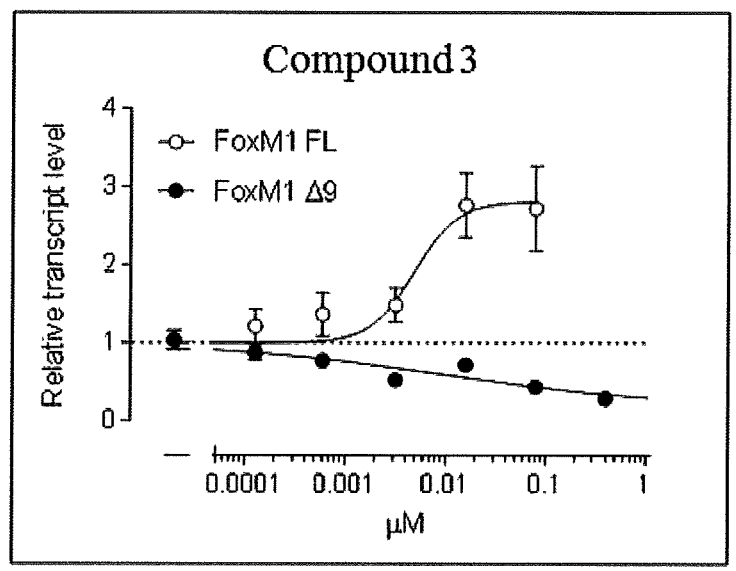
Figure 1D:
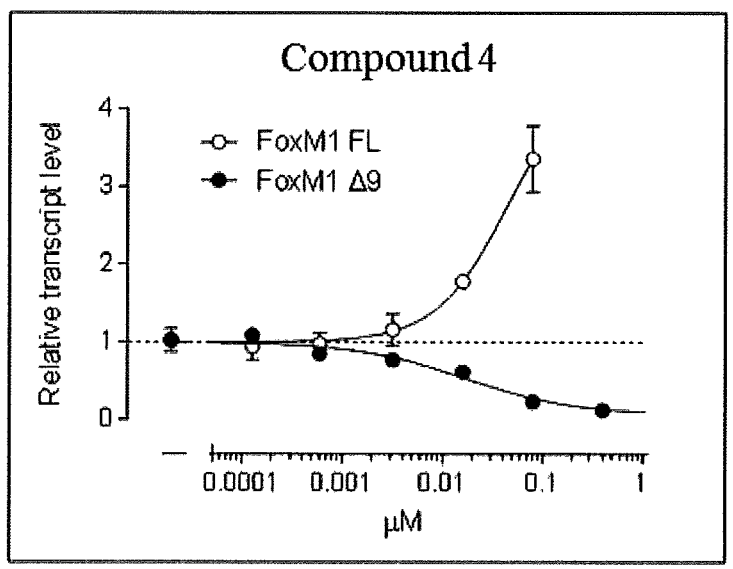
Figure 1E:
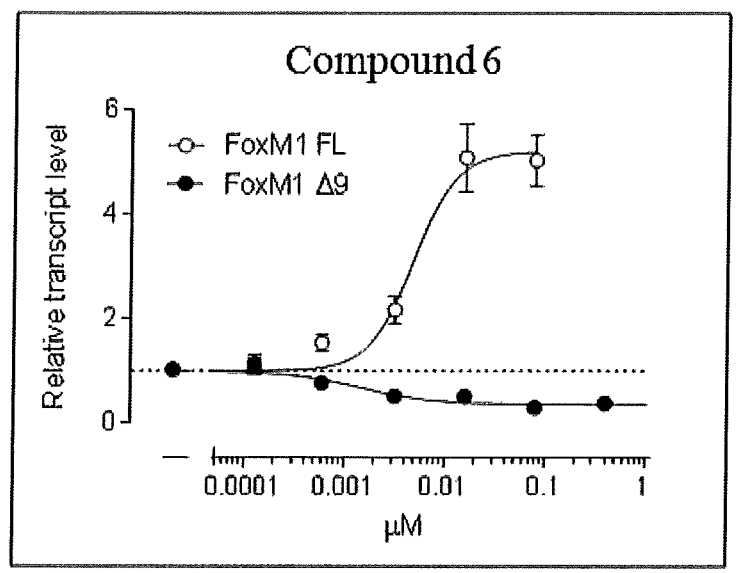
Figure 1F:
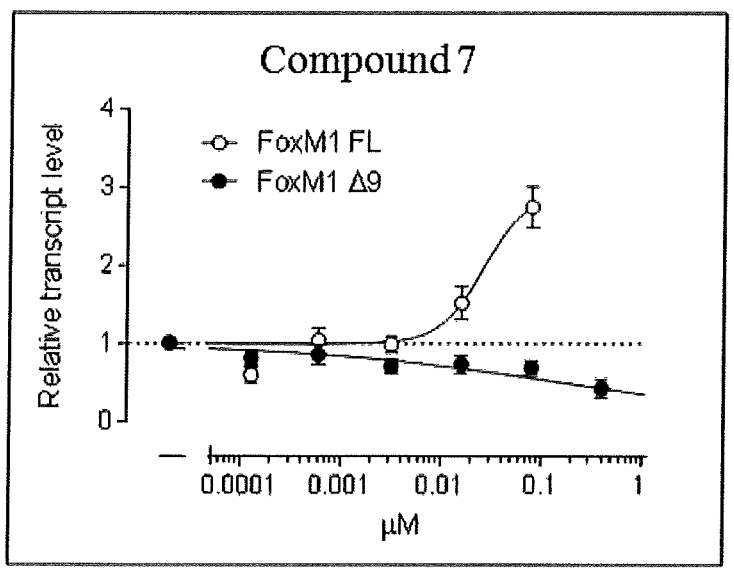
Figure 1G:
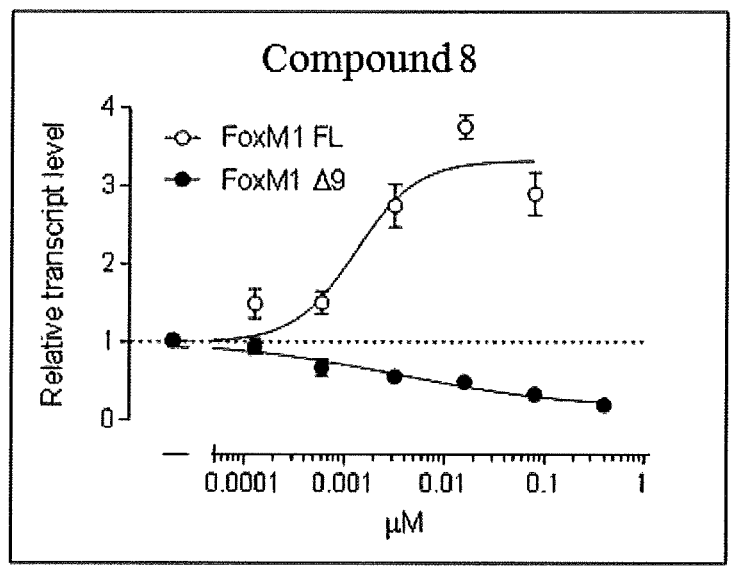
Figure 1H:
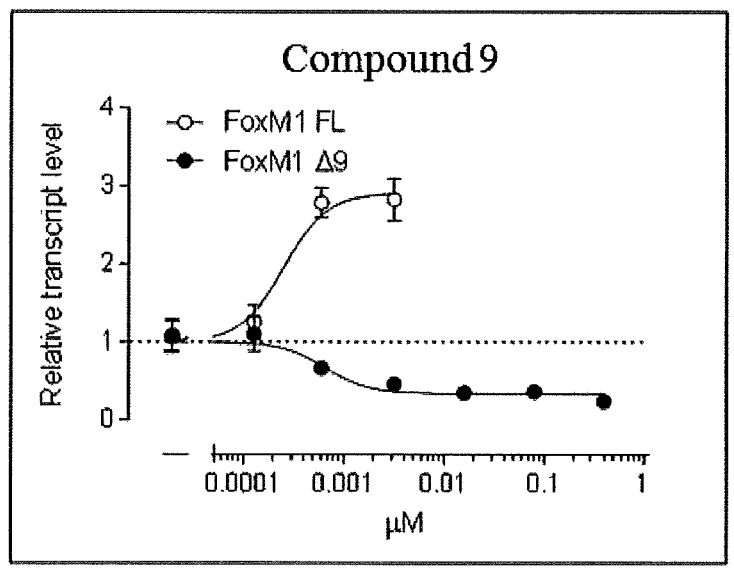
Figure 1I:
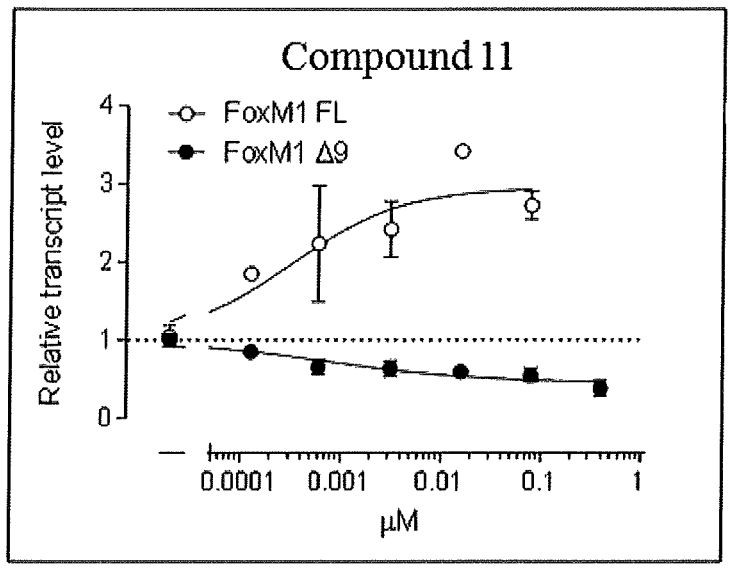

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this Application is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

The definitions described herein apply irrespective of whether the terms in question appear alone or in combination. It is contemplated that the definitions described herein can be appended to form chemically-relevant combinations, such as e.g. "heterocycloalkylaryl", "haloalkylheteroaryl", "arylalkylheterocycloalkyl", or "alkoxyalkyl". The last member of the combination is the radical which is binding to the rest of the molecule. The other members of the combination are attached to the binding radical in reversed order in respect of the literal sequence, e.g. the combination arylalkylheterocycloalkyl refers to a heterocycloalkyl-radical which is substituted by an alkyl which is substituted by an aryl.

When indicating the number of substituents, the term "one or more" refers to the range from one substituent to the highest possible number of substitution, i.e. replacement of one hydrogen up to replacement of all hydrogens by substituents.

The term "optional" or "optionally" denotes that a subsequently described event or circumstance can but need not occur, and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The terms "compound(s) of this invention", "compound(s) of the present invention", "FoxM1 gene splicing modifier", "FoxM1 splicing modifier", and "compounds modifying splicing of the FoxM1 gene" are interchangeably used herein and refer to compounds as disclosed herein and stereoisomers, tautomers, solvates, and salts (e.g., pharmaceutically acceptable salts) thereof.

When the compounds of the invention are solids, it is understood by those skilled in the art that these compounds, and their solvates and salts, may exist in different solid forms, particularly different crystal forms, all of which are intended to be within the scope of the present invention and specified formulas.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. Angew. Chem. Inter. Edit. 1966, 5, 385; errata 511). The prefixes D and L or (+) and (−) are employed to designate the sign of rotation of plane-polarized light by the compound, with (−) or L designating that the compound is levorotatory. A compound prefixed with (+) or D is dextrorotatory.

The terms "halo", "halogen", and "halide" are used interchangeably herein and denote fluoro, chloro, bromo, or iodo, most particularly fluoro or chloro.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl, particularly methyl.

The term "alkenyl" denotes a monovalent linear or branched hydrocarbon group of 2 to 7 carbon atoms with at least one double bond. In particular embodiments, alkenyl has 2 to 4 carbon atoms with at least one double bond. Examples of alkenyl include ethenyl, propenyl, prop-2-enyl, isopropenyl, n-butenyl, and iso-butenyl.

The term "alkynyl" denotes a monovalent linear or branched saturated hydrocarbon group of 2 to 7 carbon atoms comprising one, two or three triple bonds. In particular embodiments alkynyl has from 2 to 4 carbon atoms comprising one or two triple bonds. Examples of alkynyl include ethynyl, propynyl, prop-2-ynyl, isopropynyl, and n-butynyl.

The term "alkoxy" denotes a group of the formula —O—R', wherein R' is an alkyl group. Examples of alkoxy moieties include methoxy, ethoxy, isopropoxy, and tert-butoxy, particularly methoxy.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms.

The term "haloalkoxy" denotes an alkoxy group wherein at least one of the hydrogen atoms of the alkoxy group has been replaced by same or different halogen atoms, particularly fluoro atoms. Examples of haloalkoxyl include monofluoro-, difluoro- or trifluoro-methoxy, -ethoxy or -propoxy, for example 3,3,3-trifluoropropoxy, 2-fluoroethoxy, 2,2,2-trifluoroethoxy, fluoromethoxy, or trifluoromethoxy. The term "perhaloalkoxy" denotes an alkoxy group where all hydrogen atoms of the alkoxy group have been replaced by the same or different halogen atoms.

The term "hydroxyalkyl" denotes an alkyl group wherein at least one of the hydrogen atoms of the alkyl group has been replaced by a hydroxy group. Examples of hydroxyalky include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl or 2-(hydroxymethyl)-3-hydroxypropyl.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "cycloalkenyl" denotes a monovalent unsaturated non-aromatic monocyclic or bicyclic hydrocarbon group of 3 to 8 ring carbon atoms. Particular cycloalkenyl groups are monocyclic. Examples of cycloalkenyl groups include cyclobuten-1-yl, and cyclopenten-1-yl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-azabicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl.

The term "aromatic" denotes the conventional idea of aromaticity as defined in the literature, in particular in IUPAC-Compendium of Chemical Terminology, 2nd, A. D. McNaught & A. Wilkinson (Eds). Blackwell Scientific Publications, Oxford (1997).

The term "aryl" denotes a monovalent aromatic carbocyclic mono- or bicyclic ring system comprising 6 to 10 carbon ring atoms. Examples of aryl moieties include phenyl and naphthyl.

The term "aryloxy" denotes a group of the formula —O—R', wherein R' is aryl. An example of aryloxy is phenoxy.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl, most particularly pyrazolyl or pyridinyl.

The term "pyridinyl substituted with hydroxy" equally refers to its tautomeric form pyridine-one, such as for example "pyridin-2-ol" and its tautomer "3H-pyridin-2-one"

The term "alkylene" denotes a linear saturated divalent hydrocarbon group of 1 to 7 carbon atoms or a divalent branched saturated divalent hydrocarbon group of 3 to 7 carbon atoms. Examples of alkylene groups include methylene, ethylene, propylene, 2-methylpropylene, butylene, 2-ethylbutylene, pentylene, hexylene.

The term "alkylamino" denotes a group —NR'R", wherein R' is hydrogen and R" is a alkyl. The term "dialkylamino" as used herein denotes a group —NR'R", wherein R' and R" are both alkyl. Examples of alkylamino groups include methylamino and ethylamino. Examples of alkylamino groups include dimethylamino, methylethylamino, diethylamino and di(1-methylethyl)amino.

The term "active pharmaceutical ingredient" (or "API") denotes the compound or molecule in a pharmaceutical composition that has a particular biological activity.

The terms "pharmaceutical composition" and "pharmaceutical formulation" (or "formulation") are used interchangeably and denote a mixture or solution comprising a therapeutically effective amount of an active pharmaceutical ingredient together with one or more pharmaceutically acceptable excipients to be administered to a mammal, e.g., a human in need thereof.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "animal" as used herein comprises human beings and non-human animals. In one embodiment, a "non-human animal" is a mammal, for example a rodent such as rat or a mouse. In one embodiment, a non-human animal is a mouse.

The term "treating" or "treatment" of a disease state includes inhibiting the disease state, i.e., arresting the development of the disease state or its clinical symptoms, or relieving the disease state, i.e., causing temporary or permanent regression of the disease state or its clinical symptoms.

The term "preventing" or "prevention" of a disease state denotes causing the clinical symptoms of the disease state not to develop in a subject that can be exposed to or predisposed to the disease state, but does not yet experience or display symptoms of the disease state.

The term "FoxM1 polypeptide" is used herein to refer to native FoxM1 polypeptide from any animal, e.g. mammalian, species, including humans, and FoxM1 variants. The amino acid sequence of human FoxM1A polypeptide is given in Seq. Id. No. 1, the amino acid sequence of human FoxM1B is given in Seq. Id. No. 2 and the amino acid sequence of FoxM1C polypeptide is given in Seq. Id. No. 3.

The nucleotide sequences of the three FoxM1 variants are set forth in Seq. Id. No. 4 (FoxM1A), Seq. Id. No. 5 (FoxM1B) and Seq. Id. No. 6 (FoxM1C).

The term "compound modifying splicing of the FoxM1 gene" is used herein to refer to compounds which lead to the production of transcriptionally inactive forms of the FoxM1 polypeptide, in particular to the production of FoxM1A variant, by modifying the FoxM1 splicing such that transcriptionally inactive forms are generated, in particular FoxM1A, and by suppressing the production of transcriptionally active FoxM1 variants, in particular FoxM1B and FoxM1C.

Methods for detection and/or measurement of polypeptides in biological material are well known in the art and include, but are not limited to, Western-blotting, Flow cytometry, ELISAs or RIAs, or various proteomics techniques. An example for a method to measure a polypeptide is an ELISA. This type of protein quantitation is based on an antibody capable of capturing a specific antigen, and a second antibody capable of detecting the captured antigen. The assays mentioned hereinbefore are described in Harlow, E. and Lane, D. Antibodies: A Laboratory Manual, (1988), Cold Spring Harbor Laboratory Press.

Methods for detection and/or measurement of RNA in biological material are well known in the art and include, but are not limited to, Northern-blotting, RNA protection assay, RT PCR. Suitable methods are described in Molecular Cloning: A Laboratory Manual (Fourth Edition) By Michael R. Green, Joseph Sambrook, Peter MacCallum 2012, 2,028 pp, ISBN 978-1-936113-42-2.

In a first aspect, the present invention provides compounds modifying splicing of the FoxM1 gene for use in the treatment, prevention and/or delay of progression of cancer, wherein the compounds induce a transcriptionally inactive FoxM1 variant. In a particular embodiment of the present invention, the transcriptionally inactive FoxM1 variant is FoxM1A.

In a particular embodiment, the present invention relates to a FoxM1 gene splicing modifier for use in the treatment, prevention and/or delay of progression of cancer, wherein the FoxM1 gene splicing modifier induces a transcriptionally inactive FoxM1 variant.

In a particular embodiment, the present invention relates to a FoxM1 gene splicing modifier for use in the treatment, prevention and/or delay of progression of cancer, wherein the FoxM1 gene splicing modifier induces the transcriptionally inactive FoxM1A variant.

In a particular embodiment of the present invention the FoxM1 gene is the human FoxM1 gene.

In a particular embodiment, the present invention relates to a FoxM1 gene splicing modifier for use in the treatment, prevention and/or delay of progression of cancer, wherein the FoxM1 gene is the human FoxM1 gene.

In a particular embodiment of the present invention the cancer is selected from the group consisting of cancer of the liver, prostate, brain, breast, lung, colon, pancreas, skin, cervix, ovary, mouth, blood and nervous system.

In a particular embodiment, the present invention relates to a FoxM1 gene splicing modifier for use in the treatment, prevention and/or delay of progression of cancer, wherein the cancer is selected from the group consisting of cancer of the liver, prostate, brain, breast, lung, colon, pancreas, skin, cervix, ovary, mouth, blood and nervous system.

In more detail, the present invention relates to a FoxM1 gene splicing modifier selected from a compound of formula (I) or a compound of formula (VI)

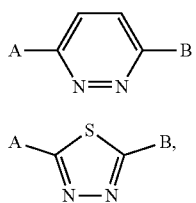

wherein
A is 2-hydroxy-phenyl which is substituted with: 0, 1, 2, or 3 substituents independently selected from $C_{1-4}$ alkyl, oxo, oxime, hydroxy, halo-$C_{1-4}$ alkyl, dihalo-$C_{1-4}$ alkyl, trihalo-$C_{1-4}$ alkyl, $C_{1-4}$ alkoxy, $C_{1-4}$ alkoxy-$C_{3-7}$ cycloalkyl, halo-$C_{1-4}$ alkoxy, dihalo-$C_{1-4}$alkoxy, trihalo-$C_{1-4}$ alkoxy, hydroxy, cyano, halogen, amino, mono-$C_{1-4}$ alkylamino, di-$C_{1-4}$ alkylamino, heteroaryl, $C_{1-4}$ alkyl substituted with hydroxy, $C_{1-4}$ alkoxy substituted with aryl, amino, —C(O)NH—$C_{1-4}$alkyl-heteroaryl, —NHC(O)—$C_{1-4}$ alkylheteroaryl, $C_{1-4}$ alkyl-C(O)NH-heteroaryl, $C_{1-4}$alkyl-NHC(O)-heteroaryl, $C_{3-7}$ cycloalkyl, 5-7 membered cycloalkenyl, or 5, 6 or 9 membered heterocycle containing 1 or 2 heteroatoms independently, selected from S, O and N, wherein two $C_{1-4}$ alkyl groups can combine with the atoms to which they are bound to form a 5-6 membered ring; wherein heteroaryl has 5, 6 or 9 ring atoms, 1, 2 or 3 ring heteroatoms selected from N, O and S, and is substituted with 0, 1, or 2 substituents independently selected from oxo, hydroxy, nitro, halogen, $C_{1-4}$ alkyl, $C_{1-4}$ alkenyl, $C_{1-4}$ alkoxy, $C_{3-7}$ cycloalkyl, $C_{1-4}$ alkyl-OH, trihalo-$C_{1-4}$ alkyl, mono-$C_{1-4}$ alkylamino, di-$C_{1-4}$ alkylamino, —C(O)NH$_2$, —NH$_2$, NO$_2$, hydroxy-$C_{1-4}$alkylamino, hydroxy-$C_{1-4}$ alkyl, 4-7 membered heterocycle-$C_{1-4}$ alkyl, amino-$C_{1-4}$ alkyl, mono-$C_{1-4}$ alkylamino-$C_{1-4}$ alkyl, and di-$C_{1-4}$alkylamino-$C_{1-4}$ alkyl; or A is 2-naphthyl optionally substituted at the 3 position with hydroxy and additionally substituted with 0, 1, or 2 substituents selected from hydroxy, cyano, halogen, $C_{1-4}$ alkyl, $C_{2-4}$ alkenyl, $C_{1-5}$ alkoxy, wherein the alkoxy is unsubstituted or substituted with hydroxy, $C_{1-4}$ alkoxy, amino, —NHC(O)—$C_{1-4}$ alkyl, —NHC(O)O—$C_{1-4}$ alkyl, $C_{1-4}$ alkylene-4-7 membered heterocycle, 4-7 membered heterocycle, mono-$C_{1-4}$ alkylamino, and di-$C_{1-4}$ alkylamino; or A is 6 membered heteroaryl having 1-3 ring nitrogen atoms and which is substituted by phenyl or a heteroaryl having 5 or 6 ring atoms, 1 or 2 ring heteroatoms independently selected from N, O and S and is substituted with 0, 1, or 2 substituents independently selected from $C_{1-4}$ alkyl, mono-$C_{1-4}$ alkylamino, di-$C_{1-4}$ alkylamino, hydroxy-$C_{1-4}$ alkylamino, hydroxy-$C_{1-4}$ alkyl, amino-$C_{1-4}$ alkyl and mono-$C_{1-4}$ alkylamino-$C_{1-4}$ alkyl, and di-$C_{1-4}$alkylamino-$C_{1-4}$ alkyl; or A is bicyclic heteroaryl having 9 to 10 ring atoms, 1, 2, or 3 ring heteroatoms independently selected from N, O or S, and which is substituted with 0, 1, or 2 substituents independently selected from cyano, oxime, halogen, hydroxy, $C_{1-4}$ alkyl, $C_{2-4}$ alkenyl, $C_{2-4}$ alkynyl, $C_{1-4}$ alkoxy, $C_{1-4}$ alkoxy substituted with hydroxy, amino, mono-$C_{1-4}$ alkylamino, and di-$C_{1-4}$ alkylamino; or A is tricyclic heteroaryl having 12 or 13 ring atoms, 1, 2, or 3 ring heteroatoms independently selected from N, O or S, and which is substituted with 0, 1, or 2 substituents independently selected from cyano, halogen, hydroxy, $C_{1-4}$ alkyl, $C_{1-4}$ alkenyl, $C_{2-4}$ alkynyl, $C_{1-4}$ alkoxy, $C_{1-4}$ alkoxy substituted with hydroxy, amino, alkylamino, alkylamino, and heteroaryl having 5, 6 or 9 ring atoms, 1, 2 or 3 ring heteroatoms selected from N, O and S, and which is substituted with 0, 1, or 2 substituents independently selected from oxo, hydroxy, nitro, halogen, $C_{1-4}$ alkyl, $C_{1-4}$ alkenyl, $C_{1-4}$ alkoxy, $C_{3-7}$ cycloalkyl, $C_{1-4}$ alkyl-OH, trihalo-$C_{1-4}$ alkyl, mono-$C_{1-4}$ alkylamino, di-$C_{1-4}$ alkylamino, —C(O)NH$_2$, —NH$_2$, —NO$_2$, hydroxy-$C_{1-4}$ alkylamino, hydroxy-$C_{1-4}$ alkyl, 4-7 membered heterocycle-$C_{1-4}$ alkyl, amino-$C_{1-4}$ alkyl, mono-$C_{1-4}$ alkylamino-$C_{1-4}$ alkyl and di-$C_{1-4}$ alkylamino-$C_{1-4}$ alkyl; or A is phenyl which is substituted with 0, 1, 2, or 3 substituents independently selected from $C_{1-4}$ alkyl, oxo, oxime, hydroxy, halo-$C_{1-4}$ alkyl, dihalo-$C_{1-4}$ alkyl, trihalo-$C_{1-4}$ alkyl, $C_{1-4}$ alkoxy, $C_{1-4}$ alkoxy-$C_{3-7}$ cycloalkyl, halo-$C_{1-4}$ alkoxy, dihalo-$C_{1-4}$ alkoxy, trihalo-$C_{1-4}$ alkoxy, cyano, halogen, amino, mono-$C_{1-4}$ alkylamino, di-$C_{1-4}$ alkylamino, heteroaryl, $C_{1-4}$ alkyl substituted with hydroxy, $C_{1-4}$ alkoxy substituted with aryl, —C(O)NH—$C_{1-4}$ alkyl-heteroaryl, —NHC(O)—$C_{1-4}$ alkylheteroaryl, $C_{1-4}$ alkyl-C(O)NH-heteroaryl, $C_{1-4}$ alkyl-NHC(O)-heteroaryl, $C_{3-7}$ cycloalkyl, 5-7 membered cycloalkenyl or 5, 6 or 9 membered heterocycle containing 1 or 2 heteroatoms, independently, selected from S, O and N; wherein two $C_{1-4}$ alkyl groups can combine with the atoms to which they are bound to form a 5-6 membered ring;
wherein heteroaryl has 5, 6 or 9 ring atoms, 1, 2 or 3 ring heteroatoms selected from N, O and S and is substituted with 0, 1, or 2 substituents independently selected from oxo, hydroxy, nitro, halogen, $C_{1-4}$ alkyl, $C_{1-4}$ alkenyl, $C_{1-4}$ alkoxy, $C_{3-7}$ cycloalkyl, $C_{1-4}$ alkyl-OH, trihalo-$C_{1-4}$ alkyl, mono-$C_{1-4}$ alkylamino, di-$C_{1-4}$ alkylamino, —C(O)NH$_2$, —NH$_2$, —NO$_2$, hydroxy-$C_{1-4}$ alkylamino, hydroxy-$C_{1-4}$ alkyl, 4-7 membered heterocycle-$C_{1-4}$ alkyl, amino-$C_{1-4}$ alkyl, mono-$C_{1-4}$ alkylamino-$C_{1-4}$ alkyl, and di-$C_{1-4}$ alkylamino-$C_{1-4}$ alkyl;

B is a group of the formula

[chemical structure showing a ring with substituents X, Z, R, R1, R2, R3, R4, R5, R6, N, with indices m, n, p]

wherein m, n and p are independently selected from 0 or 1;

R, $R_1$, $R_2$, $R_3$, and $R_4$ are independently selected from the group consisting of hydrogen and $C_{1-4}$ alkyl, wherein alkyl is optionally substituted with hydroxy, amino, mono-$C_{1-4}$ akylamino or di-$C_{1-4}$ akylamino;

$R_5$ and $R_6$ are independently selected from hydrogen and fluorine; or

R and $R_3$, taken in combination form a fused 5 or 6 membered heterocyclic ring having 0 or 1 additional ring heteroatoms selected from N, O or S; or $R_1$ and $R_3$, taken in combination form a $C_{1-3}$ alkylene group; or $R_1$ and $R_5$, taken in combination form a $C_{1-3}$ alkylene group; or $R_3$ and $R_4$, taken in combination with the carbon atom to which they attach, form a spirocyclic $C_{3-6}$ cycloalkyl;

X is $CR_AR_B$, O, $NR_7$ or a bond;

$R_7$ is hydrogen, or $C_{1-4}$ alkyl;

$R_A$ and $R_B$ are independently selected from hydrogen and $C_{1-4}$ alkyl, or $R_A$ and $R_B$, taken in combination, form a divalent $C_{2-5}$ alkylene group;

Z is $CR_8$ or N; with the proviso that when Z is N, X is a bond;

$R_8$ is hydrogen or taken in combination with $R_6$ form a double bond; or

B is a group of the formula

[chemical structure showing a piperidine-like ring with N, R9, R10, R11, R12, R13, R14, R15, with indices p, q]

wherein p and q are independently selected from the group consisting of 0, 1, and 2;

$R_9$ and $R_{13}$ are independently selected from hydrogen and $C_{1-4}$ alkyl;

$R_{10}$ and $R_{14}$ are independently selected from hydrogen, amino, mono-$C_{1-4}$ alkylamino, alkylamino, and $C_{1-4}$ alkyl optionally substituted with hydroxy, amino, mono-$C_{1-4}$ alkylamino or di-$C_{1-4}$ alkylamino;

$R_{11}$ is hydrogen, $C_{1-4}$ alkyl, amino, mono-$C_{1-4}$ alkylamino, or di-$C_{1-4}$ alkylamino;

$R_{12}$ is hydrogen or $C_{1-4}$ alkyl; or $R_9$ and $R_{11}$ taken in combination form a saturated azacycle having 4 to 7 ring atoms which is optionally substituted with one to three $C_{1-4}$ alkyl groups; or $R_{11}$ and $R_{12}$, taken in combination form a saturated azacycle having 4 to 7 ring atoms which is optionally substituted with one to three $C_{1-4}$ alkyl groups.

or a pharmaceutically acceptable salt thereof;

for use in the treatment, prevention and/or delay of progression of cancer.

In a particular embodiment of the present invention, the FoxM1 gene splicing modifier is selected from a compound of formula (I):

(I)

[chemical structure: A—pyridazine ring (N=N)—B]

wherein

A is 2-hydroxy-phenyl which is substituted with:

0, 1, 2, or 3 substituents independently selected from $C_{1-4}$ alkyl, oxo, oxime, hydroxy, halo-$C_{1-4}$ alkyl, dihalo-$C_{1-4}$ alkyl, trihalo-$C_{1-4}$ alkyl, $C_{1-4}$ alkoxy, $C_{1-4}$ alkoxy-$C_{3-7}$ cycloalkyl, halo-$C_{1-4}$ alkoxy, dihalo-$C_{1-4}$alkoxy, trihalo-$C_{1-4}$alkoxy, hydroxy, cyano, halogen, amino, mono-$C_{1-4}$ alkylamino, alkylamino, heteroaryl, $C_{1-4}$ alkyl substituted with hydroxy, $C_{1-4}$ alkoxy substituted with aryl, amino, —C(O)NH—$C_{1-4}$alkyl-heteroaryl, —NHC(O)—$C_{1-4}$alkylheteroaryl, $C_{1-4}$ alkyl-C(O)NH-heteroaryl, $C_{1-4}$alkyl-NHC(O)-heteroaryl, $C_{3-7}$ cycloalkyl, 5-7 membered cycloalkenyl, or 5, 6 or 9 membered heterocycle containing 1 or 2 heteroatoms independently, selected from S, O and N, wherein two $C_{1-4}$ alkyl groups can combine with the atoms to which they are bound to form a 5-6 membered ring;

wherein heteroaryl has 5, 6 or 9 ring atoms, 1, 2 or 3 ring heteroatoms selected from N, O and S, and is substituted with 0, 1, or 2 substituents independently selected from oxo, hydroxy, nitro, halogen, $C_{1-4}$ alkyl, $C_{1-4}$ alkenyl, $C_{1-4}$ alkoxy, $C_{3-7}$ cycloalkyl, $C_{1-4}$ alkyl-OH, trihalo-$C_{1-4}$ alkyl, mono-$C_{1-4}$ alkylamino, di-$C_{1-4}$ alkylamino, —C(O)NH$_2$, —NH$_2$, NO$_2$, hydroxy-$C_{1-4}$alkylamino, hydroxy-$C_{1-4}$ alkyl, 4-7 membered heterocycle-$C_{1-4}$ alkyl, amino-$C_{1-4}$ alkyl, mono-$C_{1-4}$alkylamino-$C_{1-4}$ alkyl, and di-$C_{1-4}$alkylamino-$C_{1-4}$ alkyl; or A is 2-naphthyl optionally substituted at the 3 position with hydroxy and additionally substituted with 0, 1, or 2 substituents selected from hydroxy, cyano, halogen, $C_{1-4}$ alkyl, $C_{2-4}$ alkenyl, $C_{1-5}$ alkoxy, wherein the alkoxy is unsubstituted or substituted with hydroxy, $C_{1-4}$ alkoxy, amino, —NHC(O)—$C_{1-4}$ alkyl, —NHC(O)O—$C_{1-4}$ alkyl, $C_{1-4}$ alkylene-4-7 membered heterocycle, 4-7 membered heterocycle, mono-$C_{1-4}$ alkylamino, and di-$C_{1-4}$ alkylamino; or A is 6 membered heteroaryl having 1-3 ring nitrogen atoms and which is substituted by phenyl or a heteroaryl having 5 or 6 ring atoms, 1 or 2 ring heteroatoms independently selected from N, O and S and is substituted with 0, 1, or 2 substituents independently selected from $C_{1-4}$ alkyl, mono-$C_{1-4}$ alkylamino, di-$C_{1-4}$ alkylamino, hydroxy-$C_{1-4}$ alkylamino, hydroxy-$C_{1-4}$ alkyl, amino-$C_{1-4}$ alkyl and mono-$C_{1-4}$ alkylamino-$C_{1-4}$ alkyl, and di-$C_{1-4}$alkylamino-$C_{1-4}$ alkyl; or A is bicyclic heteroaryl having 9 to 10 ring atoms, 1, 2, or 3 ring heteroatoms independently selected from N, O or S, and which is substituted with 0, 1, or 2 substituents independently selected from cyano, oxime, halogen, hydroxy, $C_{1-4}$ alkyl, $C_{2-4}$ alkenyl, $C_{2-4}$ alkynyl, $C_{1-4}$ alkoxy, $C_{1-4}$ alkoxy substituted with hydroxy, amino, mono-$C_{1-4}$ alkylamino, and di-$C_{1-4}$ alkylamino; or A is tricyclic heteroaryl having 12 or 13 ring atoms, 1, 2, or 3 ring heteroatoms independently selected from N, O or S, and which is substituted with 0, 1, or 2 substituents independently selected from cyano, halogen, hydroxy, $C_{1-4}$ alkyl, $C_{1-4}$ alkenyl, $C_{2-4}$ alkynyl, $C_{1-4}$ alkoxy, $C_{1-4}$ alkoxy substituted with hydroxy, amino, alkylamino, alkylamino, and heteroaryl having 5, 6 or 9 ring atoms, 1, 2 or 3 ring heteroatoms selected from N, O and S, and which is substituted with 0, 1, or 2 substituents independently selected from oxo, hydroxy, nitro, halogen, $C_{1-4}$ alkyl, $C_{1-4}$ alkenyl, $C_{1-4}$ alkoxy, $C_{3-7}$ cycloalkyl, $C_{1-4}$ alkyl-OH, trihalo-$C_{1-4}$ alkyl, mono-$C_{1-4}$ alkylamino, alkylamino, —C(O)NH$_2$, —NH$_2$, —NO$_2$, hydroxy-$C_{1-4}$ alkylamino, hydroxy-$C_{1-4}$ alkyl, 4-7 membered heterocycle-$C_{1-4}$ alkyl, amino-$C_{1-4}$ alkyl, mono-$C_{1-4}$ alkylamino-$C_{1-4}$ alkyl and di-$C_{1-4}$ alkylamino-$C_{1-4}$ alkyl;

B is a group of the formula wherein
  m, n and p are independently selected from 0 or 1;
  R, $R_1$, $R_2$, $R_3$, and $R_4$ are independently selected from the group consisting of hydrogen and $C_{1-4}$ alkyl, wherein alkyl is optionally substituted with hydroxy, amino, mono-$C_{1-4}$ akylamino or di-$C_{1-4}$ akylamino;
  $R_5$ and $R_6$ are independently selected from hydrogen and fluorine; or
  R and $R_3$, taken in combination form a fused 5 or 6 membered heterocyclic ring having 0 or 1 additional ring heteroatoms selected from N, O or S; or
  $R_1$ and $R_3$, taken in combination form a $C_{1-3}$ alkylene group; or
  $R_1$ and $R_5$, taken in combination form a $C_{1-3}$ alkylene group; or
  $R_3$ and $R_4$, taken in combination with the carbon atom to which they attach, form a spirocyclic $C_{3-6}$ cycloalkyl;
  X is $CR_AR_B$, O, $NR_7$ or a bond;
  $R_7$ is hydrogen, or $C_{1-4}$ alkyl;
  $R_A$ and $R_B$ are independently selected from hydrogen and $C_{1-4}$ alkyl, or $R_A$ and $R_B$, taken in combination, form a divalent $C_{2-5}$ alkylene group;
  Z is $CR_8$ or N; with the proviso that when Z is N, X is a bond;
  $R_8$ is hydrogen or taken in combination with $R_6$ form a double bond; or B is a group of the formula wherein
  p and q are independently selected from the group consisting of 0, 1, and 2;
  $R_9$ and $R_{13}$ are independently selected from hydrogen and $C_{1-4}$ alkyl;
  $R_{10}$ and $R_{14}$ are independently selected from hydrogen, amino, mono-$C_{1-4}$ alkylamino, di-$C_{1-4}$ alkylamino, and $C_{1-4}$ alkyl optionally substituted with hydroxy, amino, mono-$C_{1-4}$ alkylamino or di-$C_{1-4}$ alkylamino;
  $R_{11}$ is hydrogen, $C_{1-4}$ alkyl, amino, mono-$C_{1-4}$ alkylamino, or di-$C_{1-4}$ alkylamino;
  $R_{12}$ is hydrogen or $C_{1-4}$ alkyl; or
  $R_9$ and $R_{11}$ taken in combination form a saturated azacycle having 4 to 7 ring atoms which is optionally substituted with one to three $C_{1-4}$ alkyl groups; or
  $R_{11}$ and $R_{12}$, taken in combination form a saturated azacycle having 4 to 7 ring atoms which is optionally substituted with one to three $C_{1-4}$ alkyl group;

or a pharmaceutically acceptable salt thereof;
for use in the treatment, prevention and/or delay of progression of cancer.

In a particular embodiment of the present invention, the FoxM1 gene splicing modifier is selected from a compound of formula (VI)

(VI)

wherein
  A is 6 membered heteroaryl having 1-3 ring nitrogen atoms and which is substituted by phenyl or a heteroaryl having 5 or 6 ring atoms, 1 or 2 ring heteroatoms independently selected from N, O and S and is substituted with 0, 1, or 2 substituents independently selected from $C_{1-4}$ alkyl, mono-$C_{1-4}$ alkylamino, di-$C_{1-4}$ alkylamino, hydroxy-$C_{1-4}$ alkylamino, hydroxy-$C_{1-4}$ alkyl, amino-$C_{1-4}$ alkyl and mono-$C_{1-4}$ alkylamino-$C_{1-4}$ alkyl, and di-$C_{1-4}$alkylamino-$C_{1-4}$ alkyl; or
  A is bicyclic heteroaryl having 9 to 10 ring atoms, 1, 2, or 3 ring heteroatoms independently selected from N, O or S, and which is substituted with 0, 1, or 2 substituents independently selected from cyano, oxime, halogen, hydroxy, $C_{1-4}$ alkyl, $C_{2-4}$ alkenyl, $C_{2-4}$ alkynyl, $C_{1-4}$ alkoxy, $C_{1-4}$ alkoxy substituted with hydroxy, amino, mono-$C_{1-4}$ alkylamino, and di-$C_{1-4}$ alkylamino; or
  A is phenyl which is substituted with 0, 1, 2, or 3 substituents independently selected from $C_{1-4}$ alkyl, oxo, oxime, hydroxy, halo-$C_{1-4}$ alkyl, dihalo-$C_{1-4}$ alkyl, trihalo-$C_{1-4}$ alkyl, $C_{1-4}$ alkoxy, $C_{1-4}$ alkoxy-$C_{3-7}$ cycloalkyl, halo-$C_{1-4}$ alkoxy, dihalo-$C_{1-4}$ alkoxy, trihalo-$C_{1-4}$ alkoxy, cyano, halogen, amino, mono-$C_{1-4}$ alkylamino, alkylamino, heteroaryl, $C_{1-4}$ alkyl substituted with hydroxy, $C_{1-4}$ alkoxy substituted with aryl, —C(O)NH—$C_{1-4}$ alkyl-heteroaryl, —NHC(O)—$C_{1-4}$ alkylheteroaryl, $C_{1-4}$ alkyl-C(O)NH-heteroaryl, $C_{1-4}$ alkyl-NHC(O)-heteroaryl, $C_{3-7}$ cycloalkyl, 5-7 membered cycloalkenyl or 5, 6 or 9 membered heterocycle containing 1 or 2 heteroatoms, independently, selected from S, O and N;

wherein two $C_{1-4}$ alkyl groups can combine with the atoms to which they are bound to form a 5-6 membered ring;

wherein heteroaryl has 5, 6 or 9 ring atoms, 1, 2 or 3 ring heteroatoms selected from N, O and S and is substituted with 0, 1, or 2 substituents independently selected from oxo, hydroxy, nitro, halogen, $C_{1-4}$ alkyl, $C_{1-4}$ alkenyl, $C_{1-4}$ alkoxy, $C_{3-7}$ cycloalkyl, $C_{1-4}$ alkyl-OH, trihalo-$C_{1-4}$ alkyl, mono-$C_{1-4}$ alkylamino, di-$C_{1-4}$ alkylamino, —C(O)NH$_2$, —NH$_2$, —NO$_2$, hydroxy-$C_{1-4}$ alkylamino, hydroxy-$C_{1-4}$ alkyl, 4-7 membered heterocycle-$C_{1-4}$ alkyl, amino-$C_{1-4}$ alkyl, mono-$C_{1-4}$ alkylamino-$C_{1-4}$ alkyl, and di-$C_{1-4}$ alkylamino-$C_{1-4}$ alkyl;

B is a group of the formula

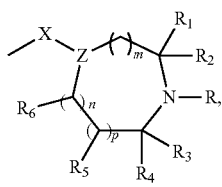

wherein m, n and p are independently selected from 0 or 1;

R, $R_1$, $R_2$, $R_3$, and $R_4$ are independently selected from the group consisting of hydrogen and $C_{1-4}$ alkyl, wherein alkyl is optionally substituted with hydroxy, amino, mono-$C_{1-4}$ akylamino or di-$C_{1-4}$ akylamino;

$R_5$ and $R_6$ are independently selected from hydrogen and fluorine; or

R and $R_3$, taken in combination form a fused 5 or 6 membered heterocyclic ring having 0 or 1 additional ring heteroatoms selected from N, O or S; or $R_1$ and $R_3$, taken in combination form a $C_{1-3}$ alkylene group; or $R_1$ and $R_5$, taken in combination form a $C_{1-3}$ alkylene group; or $R_3$ and $R_4$, taken in combination with the carbon atom to which they attach, form a spirocyclic $C_{3-6}$ cycloalkyl;

X is $CR_AR_B$, O, $NR_7$ or a bond;

$R_7$ is hydrogen, or $C_{1-4}$ alkyl;

$R_A$ and $R_B$ are independently selected from hydrogen and $C_{1-4}$ alkyl, or $R_A$ and $R_B$, taken in combination, form a divalent $C_{2-5}$ alkylene group;

Z is $CR_8$ or N; with the proviso that when Z is N, X is a bond;

$R_8$ is hydrogen or taken in combination with $R_6$ form a double bond; or

B is a group of the formula

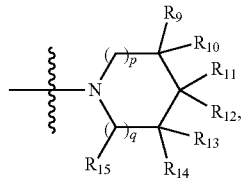

wherein
  p and q are independently selected from the group consisting of 0, 1, and 2;
  $R_9$ and $R_{13}$ are independently selected from hydrogen and $C_{1-4}$ alkyl;
  $R_{10}$ and $R_{14}$ are independently selected from hydrogen, amino, mono-$C_{1-4}$ alkylamino, di-$C_{1-4}$ alkylamino, and $C_{1-4}$ alkyl optionally substituted with hydroxy, amino, mono-$C_{1-4}$ alkylamino or di-$C_{1-4}$ alkylamino;
  $R_{11}$ is hydrogen, $C_{1-4}$ alkyl, amino, mono-$C_{1-4}$ alkylamino, or di-$C_{1-4}$ alkylamino;
  $R_{12}$ is hydrogen or $C_{1-4}$ alkyl; or
  $R_9$ and $R_{11}$ taken in combination form a saturated azacycle having 4 to 7 ring atoms which is optionally substituted with one to three $C_{1-4}$ alkyl groups; or
  $R_{11}$ and $R_{12}$, taken in combination form a saturated azacycle having 4 to 7 ring atoms which is optionally substituted with one to three $C_{1-4}$ alkyl groups.
or a pharmaceutically acceptable salt thereof;
for use in the treatment, prevention and/or delay of progression of cancer.

In a particular embodiment, the present invention relates to a FoxM1 gene splicing modifier selected from a compound of formula (I) or of formula (VI), wherein
  A is 2-hydroxy-phenyl which is substituted with:
    0, 1, 2, or 3 substituents independently selected from $C_{1-4}$ alkyl, oxo, oxime, hydroxy, halo-$C_{1-4}$ alkyl, dihalo-$C_{1-4}$ alkyl, trihalo-$C_{1-4}$ alkyl, $C_{1-4}$ alkoxy, $C_{1-4}$ alkoxy-$C_{3-7}$ cycloalkyl, halo-$C_{1-4}$ alkoxy, dihalo-$C_{1-4}$alkoxy, trihalo-$C_{1-4}$alkoxy, hydroxy, cyano, halogen, amino, mono-$C_{1-4}$ alkylamino, di-$C_{1-4}$ alkylamino, heteroaryl, $C_{1-4}$ alkyl substituted with hydroxy, $C_{1-4}$ alkoxy substituted with aryl, amino, —C(O)NH—$C_{1-4}$alkyl-heteroaryl, —NHC(O)—$C_{1-4}$alkylheteroaryl, $C_{1-4}$ alkyl-C(O)NH-heteroaryl, $C_{1-4}$alkyl-NHC(O)-heteroaryl, $C_{3-7}$ cycloalkyl, 5-7 membered cycloalkenyl, or 5, 6 or 9 membered heterocycle containing 1 or 2 heteroatoms independently, selected from S, O and N,
    wherein two $C_{1-4}$ alkyl groups can combine with the atoms to which they are bound to form a 5-6 membered ring;
    wherein heteroaryl has 5, 6 or 9 ring atoms, 1, 2 or 3 ring heteroatoms selected from N, O and S, and is substituted with 0, 1, or 2 substituents independently selected from oxo, hydroxy, nitro, halogen, $C_{1-4}$ alkyl, $C_{1-4}$ alkenyl, $C_{1-4}$ alkoxy, $C_{3-7}$ cycloalkyl, $C_{1-4}$ alkyl-OH, trihalo-$C_{1-4}$ alkyl, mono-$C_{1-4}$ alkylamino, di-$C_{1-4}$ alkylamino, —C(O)NH$_2$, —NH$_2$, NO$_2$, hydroxy-$C_{1-4}$alkylamino, hydroxy-$C_{1-4}$ alkyl, 4-7 membered heterocycle-$C_{1-4}$ alkyl, amino-$C_{1-4}$ alkyl, mono-$C_{1-4}$alkylamino-$C_{1-4}$ alkyl, and di-$C_{1-4}$alkylamino-$C_{1-4}$alkyl; or
  A is 2-naphthyl optionally substituted at the 3 position with hydroxy and additionally substituted with 0, 1, or 2 substituents selected from hydroxy, cyano, halogen, C$_{1-4}$ alkyl, C$_{2-4}$ alkenyl, C$_{1-5}$ alkoxy, wherein the alkoxy is unsubstituted or substituted with hydroxy, C$_{1-4}$ alkoxy, amino, —NHC(O)—C$_{1-4}$ alkyl, —NHC(O)O—C$_{1-4}$ alkyl, C$_{1-4}$ alkylene-4-7 membered heterocycle, 4-7 membered heterocycle, mono-C$_{1-4}$ alkylamino, and di-C$_{1-4}$ alkylamino; or A is phenyl which is substituted with 0, 1, 2, or 3 substituents independently selected from C$_{1-4}$ alkyl, oxo, oxime, hydroxy, halo-C$_{1-4}$ alkyl, dihalo-C$_{1-4}$ alkyl, trihalo-C$_{1-4}$ alkyl, C$_{1-4}$ alkoxy, C$_{1-4}$ alkoxy-C$_{3-7}$ cycloalkyl, halo-C$_{1-4}$ alkoxy, dihalo-C$_{1-4}$ alkoxy, trihalo-C$_{1-4}$ alkoxy, cyano, halogen, amino, mono-C$_{1-4}$ alkylamino, di-C$_{1-4}$ alkylamino, heteroaryl, C$_{1-4}$ alkyl substituted with hydroxy, C$_{1-4}$ alkoxy substituted with aryl, —C(O)NH—C$_{1-4}$ alkyl-heteroaryl, —NHC(O)—C$_{1-4}$ alkylheteroaryl, C$_{1-4}$ alkyl-C(O)NH-heteroaryl, C$_{1-4}$ alkyl-NHC(O)-heteroaryl, C$_{3-7}$ cycloalkyl, 5-7 membered cycloalkenyl or 5, 6 or 9 membered heterocycle containing 1 or 2 heteroatoms, independently, selected from S, O and N;

wherein two C$_{1-4}$ alkyl groups can combine with the atoms to which they are bound to form a 5-6 membered ring;

wherein heteroaryl has 5, 6 or 9 ring atoms, 1, 2 or 3 ring heteroatoms selected from N, O and S and is substituted with 0, 1, or 2 substituents independently selected from oxo, hydroxy, nitro, halogen, C$_{1-4}$ alkyl, C$_{1-4}$ alkenyl, C$_{1-4}$ alkoxy, C$_{3-7}$ cycloalkyl, C$_{1-4}$ alkyl-OH, trihalo-C$_{1-4}$ alkyl, mono-C$_{1-4}$ alkylamino, di-C$_{1-4}$ alkylamino, —C(O)NH$_2$, —NH$_2$, —NO$_2$, hydroxy-C$_{1-4}$ alkylamino, hydroxy-C$_{1-4}$ alkyl, 4-7 membered heterocycle-C$_{1-4}$ alkyl, amino-C$_{1-4}$ alkyl, mono-C$_{1-4}$ alkylamino-C$_{1-4}$ alkyl, and di-C$_{1-4}$ alkylamino-C$_{1-4}$ alkyl;

or a pharmaceutically acceptable salt thereof;

for use in the treatment, prevention and/or delay of progression of cancer.

In a particular embodiment, the present invention relates to a FoxM1 gene splicing modifier selected from a compound of formula (I) or a compound of formula (VI), wherein A is 2-hydroxy-phenyl substituted with 0, 1, 2, or 3 substituents independently selected from C$_{1-4}$ alkyl, halo-C$_{1-4}$ alkyl, C$_{1-4}$ alkoxy, hydroxy, cyano, halogen, amino, mono-C$_{1-4}$ alkylamino, di-C$_{1-4}$ alkylamino, heteroaryl, and C$_{1-4}$ alkyl substituted with hydroxy or amino, wherein heteroaryl has 5 or 6 ring atoms, 1 or 2 ring heteroatoms selected from N, O and S and is substituted with 0, 1, or 2 substituents independently selected from C$_{1-4}$ alkyl, mono-C$_{1-4}$ alkylamino, di-C$_{1-4}$ alkylamino, hydroxy-C$_{1-4}$ alkylamino, hydroxy-C$_{1-4}$ alkyl, 4-7 membered heterocycle-C$_{1-4}$ alkyl, amino-C$_{1-4}$ alkyl, mono-C$_{1-4}$ alkylamino-C$_{1-4}$ alkyl, and di-C$_{1-4}$ alkylamino-C$_{1-4}$ alkyl; or a pharmaceutically acceptable salt thereof; for use in the treatment, prevention and/or delay of progression of cancer.

In a particular embodiment, the present invention relates to a FoxM1 gene splicing modifier selected from a compound of formula (I) or a compound of formula (VI), wherein A is 2-naphthyl optionally substituted at the 3 position with hydroxy and additionally substituted with 0, 1, or 2 substituents selected from hydroxy, cyano, halogen, C$_{1-4}$ alkyl, C$_{2-4}$ alkenyl, C$_{1-4}$ alkoxy, wherein alkoxy is unsubstituted or substituted with hydroxy, C$_{1-4}$ alkoxy, amino, —N(H)C(O)—C$_{1-4}$ alkyl, —N(H)C(O)O—C$_{1-4}$ alkyl, 4 to 7 membered heterocycle, mono-C$_{1-4}$ alkylamino and di-C$_{1-4}$ alkylamino; or a pharmaceutically acceptable salt thereof; for use in the treatment, prevention and/or delay of progression of cancer.

In a particular embodiment, the present invention relates to a FoxM1 gene splicing modifier selected from a compound of formula (I) or a compound of formula (VI), wherein A is phenyl substituted with 0, 1, 2, or 3 substituents independently selected from C$_{1-4}$ alkyl, halo-C$_{1-4}$ alkyl, C$_{1-4}$ alkoxy, hydroxy, cyano, halogen, amino, mono-C$_{1-4}$ alkylamino, di-C$_{1-4}$ alkylamino, heteroaryl, and C$_{1-4}$ alkyl substituted with hydroxy or amino, wherein heteroaryl has 5 or 6 ring atoms, 1 or 2 ring heteroatoms selected from N, O and S and is substituted with 0, 1, or 2 substituents independently selected from C$_{1-4}$ alkyl, mono-C$_{1-4}$ alkylamino, di-C$_{1-4}$ alkylamino, hydroxy-C$_{1-4}$ alkylamino, hydroxy-C$_{1-4}$ alkyl, 4-7 membered heterocycle-C$_{1-4}$ alkyl, amino-C$_{1-4}$ alkyl, mono-C$_{1-4}$ alkylamino-C$_{1-4}$ alkyl, and di-C$_{1-4}$ alkylamino-C$_{1-4}$ alkyl; or a pharmaceutically acceptable salt thereof; for use in the treatment, prevention and/or delay of progression of cancer.

In a particular embodiment, the present invention relates to a FoxM1 gene splicing modifier selected from a compound of formula (I) or a compound of formula (VI), wherein A is 2-hydroxy-phenyl substituted with one additional substituent selected from cyano and heteroaryl; or A is 2-naphthyl optionally substituted at the 3 position with hydroxy and additionally substituted with 0 or 1 substituents selected from hydroxy and C$_{1-4}$ alkoxy; or A is phenyl which is substituted with two or three substituents independently selected from halogen and heteroaryl;

wherein heteroaryl has 5 or 6 ring atoms of which 1 or 2 are nitrogen and is substituted with 0, 1, or 2 substituents independently selected from C$_{1-4}$ alkyl and hydroxy; or a pharmaceutically acceptable salt thereof;

for use in the treatment, prevention and/or delay of progression of cancer.

In a particular embodiment, the present invention relates to a FoxM1 gene splicing modifier selected from a compound of formula (I) or a compound of formula (VI), wherein A is 2-hydroxy-phenyl substituted with one additional substituent selected from cyano and heteroaryl; or A is 2-naphthyl optionally substituted at the 3 position with hydroxy and additionally substituted with 0 or 1 substituents selected from hydroxy and methoxy; or A is phenyl which is substituted with two or three substituents independently selected from chloro, fluoro and heteroaryl;

wherein heteroaryl is pyrazolyl or pyridinyl substituted with 0, 1, or 2 substituents independently selected from methyl and hydroxy;

or a pharmaceutically acceptable salt thereof;

for use in the treatment, prevention and/or delay of progression of cancer.

In a particular embodiment, the present invention relates to a FoxM1 gene splicing modifier selected from a compound of formula (I) or of formula (VI), wherein A is selected from:

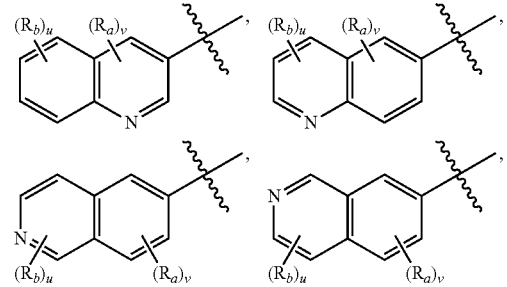

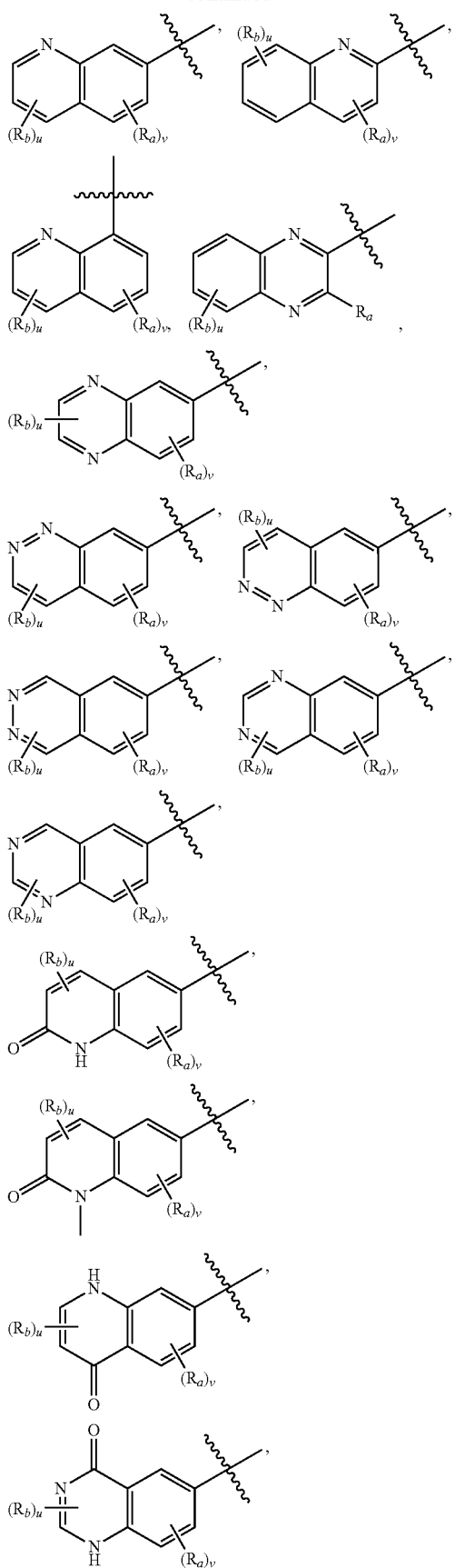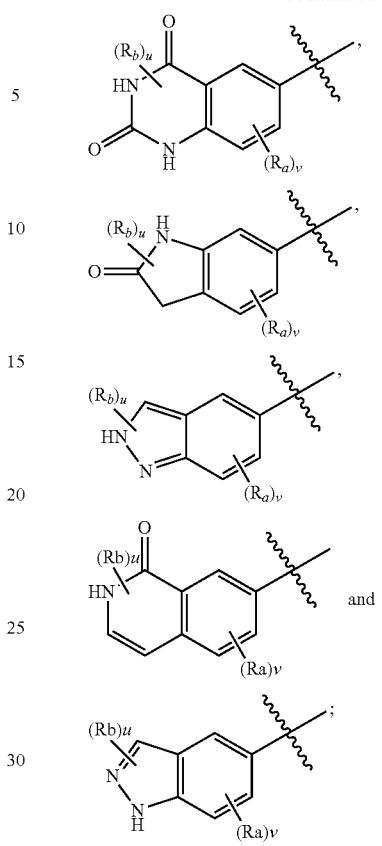

wherein u and v are each, independently, 0, 1, 2 or 3; and
each $R_a$ and $R_b$ are, independently, selected from cyano, halogen, hydroxy, $C_{1-4}$ alkyl, $C_{2-4}$ alkenyl, $C_{2-4}$ alkynyl, $C_{1-4}$ alkoxy, $C_{3-7}$ cycloalkyl, heterocyclyl, heteroaryl, heterocyclyl-$C_{1-4}$ alkyl, $C_{1-4}$ alkyl-aryl, $C_{1-4}$ alkyl-heterocyclyl, $C_{1-4}$ alkyl-heteroaryl, $C_{1-4}$ alkoxy-aryl, $C_{1-4}$ alkoxy-heterocyclyl, $C_{1-4}$ alkoxy-heteroaryl, and $C_{1-4}$ alkoxy substituted with hydroxy, $C_{1-4}$ alkoxy, amino, mono-$C_{1-4}$ alkylamino and di-$C_{1-4}$ alkylamino; or a pharmaceutically acceptable salt thereof; for use in the treatment, prevention and/or delay of progression of cancer.

In a particular embodiment, the present invention relates to a FoxM1 gene splicing modifier selected from a compound of formula (I) or of formula (VI), wherein A is selected from:

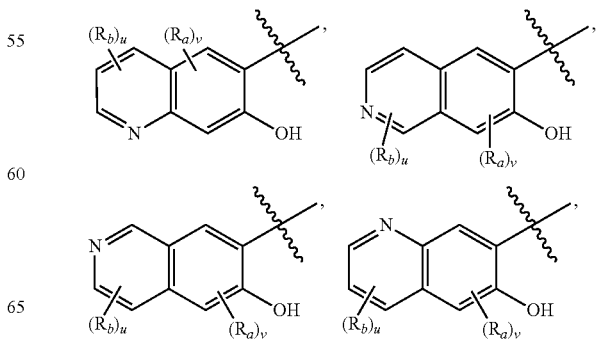

-continued

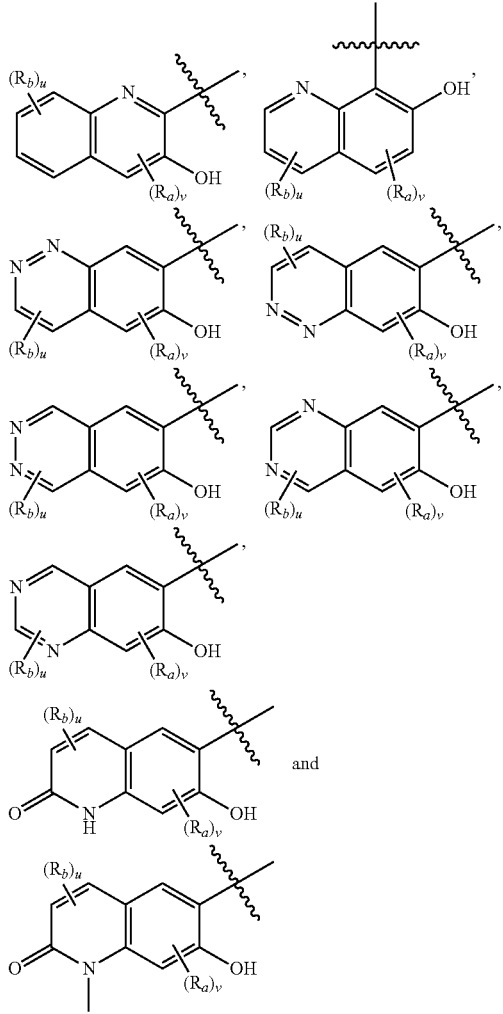

and wherein u and v are each, independently, 0, 1, 2 or 3; and each $R_a$ and $R_b$ are, independently, selected from cyano, halogen, hydroxy, $C_{1-4}$ alkyl, $C_{2-4}$ alkenyl, $C_{2-4}$ alkynyl, $C_{1-4}$ alkoxy, $C_{3-7}$ cycloalkyl, heterocyclyl, heteroaryl, heterocyclyl-$C_{1-4}$ alkyl, $C_{1-4}$ alkyl-aryl, $C_{1-4}$ alkyl-heterocyclyl, $C_{1-4}$ alkyl-heteroaryl, $C_{1-4}$ alkoxy-aryl, $C_{1-4}$ alkoxy-heterocyclyl, $C_{1-4}$ alkoxy-heteroaryl, $C_{1-4}$ alkoxy substituted with hydroxy, $C_{1-4}$ alkoxy, amino, mono-$C_{1-4}$ alkylamino and di-$C_{1-4}$ alkylamino; or a pharmaceutically acceptable salt thereof; for use in the treatment, prevention and/or delay of progression of cancer.

In a particular embodiment, the present invention relates to a FoxM1 gene splicing modifier selected from a compound of formula (I) or a compound of formula (VI), wherein A is substituted by one or more substituents as described herein, wherein one of the substituents of A is hydroxy in ortho-positon to the pyridazine of formula (I) or to the thiadiazole of formula (VI); or a pharmaceutically acceptable salt thereof; for use in the treatment, prevention and/or delay of progression of cancer.

In a particular embodiment, the present invention relates to a FoxM1 gene splicing modifier selected from a compound of formula (I) or a compound of formula (VI), wherein A is substituted by one or more substituents as described herein, wherein one of the substituents of A is hydroxy in 2-positon to the pyridazine of formula (I) or to the thiadiazole of formula (VI); or a pharmaceutically acceptable salt thereof; for use in the treatment, prevention and/or delay of progression of cancer.

In a particular embodiment, the present invention relates to a FoxM1 gene splicing modifier selected from a compound of formula (I), wherein A is substituted by one or more substituents as described herein, wherein one of the substituents of A is hydroxy in ortho-positon to the pyridazine of formula (I); or a pharmaceutically acceptable salt thereof; for use in the treatment, prevention and/or delay of progression of cancer.

In a particular embodiment, the present invention relates to a FoxM1 gene splicing modifier selected from a compound of formula (VI), wherein A is substituted by one or more substituents as described herein, wherein one of the substituents of A is hydroxy in ortho-positon to the thiadiazole of formula (VI); or a pharmaceutically acceptable salt thereof; for use in the treatment, prevention and/or delay of progression of cancer.

In a particular embodiment, the present invention relates to a FoxM1 gene splicing modifier selected from a compound of formula (I) or a compound of formula (VI), wherein B is a group of the formula

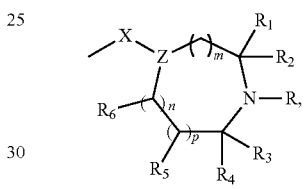

wherein m, n and p are independently selected from 0 or 1; R, $R_1$, $R_2$, $R_3$, and $R_4$ are independently selected from the group consisting of hydrogen, and $C_{1-4}$ alkyl, which alkyl is optionally substituted with hydroxy, amino, mono-$C_{1-4}$ alkylamino or di-$C_{1-4}$ alkylamino; $R_5$ and $R_6$ are hydrogen; or R and $R_3$ taken in combination form a fused 5 or 6 membered heterocyclic ring having 0 or 1 additional ring heteroatoms selected from N, O or S; $R_1$ and $R_3$, taken in combination form a $C_{1-3}$ alkylene group; $R_1$ and $R_5$ taken in combination form a $C_{1-3}$ alkylene group; $R_3$ and $R_4$ taken in combination with the carbon atom to which they attach, form a spirocyclic $C_{3-6}$ cycloalkyl; X is $CR_AR_B$, O, $NR_7$ or a bond; $R_A$ and $R_B$ are independently selected from hydrogen and $C_{1-4}$ alkyl, or $R_A$ and $R_B$ taken in combination, form a divalent $C_{2-5}$ alkylene group; Z is $CR_8$ or N; when Z is N, X is a bond; $R_8$ is hydrogen or taken in combination with $R_6$ form a double bond;

or a pharmaceutically acceptable salt thereof;

for use in the treatment, prevention and/or delay of progression of cancer.

In a particular embodiment, the present invention relates to a FoxM1 gene splicing modifier selected from a compound of formula (I) or a compound of formula (VI), wherein B is a group of the formula

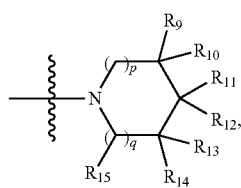

wherein p and q are independently selected from the group consisting of 0, 1, and 2; $R_9$ and $R_{13}$ are independently selected from hydrogen and $C_{1-4}$ alkyl; $R_{10}$ and $R_{14}$ are independently selected from hydrogen, amino, mono-$C_{1-4}$ alkylamino, di-$C_{1-4}$ alkylamino and $C_{1-4}$ alkyl, which alkyl is optionally substituted with hydroxy, amino, mono-$C_{1-4}$ alkylamino or di-$C_{1-4}$ alkylamino; $R_{11}$ is hydrogen, $C_{1-4}$ alkyl, amino, mono-$C_{1-4}$ alkylamino or di-$C_{1-4}$ alkylamino; $R_{12}$ is hydrogen or $C_{1-4}$ alkyl; or $R_9$ and $R_{11}$ taken in combination form a saturated azacycle having 4 to 7 ring atoms which is optionally substituted with one to three $C_{1-4}$ alkyl groups; or $R_{11}$ and $R_{12}$ taken in combination form a saturated azacycle having 4 to 7 ring atoms which is optionally substituted with one to three $C_{1-4}$ alkyl groups;

or a pharmaceutically acceptable salt thereof;

for use in the treatment, prevention and/or delay of progression of cancer.

In a particular embodiment, the present invention relates to a FoxM1 gene splicing modifier selected from a compound of formula (I) or a compound of formula (VI), wherein B is selected from the group consisting of

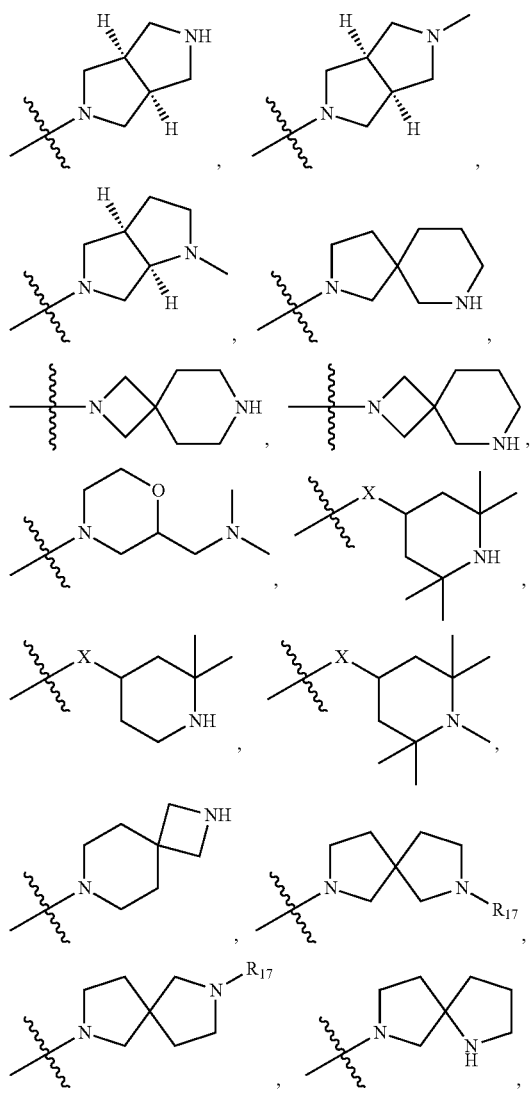

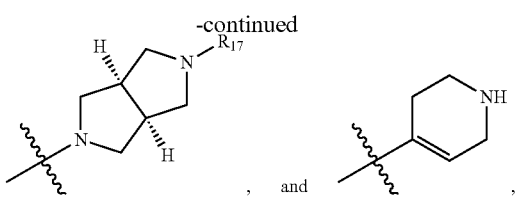

wherein X is O or —N(CH$_3$)—; and $R_{17}$ is hydrogen or methyl;

or a pharmaceutically acceptable salt thereof;

for use in the treatment, prevention and/or delay of progression of cancer.

In a particular embodiment, the present invention relates to a FoxM1 gene splicing modifier selected from a compound of formula (I) or a compound of formula (VI), wherein B is

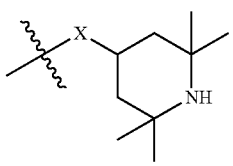

and X is O or —N(CH$_3$)—; or a pharmaceutically acceptable salt thereof; for use in the treatment, prevention and/or delay of progression of cancer.

In a particular embodiment, the present invention relates to a FoxM1 gene splicing modifier selected from a compound of formula (I) or a compound of formula (VI), wherein X is O; or a pharmaceutically acceptable salt thereof;

for use in the treatment, prevention and/or delay of progression of cancer.

In a particular embodiment, the present invention relates to a FoxM1 gene splicing modifier selected from a compound of formula (I) or a compound of formula (VI), wherein X is —N(CH$_3$)—; or a pharmaceutically acceptable salt thereof;

for use in the treatment, prevention and/or delay of progression of cancer.

In a particular embodiment, the present invention relates to a FoxM1 gene splicing modifier selected from a compound of formula (I) or a compound of formula (VI), wherein B is

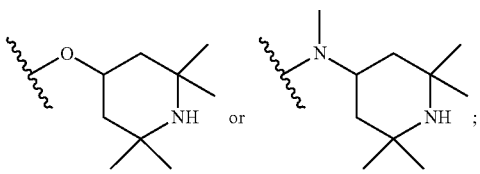 [SMILES: *OC1CC(C)(C)NC(C)(C)C1 ; *N(C)C1CC(C)(C)NC(C)(C)C1]

or a pharmaceutically acceptable salt thereof;

for use in the treatment, prevention and/or delay of progression of cancer.

In a particular embodiment, the present invention relates to a FoxM1 gene splicing modifier selected from a compound of formula (I) or a compound of formula (VI), wherein B is

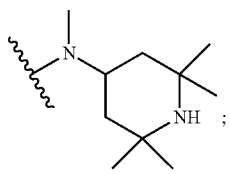 [SMILES: *N(C)C1CC(C)(C)NC(C)(C)C1]

or a pharmaceutically acceptable salt thereof;
for use in the treatment, prevention and/or delay of progression of cancer.

In a particular embodiment, the present invention relates to a FoxM1 gene splicing modifier selected from a compound of formula (I) or a compound of formula (VI), wherein B is

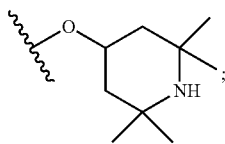 [SMILES: *OC1CC(C)(C)NC(C)(C)C1]

or a pharmaceutically acceptable salt thereof;
for use in the treatment, prevention and/or delay of progression of cancer.

In a particular embodiment, the present invention relates to a FoxM1 gene splicing modifier selected from a compound of formula (II):

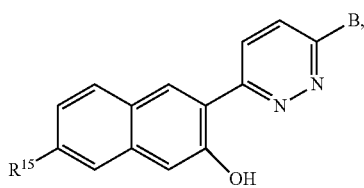

wherein $R^{15}$ is hydrogen, hydroxy, or $C_{1-4}$ alkoxy, wherein alkoxy is optionally substituted with hydroxy, methoxy, amino, mono-methylamino, dimethylamino or morpholine; or a pharmaceutically acceptable salt thereof; for use in the treatment, prevention and/or delay of progression of cancer.

In a particular embodiment, the present invention relates to a FoxM1 gene splicing modifier selected from a compound of formula (II), wherein $R^{15}$ is hydrogen, hydroxy or methoxy; or a pharmaceutically acceptable salt thereof; for use in the treatment, prevention and/or delay of progression of cancer.

In a particular embodiment, the present invention relates to a FoxM1 gene splicing modifier selected from a compound of formula (III):

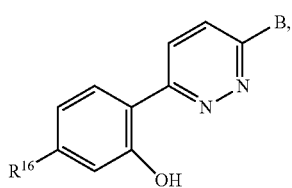

wherein $R^{16}$ is cyano, 5-membered heteroaryl having two ring nitrogen atoms, or 6-membered heteroaryl having one ring nitrogen atom; wherein the 5-membered heteroaryl is optionally substituted with $C_{1-4}$ alkyl; wherein the 6-membered heteroaryl is optionally substituted with one or two substituents selected from $C_{1-4}$ alkyl and hydroxy; or a pharmaceutically acceptable salt thereof; for use in the treatment, prevention and/or delay of progression of cancer.

In a particular embodiment, the present invention relates to a FoxM1 gene splicing modifier selected from a compound of formula (III), wherein $R^{16}$ is cyano, pyrazolyl or pyridinyl, wherein pyrazolyl is optionally substituted with methyl and wherein pyridinyl is optionally substituted with one or two substituents selected from methyl and hydroxy; or a pharmaceutically acceptable salt thereof; for use in the treatment, prevention and/or delay of progression of cancer.

In a particular embodiment, the present invention relates to a FoxM1 gene splicing modifier selected from a compound of formula (III), wherein $R^{16}$ is

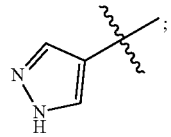 [SMILES: *c1cn[nH]c1]

or a pharmaceutically acceptable salt thereof; for use in the treatment, prevention and/or delay of progression of cancer.

In a particular embodiment, the present invention relates to a FoxM1 gene splicing modifier selected from a compound of formula (VII):

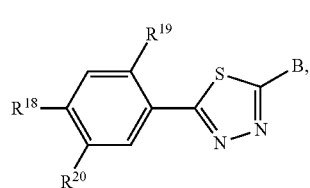

wherein $R^{18}$ is 5-membered heteroaryl having two ring nitrogen atoms or 6-membered heteroaryl having one ring nitrogen atom; wherein the 5-membered heteroaryl is optionally substituted with $C_{1-4}$ alkyl; wherein the 6-membered heteroaryl is optionally substituted with one or two substituents selected from $C_{1-4}$ alkyl and hydroxy; $R^{19}$ is hydrogen or halogen; and $R^{20}$ is hydrogen or halogen; or a pharmaceutically acceptable salt thereof; for use in the treatment, prevention and/or delay of progression of cancer.

In a particular embodiment, the present invention relates to a FoxM1 gene splicing modifier selected from a compound of formula (VII), wherein $R^{18}$ is pyrazolyl optionally substituted with methyl, or pyridinyl substituted with methyl and hydroxy; $R^{19}$ is hydrogen, chloro or fluoro; and $R^{20}$ is hydrogen, chloro or fluoro; or a pharmaceutically acceptable salt thereof; for use in the treatment, prevention and/or delay of progression of cancer.

In a particular embodiment, the present invention relates to a FoxM1 gene splicing modifier selected from a compound of formula (IV) or of formula (V) or of formula (VIII):

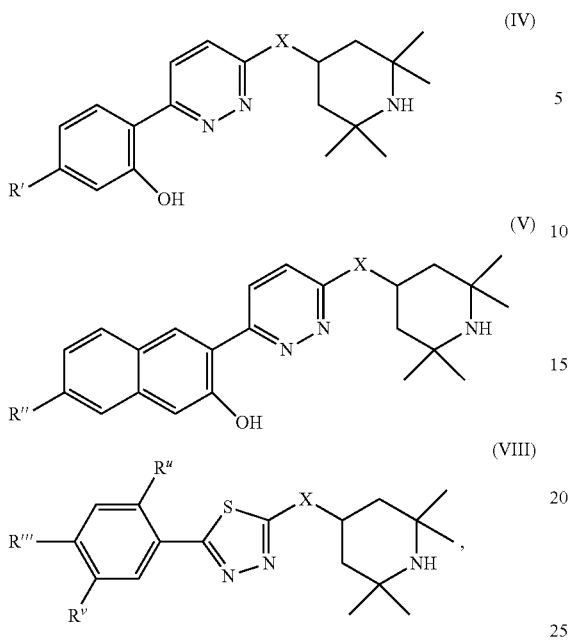

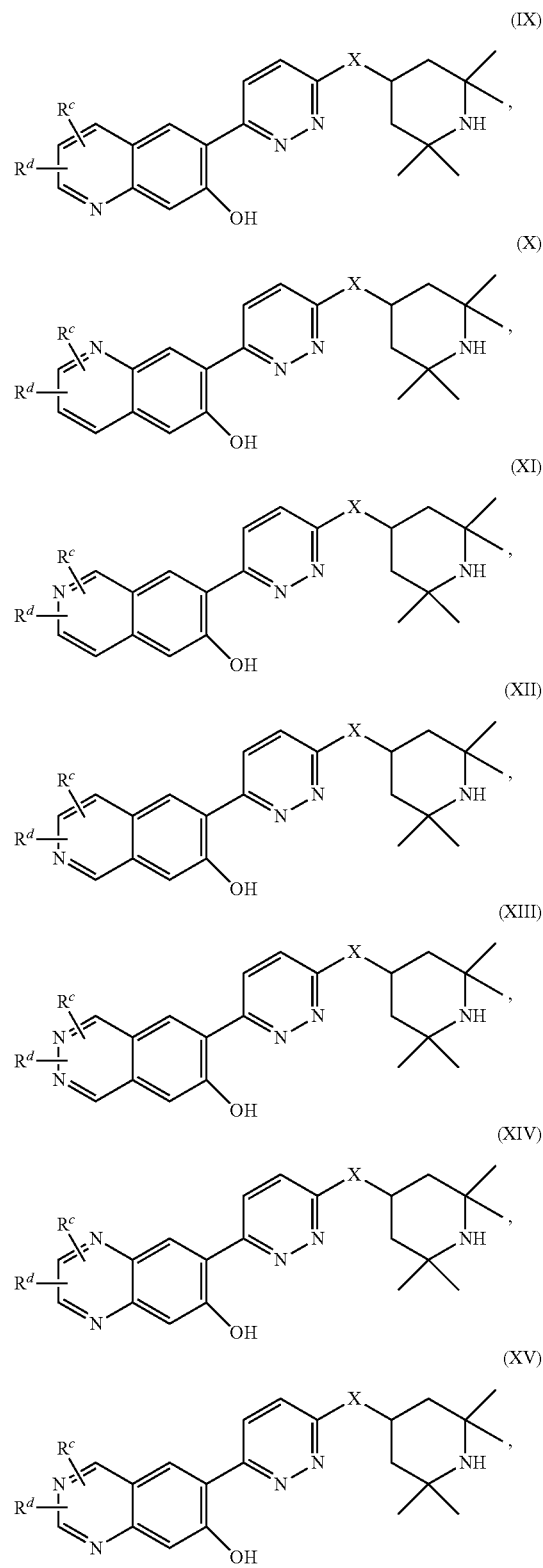

wherein X is —O— or —N(CH₃)—; R' is cyano, pyrazolyl optionally substituted with methyl, or pyridinyl substituted with methyl and hydroxy; R'' is hydrogen, methyl or methoxy; R''' is pyrazolyl optionally substituted with methyl, or pyridinyl substituted with methyl and hydroxy; R" is hydrogen, chloro or fluoro; R' is hydrogen, chloro or fluoro; or a pharmaceutically acceptable salt thereof; for use in the treatment, prevention and/or delay of progression of cancer.

In a particular embodiment, the present invention relates to a FoxM1 gene splicing modifier selected from a compound of formula (IV), wherein X is —O— or —N(CH₃)—; R' is cyano, pyrazolyl optionally substituted with methyl, or pyridinyl substituted with methyl and hydroxy; or a pharmaceutically acceptable salt thereof; for use in the treatment, prevention and/or delay of progression of cancer.

In a particular embodiment, the present invention relates to a FoxM1 gene splicing modifier selected from a compound of formula (V), wherein X is —O— or —N(CH₃)—; R'' is hydrogen, methyl or methoxy; or a pharmaceutically acceptable salt thereof; for use in the treatment, prevention and/or delay of progression of cancer.

In a particular embodiment, the present invention relates to a FoxM1 gene splicing modifier selected from a compound of formula (VIII), wherein X is —O— or —N(CH₃)—; R''' is pyrazolyl optionally substituted with methyl, or pyridinyl substituted with methyl and hydroxy; R" is hydrogen, chloro or fluoro; R' is hydrogen, chloro or fluoro; or a pharmaceutically acceptable salt thereof; for use in the treatment, prevention and/or delay of progression of cancer.

In a particular embodiment, the present invention relates to a FoxM1 gene splicing modifier selected from a compound of formula (IX) or of formula (X) or of formula (XI) or of formula (XII) or of formula (XIII) or of formula (XIV) or of formula (XV):

wherein X is —O— or —N(CH₃)—; and each $R^c$ and $R^d$ are, independently, selected from hydrogen, cyano, halogen, hydroxy, $C_{1-4}$ alkyl, $C_{2-4}$ alkenyl, $C_{2-4}$ alkynyl, $C_{1-4}$ alkoxy, $C_{3-7}$ cycloalkyl, heterocyclyl, heteroaryl, heterocyclyl-$C_{1-4}$ alkyl, $C_{1-4}$ alkyl-aryl, $C_{1-4}$ alkyl-heterocyclyl, $C_{1-4}$ alkyl-heteroaryl, $C_{1-4}$ alkoxy-aryl, $C_{1-4}$ alkoxy-heterocyclyl, $C_{1-4}$ alkoxy-heteroaryl, $C_{1-4}$ alkoxy substituted with hydroxy, $C_{1-4}$ alkoxy, amino, mono-$C_{1-4}$ alkylamino and di-$C_{1-4}$ alkylamino; or a pharmaceutically acceptable salt thereof; for use in the treatment, prevention and/or delay of progression of cancer.

In a particular embodiment, the present invention relates to a FoxM1 gene splicing modifier as described herein selected from the group consisting of:

6-(naphthalen-2-yl)-N-(2,2,6,6-tetramethylpiperidin-4-yl) pyridazin-3-amine;
6-(benzo[b]thio-phen-2-yl)-N-methyl-N-(2,2,6,6-tetramethylpiperidin-4-yl)pyridazin-3-amine;
2-(6-(2,2,6,6-tetramethylpiperidin-4-ylamino)-pyridazin-3-yl)phenol;
2-(6-(methyl-(2,2,6,6-tetra-methylpiperidin-4-yl)amino) pyridazin-3-yl)benzo[b]-thiophene-5-carbonitrile;
6-(quinolin-3-yl)-N-(2,2,6,6-tetramethyl-piperidin-4-yl) pyridazin-3-amine;
3-(benzo[b]-thiophen-2-yl)-6-(2,2,6,6-tetra-methylpiperidin-4-yloxy)pyridazine;
2-(6-(methyl-(2,2,6,6-tetra-methylpiperidin-4-yl)amino)-pyridazin-3-yl)phenol;
6-(6-(methyl-(2,2,6,6-tetra-methylpiperidin-4-yl)amino)-pyridazin-3-yl)naphthalen-2-ol;
6-(benzo[b]-thiophen-2-yl)-N-(2,2,6,6-tetra-methylpiperidin-4-yl)pyridazin-3-amine;
7-(6-((2,2,6,6-tetramethylpiperidin-4-yl)oxy)pyridazin-3-yl)isoquinoline;
6-(6-((2,2,6,6-tetramethylpiperidin-4-yl)oxy)pyridazin-3-yl)isoquinoline;
N-methyl-6-(quinolin-7-yl)-N-(2,2,6,6-tetramethyl-piperidin-4-yl)pyridazin-3-amine;
N-methyl-6-(quinolin-6-yl)-N-(2,2,6,6-tetramethylpiperidin-4-yl)pyridazin-3-amine;
6-(isoquinolin-7-yl)-N-methyl-N-(2,2,6,6-tetramethylpiperidin-4-yl)pyridazin-3-amine;
6-(isoquinolin-6-yl)-N-methyl-N-(2,2,6,6-tetramethylpiperidin-4-yl)pyridazin-3-amine;
6-(imidazo[1,2-a]pyridin-6-yl-pyridazin-3-yl)-methyl-(2,2,6,6-tetramethyl-piperidin-4-yl)-amine
methyl-[6-(6-phenyl-pyridin-3-yl)-pyridazin-3-yl]-(2,2,6,6-tetramethyl-piperidin-4-yl)-amine;
methyl-[6-(6-pyrrol-1-yl-pyridin-3-yl)-pyridazin-3-yl]-(2,2,6,6-tetramethyl-piperidin-4-yl)-amine;
methyl-(6-quinoxalin-2-yl-pyridazin-3-yl)-(2,2,6,6-tetramethyl-piperidin-4-yl)-amine;
methyl-(6-quinolin-3-yl-pyridazin-3-yl)-(2,2,6,6-tetramethyl-piperidin-4-yl)-amine;
N-methyl-6-(phthalazin-6-yl)-N-(2,2,6,6-tetramethylpiperidin-4-yl)pyridazin-3-amine;
6-(benzo[c][1,2,5]oxa-diazol-5-yl)-N-(2,2,6,6-tetramethyl-piperidin-4-yl)pyridazin-3-amine;
6-(benzo[d]thiazol-5-yl)-N-(2,2,6,6-tetramethyl-piperidin-4-yl)pyridazin-3-amine;
6-(2-methylbenzo-[d]oxazol-6-yl)-N-(2,2,6,6-tetramethyl-piperidin-4-yl)pyridazin-3-amine;
3-(6-(methyl(2,2,6,6-tetramethylpiperidin-4-yl)amino) pyridazin-3-yl)naphthalen-2-ol;
5-chloro-2-(6-(methyl(1,2,2,6,6-pentamethylpiperidin-4-yl) amino)pyridazin-3-yl)phenol;
3-(6-(2,2,6,6-tetramethylpiperidin-4-ylamino)pyridazin-3-yl)naphthalen-2-ol;
5-chloro-2-(6-(1,2,2,6,6-pentamethylpiperidin-4-ylamino) pyridazin-3-yl)phenol;
4-hydroxy-3-(6-(methyl(2,2,6,6-tetramethylpiperidin-4-yl) amino)pyridazin-3-yl)benzonitrile;
3-[6-(2,2,6,6-tetramethyl-piperidin-4-yloxy)-pyridazin-3-yl]-naphthalen-2-ol;
2-{6-[methyl-(2,2,6,6-tetramethyl-piperidin-4-yl)-amino]-pyridazin-3-yl}-4-trifluoromethylphenol;
2-fluoro-6-{6-[methyl-(2,2,6,6-tetramethyl-piperidin-4-yl)-amino]-pyridazin-3-yl}-phenol;
3,5-dimethoxy-2-{6-[methyl-(2,2,6,6-tetramethyl-piperidin-4-yl)-amino]-pyridazin-3-yl}-phenol;
4,5-dimethoxy-2-{6-[methyl-(2,2,6,6-tetramethyl-piperidin-4-yl)-amino]-pyridazin-3-yl}-phenol;
5-methoxy-2-{6-[methyl-(2,2,6,6-tetramethyl-piperidin-4-yl)-amino]-pyridazin-3-yl}-phenol;
4,5-difluoro-2-{6-[methyl-(2,2,6,6-tetramethyl-piperidin-4-yl)-amino]-pyridazin-3-yl}-phenol;
5-fluoro-2-{6-[methyl-(2,2,6,6-tetramethyl-piperidin-4-yl)-amino]-pyridazin-3-yl}-phenol;
3-hydroxy-4-(6-(methyl(2,2,6,6-tetramethylpiperidin-4-yl) amino)pyridazin-3-yl)benzonitrile;
1-allyl-6-(6-(methyl(2,2,6,6-tetramethylpiperidin-4-yl) amino)pyridazin-3-yl)naphthalen-2-ol;
6-(benzo[b]thiophen-2-yl)-N-(1,2,2,6,6-pentamethylpiperidin-4-yl)pyridazin-3-amine;
N-allyl-3-hydroxy-4-(6-(methyl(2,2,6,6-tetramethylpiperidin-4-yl)amino)pyridazin-3-yl)benzamide;
2-(6-(methyl(2,2,6,6-tetramethylpiperidin-4-yl)amino) pyridazin-3-yl)-5-(1H-pyrazol-1-yl)phenol;
5-(5-methyl-oxazol-2-yl)-2-{6-[methyl-(2,2,6,6-tetramethyl-piperidin-4-yl)-amino]-pyridazin-3-yl}-phenol;
5-(4-hydroxymethyl)-1H-pyrazole-1-yl)-2-(6-(methyl(2,2,6,6-tetramethylpiperidin-4yl)amino)pyridazin-3-yl)phenol;
5-(1H-imidazole-1-yl)-2-(6-(methyl(2,2,6,6-tetramethyl-piperidin-4-yl)amino)pyridazin-3-yl)phenol;
5-(4-amino-1H-pyrazole-1-yl)-2-(6-(methyl(2,2,6,6-tetramethylpiperidin-4-yl)amino)pyridazin-3-yl)phenol;
5-(4-amino-1H-pyrazol-1-yl)-2-(6-(methyl(2,2,6,6-tetramethylpiperidin-4-yl)amino)pyridazin-3-yl)phenol;
5-(3-amino-pyrazol-1-yl)-2-{6-[methyl-(2,2,6,6-tetramethyl-piperidin-4-yl)-amino]-pyridazin-3-yl}-phenol;
2-(6-(methyl-(2,2,6,6-tetramethylpiperidin-4-yl)amino) pyridazin-3-yl)-5-(1-(2-morpholinoethyl)-1H-pyrazol-4-yl)phenol;
2-(6-(methyl-(2,2,6,6-tetramethylpiperidin-4-yl)amino) pyridazin-3-yl)-5-(1-methyl-1H-pyrazol-4-yl)phenol;
5-(5-amino-1H-pyrazol-1-yl)-2-(6-(methyl-(2,2,6,6-tetramethyl-piperidin-4-yl)amino)pyridazin-3-yl)phenol;
2-(6-(methyl-(2,2,6,6-tetramethylpiperidin-4-yl)amino) pyridazin-3-yl)-4-(1H-pyrazol-1-yl)phenol;
2-{6-[(2-hydroxy-ethyl)-(2,2,6,6-tetramethyl-piperidin-4-yl)-amino]-pyridazin-3-yl}-5-pyrazol-1-yl-phenol;
2-(6-(piperidin-4-yloxy)pyridazin-3-yl)-5-(1H-pyrazol-1-yl)phenol;
2-(6-(((2S,4R,6R)-2,6-dimethylpiperidin-4-yl)oxy) pyridazin-3-yl)-5-(1H-pyrazol-1-yl)phenol;
5 2-(6-((2,6-di-methylpiperidin-4-yl)oxy)pyridazin-3-yl)-5-(1H-pyrazol-1-yl)phenol;
2-(6-((2,6-di-methylpiperidin-4-yl)oxy)pyridazin-3-yl)-5-(1H-pyrazol-1-yl)phenol;
5-(1H-pyrazol-1-yl)-2-(6-(pyrrolidin-3-yloxy)pyridazin-3-yl)phenol;
2-(6-((-2-methylpiperidin-4-yl)oxy)pyridazin-3-yl)-5-(1H-pyrazol-1-yl)phenol;
(S)-5-(1H-pyrazol-1-yl)-2-(6-(pyrrolidin-3-ylmethoxy) pyridazin-3-yl)phenol;
(R)-5-(1H-pyrazol-1-yl)-2-(6-(pyrrolidin-3-yl methoxy) pyridazin-3-yl)phenol;

2-(6-((3-fluoropiperidin-4-yl)oxy)pyridazin-3-yl)-5-(1H-pyrazol-1-yl)-phenol;
2-[6-(1,2,2,6,6-pentamethyl-piperidin-4-yloxy)-pyridazin-3-yl]-5-pyrazol-1-yl-phenol;
5-pyrazol-1-yl-2-[6-((2,2,6,6-tetramethylpiperidin-4-yloxy)-pyridazin-3-yl]-phenol;
5-(1H-pyrazol-4-yl)-2-(6-((2,2,6,6-tetramethylpiperidin-4-yl)oxy)-pyridazin-3-yl)phenol;
2-(6-piperazin-1-yl-pyridazin-3-yl)-5-pyrazol-1-yl-phenol;
3-[6-(azetidin-3-yl-amino)-pyridazin-3-yl]-naphthalen-2-ol;
2-[6-(azetidin-3-ylamino)-pyridazin-3-yl]-5-pyrazol-1-yl-phenol;
2-[6-(3,5-di methyl-piperazin-1-yl)-pyridazin-3-yl]-5-pyrazol-1-yl-phenol;
2-[6-(7-methyl-2,7-diaza-spiro[4.4]non-2-yl)-pyridazin-3-yl]-5-pyrazol-1-yl-phenol;
2-[6-[1,4]diazepan-1-yl-pyridazin-3-yl]-5-pyrazol-1-yl-phenol;
2-{6-[4-(2-hydroxy-ethyl)-piperazin-1-yl]-pyridazin-3-yl}-5-pyrazol-1-yl-phenol;
2-[6-(3,6-diaza-bicyclo[3.2.1]oct-3-yl)-pyridazin-3-yl]-5-pyrazol-1-yl-phenol;
2-[6-(2,7-diaza-spiro[3.5]non-7-yl)-pyridazin-3-yl]-5-pyrazol-1-yl-phenol;
2-[6-(3-hydroxy-methyl-piperazin-1-yl)-pyridazin-3-yl]-5-pyrazol-1-yl-phenol;
2-[6-(1,7-diaza-spiro[4.4]non-7-yl)-pyridazin-3-yl]-5-pyrazol-1-yl-phenol;
2-[6-(4-amino-4-methyl-piperidin-1-yl)-pyridazin-3-yl]-5-pyrazol-1-yl-phenol;
2-[6-(3-dimethyl-amino-piperidin-1-yl)-pyridazin-3-yl]-5-pyrazol-1-yl-phenol;
2-[6-(1,2,2,6,6-pentamethyl-piperidin-4-ylamino)-pyridazin-3-yl]-5-pyrazol-1-yl-phenol;
2-[6-(3,3-di methyl-piperazin-1-yl)-pyridazin-3-yl]-5-pyrazol-1-yl-phenol;
2-(6-(7-(2-hydroxyethyl)-2,7-diazaspiro[4.4]-nonan-2-yl)pyridazin-3-yl)-5-(1H-pyrazol-1-yl)phenol;
2-(6-(((3aR,6aS)-hexahydropyrrolo[3,4-c]pyrrol-2(1H)-yl)pyridazin-3-yl)-5-(1H-pyrazol-1-yl)phenol;
3-(6-(piperazin-1-yl)pyridazin-3-yl)naphthalene-2,7-diol;
5-pyrazol-1-yl-2-[6-(1,2,3,6-tetrahydro-pyridin-4-yl)-pyridazin-3-yl]-phenol;
2-(6-piperidin-4-yl-pyridazin-3-yl)-5-pyrazol-1-yl-phenol;
3-(6-(1,2,3,6-tetra-hydropyridin-4-yl)pyridazin-3-yl)naphthalen-2-ol;
3-(6-(1,2,3,6-tetrahydropyridin-4-yl)pyridazin-3-yl)naphthalene-2,7-diol;
3-(6-(2,2,6,6-tetramethyl-1,2,3,6-tetrahydropyridin-4-yl)pyridazin-3-yl)naphthalene-2,7-diol;
3-(6-(1-methyl-1,2,3,6-tetrahydropyridin-4-yl)pyridazin-3-yl)naphthalene-2,7-diol;
3-(6-(piperidin-4-yl)pyridazin-3-yl)naphthalene-2,7-diol;
3-(6-((2,2,6,6-tetramethylpiperidin-4-yl)oxy)pyridazin-3-yl)naphthalene-2,7-diol;
3-(6-(methyl-(2,2,6,6-tetramethylpiperidin-4-yl)amino)pyridazin-3-yl)naphthalene-2,7-diol;
3-(6-((2,2,6,6-tetramethylpiperidin-4-yl)amino)pyridazin-3-yl)naphthalene-2,7-diol;
[3-(7-hydroxy-6-{6-[methyl-(2,2,6,6-tetramethyl-piperidin-4-yl)-amino]-pyridazin-3-yl}-naphthalen-2-yloxy)-propyl]-carbamic acid tert-butyl ester;
7-(3-amino-propoxy)-3-{6-[methyl-(2,2,6,6-tetramethyl-piperidin-4-yl)-amino]-pyridazin-3-yl}naphthalen-2-ol;
N-[3-(7-hydroxy-6-{6-[methyl-(2,2,6,6-tetramethyl-piperidin-4-yl)-amino]-pyridazin-3-yl}naphthalen-2-yloxy)-propyl]-acetamide de;
7-(3-hydroxypropoxy)-3-(6-(methyl(2,2,6,6-tetramethylpiperidin-4-yl)amino)pyridazin-3-yl)naphthalen-2-ol;
7-(3-methoxypropoxy)-3-(6-(methyl(2,2,6,6-tetramethylpiperidin-4-yl)amino)pyridazin-3-yl)naphthalen-2-ol;
7-(2-morpholinoethoxy)-3-(6-((2,2,6,6-tetramethylpiperidin-4-yl)oxy)pyridazin-3-yl)naphthalen-2-ol;
3-(6-(piperidin-4-ylmethyl)pyridazin-3-yl)naphthalen-2-ol;
5-(1H-pyrazol-1-yl)-2-(6-((2,2,6,6-tetramethylpiperidin-4-yl)methyl)pyridazin-3-yl)phenol;
3-methoxy-2-(6-(methyl(2,2,6-trimethylpiperidin-4-yl)amino)pyridazin-3-yl)-5-(5-methyloxazol-2-yl)phenol;
2-(6-(((6S)-6-((S)-1-hydroxyethyl)-2,2-dimethylpiperidin-4-yloxy)pyridazin-3-yl)-5-(1H pyrazol-1-yl)phenol;
7-hydroxy-6-(6-(methyl(2,2,6,6-tetramethylpiperidin-4-yl)amino)pyridazin-3-yl)-2-naphthonitrile;
3-(6-(methyl(2,2,6,6-tetramethylpiperidin-4-yl)amino)pyridazin-3-yl)-7-(piperidin-1-ylmethyl)naphthalen-2-ol;
3-(6-(methyl(2,2,6,6-tetramethylpiperidin-4-yl)amino)pyridazin-3-yl)-7-(pyrrolidin-1-ylmethyl)naphthalen-2-ol;
1-bromo-6-(6-(methyl(2,2,6,6-tetramethylpiperidin-4-yl)amino)pyridazin-3-yl)naphthalene-2,7-diol;
1-chloro-6-(6-(methyl(2,2,6,6-tetramethylpiperidin-4-yl)amino)pyridazin-3-yl)naphthalene-2,7-diol;
7-methoxy-3-(6-(methyl(2,2,6,6-tetramethylpiperidin-4-yl)amino)pyridazin-3-yl)naphthalen-2-ol;
7-methoxy-3-(6-(methyl(1,2,2,6,6-pentamethylpiperidin-4-yl)amino)pyridazin-3-yl)naphthalen-2-ol;
7-(3,6-dihydro-2H-pyran-4-yl)-3-(6-(methyl(2,2,6,6-tetramethylpiperidin-4-yl)amino)pyridazin-3-yl)naphthalen-2-ol;
3-(6-(methyl-(2,2,6,6-tetramethylpiperidin-4-yl)amino)pyridazin-3-yl)-7-(tetrahydro-2H-pyran-4-yl)naphthalen-2-ol;
7-(difluoromethyl)-3-(6-(methyl-(2,2,6,6-tetramethylpiperidin-4-yl)amino)pyridazin-3-yl)naphthalen-2-ol;
7-((4-hydroxy-2-methyl butan-2-yl)oxy)-3-(6-(methyl(2,2,6,6-tetramethylpiperidin-4-yl)amino)pyridazin-3-yl)naphthalen-2-ol;
7-(3-hydroxy-3-methylbutoxy)-3-(6-(methyl-(2,2,6,6-tetramethylpiperidin-4-yl)amino)pyridazin-3-yl)naphthalen-2-ol;
2-(6-(methyl(2,2,6,6-tetramethylpiperidin-4-yl)amino)pyridazin-3-yl)-5-(1H-pyrazol-4-yl)benzene-1,3-diol;
3-methoxy-2-(6-(methyl-(2,2,6,6-tetramethylpiperidin-4-yl)amino)pyridazin-3-yl)-5-(1H pyrazol-4-yl)phenol;
5-(1H-pyrazol-4-yl)-2-(6-((2,2,6,6-tetramethylpiperidin-4-yl)amino)pyridazin-3-yl)-3-(trifluoromethoxy)phenol;
2-(6-(methyl(2,2,6,6-tetramethylpiperidin-4-yl)amino)pyridazin-3-yl)-5-(1-methyl-1H-pyrazol-4-yl)-3-(trifluoromethoxy)phenol;
2-(6-(methyl(2,2,6,6-tetramethylpiperidin-4-yl)amino)pyridazin-3-yl)-5-(1H-pyrazol-4-yl)-3-(trifluoromethoxy)phenol;
4-(3-hydroxy-4-(6-(methyl-(2,2,6,6-tetramethylpiperidin-4-yl)amino)pyridazin-3-yl)-5-(trifluoromethoxy)phenyl)-1-methylpyridin-2(1H)-one;
3-methoxy-2-(6-(methyl(2,2,6,6-tetramethylpiperidin-4-yl)amino)pyridazin-3-yl)-5-(1-methyl-1H-pyrazol-4-yl)phenol;
3-methoxy-2-(6-(methyl(2,2,6,6-tetramethylpiperidin-4-yl)amino)pyridazin-3-yl)-5-(5,6,7,8-tetrahydroimidazo[1,2-a]pyridin-3-yl)phenol;
3-methoxy-2-(6-(methyl(2,2,6,6-tetramethylpiperidin-4-yl)amino)pyridazin-3-yl)-5-(pyridin-3-yl)phenol;

5-(1-cyclopentyl-1H-pyrazol-4-yl)-3-methoxy-2-(6-(methyl (2,2,6,6-tetramethylpiperidin-4-yl)amino)pyridazin-3-yl) phenol;

3'5-dimethoxy-4-(6-(methyl-(2,2,6,6-tetramethylpiperidin-4-yl)amino)pyridazin-3-yl)-[1,1'-biphenyl]-3-ol;

3-(benzyloxy)-2-(6-(methyl-(2,2,6,6-tetramethylpiperidin-4-yl)amino)pyridazin-3-yl)-5-(5-methyloxazol-2-yl)phenol;

3-ethoxy-2-(6-(methyl-(2,2,6,6-tetramethylpiperidin-4-yl) amino)pyridazin-3-yl)-5-(5-methyloxazol-2-yl)phenol;

3-(cyclopropylmethoxy)-2-(6-(methyl-(2,2,6,6-tetramethylpiperidin-4-yl)amino)-pyridazin-3-yl)-5-(5-methyloxazol-2-yl)phenol;

2-methyl-5-(6-(methyl-(2,2,6,6-tetramethylpiperidin-4-yl) amino)pyridazin-3-yl)-1H benzo[d]imidazol-6-ol;

5-chloro-2-(6-(methyl-(2,2,6,6-tetramethylpiperidin-4-yl) amino)pyridazin-3-yl)phenol;

5-(1H-pyrazol-1-yl)-2-(6-((2,2,6,6-tetramethylpiperidin-4-yl)amino)pyridazin-3-yl)phenol;

3-hydroxy-4-(6-((2,2,6,6-tetramethylpiperidin-4-yl)amino) pyridazin-3-yl)benzonitrile;

2-(6-((2,2-dimethylpiperidin-4-yl)oxy)pyridazin-3-yl)-5-(1H-pyrazol-1-yl)phenol;

2-(6-(methyl-(2,2,6,6-tetramethylpiperidin-4-yl)amino) pyridazin-3-yl)-4-(1H-pyrazol-4-yl)phenol;

2-(6-(methyl-(2,2,6,6-tetramethylpiperidin-4-yl)amino) pyridazin-3-yl)-4-(4,5,6,7-tetrahydropyrazolo[1,5-a]pyridin-3-yl)phenol;

2-(6-(methyl-(2,2,6,6-tetramethylpiperidin-4-yl)amino) pyridazin-3-yl)-4-(4,5,6,7-tetrahydropyrazolo[1,5-a] pyrazin-3-yl)phenol;

4-(1H-indol-2-yl)-2-(6-(methyl-(2,2,6,6-tetramethylpiperidin-4-yl)amino)pyridazin-3-yl)phenol;

4-(cyclopent-1-en-1-yl)-2-(6-(methyl(2,2,6,6-tetramethylpiperidin-4-yl)amino)pyridazin-3-yl)phenol;

2-(6-(methyl-(2,2,6,6-tetramethylpiperidin-4-yl)amino) pyridazin-3-yl)-4-(1H-pyrazol-3-yl)phenol;

4-(4-hydroxy-3-(6-(methyl-(2,2,6,6-tetramethylpiperidin-4-yl)amino)pyridazin-3yl)phenyl)pyridin-2-ol;

4-(4-hydroxy-3-(6-((2,2,6,6-tetramethylpiperidin-4-yl)oxy) pyridazin-3-yl)phenyl)-1-methylpyridin-2-(1H)-one;

4-(4-hydroxy-3-(6-((2,2,6,6-tetramethylpiperidin-4-yl)oxy) pyridazin-3-yl)phenyl)pyridin-2-ol;

5-(1H-indazol-7-yl)-2-(6-(methyl-(2,2,6,6-tetramethylpiperidin-4-yl)amino)pyridazin-3-yl)phenol;

4-chloro-2-(6-(methyl-(2,2,6,6-tetramethylpiperidin-4-yl) amino)pyridazin-3-yl)-5-(1H-pyrazol-4-yl)phenol;

4-fluoro-2-(6-(methyl-(2,2,6,6-tetramethylpiperidin-4-yl) amino)pyridazin-3-yl)-5-(1H-pyrazol-4-yl)phenol;

5-fluoro-4-(1H-imidazol-4-yl)-2-(6-(methyl-(2,2,6,6-tetramethylpiperidin-4-yl)amino)pyridazin-3-yl)phenol;

5-fluoro-2-(6-(methyl-(2,2,6,6-tetramethylpiperidin-4-yl) amino)pyridazin-3-yl)-4-(1H-pyrazol-4-yl)phenol;

5-fluoro-2-(6-(methyl-(2,2,6,6-tetramethylpiperidin-4-yl) amino)pyridazin-3-yl)-4-(1H-pyrazol-5-yl)phenol;

5,6-hydroxy-5-(6-(methyl-(2,2,6,6-tetramethylpiperidin-4-yl)amino)pyridazin-3-yl)-2,3-dihydro-1H-inden-1-one;

6-(6-(methyl-(2,2,6,6-tetramethylpiperidin-4-yl)amino) pyridazin-3-yl)-1,4-dihydroindeno[1,2-c]pyrazol-7-ol;

6-hydroxy-5-(6-(methyl-(2,2,6,6-tetramethylpiperidin-4-yl) amino)pyridazin-3-yl)-2,3-dihydro-1H-inden-1-one oxime hydrochloride salt;

5-(6-(methyl-(2,2,6,6-tetramethylpiperidin-4-yl)amino) pyridazin-3-yl)-2,3-dihydro-1H-indene-1,6-diol;

2-amino-6-(6-(methyl-(2,2,6,6-tetramethylpiperidin-4-yl) amino)pyridazin-3-yl)-8H-indeno[1,2-d]thiazol-5-ol hydrochloride salt;

9-(6-(methyl-(2,2,6,6-tetramethylpiperidin-4-yl)amino) pyridazin-3-yl)-5,6-dihydroimidazo[5,1-a]isoquinolin-8-ol hydrochloride salt;

4-hydroxy-3-(6-(methyl-(2,2,6,6-tetramethylpiperidin-4-yl) amino)pyridazin-3-yl)-N-((1-methyl-1H-pyrazol-4-yl) methyl)benzamide;

4-(4-(hydroxymethyl)-1H-pyrazol-1-yl)-2-(6-(methyl(2,2,6, 6-tetramethylpiperidin-4-yl)amino)pyridazin-3-yl)phenol;

5-(1H-pyrazol-4-yl)-2-(6-((2,2,6,6-tetramethylpiperidin-4-yl)methyl)pyridazin-3-yl)phenol;

6-(3-(benzyloxy)isoquinolin-6-yl)-N-methyl-N-(2,2,6,6-tetramethylpiperidin-4-yl)pyridazin-3-amine;

6-(1-(benzyloxy)isoquinolin-7-yl)-N-methyl-N-(2,2,6,6-tetramethylpiperidin-4-yl)pyridazin-3-amine;

3-fluoro-5-(2-methoxypyridin-4-yl)-2-(6-(methyl-(2,2,6,6-tetramethylpiperidin-4-yl)amino)pyridazin-3-yl)phenol hydrochloride salt;

4-(3-fluoro-5-hydroxy-4-(6-(methyl-(2,2,6,6-tetramethylpiperidin-4-yl)amino)pyridazin-3-yl)phenyl)pyridin-2(1H)-one hydrochloride salt;

4-(3-fluoro-5-hydroxy-4-(6-(methyl-(2,2,6,6-tetramethylpiperidin-4-yl)amino)pyridazin-3-yl)phenyl)-1-methylpyridin-2(1H)-one hydrochloride salt;

5-(3-fluoro-5-hydroxy-4-(6-(methyl-(2,2,6,6-tetramethylpiperidin-4-yl)amino)pyridazin-3-yl)phenyl)-1-methylpyridin-2(1H)-one hydrochloride salt;

3-fluoro-5-(1H-pyrazol-4-yl)-2-(6-((2,2,6,6-tetramethylpiperidin-4-yl)oxy)pyridazin-3-yl)phenol hydrochloride salt;

5-chloro-3-fluoro-2-(6-(methyl-(2,2,6,6-tetramethylpiperidin-4-yl)amino)pyridazin-3-yl)phenol hydrochloride salt;

3-fluoro-2-(6-(methyl-(2,2,6,6-tetramethylpiperidin-4-yl) amino)pyridazin-3-yl)-5-(1H-pyrazol-4-yl)phenol hydrochloride salt;

3-fluoro-2-(6-(methyl-(2,2,6,6-tetramethylpiperidin-4-yl) amino)pyridazin-3-yl)-5-(1-methyl-1H pyrazol-4-yl)phenol hydrochloride salt;

5-(5-methoxypyridin-3-yl)-2-(6-(methyl-(2,2,6,6-tetramethylpiperidin-4-yl)amino)pyridazin-3-yl)phenol;

5-(3-hydroxy-4-(6-methyl-2,2,6,6-tetramethylpiperidin-4-yl)amino)pyridazin-3-yl)phenyl)pyridin-2-ol;

4-(3-hydroxy-4-(6-methyl-(2,2,6,6-tetramethylpiperidin-4-yl)amino)pyridazin-3-yl)phenyl)pyridin-2-ol;

5-(6-methoxypyridin-3-yl)-2-(6-(methyl-(2,2,6,6-tetramethylpiperidin-4-yl)amino)pyridazin-3-yl)phenol;

5-(3-hydroxy-4-(6-(methyl-(2,2,6,6-tetramethylpiperidin-4-yl)amino)pyridazin-3-yl)phenyl)-3-(trifluoromethyl)pyridin-2-ol;

5-(3-hydroxy-4-(6-(methyl-(2,2,6,6-tetramethylpiperidin-4-yl)amino)pyridazin-3-yl)phenyl)-1-methylpyridin-2(1H)-one;

4-(3-hydroxy-4-(6-(methyl-(2,2,6,6-tetramethylpiperidin-4-yl)amino)pyridazin-3-yl)phenyl)-1-methylpyridin-2(1H)-one;

5-(2-methoxypyridin-4-yl)-2-(6-(methyl-(2,2,6,6-tetramethylpiperidin-4-yl)amino)pyridazin-3-yl)phenol;

4-(3-hydroxy-4-(6-((2,2,6,6-tetramethylpiperidin-4-yl)oxy) pyridazin-3-yl)phenyl)pyridin-2-ol;

5-(6-(dimethylamino)pyridin-3-yl)-2-(6-(methyl(2,2,6,6-tetramethylpiperidin-4-yl)amino)pyridazin-3-yl)phenol;

4-(3-hydroxy-4-(6-((2,2,6,6-tetramethylpiperidin-4-yl)oxy) pyridazin-3-yl)phenyl)-1-methylpyridin-2(1H)-one;

2-(6-(methyl-(2,2,6,6-tetramethylpiperidin-4-yl)amino) pyridazin-3-yl)-5-(pyrimidin-5-yl)phenol;

5-(3-hydroxy-4-(6-(methyl-(2,2,6,6-tetramethylpiperidin-4-yl)amino)pyridazin-3-yl)phenyl)pyridin-3-ol;

1-cyclopropyl-4-(3-hydroxy-4-(6-(methyl(2,2,6,6-tetramethylpiperidin-4-yl)amino)pyridazin-3-yl)phenyl)pyridin-2(1H)-one;
2-(6-(methyl(2,2,6,6-tetramethylpiperidin-4-yl)amino)pyridazin-3-yl)-5-(1,2,3,6-tetrahydropyridin-4-yl)phenol;
5-(cyclopent-1-en-1-yl)-2-(6-(methyl(2,2,6,6-tetramethylpiperidin-4-yl)amino)pyridazin-3-yl)phenol;
5-(3,6-dihydro-2H-pyran-4-yl)-2-(6-(methyl(2,2,6,6-tetramethylpiperidin-4-yl)amino)pyridazin-3-yl)phenol;
5-(imidazo[1,5-a]pyridin-7-yl)-2-(6-(methyl(2,2,6,6-tetramethylpiperidin-4-yl)amino)pyridazin-3-yl)phenol;
5-(imidazo[1,2-a]pyridin-7-yl)-2-(6-(methyl(2,2,6,6-tetramethylpiperidin-4-yl)amino)pyridazin-3-yl)phenol;
2-(6-(methyl(2,2,6,6-tetramethylpiperidin-4-yl)amino)pyridazin-3-yl)-5-(2-methylpyridin-4-yl)phenol;
5-(1H-imidazol-2-yl)-2-(6-(methyl-(2,2,6,6-tetramethylpiperidin-4-yl)amino)pyridazin-3-yl)phenol;
5-(1H-imidazol-4-yl)-2-(6-(methyl-(2,2,6,6-tetramethylpiperidin-4-yl)amino)pyridazin-3-yl)phenol;
5-(imidazo[1,2-a]pyrazin-3-yl)-2-(6-(methyl(2,2,6,6-tetramethylpiperidin-4-yl)amino)pyridazin-3-yl)phenol;
2-(6-(methyl-(2,2,6,6-tetramethylpiperidin-4-yl)amino)pyridazin-3-yl)-5-(5,6,7,8-tetrahydroimidazo[1,2-a]pyrazin-3-yl)phenol;
2-(6-(methyl-(2,2,6,6-tetramethylpiperidin-4-yl)amino)pyridazin-3-yl)-5-(4-methyl-1H-imidazol-2-yl)phenol;
2-(6-(methyl-(2,2,6,6-tetramethylpiperidin-4-yl)amino)pyridazin-3-yl)-5-(1-methyl-1H-imidazol-4-yl)phenol;
2-(6-(methyl-(2,2,6,6-tetramethylpiperidin-4-yl)amino)pyridazin-3-yl)-5-(1-methyl-1H imidazol-5-yl)phenol;
2-(6-(methyl-(2,2,6,6-tetramethylpiperidin-4-yl)amino)pyridazin-3-yl)-5-(4-nitro-1H-imidazol-2-yl)phenol;
2-(6-(methyl-(2,2,6,6-tetramethylpiperidin-4-yl)amino)pyridazin-3-yl)-5-(2-methyl-1H imidazol-4-yl)phenol;
5-(1,2-dimethyl-1H-imidazol-4-yl)-2-(6-(methyl(2,2,6,6-tetramethylpiperidin-4-yl)amino)pyridazin-3-yl)phenol;
1-(3-hydroxy-4-(6-(methyl-(2,2,6,6-tetramethylpiperidin-4-yl)amino)pyridazin-3-yl)phenyl)-1H-pyrazole-4-carboxamide;
2-(6-((3aR,6aS)-5-(2-hydroxyethyphexahydropyrrolo[3,4-c]pyrrol-2 (1H)-yl)pyridazin-3-yl)-5-(1H-pyrazol-4-yl)phenol;
2-(6-((3aR,6aS)-hexahydropyrrolo[3,4-c]pyrrol-2(1H)-yl)pyridazin-3-yl)-5-(1H-pyrazol-4-yl)phenol;
2-(6-((3aR,6aS)-5-methylhexahydropyrrolo[3,4-c]pyrrol-2(1H)-yl)pyridazin-3-yl)-5-(1Hpyrazol-4-yl)phenol;
4-(3-hydroxy-4-(6-(5-methylhexahydropyrrolo[3,4-c]pyrrol-2(1H)-yl)pyridazin-3-yl)phenyl)-1-methylpyridin-2 (1H)-one;
4-(3-hydroxy-4-(6-((3aR,6aR)-1-methylhexahydropyrrolo[3,4-b]pyrrol-5(1H)-yl)pyridazin-3-yl)phenyl)-1-methylpyridin-2(1H)-one;
2-(6-(2,7-diazaspiro[4.5]decan-2-yl)pyridazin-3-yl)-5-(1H-pyrazol-4-yl)phenol; and
4-(4-(6-(2,7-diazaspiro[4.5]decan-2-yl)pyridazin-3-yl)-3-hydroxyphenyl)-1-methylpyridin-2(1H)-one;
5-(2-Methoxy-4-(1H-pyrazol-1-yl)phenyl)-N-methyl-N-(2,2,6,6-tetramethylpiperidin-4-yl)-1,3,4-thiadiazol-2-amine;
6-(5-(Methyl(2,2,6,6-tetramethylpiperidin-4-yl)amino)-1,3,4-thiadiazol-2-yl)naphthalen-2-ol;
5-(2-Methoxyquinolin-3-yl)-N-methyl-N-(2,2,6,6-tetramethylpiperidin-4-yl)-1,3,4-thiadiazol-2-amine;
5-(3-Methoxynaphthalen-2-yl)-N-methyl-N-(2,2,6,6-tetramethylpiperidin-4-yl)-1,3,4-thiadiazol-2-amine;
5-(2-Methoxy-4-(1H-pyrazol-1-yl)phenyl)-N-(1,2,2,6,6-pentamethylpiperidin-4-yl)-1,3,4-thiadiazol-2-amine;
5-(2-Methoxy-4-(1-methyl-1H-pyrazol-4-yl)phenyl)-N-methyl-N-(2,2,6,6-tetramethylpiperidin-4-yl)-1,3,4-thiadiazol-2-amine;
5-(2-Methoxy-4-(1H-pyrazol-4-yl)phenyl)-N-methyl-N-(2,2,6,6-tetramethylpiperidin-4-yl)-1,3,4-thiadiazol-2-amine;
4-(3-Methoxy-4-(5-(methyl(2,2,6,6-tetramethylpiperidin-4-yl)amino)-1,3,4-thiadiazol-2-yl)phenyl)-1-methylpyridin-2(1H)-one;
5-(3-Methoxy-4-(5-(methyl(2,2,6,6-tetramethylpiperidin-4-yl)amino)-1,3,4-thiadiazol-2-yl)phenyl)pyridin-2-ol;
5-(3-Methoxy-4-(5-(methyl(2,2,6,6-tetramethylpiperidin-4-yl)amino)-1,3,4-thiadiazol-2-yl)phenyl)-1-methylpyridin-2(1H)-one;
N-Methyl-5-(2-methyl-4-(1-methyl-1H-pyrazol-4-yl)phenyl)-N-(2,2,6,6-tetramethylpiperidin-4-yl)-1,3,4-thiadiazol-2-amine;
1-Methyl-4-(4-(5-(methyl(2,2,6,6-tetramethylpiperidin-4-yl)amino)-1,3,4-thiadiazol-2-yl)-3-(trifluoromethoxy)phenyl)pyridin-2(1H)-one;
5-(4-(3,5-Dimethyl-1H-pyrazol-4-yl)-2-methoxyphenyl)-N-methyl-N-(2,2,6,6-tetramethylpiperidin-4-yl)-1,3,4-thiadiazol-2-amine;
5-(2-Methoxy-4-(1-methyl-1H-pyrazol-4-yl)phenyl)-N-methyl-N-(2,2,6,6-tetramethylpiperidin-4-yl)-1,3,4-thiadiazol-2-amine;
2-(5-(Methyl(2,2,6,6-tetramethylpiperidin-4-yl)amino)-1,3,4-thiadiazol-2-yl)-5-(1-methyl-1H-pyrazol-4-yl)phenol;
2-(5-(Methyl(2,2,6,6-tetramethylpiperidin-4-yl)amino)-1,3,4-thiadiazol-2-yl)-5-(1H-pyrazol-1-yl)phenol;
5-(3-Hydroxy-4-(5-(methyl(2,2,6,6-tetramethylpiperidin-4-yl)amino)-1,3,4-thiadiazol-2-yl)phenyl)-1-methylpyridin-2(1H)-one;
4-(3-Hydroxy-4-(5-(methyl(2,2,6,6-tetramethylpiperidin-4-yl)amino)-1,3,4-thiadiazol-2-yl)phenyl)-1-methylpyridin-2(1H)-one;
5-(3-Hydroxy-4-(5-(methyl(2,2,6,6-tetramethylpiperidin-4-yl)amino)-1,3,4-thiadiazol-2-yl)phenyl)pyridin-2-ol;
3-(5-(Methyl(2,2,6,6-tetramethylpiperidin-4-yl)amino)-1,3,4-thiadiazol-2-yl)naphthalene-2,7-diol;
3-(5-((3 aR,6aS)-Hexahydropyrrolo[3,4-c]pyrrol-2(1H)-yl)-1,3,4-thiadiazol-2-yl)naphthalene-2,7-diol;
3-(5-(Methyl(2,2,6,6-tetramethylpiperidin-4-yl)amino)-1,3,4-thiadiazol-2-yl)naphthalen-2-ol hydrobromide salt;
3-(5-(Methyl(2,2,6,6-tetramethylpiperidin-4-yl)amino)-1,3,4-thiadiazol-2-yl)quinolin-2-ol;
2-(5-(Methyl(2,2,6,6-tetramethylpiperidin-4-yl)amino)-1,3,4-thiadiazol-2-yl)-4-(1H-pyrazol-1-yl)phenol;
5-(2-Chloro-4-(1-methyl-1H-pyrazol-4-yl)phenyl)-N-methyl-N-(2,2,6,6-tetramethylpiperidin-4-yl)-1,3,4-thiadiazol-2-amine;
3-Chloro-2-(5-(methyl(2,2,6,6-tetramethylpiperidin-4-yl)amino)-1,3,4-thiadiazol-2-yl)-5-(1-methyl-1H-pyrazol-4-yl)phenol;
5-(2-Chloro-4-(1-methyl-1H-pyrazol-4-yl)phenyl)-N-(2,2,6,6-tetramethylpiperidin-4-yl)-1,3,4-thiadiazol-2-amine;
3-Methoxy-2-(5-(methyl(2,2,6,6-tetramethylpiperidin-4-yl)amino)-1,3,4-thiadiazol-2-yl)-5-(5-methyloxazol-2-yl)phenol;
2-(2-Methoxy-4-(1H-pyrazol-1-yl)phenyl)-5-(1,2,3,6-tetrahydropyridin-4-yl)-1,3,4-thiadiazole;
2-(5-(piperazin-1-yl)-1,3,4-thiadiazol-2-yl)-5-(1H-pyrazol-1-yl)phenol;
5-(7-Methoxyquinolin n-6-yl)-N-methyl-N-(2,2,6,6-tetramethylpiperidin-4-yl)-1,3,4-thiadiazol-2-amine;
6-(5-(Methyl(2,2,6,6-tetramethylpiperidin-4-yl)amino)-1,3,4-thiadiazol-2-yl)quinolin-7-ol;

3-methoxy-4-(5-(methyl(2,2,6,6-tetramethylpiperidin-4-yl)amino)-1,3,4-thiadiazol-2-yl)benzonitrile;

3-fluoro-4-(5-(methyl(2,2,6,6-tetramethylpiperidin-4-yl)amino)-1,3,4-thiadiazol-2-yl)benzonitrile;

methyl 3-fluoro-4-(5-(methyl(2,2,6,6-tetramethylpiperidin-4-yl)amino)-1,3,4-thiadiazol-2-yl)benzoate;

5-(2-methoxy-4-(3-(methylamino)-1H-pyrazol-1-yl)phenyl)-N-methyl-N-(2,2,6,6-tetramethylpiperidin-4-yl)-1,3,4-thiadiazol-2-amine;

7-methoxy-6-(5-(methyl(2,2,6,6-tetramethylpiperidin-4-yl)amino)-1,3,4-thiadiazol-2-yl)quinoline-2-carbonitrile;

4-(3-methoxy-4-(5-((2,2,6,6-tetramethylpiperidin-4-yl)oxy)-1,3,4-thiadiazol-2-yl)phenyl)-1-methylpyridin-2(1H)-one;

4-(3-chloro-4-(5-(methyl(2,2,6,6-tetramethylpiperidin-4-yl)amino)-1,3,4-thiadiazol-2-yl)phenyl)-1-methylpyridin-2(1H)-one;

5-(2-Chloro-4-(1H-pyrazol-4-yl)phenyl)-N-methyl-N-(2,2,6,6-tetramethylpiperidin-4-yl)-1,3,4-thiadiazol-2-amine;

5-(2-Chloro-4-(4,5,6,7-tetrahydropyrazolo[1,5-a]pyridin-3-yl)phenyl)-N-methyl-N-(2,2,6,6-tetramethylpiperidin-4-yl)-1,3,4-thiadiazol-2-amine;

N-methyl-5-(5-(1-methyl-1H-pyrazol-4-yl)pyridin-2-yl)-N-(2,2,6,6-tetramethylpiperidin-4-yl)-1,3,4-thiadiazol-2-amine Hydrochloride salt;

2-(2-chloro-4-(1-methyl-1H-pyrazol-4-yl)phenyl)-5-((2,2,6,6-tetramethylpiperidin-4-yl)oxy)-1,3,4-thiadiazole;

5-(2-chloro-4-(6-methoxypyridin-3-yl)phenyl)-N-methyl-N-(2,2,6,6-tetramethylpiperidin-4-yl)-1,3,4-thiadiazol-2-amine;

5-(4-(6-aminopyridin-3-yl)-2-fluorophenyl)-N-methyl-N-(2,2,6,6-tetramethylpiperidin-4-yl)-1,3,4-thiadiazol-2-amine;

5-(2-fluoro-4-(3-methyl-1H-pyrazol-5-yl)phenyl)-N-methyl-N-(2,2,6,6-tetramethylpiperidin-4-yl)-1,3,4-thiadiazol-2-amine;

5-(2-fluoro-4-(1H-pyrazol-5-yl)phenyl)-N-methyl-N-(2,2,6,6-tetramethylpiperidin-4-yl)-1,3,4-thiadiazol-2-amine;

5-(2,3-difluoro-4-(1H-pyrazol-4-yl)phenyl)-N-methyl-N-(2,2,6,6-tetramethylpiperidin-4-yl)-1,3,4-thiadiazol-2-amine;

5-(2,3-difluoro-4-(1H-pyrazol-5-yl)phenyl)-N-methyl-N-(2,2,6,6-tetramethylpiperidin-4-yl)-1,3,4-thiadiazol-2-amine;

5-(2,5-difluoro-4-(1H-pyrazol-4-yl)phenyl)-N-methyl-N-(2,2,6,6-tetramethylpiperidin-4-yl)-1,3,4-thiadiazol-2-amine;

5-(2,5-difluoro-4-(1H-pyrazol-5-yl)phenyl)-N-methyl-N-(2,2,6,6-tetramethylpiperidin-4-yl)-1,3,4-thiadiazol-2-amine;

5-(2,6-difluoro-4-(1H-pyrazol-4-yl)phenyl)-N-methyl-N-(2,2,6,6-tetramethylpiperidin-4-yl)-1,3,4-thiadiazol-2-amine;

2-(2,5-difluoro-4-(1H-pyrazol-4-yl)phenyl)-5-((3aR,6aS)-hexahydropyrrolo[3,4-c]pyrrol-2(1H)-yl)-1,3,4-thiadiazole;

5-(2-chloro-5-fluoro-4-(1H-pyrazol-4-yl)phenyl)-N-methyl-N-(2,2,6,6-tetramethylpiperidin-4-yl)-1,3,4-thiadiazol-2-amine;

5-(3-fluoro-5-(1H-pyrazol-4-yl)pyridin-2-yl)-N-methyl-N-(2,2,6,6-tetramethylpiperidin-4-yl)-1,3,4-thiadiazol-2-amine;

5-(4-(2-aminopyrimidin-4-yl)-2-chlorophenyl)-N-methyl-N-(2,2,6,6-tetramethylpiperidin-4-yl)-1,3,4-thiadiazol-2-amine;

5-(5-(2-aminopyrimidin-4-yl)-2-chlorophenyl)-N-methyl-N-(2,2,6,6-tetramethylpiperidin-4-yl)-1,3,4-thiadiazol-2-amine;

5-(4-(2,4-dimethylthiazol-5-yl)-2,5-difluorophenyl)-N-methyl-N-(2,2,6,6-tetramethylpiperidin-4-yl)-1,3,4-thiadiazol-2-amine;

5-(4-(2,4-dimethylthiazol-5-yl)-2,3-difluorophenyl)-N-methyl-N-(2,2,6,6-tetramethylpiperidin-4-yl)-1,3,4-thiadiazol-2-amine;

4-(3-hydroxy-4-(5-(methyl(2,2,6,6-tetramethylpiperidin-4-yl)amino)-1,3,4-thiadiazol-2-yl)-5-(trifluoromethoxy)phenyl)-1-methylpyridin-2(1H)-one;

5-(2-fluoro-6-methoxy-4-(1H-pyrazol-4-yl)phenyl)-N-methyl-N-(2,2,6,6-tetramethylpiperidin-4-yl)-1,3,4-thiadiazol-2-amine;

2-(2-fluoro-6-methoxy-4-(1H-pyrazol-4-yl)phenyl)-5-((3aR,6aS)-5-methylhexahydropyrrolo[3,4-c]pyrrol-2(1H)-yl)-1,3,4-thiadiazole;

5-(2,3-difluoro-6-methoxy-4-(1H-pyrazol-4-yl)phenyl)-N-methyl-N-(2,2,6,6-tetramethylpiperidin-4-yl)-1,3,4-thiadiazol-2-amine;

6-methoxy-2-(5-(methyl(2,2,6,6-tetramethylpiperidin-4-yl)amino)-1,3,4-thiadiazol-2-yl)-3,4-dihydroisoquinolin-1(2H)-one;

5-(2-Chloro-4-(1H-pyrazol-1-yl)phenyl)-N-methyl-N-(2,2,6,6-tetramethylpiperidin-4-yl)-1,3,4-thiadiazol-2-amine;

5-(2-Chloro-4-(1H-1,2,3-triazol-1-yl)phenyl)-N-methyl-N-(2,2,6,6-tetramethylpiperidin-4-yl)-1,3,4-thiadiazol-2-amine;

5-(2-chloro-4-(2H-1,2,3-triazol-2-yl)phenyl)-N-methyl-N-(2,2,6,6-tetramethylpiperidin-4-yl)-1,3,4-thiadiazol-2-amine;

5-(2-chloro-4-(1H-1,2,4-triazol-1-yl)phenyl)-N-methyl-N-(2,2,6,6-tetramethylpiperidin-4-yl)-1,3,4-thiadiazol-2-amine;

5-(4-(3-amino-1H-pyrazol-1-yl)-2-chlorophenyl)-N-methyl-N-(2,2,6,6-tetramethylpiperidin-4-yl)-1,3,4-thiadiazol-2-amine;

2-(2-chloro-4-(1H-imidazol-1-yl)phenyl)-5-((3aR,6aS)-5-methyl hexahydropyrrolo[3,4-c]pyrrol-2(1H)-yl)-1,3,4-thiadiazole;

5-(2-Chloro-4-(1H-imidazol-1-yl)phenyl)-N-methyl-N-(2,2,6,6-tetramethylpiperidin-4-yl)-1,3,4-thiadiazol-2-amine;

5-(2-fluoro-4-(1H-imidazol-1-yl)phenyl)-N-methyl-N-(2,2,6,6-tetramethylpiperidin-4-yl)-1,3,4-thiadiazol-2-amine;

5-(2-methoxy-4-(1H-pyrazol-5-yl)phenyl)-N-methyl-N-(2,2,6,6-tetramethylpiperidin-4-yl)-1,3,4-thiadiazol-2-amine;

5-(4-(2,4-dimethylthiazol-5-yl)-2-methoxyphenyl)-N-methyl-N-(2,2,6,6-tetramethylpiperidin-4-yl)-1,3,4-thiadiazol-2-amine;

5-(2-methoxy-4-(pyridin-3-yl)phenyl)-N-methyl-N-(2,2,6,6-tetramethylpiperidin-4-yl)-1,3,4-thiadiazol-2-amine;

5-(2-fluoro-4-(1H-pyrazol-4-yl)phenyl)-N-methyl-N-(2,2,6,6-tetramethylpiperidin-4-yl)-1,3,4-thiadiazol-2-amine;

5-(2-methoxy-4-(2-methoxypyridin-4-yl)phenyl)-N-methyl-N-(2,2,6,6-tetramethylpiperidin-4-yl)-1,3,4-thiadiazol-2-amine;

5-(2-methoxy-4-(6-methoxypyridin-3-yl)phenyl)-N-methyl-N-(2,2,6,6-tetramethylpiperidin-4-yl)-1,3,4-thiadiazol-2-amine;

2-(2-Chloro-4-(1-methyl-1H-pyrazol-4-yl)phenyl)-5-((3aR,6aS)-5-methylhexahydropyrrolo[3,4-c]pyrrol-2(1H)-yl)-1,3,4-thiadiazole;

2-(2-chloro-4-(1H-pyrazol-4-yl)phenyl)-5-((3aR,6aS)-5-methylhexahydropyrrolo[3,4-c]pyrrol-2(1H)-yl)-1,3,4-thiadiazole;

2-(2-Chloro-4-(1H-pyrazol-4-yl)phenyl)-5-((3aR,6aR)-1-methylhexahydropyrrolo[3,4-b]pyrrol-5(1H)-yl)-1,3,4-thiadiazole;

1-(4-(5-(2-chloro-4-(1H-pyrazol-4-yl)phenyl)-1,3,4-thiadiazol-2-yl)morpholin-2-yl)-N,N-dimethylmethanamine;

2-(2-chloro-4-(1H-pyrazol-4-yl)phenyl)-5-(2-methyl-2,7-diazaspiro[4.5]decan-7-yl)-1,3,4-thiadiazole;

2-(2-fluoro-4-(1H-pyrazol-4-yl)phenyl)-5-((3aR,6aS)-5-methylhexahydropyrrolo[3,4-c]pyrrol-2(1H)-yl)-1,3,4-thiadiazole;

2-(2-methoxy-4-(1-methyl-1H-pyrazol-4-yl)phenyl)-5-(2,6-diazaspiro[3.5]nonan-2-yl)-1,3,4-thiadiazole;

2-(2-methoxy-4-(1-methyl-1H-pyrazol-4-yl)phenyl)-5-(2,7-diazaspiro[3.5]nonan-2-yl)-1,3,4-thiadiazole;

2-(5-(Methyl(2,2,6,6-tetramethylpiperidin-4-yl)amino)-1,3,4-thiadiazol-2-yl)-5-(1H-pyrazol-1-yl)phenol;

5-(3-chloro-4-(5-(methyl(2,2,6,6-tetramethylpiperidin-4-yl)amino)-1,3,4-thiadiazol-2-yl)phenyl)pyridin-2(1H)-one;

2-(5-(methyl(2,2,6,6-tetramethylpiperidin-4-yl)amino)-1,3,4-thiadiazol-2-yl)-5-(3-(methylamino)-1H-pyrazol-1-yl)phenol;

3-fluoro-2-(5-(methyl(2,2,6,6-tetramethylpiperidin-4-yl)amino)-1,3,4-thiadiazol-2-yl)-5-(1H-pyrazol-4-yl)phenol;

3,4-difluoro-2-(5-(methyl(2,2,6,6-tetramethylpiperidin-4-yl)amino)-1,3,4-thiadiazol-2-yl)-5-(1H-pyrazol-4-yl)phenol;

6-hydroxy-5-(5-(methyl(2,2,6,6-tetramethylpiperidin-4-yl)amino)-1,3,4-thiadiazol-2-yl)-2,3-dihydro-1H-inden-1-one;

2-(5-(methyl(2,2,6,6-tetramethylpiperidin-4-yl)amino)-1,3,4-thiadiazol-2-yl)-5-(1H-pyrazol-4-yl)phenol;

2-(5-(2,6-diazaspiro[3.5]nonan-2-yl)-1,3,4-thiadiazol-2-yl)-5-(1-methyl-1H-pyrazol-4-yl)phenol;

2-(5-(2,7-diazaspiro[3.5]nonan-2-yl)-1,3,4-thiadiazol-2-yl)-5-(1-methyl-1H-pyrazol-4-yl)phenol;

3-fluoro-2-(5-((3aR,6aS)-hexahydropyrrolo[3,4-c]pyrrol-2(1H)-yl)-1,3,4-thiadiazol-2-yl)-5-(1H-pyrazol-4-yl)phenol Di-hydrochloride salt;

3-Chloro-2-(5-(methyl(2,2,6,6-tetramethylpiperidin-4-yl)amino)-1,3,4-thiadiazol-2-yl)-5-(1H-pyrazol-4-yl)phenol;

2-(2-methoxy-4-(1H-pyrazol-1-yl)phenyl)-5-((2,2,6,6-tetramethylpiperidin-4-yl)methyl)-1,3,4-thiadiazole;

2-(2,3-difluoro-4-(1H-pyrazol-4-yl)phenyl)-5-(2,7-diazaspiro[3.5]nonan-2-yl)-1,3,4-thiadiazole;

2-(5-(2,7-diazaspiro[3.5]nonan-2-yl)-1,3,4-thiadiazol-2-yl)-3-fluoro-5-(1H-pyrazol-4-yl)phenol;

4-methoxy-1-methyl-3-(5-(methyl(2,2,6,6-tetramethylpiperidin-4-yl)amino)-1,3,4-thiadiazol-2-yl)quinolin-2(1H)-one;

4-hydroxy-1-methyl-3-(5-(methyl(2,2,6,6-tetramethylpiperidin-4-yl)amino)-1,3,4-thiadiazol-2-yl)quinolin-2(1H)-one;

3-(5-(methyl(2,2,6,6-tetramethylpiperidin-4-yl)amino)-1,3,4-thiadiazol-2-yl)quinolin-2(1H)-one;

1-methyl-3-(5-(methyl(2,2,6,6-tetramethylpiperidin-4-yl)amino)-1,3,4-thiadiazol-2-yl)quinolin-2(1H)-one;

2-(2-Chloro-4-(1H-pyrazol-4-yl)phenyl)-5-((3aR,6aS)-hexahydropyrrolo[3,4-c]pyrrol-2(1H)yl)-1,3,4-thiadiazole Hydrochloride Salt;

2-(2-Chloro-4-(1H-pyrazol-4-yl)phenyl)-5-(2,7-diazaspiro[4.5]decan-2-yl)-1,3,4-thiadiazole Hydrochloride Salt;

(R)-(4-(5-(2-chloro-4-(1H-pyrazol-4-yl)phenyl)-1,3,4-thiadiazol-2-yl)piperazin-2-yl)methanol Hydrochloride Salt;

2-(5-(methyl(2,2,6,6-tetramethylpiperidin-4-yl)amino)-1,3,4-thiadiazol-2-yl)benzo[b]thiophene-5-carbonitrile; and 5-(3-chlorobenzo[b]thiophen-2-yl)-N-methyl-N-(2,2,6,6-tetramethylpiperidin-4-yl)-1,3,4-thiadiazol-2-amine;

7-hydroxy-6-(6-(methyl(2,2,6,6-tetramethylpiperidin-4-yl)amino)pyridazin-3-yl)quinolin-2(1H)-one;

6-(6-((3aR,6aS)-5-methylhexahydropyrrolo[3,4-c]pyrrol-2(1H)-yl)pyridazin-3-yl)quinolin-7-ol;

7-hydroxy-1-methyl-6-(6-(methyl(2,2,6,6-tetramethylpiperidin-4-yl)amino)pyridazin-3-yl)quinolin-2(1H)-one;

6-(6-(methyl(1,2,2,6,6-pentamethylpiperidin-4-yl)amino)pyridazin-3-yl)quinolin-7-ol;

2-methyl-6-(6-(methyl(2,2,6,6-tetramethylpiperidin-4-yl)amino)pyridazin-3-yl)-4-morpholinoquinolin-7-ol;

4-chloro-2-methyl-6-(6-(methyl(2,2,6,6-tetramethylpiperidin-4-yl)amino)pyridazin-3-yl)quinolin-7-ol;

3-bromo-6-(6-(methyl(2,2,6,6-tetramethylpiperidin-4-yl)amino)pyridazin-3-yl)quinolin-7-ol;

3-ethyl-6-(6-(methyl(2,2,6,6-tetramethylpiperidin-4-yl)amino)pyridazin-3-yl)quinolin-7-ol;

3-(1H-imidazol-1-yl)-6-(6-(methyl(2,2,6,6-tetramethylpiperidin-4-yl)amino)pyridazin-3-yl)quinolin-7-ol;

6-(6-(methyl(2,2,6,6-tetramethylpiperidin-4-yl)amino)pyridazin-3-yl)-3-(1-methyl-1H-imidazol-4-yl)quinolin-7-ol;

3-isopropyl-6-(6-(methyl(2,2,6,6-tetramethylpiperidin-4-yl)amino)pyridazin-3-yl)quinolin-7-ol;

6-(6-(methyl(2,2,6,6-tetramethylpiperidin-4-yl)amino)pyridazin-3-yl)quinoline-3,7-diol;

7-hydroxy-6-(6-(methyl(2,2,6,6-tetramethylpiperidin-4-yl)amino)pyridazin-3-yl)quinoline-3-carbonitrile;

6-(6-(methyl(2,2,6,6-tetramethylpiperidin-4-yl)amino)pyridazin-3-yl)quinolin-7-ol;

4-(dimethylamino)-2-methyl-6-(6-(methyl(2,2,6,6-tetramethylpiperidin-4-yl)amino)pyridazin-3-yl)quinolin-7-ol;

3-chloro-6-(6-(methyl(2,2,6,6-tetramethylpiperidin-4-yl)amino)pyridazin-3-yl)quinolin-7-ol;

4-methoxy-2-methyl-6-(6-(methyl(2,2,6,6-tetramethylpiperidin-4-yl)amino)pyridazin-3-yl)quinolin-7-ol;

6-(3-(benzyloxy)isoquinolin-6-yl)-N-methyl-N-(2,2,6,6-tetramethylpiperidin-4-yl)pyridazin-3-amine;

8-(6-(methyl(2,2,6,6-tetramethylpiperidin-4-yl)amino)pyridazin-3-yl)quinolin-7-ol;

7-(6-(methyl(2,2,6,6-tetramethylpiperidin-4-yl)amino)pyridazin-3-yl)isoquinoline-1,6-diol;

7-(6-(methyl(1,2,2,6,6-pentamethylpiperidin-4-yl)amino)pyridazin-3-yl)isoquinolin-6-ol;

1-cyclopropyl-7-(6-(methyl(2,2,6,6-tetramethylpiperidin-4-yl)amino)pyridazin-3-yl)isoquinolin-6-ol;

7-(6-(methyl(2,2,6,6-tetramethylpiperidin-4-yl)amino)pyridazin-3-yl)isoquinolin-6-ol;

6-(1-(benzyloxy)isoquinolin-7-yi)-N-methyl-N-(2,2,6,6-tetramethylpiperidin-4-yl)pyridazin-3-amine;

7-(6-(methyl(2,2,6,6-tetramethylpiperidin-4-yl)amino)pyridazin-3-yl)quinolin-6-ol;

2-methyl-7-(6-(methyl(2,2,6,6-tetramethylpiperidin-4-yl)amino)pyridazin-3-yl)quinolin-6-ol;

2-methyl-6-(6-(methyl(2,2,6,6-tetramethylpiperidin-4-yl)amino)pyridazin-3-yl)-4-(1-methyl-1Hpyrazol-4-yl)quinolin-7-ol;

2-methyl-6-(6-(methyl(2,2,6,6-tetramethylpiperidin-4-yl)amino)pyridazin-3-yl)quinolin-7-ol;

4-ethoxy-2-methyl-6-(6-(methyl(2,2,6,6-tetramethylpiperidin-4-yl)amino)pyridazin-3-yl)quinolin-7-ol;

4-chloro-7-(6-(methyl(2,2,6,6-tetramethylpiperidin-4-yl) amino)pyridazin-3-yl)quinolin-6-ol;
6-(6-(methyl(2,2,6,6-tetramethylpiperidin-4-yl)amino) pyridazin-3-yl)-3-(tetrahydro-2H-pyran-4-yl)quinolin-7-ol;
3-chloro-7-(6-(methyl(2,2,6,6-tetramethylpiperidin-4-yl) amino)pyridazin-3-yl)quinolin-6-ol;
3-bromo-7-(6-(methyl(2,2,6,6-tetramethylpiperidin-4-yl) amino)pyridazin-3-yl)quinolin-6-ol;
3-methyl-7-(6-(methyl(2,2,6,6-tetramethylpiperidin-4-yl) amino)pyridazin-3-yl)quinolin-6-ol;
5-bromo-3-methyl-7-(6-(methyl(2,2,6,6-tetramethylpiperidin-4-yl)amino)pyridazin-3-yl)quinolin-6-ol;
6-hydroxy-1-methyl-7-(6-(methyl(2,2,6,6-tetramethylpiperidin-4-yl)amino)pyridazin-3-yl)quinolin-4(1H)-one;
2,3-dimethyl-7-(6-(methyl(2,2,6,6-tetramethylpiperidin-4-yl)amino)pyridazin-3-yl)quinoxalin-6-ol;
2-methyl-7-(6-(methyl(2,2,6,6-tetramethylpiperidin-4-yl) amino)pyridazin-3-yl)quinoxalin-6-ol;
3-methyl-7-(6-(methyl(2,2,6,6-tetramethylpiperidin-4-yl) amino)pyridazin-3-yl)quinoxalin-6-ol;
4-methoxy-6-(6-(methyl(2,2,6,6-tetramethylpiperidin-4-yl) amino)pyridazin-3-yl)quinolin-7-ol;
4-(azetidin-1-yl)-2-methyl-6-(6-(methyl(2,2,6,6-tetramethylpiperidin-4-yl)amino)pyridazin-3-yl)quinolin-7-ol;
7-hydroxy-2-methyl-6-(6-(methyl(2,2,6,6-tetramethylpiperidin-4-yl)amino)pyridazin-3-yl)quinoline-4-carbonitrile;
4-cyclopropyl-2-methyl-6-(6-(methyl(2,2,6,6-tetramethylpiperidin-4-yl)amino)pyridazin-3-yl)quinolin-7-ol;
4-(3,6-dihydro-2H-pyran-4-yl)-2-methyl-6-(6-(methyl(2,2,6,6-tetramethylpiperidin-4-yl)amino)pyridazin-3-yl)quinolin-7-ol;
2-methyl-6-(6-(methyl(2,2,6,6-tetramethylpiperidin-4-yl) amino)pyridazin-3-yl)-4-(tetrahydro-2Hpyran-4-yl)quinolin-7-ol;
2-methyl-6-(6-(methyl(2,2,6,6-tetramethylpiperidin-4-yl) amino)pyridazin-3-yl)-4-(oxetan-3-yl)quinolin-7-ol;
4-(dimethylamino)-6-(6-(methyl(2,2,6,6-tetramethylpiperidin-4-yl)amino)pyridazin-3-yl)quinolin-7-ol;
7-hydroxy-6-(6-(methyl(2,2,6,6-tetramethylpiperidin-4-yl) amino)pyridazin-3-yl)quinazolin-4(1H)-one;
6-(6-(methyl(2,2,6,6-tetramethylpiperidin-4-yl)amino) pyridazin-3-yl)quinazolin-7-ol;
7-hydroxy-1-methyl-6-(6-(methyl(2,2,6,6-tetramethylpiperidin-4-yl)amino)pyridazin-3-yl)-3,4-dihydroquinolin-2 (1H)-one;
7-hydroxy-1-methyl-6-(6-(methyl(2,2,6,6-tetramethylpiperidin-4-yl)amino)pyridazin-3-yl)-3,4-dihydroquinolin-2 (1H)-one;
7-hydroxy-6-(6-(methyl(2,2,6,6-tetramethylpiperidin-4-yl) amino)pyridazin-3-yl)isoquinoline-1-carbonitrile;
7-hydroxy-6-(6-(methyl(2,2,6,6-tetramethylpiperidin-4-yl) amino)pyridazin-3-yl)quinoline-2-carbonitrile;
6-hydroxy-7-(6-(methyl(2,2,6,6-tetramethylpiperidin-4-yl) amino)pyridazin-3-yl)quinoline-2-carbonitrile;
6-hydroxy-7-(6-(methyl(2,2,6,6-tetramethylpiperidin-4-yl) amino)pyridazin-3-yl)isoquinoline-1-carboxamide;
7-hydroxy-6-(6-(methyl(2,2,6,6-tetramethylpiperidin-4-yl) amino)pyridazin-3-yl)quinoline-2-carboxamide;
6-hydroxy-7-(6-(methyl(2,2,6,6-tetramethylpiperidin-4-yl) amino)pyridazin-3-yl)quinoline-2-carboxamide;
methyl 6-hydroxy-7-(6-(methyl(2,2,6,6-tetramethylpiperidin-4-yl)amino)pyridazin-3-yl)quinoline-2-carboxylate;
6-hydroxy-7-(6-(piperazin-1-yl)pyridazin-3-yl)quinoline-2-carbonitrile;
7-hydroxy-6-(6-(piperazin-1-yl)pyridazin-3-yl)quinoline-2-carbonitrile;
7-(6-(piperazin-1-yl)pyridazin-3-yl)isoquinolin-6-ol;
7-(6-(1,2,3,6-tetrahydropyridin-4-yl)pyridazin-3-yl)quinolin-6-ol;
1-methyl-6-(6-(methyl(2,2,6,6-tetramethylpiperidin-4-yl) amino)pyridazin-3-yl)isoquinolin-7-ol;
1-methyl-7-(6-(methyl(2,2,6,6-tetramethylpiperidin-4-yl) amino)pyridazin-3-yl)isoquinolin-6-ol;
1,3-dimethyl-7-(6-(methyl(2,2,6,6-tetramethylpiperidin-4-yl)amino)pyridazin-3-yl)isoquinolin-6-ol;
7-hydroxy-3-methyl-6-(6-(methyl(2,2,6,6-tetramethylpiperidin-4-yl)amino)pyridazin-3-yl)isoquinoline-1-carbonitrile;
1-amino-7-(6-(methyl(2,2,6,6-tetramethylpiperidin-4-yl) amino)pyridazin-3-yl)isoquinolin-6-ol;
7-hydroxy-1,3-dimethyl-6-(6-(methyl(2,2,6,6-tetramethylpiperidin-4-yl)amino)pyridazin-3-yl)quinazoline-2,4 (1H,3H)-di one;
6-hydroxy-5-(6-(methyl(2,2,6,6-tetramethylpiperidin-4-yl) amino)pyridazin-3-yl)benzo[d]oxazoi-2(3H)-one;
2-methyl-5-(6-(methyl(2,2,6,6-tetramethylpiperidin-4-yl) amino)pyridazin-3-yl)-2H-indazol-6-ol;
1-methyl-5-(6-(methyl(2,2,6,6-tetramethylpiperidin-4-yl) amino)pyridazin-3-yl)-1H-indazol-6-ol;
6-hydroxy-2-methyl-7-(6-(methyl(2,2,6,6-tetramethylpiperidin-4-yl)amino)pyridazin-3-yl)isoquinolin-1(2H)-one;
2-ethyl-6-hydroxy-7-(6-((2,2,6,6-tetramethylpiperidin-4-yl) oxy)pyridazin-3-yl)isoquinolin-1(2H)-one;
1-ethoxy-7-(6-(methyl(2,2,6,6-tetramethylpiperidin-4-yl) amino)pyridazin-3-yl)isoquinolin-6-ol;
7-(6-((2,2,6,6-tetramethylpiperidin-4-yl)oxy)pyridazin-3-yl)isoquinoline-1,6-diol;
7-(6-(methyl(2,2,6,6-tetramethyl-piperidin-4-yl)amino)-pyridazin-3-yl)-3-phenylisoquinolin-6-ol;
3-methyl-7-(6-(methyl(2,2,6,6-tetramethylpiperidin-4-yl) amino)pyridazin-3-yl)isoquinolin-6-ol;
3-cyclopropyl-7-(6-(methyl(2,2,6,6-tetramethyl-piperidin-4-yl)amino)pyridazin-3-yl)isoquinolin-6-ol;
3-isopropyl-7-(6-(methyl(2,2,6,6-tetramethyl-piperidin-4-yl)amino)pyridazin-3-yl)isoquinolin-6-ol;
3-propyl-7-(6-((2,2,6,6-tetramethylpiperidin-4-yl)oxy)-pyridazin-3-yl)isoquinolin-6-ol;
3-isopropyl-7-(6-((2,2,6,6-tetramethylpiperidin-4-yl)oxy)-pyridazin-3-yl)isoquinolin-6-ol; and
3-methyl-7-(6-(piperazin-1-yl)pyridazin-3-yl)isoquinolin-6-ol;
or a pharmaceutically acceptable salt thereof;
for use in the treatment, prevention and/or delay of progression of cancer.

In a particular embodiment, the present invention relates to a FoxM1 gene splicing modifier as described herein selected from the group consisting of:
6-(naphthalen-2-yl)-N-(2,2,6,6-tetramethylpiperidin-4-yl) pyridazin-3-amine;
6-(benzo[b]thio-phen-2-yl)-N-methyl-N-(2,2,6,6-tetramethylpiperidin-4-yl)pyridazin-3-amine;
2-(6-(2,2,6,6-tetramethylpiperidin-4-ylamino)-pyridazin-3-yl)phenol;
2-(6-(methyl-(2,2,6,6-tetra-methylpiperidin-4-yl)amino) pyridazin-3-yl)benzo[b]-thiophene-5-carbonitrile;
6-(quinolin-3-yl)-N-(2,2,6,6-tetramethyl-piperidin-4-yl) pyridazin-3-amine;
3-(benzo[b]-thiophen-2-yl)-6-(2,2,6,6-tetra-methylpiperidin-4-yloxy)pyridazine;
2-(6-(methyl-(2,2,6,6-tetra-methylpiperidin-4-yl)amino)-pyridazin-3-yl)phenol;

6-(6-(methyl-(2,2,6,6-tetra-methylpiperidin-4-yl)amino)-pyridazin-3-yl)naphthalen-2-ol;

6-(benzo[b]-thiophen-2-yl)-N-(2,2,6,6-tetra-methylpiperidin-4-yl)pyridazin-3-amine;

7-(6-((2,2,6,6-tetramethylpiperidin-4-yl)oxy)pyridazin-3-yl)isoquinoline;

6-(6-((2,2,6,6-tetramethylpiperidin-4-yl)oxy)pyridazin-3-yl)isoquinoline;

N-methyl-6-(quinolin-7-yl)-N-(2,2,6,6-tetramethyl-piperidin-4-yl)pyridazin-3-amine;

N-methyl-6-(quinolin-6-yl)-N-(2,2,6,6-tetramethylpiperidin-4-yl)pyridazin-3-amine;

6-(isoquinolin-7-yl)-N-methyl-N-(2,2,6,6-tetramethylpiperidin-4-yl)pyridazin-3-amine;

6-(isoquinolin-6-yl)-N-methyl-N-(2,2,6,6-tetramethylpiperidin-4-yl)pyridazin-3-amine;

6-(imidazo[1,2-a]pyridin-6-yl-pyridazin-3-yl)-methyl-(2,2,6,6-tetramethyl-piperidin-4-yl)-amine methyl-[6-(6-phenyl-pyridin-3-yl)-pyridazin-3-yl]-(2,2,6,6-tetramethyl-piperidin-4-yl)-amine;

methyl-[6-(6-pyrrol-1-yl-pyridin-3-yl)-pyridazin-3-yl]-(2,2,6,6-tetramethyl-piperidin-4-yl)-amine;

methyl-(6-quinoxalin-2-yl-pyridazin-3-yl)-(2,2,6,6-tetramethyl-piperidin-4-yl)-amine;

methyl-(6-quinolin-3-yl-pyridazin-3-yl)-(2,2,6,6-tetramethyl-piperidin-4-yl)-amine;

N-methyl-6-(phthalazin-6-yl)-N-(2,2,6,6-tetramethylpiperidin-4-yl)pyridazin-3-amine;

6-(benzo[c][1,2,5]oxa-diazol-5-yl)-N-(2,2,6,6-tetramethyl-piperidin-4-yl)pyridazin-3-amine;

6-(benzo[d]thiazol-5-yl)-N-(2,2,6,6-tetramethyl-piperidin-4-yl)pyridazin-3-amine;

6-(2-methylbenzo-[d]oxazol-6-yl)-N-(2,2,6,6-tetramethyl-piperidin-4-yl)pyridazin-3-amine;

3-(6-(methyl(2,2,6,6-tetramethylpiperidin-4-yl)amino)pyridazin-3-yl)naphthalen-2-ol;

5-chloro-2-(6-(methyl(1,2,2,6,6-pentamethylpiperidin-4-yl)amino)pyridazin-3-yl)phenol;

3-(6-(2,2,6,6-tetramethylpiperidin-4-ylamino)pyridazin-3-yl)naphthalen-2-ol;

5-chloro-2-(6-(1,2,2,6,6-pentamethylpiperidin-4-ylamino)pyridazin-3-yl)phenol;

4-hydroxy-3-(6-(methyl(2,2,6,6-tetramethylpiperidin-4-yl)amino)pyridazin-3-yl)benzonitrile;

3-[6-(2,2,6,6-tetramethyl-piperidin-4-yloxy)-pyridazin-3-yl]-naphthalen-2-ol;

2-{6-[methyl-(2,2,6,6-tetramethyl-piperidin-4-yl)-amino]-pyridazin-3-yl}-4-trifluoromethylphenol;

2-fluoro-6-{6-[methyl-(2,2,6,6-tetramethyl-piperidin-4-yl)-amino]-pyridazin-3-yl}-phenol;

3,5-dimethoxy-2-{6-[methyl-(2,2,6,6-tetramethyl-piperidin-4-yl)-amino]-pyridazin-3-yl}-phenol;

4,5-dimethoxy-2-{6-[methyl-(2,2,6,6-tetramethyl-piperidin-4-yl)-amino]-pyridazin-3-yl}-phenol;

5-methoxy-2-{6-[methyl-(2,2,6,6-tetramethyl-piperidin-4-yl)-amino]-pyridazin-3-yl}-phenol;

4,5-difluoro-2-{6-[methyl-(2,2,6,6-tetramethyl-piperidin-4-yl)-amino]-pyridazin-3-yl}-phenol;

5-fluoro-2-{6-[methyl-(2,2,6,6-tetramethyl-piperidin-4-yl)-amino]-pyridazin-3-yl}-phenol;

3-hydroxy-4-(6-(methyl(2,2,6,6-tetramethylpiperidin-4-yl)amino)pyridazin-3-yl)benzonitrile;

1-allyl-6-(6-(methyl(2,2,6,6-tetramethylpiperidin-4-yl)amino)pyridazin-3-yl)naphthalen-2-ol;

6-(benzo[b]thiophen-2-yl)-N-(1,2,2,6,6-pentamethylpiperidin-4-yl)pyridazin-3-amine;

N-allyl-3-hydroxy-4-(6-(methyl(2,2,6,6-tetramethylpiperidin-4-yl)amino)pyridazin-3-yl)benzamide;

2-(6-(methyl(2,2,6,6-tetramethylpiperidin-4-yl)amino)pyridazin-3-yl)-5-(1H-pyrazol-1-yl)phenol;

5-(5-methyl-oxazol-2-yl)-2-{6-[methyl-(2,2,6,6-tetramethyl-piperidin-4-yl)-amino]-pyridazin-3-yl}-phenol;

5-(4-hydroxymethyl)-1H-pyrazole-1-yl)-2-(6-(methyl(2,2,6,6-tetramethylpiperidin-4 yl)amino)pyridazin-3-yl)phenol;

5-(1H-imidazole-1-yl)-2-(6-(methyl(2,2,6,6-tetramethyl-piperidin-4-yl)amino)pyridazin-3-yl)phenol;

5-(4-amino-1H-pyrazole-1-yl)-2-(6-(methyl(2,2,6,6-tetramethylpiperidin-4-yl)amino)pyridazin-3-yl)phenol;

5-(4-amino-1H-pyrazol-1-yl)-2-(6-(methyl(2,2,6,6-tetramethylpiperidin-4-yl)amino)pyridazin-3-yl)phenol;

5-(3-amino-pyrazol-1-yl)-2-{6-[methyl-(2,2,6,6-tetramethyl-piperidin-4-yl)-amino]-pyridazin-3-yl}-phenol;

2-(6-(methyl-(2,2,6,6-tetramethylpiperidin-4-yl)amino)pyridazin-3-yl)-5-(1-(2-morpholinoethyl)-1H-pyrazol-4-yl)phenol;

2-(6-(methyl-(2,2,6,6-tetramethylpiperidin-4-yl)amino)pyridazin-3-yl)-5-(1-methyl-1H-pyrazol-4-yl)phenol;

5-(5-amino-1H-pyrazol-1-yl)-2-(6-(methyl-(2,2,6,6-tetramethyl-piperidin-4-yl)amino)pyridazin-3-yl)phenol;

2-(6-(methyl-(2,2,6,6-tetramethylpiperidin-4-yl)amino)pyridazin-3-yl)-4-(1H-pyrazol-1-yl)phenol;

2-{6-[(2-hydroxy-ethyl)-(2,2,6,6-tetramethyl-piperidn-4-yl)-amino]-pyridazin-3-yl}-5-pyrazol-1-yl-phenol;

2-(6-(piperidin-4-yloxy)pyridazin-3-yl)-5-(1H-pyrazol-1-yl)phenol;

2-(6-(((2S,4R,6R)-2,6-dimethylpiperidin-4-yl)oxy)pyridazin-3-yl)-5-(1H-pyrazol-1-yl)phenol;

2-(6-((2,6-di-methylpiperidin-4-yl)oxy)pyridazin-3-yl)-5-(1H-pyrazol-1-yl)phenol;

2-(6-((2,6-di-methylpiperidin-4-yl)oxy)pyridazin-3-yl)-5-(1H-pyrazol-1-yl)phenol;

5-(1H-pyrazol-1-yl)-2-(6-(pyrrolidin-3-yloxy)pyridazin-3-yl)phenol;

2-(6-((-2-methylpiperidin-4-yl)oxy)pyridazin-3-yl)-5-(1H-pyrazol-1-yl)phenol;

(S)-5-(1H-pyrazol-1-yl)-2-(6-(pyrrolidin-3-ylmethoxy)pyridazin-3-yl)phenol;

(R)-5-(1H-pyrazol-1-yl)-2-(6-pyrrolidin-3-yl methoxy)pyridazin-3-yl)phenol;

2-(64(3-fluoropiperidin-4-yl)oxy)pyridazin-3-yl)-5-(1H-pyrazol-1-yl)-phenol;

2-[6-(1,2,2,6,6-pentamethyl-piperidin-4-yloxy)-pyridazin-3-yl]-5-pyrazol-1-yl-phenol;

5-pyrazol-1-yl-2-[6-((2,2,6,6-tetramethylpiperidin-4-yloxy)-pyridazin-3-yl]-phenol;

5-(1H-pyrazol-4-yl)-2-(6-((2,2,6,6-tetramethylpiperidin-4-yl)oxy)pyridazin-3-yl)phenol;

2-(6-piperazin-1-yl-pyridazin-3-yl)-5-pyrazol-1-yl-phenol;

3-[6-(azetidin-3-yl-amino)-pyridazin-3-yl]-naphthalen-2-ol;

2-[6-(azetidin-3-ylamino)-pyridazin-3-yl]-5-pyrazol-1-yl-phenol;

2-[6-(3,5-di methyl-piperazin-1-yl)-pyridazin-3-yl]-5-pyrazol-1-yl-phenol;

2-[6-(7-methyl-2,7-diaza-spiro[4.4]non-2-yl)-pyridazin-3-yl]-5-pyrazol-1-yl-phenol;

2-(6-[1,4]diazepan-1-yl-pyridazin-3-yl)-5-pyrazol-1-yl-phenol;

2-{6-[4-(2-hydroxy-ethyl)-piperazin-1-yl]-pyridazin-3-yl}-5-pyrazol-1-yl-phenol;

2-[6-(3,6-diaza-bicyclo[3.2.1]oct-3-yl)-pyridazin-3-yl]-5-pyrazol-1-yl-phenol;

2-[6-(2,7-diaza-spiro[3.5]non-7-yl)-pyridazin-3-yl]-5-pyrazol-1-yl-phenol;
2-[6-(3-hydroxy-methyl-piperazin-1-yl)-pyridazin-3-yl]-5-pyrazol-1-yl-phenol;
2-[6-(1,7-diaza-spiro[4.4]non-7-yl)-pyridazin-3-yl]-5-pyrazol-1-yl-phenol;
2-[6-(4-amino-4-methyl-piperidin-1-yl)-pyridazin-3-yl]-5-pyrazol-1-yl-phenol;
2-[6-(3-dimethyl-amino-piperidin-1-yl)-pyridazin-3-yl]-5-pyrazol-1-yl-phenol;
2-[6-(1,2,2,6,6-pentamethyl-piperidin-4-ylamino)-pyridazin-3-yl]-5-pyrazol-1-yl-phenol;
2-[6-(3,3-di methyl-piperazin-1-yl)-pyridazin-3-yl]-5-pyrazol-1-yl-phenol;
2-(6-(7-(2-hydroxyethyl)-2,7-diazaspiro[4.4]-nonan-2-yl)pyridazin-3-yl)-5-(1H-pyrazol-1-yl)phenol;
2-(6-((3aR,6aS)-hexahydropyrrolo[3,4-c]pyrrol-2(1H)-yl)pyridazin-3-yl)-5-(1H-pyrazol-1-yl)phenol;
3-(6-(piperazin-1-yl)pyridazin-3-yl)naphthalene-2,7-diol;
5-pyrazol-1-yl-2-[6-(1,2,3,6-tetrahydro-pyridin-4-yl)-pyridazin-3-yl]-phenol;
2-(6-piperidin-4-yl-pyridazin-3-yl)-5-pyrazol-1-yl-phenol;
3-(6-(1,2,3,6-tetra-hydropyridin-4-yl)pyridazin-3-yl)naphthalen-2-ol;
3-(6-(1,2,3,6-tetrahydropyridin-4-yl)pyridazin-3-yl)naphthalene-2,7-diol;
3-(6-(2,2,6,6-tetramethyl-1,2,3,6-tetrahydropyridin-4-yl)pyridazin-3-yl)naphthalene-2,7-diol;
3-(6-(1-methyl-1,2,3,6-tetrahydropyridin-4-yl)pyridazin-3-yl)naphthalene-2,7-diol;
3-(6-(piperidin-4-yl)pyridazin-3-yl)naphthalene-2,7-diol;
3-(6-((2,2,6,6-tetramethylpiperidin-4-yl)oxy)pyridazin-3-yl)naphthalene-2,7-diol;
3-(6-(methyl-(2,2,6,6-tetramethylpiperidin-4-yl)amino)pyridazin-3-yl)naphthalene-2,7-diol;
3-(6-((2,2,6,6-tetramethylpiperidin-4-yl)amino)pyridazin-3-yl)naphthalene-2,7-diol;
[3-(7-hydroxy-6-{6-[methyl-(2,2,6,6-tetramethyl-piperidin-4-yl)-amino]-pyridazin-3-yl}-naphthalen-2-yloxy)-propyl]-carbamic acid tert-butyl ester;
7-(3-amino-propoxy)-3-{6-[methyl-(2,2,6,6-tetramethyl-piperidin-4-yl)-amino]-pyridazin-3-yl}naphthalen-2-ol;
N-[3-(7-hydroxy-6-{6-[methyl-(2,2,6,6-tetramethyl-piperidin-4-yl)-amino]-pyridazin-3-yl}naphthalen-2-yloxy)-propyl]-acetamide;
7-(3-hydroxypropoxy)-3-(6-(methyl(2,2,6,6-tetramethylpiperidin-4-yl)amino)pyridazin-3-yl)naphthalen-2-ol;
7-(3-methoxypropoxy)-3-(6-(methyl(2,2,6,6-tetramethylpiperidin-4-yl)amino)pyridazin-3-yl)naphthalen-2-ol;
7-(2-morpholinoethoxy)-3-(6-((2,2,6,6-tetramethylpiperidin-4-yl)oxy)pyridazin-3-yl)naphthalen-2-ol;
3-(6-(piperidin-4-ylmethyl)pyridazin-3-yl)naphthalen-2-ol;
5-(1H-pyrazol-1-yl)-2-(6-(2,2,6,6-tetramethylpiperidin-4-yl)methyl)pyridazin-3-yl)phenol;
3-methoxy-2-(6-(methyl(2,2,6-trimethylpiperidin-4-yl)amino)pyridazin-3-yl)-5-(5-methyloxazol-2-yl)phenol;
2-(6-(((6S)-6-((S)-1-hydroxyethyl)-2,2-dimethylpiperidin-4-yloxy)pyridazin-3-yl)-5-(1H pyrazol-1-yl)phenol;
7-hydroxy-6-(6-(methyl(2,2,6,6-tetramethylpiperidin-4-yl)amino)pyridazin-3-yl)-2-naphthonitrile;
3-(6-(methyl(2,2,6,6-tetramethylpiperidin-4-yl)amino)pyridazin-3-yl)-7-(piperidin-1-ylmethyl)naphthalen-2-ol;
3-(6-(methyl(2,2,6,6-tetramethylpiperidin-4-yl)amino)pyridazin-3-yl)-7-(pyrrolidin-1-ylmethyl)naphthalen-2-ol;
1-bromo-6-(6-(methyl(2,2,6,6-tetramethylpiperidin-4-yl)amino)pyridazin-3-yl)naphthalene-2,7-diol;
1-chloro-6-(6-(methyl(2,2,6,6-tetramethylpiperidin-4-yl)amino)pyridazin-3-yl)naphthalene-2,7-diol;
7-methoxy-3-(6-(methyl(2,2,6,6-tetramethylpiperidin-4-yl)amino)pyridazin-3-yl)naphthalen-2-ol;
7-methoxy-3-(6-(methyl(1,2,2,6,6-pentamethylpiperidin-4-yl)amino)pyridazin-3-yl)naphthalen-2-ol;
7-(3,6-dihydro-2H-pyran-4-yl)-3-(6-(methyl(2,2,6,6-tetramethylpiperidin-4-yl)amino)pyridazin-3-yl)naphthalen-2-ol;
3-(6-(methyl-(2,2,6,6-tetramethylpiperidin-4-yl)amino)pyridazin-3-yl)-7-(tetrahydro-2H-pyran-4-yl)naphthalen-2-ol;
7-(difluoromethyl)-3-(6-(methyl-(2,2,6,6-tetramethylpiperidin-4-yl)amino)pyridazin-3-yl)naphthalen-2-ol;
7-((4-hydroxy-2-methyl butan-2-yl)oxy)-3-(6-(methyl(2,2,6,6-tetramethylpiperidin-4-yl)amino)pyridazin-3-yl)naphthalen-2-ol;
7-(3-hydroxy-3-methylbutoxy)-3-(6-(methyl-(2,2,6,6-tetramethylpiperidin-4-yl)amino)pyridazin-3-yl)naphthalen-2-ol;
2-(6-(methyl(2,2,6,6-tetramethylpiperidin-4-yl)amino)pyridazin-3-yl)-5-(1H-pyrazol-4-yl)benzene-1,3-diol;
3-methoxy-2-(6-(methyl-(2,2,6,6-tetramethylpiperidin-4-yl)amino)pyridazin-3-yl)-5-(1H pyrazol-4-yl)phenol;
5-(1H-pyrazol-4-yl)-2-(6-(((2,2,6,6-tetramethylpiperidin-4-yl)amino)pyridazin-3-yl)-3-(trifluoromethoxy)phenol;
2-(6-(methyl(2,2,6,6-tetramethylpiperidin-4-yl)amino)pyridazin-3-yl)-5-(1-methyl-1H-pyrazol-4-yl)-3-(trifluoromethoxy)phenol;
2-(6-(methyl(2,2,6,6-tetramethylpiperidin-4-yl)amino)pyridazin-3-yl)-5-(1H-pyrazol-4-yl)-3-(trifluoromethoxy)phenol;
4-(3-hydroxy-4-(6-(methyl-(2,2,6,6-tetramethylpiperidin-4-yl)amino)pyridazin-3-yl)-5-(trifluoromethoxy)phenyl)-1-methylpyridin-2(1H)-one;
3-methoxy-2-(6-(methyl-(2,2,6,6-tetramethylpiperidin-4-yl)amino)pyridazin-3-yl)-5-(1-methyl-1H-pyrazol-4-yl)phenol;
3-methoxy-2-(6-(methyl-(2,2,6,6-tetramethylpiperidin-4-yl)amino)pyridazin-3-yl)-5-(5,6,7,8-tetrahydroimidazo[1,2-a]pyridin-3-yl)phenol;
3-methoxy-2-(6-(methyl-(2,2,6,6-tetramethylpiperidin-4-yl)amino)pyridazn-3-yl)-5-(pyridin-3-yl)phenol;
5-(1-cyclopentyl-1H-pyrazol-4-yl)-3-meth oxy-2-(6-(methyl(2,2,6,6-tetramethylpiperidin-4-yl)amino)pyridazin-3-yl)phenol;
3'5-dimethoxy-4-(6-(methyl-(2,2,6,6-tetramethylpiperidin-4-yl)amino)pyridazin-3-yl)-[1,1'-biphenyl]-3-ol;
3-(benzyloxy)-2-(6-(methyl-(2,2,6,6-tetramethylpiperidin-4-yl)amino)pyridazin-3-yl)-5-(5-methyloxazol-2-yl)phenol;
3-ethoxy-2-(6-(methyl-(2,2,6,6-tetramethylpiperidin-4-yl)amino)pyridazin-3-yl)-5-(5-methyloxazol-2-yl)phenol;
5 3-(cyclopropylmethoxy)-2-(6-(methyl-(2,2,6,6-tetramethylpiperidin-4-yl)amino)-pyridazin-3-yl)-5-(5-methyloxazol-2-yl)phenol;
2-methyl-5-(6-(methyl-(2,2,6,6-tetramethylpiperidin-4-yl)amino)pyridazin-3-yl)-1H benzo[d]imidazol-6-ol;
5-chloro-2-(6-(methyl-(2,2,6,6-tetramethylpiperidin-4-yl)amino)pyridazin-3-yl)phenol;
5-(1H-pyrazol-1-yl)-2-(6-((2,2,6,6-tetramethylpiperidin-4-yl)amino)pyridazin-3-yl)phenol;
3-hydroxy-4-(6-((2,2,6,6-tetramethylpiperidin-4-yl)amino)pyridazin-3-yl)benzonitrile;
2-(6-((2,2-dimethylpiperidin-4-yl)oxy)pyridazin-3-yl)-5-(1H-pyrazol-1-yl)phenol;

2-(6-(methyl-(2,2,6,6-tetramethylpiperidin-4-yl)amino) pyridazin-3-yl)-4-(1H-pyrazol-4-yl)phenol;

2-(6-(methyl-(2,2,6,6-tetramethylpiperidin-4-yl)amino) pyridazin-3-yl)-4-(4,5,6,7-tetrahydropyrazolo[1,5-a]pyridin-3-yl)phenol;

2-(6-(methyl-(2,2,6,6-tetramethylpiperidin-4-yl)amino) pyridazin-3-yl)-4-(4,5,6,7-tetrahydropyrazolo[1,5-a] pyrazin-3-yl)phenol;

4-(1H-indol-2-yl)-2-(6-(methyl-(2,2,6,6-tetramethylpiperidin-4-yl)amino)pyridazin-3-yl)phenol;

4-cyclopent-1-en-1-yl)-2-(6-(methyl(2,2,6,6-tetramethylpiperidin-4-yl)amino)pyridazin-3-yl)phenol;

2-(6-(methyl-(2,2,6,6-tetramethylpiperidin-4-yl)amino) pyridazin-3-yl)-4-(1H-pyrazol-3-yl)phenol;

4-(4-hydroxy-3-(6-(methyl-(2,2,6,6-tetramethylpiperidin-4-yl)amino)pyridazin-3 yl)phenyl)pyridin-2-ol;

4-(4-hydroxy-3-(6-((2,2,6,6-tetramethylpiperidin-4-yl)oxy) pyridazin-3-yl)phenyl)-1-methylpyridin-2-(1H)-one;

4-(4-hydroxy-3-(6-((2,2,6,6-tetramethylpiperidin-4-yl)oxy) pyridazin-3-yl)phenyl)pyridin-2-ol;

5-(1H-indazol-7-yl)-2-(6-(methyl-(2,2,6,6-tetramethylpiperidin-4-yl)amino)pyridazin-3-yl)phenol;

4-chloro-2-(6-(methyl-(2,2,6,6-tetramethylpiperidin-4-yl) amino)pyridazin-3-yl)-5-(1H-pyrazol-4-yl)phenol;

4-fluoro-2-(6-(methyl-(2,2,6,6-tetramethylpiperidin-4-yl) amino)pyridazin-3-yl)-5-(1H-pyrazol-4-yl)phenol;

5-fluoro-4-(1H-imidazol-4-yl)-2-(6-(methyl-(2,2,6,6-tetramethylpiperidin-4-yl)amino)pyridazin-3-yl)phenol;

5-fluoro-2-(6-(methyl-(2,2,6,6-tetramethylpiperidin-4-yl) amino)pyridazin-3-yl)-4-(1H-pyrazol-4-yl)phenol;

5-fluoro-2-(6-(methyl-(2,2,6,6-tetramethylpiperidin-4-yl) amino)pyridazin-3-yl)-4-(1H-pyrazol-5-yl)phenol;

5,6-hydroxy-5-(6-(methyl-(2,2,6,6-tetramethylpiperidin-4-yl)amino)pyridazin-3-yl)-2,3-dihydro-1H-inden-1-one;

6-(6-(methyl-(2,2,6,6-tetramethylpiperidin-4-yl)amino) pyridazin-3-yl)-1,4-dihydroindeno[1,2-c]pyrazol-7-ol;

6-hydroxy-5-(6-(methyl-(2,2,6,6-tetramethylpiperidin-4-yl) amino)pyridazin-3-yl)-2,3-dihydro-1H-inden-1-one oxime hydrochloride salt;

5-(6-(methyl-(2,2,6,6-tetramethylpiperidin-4-yl)amino) pyridazin-3-yl)-2,3-dihydro-1H-indene-1,6-diol;

2-amino-6-(6-(methyl-(2,2,6,6-tetramethylpiperidin-4-yl) amino)pyridazin-3-yl)-8H-indeno[1,2-d]thiazol-5-ol hydrochloride salt;

15 9-(6-(methyl-(2,2,6,6-tetramethylpiperidin-4-yl)amino) pyridazin-3-yl)-5,6-dihydroimidazo[5,1-a]isoquinolin-8-ol hydrochloride salt;

4-hydroxy-3-(6-(methyl-(2,2,6,6-tetramethylpiperidin-4-yl) amino)pyridazin-3-yl)-N-((1-methyl-1H-pyrazol-4-yl) methyl)benzamide;

4-(4-(hydroxymethyl)-1H-pyrazol-1-yl)-2-(6-(methyl(2,2,6, 6-tetramethylpiperidin-4-yl)amino)pyridazin-3-yl)phenol;

5-(1H-pyrazol-4-yl)-2-(6-(2,2,6,6-tetramethylpiperidin-4-yl)methyl)pyridazin-3-yl)phenol;

6-(3-(benzyloxy)isoquinolin-6-yl)-N-methyl-N-(2,2,6,6-tetramethylpiperidin-4-yl)pyridazin-3-amine;

6-(1-(benzyloxy)isoquinolin-7-yl)-N-methyl-N-(2,2,6,6-tetramethylpiperidin-4-yl)pyridazin-3-amine;

3-fluoro-5-(2-methoxypyridin-4-yl)-2-(6-(methyl-(2,2,6,6-tetramethylpiperidin-4-yl)amino)pyridazin-3-yl)phenol hydrochloride salt;

4-(3-fluoro-5-hydroxy-4-(6-(methyl-(2,2,6,6-tetramethylpiperidin-4-yl)amino)pyridazin-3-yl)phenyl)pyridin-2(1H)-one hydrochloride salt;

30 4-(3-fluoro-5-hydroxy-4-(6-(methyl-(2,2,6,6-tetramethylpiperidin-4-yl)amino)pyridazin-3-yl)phenyl)-1-methylpyridin-2(1H)-one hydrochloride salt;

5-(3-fluoro-5-hydroxy-4-(6-(methyl-(2,2,6,6-tetramethylpiperidin-4-yl)amino)pyridazin-3-yl)phenyl)-1-methylpyridin-2(1H)-one hydrochloride salt;

3-fluoro-5-(1H-pyrazol-4-yl)-2-(6-(2,2,6,6-tetramethylpiperidin-4-yl)oxy)pyridazin-3-yl)phenol hydrochloride salt;

5-chloro-3-fluoro-2-(6-(methyl-(2,2,6,6-tetramethylpiperidin-4-yl)amino)pyridazin-3-yl)phenol hydrochloride salt;

3-fluoro-2-(6-(methyl-(2,2,6,6-tetramethylpiperidin-4-yl) amino)pyridazin-3-yl)-5-(1H-pyrazol-4-yl)phenol hydrochloride salt;

3-fluoro-2-(6-(methyl-(2,2,6,6-tetramethylpiperidin-4-yl) amino)pyridazin-3-yl)-5-(1-methyl-1H pyrazol-4-yl)phenol hydrochloride salt;

5-(5-methoxypyridin-3-yl)-2-(6-(methyl-(2,2,6,6-tetramethylpiperidin-4-yl)amino)pyridazin-3-yl)phenol;

5-(3-hydroxy-4-(6-methyl-(2,2,6,6-tetramethylpiperidin-4-yl)amino)pyridazin-3-yl)phenyl)pyridin-2-ol;

4-(3-hydroxy-4-(6-methyl-(2,2,6,6-tetramethylpiperidin-4-yl)amino)pyridazin-3-yl)phenyl)pyridin-2-ol;

5-(6-methoxypyridin-3-yl)-2-(6-(methyl-(2,2,6,6-tetramethylpiperidin-4-yl)amino)pyridazin-3-yl)phenol;

5-(3-hydroxy-4-(6-(methyl-(2,2,6,6-tetramethylpiperidin-4-yl)amino)pyridazin-3-yl)phenyl)-3-(trifluoromethyl)pyridin-2-ol;

5-(3-hydroxy-4-(6-(methyl-(2,2,6,6-tetramethylpiperidin-4-yl)amino)pyridazin-3-yl)phenyl)-1-methylpyridin-2(1H)-one;

4-(3-hydroxy-4-(6-(methyl-(2,2,6,6-tetramethylpiperidin-4-yl)amino)pyridazin-3-yl)phenyl)-1-methylpyridin-2(1H)-one;

5-(2-methoxypyridin-4-yl)-2-(6-(methyl-(2,2,6,6-tetramethylpiperidin-4-yl)amino)pyridazin-3-yl)phenol;

4-(3-hydroxy-4-(6-((2,2,6,6-tetramethylpiperidin-4-yl)oxy) pyridazin-3-yl)phenyl)pyridin-2-ol;

5-(6-(dimethylamino)pyridin-3-yl)-2-(6-(methyl(2,2,6,6-tetramethylpiperidin-4-yl)amino)pyridazin-3-yl)phenol;

4-(3-hydroxy-4-(6-((2,2,6,6-tetramethylpiperidin-4-yl)oxy) pyridazin-3-yl)phenyl)-1-methylpyridin-2(1H)-one;

2-(6-(methyl-(2,2,6,6-tetramethylpiperidin-4-yl)amino) pyridazin-3-yl)-5-(pyrimidin-5-yl)phenol;

5-(3-hydroxy-4-(6-(methyl-(2,2,6,6-tetramethylpiperidin-4-yl)amino)pyridazin-3-yl)phenyl)pyridin-3-ol;

1-cyclopropyl-4-(3-hydroxy-4-(6-(methyl(2,2,6,6-tetramethylpiperidin-4-yl)amino)pyridazin-3-yl)phenyl)pyridin-2(1H)-one;

2-(6-(methyl-(2,2,6,6-tetramethylpiperidin-4-yl)amino) pyridazin-3-yl)-5-(1,2,3,6-tetrahydropyridin-4-yl)phenol;

5-(cyclopent-1-en-1-yl)-2-(6-(methyl(2,2,6,6-tetramethylpiperidin-4-yl)amino)pyridazin-3-yl)phenol;

5-(3,6-dihydro-2H-pyran-4-yl)-2-(6-(methyl(2,2,6,6-tetramethylpiperidin-4-yl)amino)pyridazin-3-yl)phenol;

5-(imidazo[1,5-a]pyridin-7-yl)-2-(6-(methyl(2,2,6,6-tetramethylpiperidin-4-yl)amino)pyridazin-3-yl)phenol;

5-(imidazo[1,2-a]pyridin-7-yl)-2-(6-(methyl(2,2,6,6-tetramethylpiperidin-4-yl)amino)pyridazin-3-yl)phenol;

2-(6-(methyl(2,2,6,6-tetramethylpiperidin-4-yl)amino) pyridazin-3-yl)-5-(2-methylpyridin-4-yl)phenol;

5-(1H-imidazol-2-yl)-2-(6-(methyl-(2,2,6,6-tetramethylpiperidin-4-yl)amino)pyridazin-3-yl)phenol;

5-(1H-imidazol-4-yl)-2-(6-(methyl-(2,2,6,6-tetramethylpiperidin-4-yl)amino)pyridazin-3-yl)phenol;

5-(imidazo[1,2-a]pyrazin-3-yl)-2-(6-(methyl(2,2,6,6-tetramethylpiperidin-4-yl)amino)pyridazin-3-yl)phenol;

2-(6-(methyl-(2,2,6,6-tetramethylpiperidin-4-yl)amino) pyridazin-3-yl)-5-(5,6,7,8-tetrahydroimidazo[1,2-a] pyrazin-3-yl)phenol;
2-(6-(methyl-(2,2,6,6-tetramethylpiperidin-4-yl)amino) pyridazin-3-yl)-5-(4-methyl-1H-imidazol-2-yl)phenol;
2-(6-(methyl-(2,2,6,6-tetramethylpiperidin-4-yl)amino) pyridazin-3-yl)-5-(1-methyl-1H-imidazol-4-yl)phenol;
2-(6-(methyl-(2,2,6,6-tetramethylpiperidin-4-yl)amino) pyridazin-3-yl)-5-(1-methyl-1H imidazol-5-yl)phenol;
2-(6-(methyl-(2,2,6,6-tetramethylpiperidin-4-yl)amino) pyridazin-3-yl)-5-(4-nitro-1H-imidazol-2-yl)phenol;
2-(6-(methyl-(2,2,6,6-tetramethylpiperidin-4-yl)amino) pyridazin-3-yl)-5-(2-methyl-1H imidazol-4-yl)phenol;
5-(1,2-dimethyl-1H-imidazol-4-yl)-2-(6-(methyl(2,2,6,6-tetramethylpiperidin-4-yl)amino)pyridazin-3-yl)phenol;
1-(3-hydroxy-4-(6-(methyl-(2,2,6,6-tetramethylpiperidin-4-yl)amino)pyridazin-3-yl)phenyl)-1H-pyrazole-4-carboxamide;
2-(6-((3aR,6aS)-5-(2-hydroxyethyl)hexahydropyrrolo[3,4-c]pyrrol-2 (1H)-yl)pyridazin-3-yl)-5-(1H-pyrazol-4-yl) phenol;
2-(6-((3aR,6aS)-hexahydropyrrolo[3,4-c]pyrrol-2(1H)-yl) pyridazin-3-yl)-5-(1H-pyrazol-4-yl)phenol;
2-(6-((3aR,6aS)-5-methylhexahydropyrrolo[3,4-c]pyrrol-2 (1H)-yl)pyridazin-3-yl)-5-(1 Hpyrazol-4-yl)phenol;
4-(3-hydroxy-4-(6-(5-methylhexahydropyrrolo[3,4-c]pyrrol-2(1H)-yl)pyridazin-3-yl)phenyl)-1-methylpyridin-2 (1H)-one;
4-(3-hydroxy-4-(6-((3aR,6aR)-1-methylhexahydropyrrolo [3,4-b]pyrrol-5(1H)-yl)pyridazin-3-yl)phenyl)-1-methylpyridin-2(1H)-one;
2-(6-(2,7-diazaspiro[4.5]decan-2-yl)pyridazin-3-yl)-5-(1H-pyrazol-4-yl)phenol; and
4-(4-(6-(2,7-diazaspiro[4.5]decan-2-yl)pyridazin-3-yl)-3-hydroxyphenyl)-1-methylpyridin-2(1H)-one;
or a pharmaceutically acceptable salt thereof;
for use in the treatment, prevention and/or delay of progression of cancer.

In a particular embodiment, the present invention relates to a FoxM1 gene splicing modifier as described herein selected from the group consisting of:
5-(2-Methoxy-4-(1H-pyrazol-1-yl)phenyl)-N-methyl-N-(2,2,6,6-tetramethylpiperidin-4-yl)-1,3,4-thiadiazol-2-amine;
6-(5-(Methyl(2,2,6,6-tetramethylpiperidin-4-yl)amino)-1,3,4-thiadiazol-2-yl)naphthalen-2-ol;
5-(2-Methoxyquinolin n-3-yl)-N-methyl-N-(2,2,6,6-tetramethylpiperidin-4-yl)-1,3,4-thiadiazol-2-amine;
5-(3-Methoxynaphthalen-2-yl)-N-methyl-N-(2,2,6,6-tetramethylpiperidin-4-yl)-1,3,4-thiadiazol-2-amine;
5-(2-Methoxy-4-(1H-pyrazol-1-yl)phenyl)-N-(1,2,2,6,6-pentamethylpiperidin-4-yl)-1,3,4-thiadiazol-2-amine;
5-(2-Methoxy-4-(1-methyl-1H-pyrazol-4-yl)phenyl)-N-methyl-N-(2,2,6,6-tetramethylpiperidin-4-yl)-1,3,4-thiadiazol-2-amine;
5-(2-Methoxy-4-(1H-pyrazol-4-yl)phenyl)-N-methyl-N-(2,2,6,6-tetramethylpiperidin-4-yl)-1,3,4-thiadiazol-2-amine;
4-(3-Methoxy-4-(5-(methyl(2,2,6,6-tetramethylpiperidin-4-yl)amino)-1,3,4-thiadiazol-2-yl)phenyl)-1-methylpyridin-2(1H)-one;
5-(3-Methoxy-4-(5-(methyl(2,2,6,6-tetramethylpiperidin-4-yl)amino)-1,3,4-thiadiazol-2-yl)phenyl)pyridin-2-ol;
5-(3-Methoxy-4-(5-(methyl(2,2,6,6-tetramethylpiperidin-4-yl)amino)-1,3,4-thiadiazol-2-yl)phenyl)-1-methylpyridin-2(1H)-one;
N-Methyl-5-(2-methyl-4-(1-methyl-1H-pyrazol-4-yl)phenyl)-N-(2,2,6,6-tetramethylpiperidin-4-yl)-1,3,4-thiadiazol-2-amine;
1-Methyl-4-(4-(5-(methyl(2,2,6,6-tetramethylpiperidin-4-yl)amino)-1,3,4-thiadiazol-2-yl)-3-(trifluoromethoxy) phenyl)pyridin-2(1H)-one;
5-(4-(3,5-Dimethyl-1H-pyrazol-4-yl)-2-methoxyphenyl)-N-methyl-N-(2,2,6,6-tetramethylpiperidin-4-yl)-1,3,4-thiadiazol-2-amine;
5-(2-Methoxy-4-(1-methyl-1H-pyrazol-4-yl)phenyl)-N-methyl-N-(2,2,6,6-tetramethylpiperidin-4-yl)-1,3,4-thiadiazol-2-amine;
2-(5-(Methyl(2,2,6,6-tetramethylpiperidin-4-yl)amino)-1,3,4-thiadiazol-2-yl)-5-(1-methyl-1H-pyrazol-4-yl)phenol;
2-(5-(Methyl(2,2,6,6-tetramethylpiperidin-4-yl)amino)-1,3,4-thiadiazol-2-yl)-5-(1H-pyrazol-1-yl)phenol;
5-(3-Hydroxy-4-(5-(methyl(2,2,6,6-tetramethylpiperidin-4-yl)amino)-1,3,4-thiadiazol-2-yl)phenyl)-1-methylpyridin-2(1H)-one;
4-(3-Hydroxy-4-(5-(methyl(2,2,6,6-tetramethylpiperidin-4-yl)amino)-1,3,4-thiadiazol-2-yl)phenyl)-1-methylpyridin-2(1H)-one;
5-(3-Hydroxy-4-(5-(methyl(2,2,6,6-tetramethylpiperidin-4-yl)amino)-1,3,4-thiadiazol-2-yl)phenyl)pyridin-2-ol;
3-(5-(Methyl(2,2,6,6-tetramethylpiperidin-4-yl)amino)-1,3,4-thiadiazol-2-yl)naphthalene-2,7-diol;
3-(5-((3aR,6aS)-Hexahydropyrrolo[3,4-c]pyrrol-2(1H)-yl)-1,3,4-thiadiazol-2-yl)naphthalene-2,7-diol;
3-(5-(Methyl(2,2,6,6-tetramethylpiperidin-4-yl)amino)-1,3,4-thiadiazol-2-yl)naphthalen-2-ol hydrobromide salt;
3-(5-(Methyl(2,2,6,6-tetramethylpiperidin-4-yl)amino)-1,3,4-thiadiazol-2-yl)quinolin-2-ol;
2-(5-(Methyl(2,2,6,6-tetramethylpiperidin-4-yl)amino)-1,3,4-thiadiazol-2-yl)-4-(1H-pyrazol-1-yl)phenol;
5-(2-Chloro-4-(1-methyl-1H-pyrazol-4-yl)phenyl)-N-methyl-N-(2,2,6,6-tetramethylpiperidin-4-yl)-1,3,4-thiadiazol-2-amine;
3-Chloro-2-(5-(methyl(2,2,6,6-tetramethylpiperidin-4-yl) amino)-1,3,4-thiadiazol-2-yl)-5-(1-methyl-1H-pyrazol-4-yl)phenol;
5-(2-Chloro-4-(1-methyl-1H-pyrazol-4-yl)phenyl)-N-(2,2,6,6-tetramethylpiperidin-4-yl)-1,3,4-thiadiazol-2-amine;
3-Methoxy-2-(5-(methyl(2,2,6,6-tetramethylpiperidin-4-yl) amino)-1,3,4-thiadiazol-2-yl)-5-(5-methyloxazol-2-yl) phenol;
2-(2-Methoxy-4-(1H-pyrazol-1-yl)phenyl)-5-(1,2,3,6-tetrahydropyridin-4-yl)-1,3,4-thiadiazole;
2-(5-(piperazin-1-yl)-1,3,4-thiadiazol-2-yl)-5-(1H-pyrazol-1-yl)phenol;
5-(7-Methoxyquinolin-6-yl)-N-methyl-N-(2,2,6,6-tetramethylpiperidin-4-yl)-1,3,4-thiadiazol-2-amine;
6-(5-(Methyl(2,2,6,6-tetramethylpiperidin-4-yl)amino)-1,3,4-thiadiazol-2-yl)quinolin-7-ol;
3-methoxy-4-(5-(methyl(2,2,6,6-tetramethylpiperidin-4-yl) amino)-1,3,4-thiadiazol-2-yl)benzonitrile;
3-fluoro-4-(5-(methyl(2,2,6,6-tetramethylpiperidin-4-yl) amino)-1,3,4-thiadiazol-2-yl)benzonitrile;
methyl 3-fluoro-4-(5-(methyl(2,2,6,6-tetramethylpiperidin-4-yl)amino)-1,3,4-thiadiazol-2-yl)benzoate;
5-(2-methoxy-4-(3-(methyl amino)-1H-pyrazol-1-yl)phenyl)-N-methyl-N-(2,2,6,6-tetramethylpiperidin-4-yl)-1,3,4-thiadiazol-2-amine;
7-methoxy-6-(5-(methyl(2,2,6,6-tetramethylpiperidin-4-yl) amino)-1,3,4-thiadiazol-2-yl)quinoline-2-carbonitrile;
4-(3-methoxy-4-(5-(((2,2,6,6-tetramethylpiperidin-4-yl) oxy)-1,3,4-thiadiazol-2-yl)phenyl)-1-methylpyridin-2 (1H)-one;

4-(3-chloro-4-(5-(methyl(2,2,6,6-tetramethylpiperidin-4-yl) amino)-1,3,4-thiadiazol-2-yl)phenyl)-1-methylpyridin-2 (1H)-one;

5-(2-Chloro-4-(1H-pyrazol-4-yl)phenyl)-N-methyl-N-(2,2, 6,6-tetramethylpiperidin-4-yl)-1,3,4-thiadiazol-2-amine;

5-(2-Chloro-4-(4,5,6,7-tetrahydropyrazolo[1,5-a]pyridin-3-yl)phenyl)-N-methyl-N-(2,2,6,6-tetramethylpiperidin-4-yl)-1,3,4-thiadiazol-2-amine;

N-methyl-5-(5-(1-methyl-1H-pyrazol-4-yl)pyridin-2-yl)-N-(2,2,6,6-tetramethylpiperidin-4-yl)-1,3,4-thiadiazol-2-amine Hydrochloride salt;

2-(2-chloro-4-(1-methyl-1H-pyrazol-4-yl)phenyl)-5-((2,2,6, 6-tetramethylpiperidin-4-yl)oxy)-1,3,4-thiadiazole;

5-(2-chloro-4-(6-methoxypyridin-3-yl)phenyl)-N-methyl-N-(2,2,6,6-tetramethylpiperidin-4-yl)-1,3,4-thiadiazol-2-amine;

5-(4-(6-aminopyridin-3-yl)-2-fluorophenyl)-N-methyl-N-(2,2,6,6-tetramethylpiperidin-4-yl)-1,3,4-thiadiazol-2-amine;

5-(2-fluoro-4-(3-methyl-1H-pyrazol-5-yl)phenyl)-N-methyl-N-(2,2,6,6-tetramethylpiperidin-4-yl)-1,3,4-thiadiazol-2-amine;

5-(2-fluoro-4-(1H-pyrazol-5-yl)phenyl)-N-methyl-N-(2,2,6, 6-tetramethylpiperidin-4-yl)-1,3,4-thiadiazol-2-amine;

5-(2,3-difluoro-4-(1H-pyrazol-4-yl)phenyl)-N-methyl-N-(2, 2,6,6-tetramethylpiperidin-4-yl)-1,3,4-thiadiazol-2-amine;

5-(2,3-difluoro-4-(1H-pyrazol-5-yl)phenyl)-N-methyl-N-(2, 2,6,6-tetramethylpiperidin-4-yl)-1,3,4-thiadiazol-2-amine;

5-(2,5-difluoro-4-(1H-pyrazol-4-yl)phenyl)-N-methyl-N-(2, 2,6,6-tetramethylpiperidin-4-yl)-1,3,4-thiadiazol-2-amine;

5-(2,5-difluoro-4-(1H-pyrazol-5-yl)phenyl)-N-methyl-N-(2, 2,6,6-tetramethylpiperidin-4-yl)-1,3,4-thiadiazol-2-amine;

5-(2,6-difluoro-4-(1H-pyrazol-4-yl)phenyl)-N-methyl-N-(2, 2,6,6-tetramethylpiperidin-4-yl)-1,3,4-thiadiazol-2-amine;

2-(2,5-difluoro-4-(1H-pyrazol-4-yl)phenyl)-5-((3 aR, 6aS)-hexahydropyrrolo[3,4-c]pyrrol-2(1H)-yl)-1,3,4-thiadiazole;

5-(2-chloro-5-fluoro-4-(1H-pyrazol-4-yl)phenyl)-N-methyl-N-(2,2,6,6-tetramethylpiperidin-4-yl)-1,3,4-thiadiazol-2-amine;

5-(3-fluoro-5-(1H-pyrazol-4-yl)pyridin-2-yl)-N-methyl-N-(2,2,6,6-tetramethylpiperidin-4-yl)-1,3,4-thiadiazol-2-amine;

5-(4-(2-aminopyrimidin-4-yl)-2-chlorophenyl)-N-methyl-N-(2,2,6,6-tetramethylpiperidin-4-yl)-1,3,4-thiadiazol-2-amine;

5-(5-(2-aminopyrimidin-4-yl)-2-chlorophenyl)-N-methyl-N-(2,2,6,6-tetramethylpiperidin-4-yl)-1,3,4-thiadiazol-2-amine;

5-(4-(2,4-dimethylthiazol-5-yl)-2,5-difluorophenyl)-N-methyl-N-(2,2,6,6-tetramethylpiperidin-4-yl)-1,3,4-thiadiazol-2-amine;

5-(4-(2,4-dimethylthiazol-5-yl)-2,3-difluorophenyl)-N-methyl-N-(2,2,6,6-tetramethylpiperidin-4-yl)-1,3,4-thiadiazol-2-amine;

4-(3-hydroxy-4-(5-(methyl(2,2,6,6-tetramethylpiperidin-4-yl)amino)-1,3,4-thiadiazol-2-yl)-5-(trifluoromethoxy) phenyl)-1-methylpyridin-2(1H)-one;

5-(2-fluoro-6-methoxy-4-(1H-pyrazol-4-yl)phenyl)-N-methyl-N-(2,2,6,6-tetramethylpiperidin-4-yl)-1,3,4-thiadiazol-2-amine;

2-(2-fluoro-6-methoxy-4-(1H-pyrazol-4-yl)phenyl)-5-((3aR,6aS)-5-methylhexahydropyrrolo[3,4-c]pyrrol-2 (1H)-yl)-1,3,4-thiadiazole;

5-(2,3-difluoro-6-methoxy-4-(1H-pyrazol-4-yl)phenyl)-N-methyl-N-(2,2,6,6-tetramethylpiperidin-4-yl)-1,3,4-thiadiazol-2-amine;

6-methoxy-2-(5-(methyl(2,2,6,6-tetramethylpiperidin-4-yl) amino)-1,3,4-thiadiazol-2-yl)-3,4-dihydroisoquinolin-1 (2H)-one;

5-(2-Chloro-4-(1H-pyrazol-1-yl)phenyl)-N-methyl-N-(2,2, 6,6-tetramethylpiperidin-4-yl)-1,3,4-thiadiazol-2-amine;

5-(2-Chloro-4-(1H-1,2,3-triazol-1-yl)phenyl)-N-methyl-N-(2,2,6,6-tetramethylpiperidin-4-yl)-1,3,4-thiadiazol-2-amine;

5-(2-chloro-4-(2H-1,2,3-triazol-2-yl)phenyl)-N-methyl-N-(2,2,6,6-tetramethylpiperidin-4-yl)-1,3,4-thiadiazol-2-amine;

5-(2-chloro-4-(1H-1,2,4-triazol-1-yl)phenyl)-N-methyl-N-(2,2,6,6-tetramethylpiperidin-4-yl)-1,3,4-thiadiazol-2-amine;

5-(4-(3-amino-1H-pyrazol-1-yl)-2-chlorophenyl)-N-methyl-N-(2,2,6,6-tetramethylpiperidin-4-yl)-1,3,4-thiadiazol-2-amine;

2-(2-chloro-4-(1H-imidazol-1-yl)phenyl)-5-((3aR,6aS)-5-methylhexahydropyrrolo[3,4-c]pyrrol-2(1H)-yl)-1,3,4-thiadiazole;

5-(2-Chloro-4-(1H-imidazol-1-yl)phenyl)-N-methyl-N-(2, 2,6,6-tetramethylpiperidin-4-yl)-1,3,4-thiadiazol-2-amine;

5-(2-fluoro-4-(1H-imidazol-1-yl)phenyl)-N-methyl-N-(2,2, 6,6-tetramethylpiperidin-4-yl)-1,3,4-thiadiazol-2-amine;

5-(2-methoxy-4-(1H-pyrazol-5-yl)phenyl)-N-methyl-N-(2, 2,6,6-tetramethylpiperidin-4-yl)-1,3,4-thiadiazol-2-amine;

5-(4-(2,4-dimethylthiazol-5-yl)-2-methoxyphenyl)-N-methyl-N-(2,2,6,6-tetramethylpiperidin-4-yl)-1,3,4-thiadiazol-2-amine;

5-(2-methoxy-4-(pyridin-3-yl)phenyl)-N-methyl-N-(2,2,6, 6-tetramethylpiperidin-4-yl)-1,3,4-thiadiazol-2-amine;

5-(2-fluoro-4-(1H-pyrazol-4-yl)phenyl)-N-methyl-N-(2,2,6, 6-tetramethylpiperidin-4-yl)-1,3,4-thiadiazol-2-amine;

5-(2-methoxy-4-(2-methoxypyridin-4-yl)phenyl)-N-methyl-N-(2,2,6,6-tetramethylpiperidin-4-yl)-1,3,4-thiadiazol-2-amine;

5-(2-methoxy-4-(6-methoxypyridin-3-yl)phenyl)-N-methyl-N-(2,2,6,6-tetramethylpiperidin-4-yl)-1,3,4-thiadiazol-2-amine;

2-(2-Chloro-4-(1-methyl-1H-pyrazol-4-yl)phenyl)-5-((3 aR,6aS)-5-methylhexahydropyrrolo[3,4-c]pyrrol-2(1H)-yl)-1,3,4-thiadiazole;

2-(2-chloro-4-(1H-pyrazol-4-yl)phenyl)-5-((3aR,6aS)-5-methylhexahydropyrrolo[3,4-c]pyrrol-2(1H)-yl)-1,3,4-thiadiazole;

2-(2-Chloro-4-(1H-pyrazol-4-yl)phenyl)-5-((3aR,6aR)-1-methylhexahydropyrrolo[3,4-b]pyrrol-5(1H)-yl)-1,3,4-thiadiazole;

1-(4-(5-(2-chloro-4-(1H-pyrazol-4-yl)phenyl)-1,3,4-thiadiazol-2-yl)morpholin-2-yl)-N,N-dimethylmethanamine;

2-(2-chloro-4-(1H-pyrazol-4-yl)phenyl)-5-(2-methyl-2,7-diazaspiro[4.5]decan-7-yl)-1,3,4-thiadiazole;

2-(2-fluoro-4-(1H-pyrazol-4-yl)phenyl)-5-((3aR,6aS)-5-methylhexahydropyrrolo[3,4-c]pyrrol-2(1H)-yl)-1,3,4-thiadiazole;

2-(2-methoxy-4-(1-methyl-1H-pyrazol-4-yl)phenyl)-5-(2,6-diazaspiro[3.5]nonan-2-yl)-1,3,4-thiadiazole;

2-(2-methoxy-4-(1-methyl-1H-pyrazol-4-yl)phenyl)-5-(2,7-diazaspiro[3.5]nonan-2-yl)-1,3,4-thiadiazole;

2-(5-(Methyl(2,2,6,6-tetramethylpiperidin-4-yl)amino)-1,3,4-thiadiazol-2-yl)-5-(1H-pyrazol-1-yl)phenol;
5-(3-chloro-4-(5-(methyl(2,2,6,6-tetramethylpiperidin-4-yl)amino)-1,3,4-thiadiazol-2-yl)phenyl)pyridin-2(1H)-one;
2-(5-(methyl(2,2,6,6-tetramethylpiperidin-4-yl)amino)-1,3,4-thiadiazol-2-yl)-5-(3-(methylamino)-1H-pyrazol-1-yl)phenol;
3-fluoro-2-(5-(methyl(2,2,6,6-tetramethylpiperidin-4-yl)amino)-1,3,4-thiadiazol-2-yl)-5-(1H-pyrazol-4-yl)phenol;
3,4-difluoro-2-(5-(methyl(2,2,6,6-tetramethylpiperidin-4-yl)amino)-1,3,4-thiadiazol-2-yl)-5-(1H-pyrazol-4-yl)phenol;
6-hydroxy-5-(5-(methyl(2,2,6,6-tetramethylpiperidin-4-yl)amino)-1,3,4-thiadiazol-2-yl)-2,3-dihydro-1H-inden-1-one;
2-(5-(methyl(2,2,6,6-tetramethylpiperidin-4-yl)amino)-1,3,4-thiadiazol-2-yl)-5-(1H-pyrazol-4-yl)phenol;
2-(5-(2,6-diazaspiro[3.5]nonan-2-yl)-1,3,4-thiadiazol-2-yl)-5-(1-methyl-1H-pyrazol-4-yl)phenol;
2-(5-(2,7-diazaspiro[3.5]nonan-2-yl)-1,3,4-thiadiazol-2-yl)-5-(1-methyl-1H-pyrazol-4-yl)phenol;
3-fluoro-2-(5-((3 aR,6aS)-hexahydropyrrolo[3,4-c]pyrrol-2(1H)-yl)-1,3,4-thiadiazol-2-yl)-5-(1H-pyrazol-4-yl)phenol Di-hydrochloride salt;
3-Chloro-2-(5-(methyl(2,2,6,6-tetramethylpiperidin-4-yl)amino)-1,3,4-thiadiazol-2-yl)-5-(1H-pyrazol-4-yl)phenol;
2-(2-methoxy-4-(1H-pyrazol-1-yl)phenyl)-5-((2,2,6,6-tetramethylpiperidin-4-yl)methyl)-1,3,4-thiadiazole;
2-(2,3-difluoro-4-(1H-pyrazol-4-yl)phenyl)-5-(2,7-diazaspiro[3.5]nonan-2-yl)-1,3,4-thiadiazole;
2-(5-(2,7-diazaspiro[3.5]nonan-2-yl)-1,3,4-thiadiazol-2-yl)-3-fluoro-5-(1H-pyrazol-4-yl)phenol;
4-methoxy-1-methyl-3-(5-(methyl(2,2,6,6-tetramethylpiperidin-4-yl)amino)-1,3,4-thiadiazol-2-yl)quinolin-2(1H)-one;
4-hydroxy-1-methyl-3-(5-(methyl(2,2,6,6-tetramethylpiperidin-4-yl)amino)-1,3,4-thiadiazol-2-yl)quinolin-2(1H)-one;
3-(5-(methyl(2,2,6,6-tetramethylpiperidin-4-yl)amino)-1,3,4-thiadiazol-2-yl)quinolin-2(1H)-one;
1-methyl-3-(5-(methyl(2,2,6,6-tetramethylpiperidin-4-yl)amino)-1,3,4-thiadiazol-2-yl)quinolin-2(1H)-one;
2-(2-Chloro-4-(1H-pyrazol-4-yl)phenyl)-5-((3 aR,6aS)-hexahydropyrrolo[3,4-c]pyrrol-2(1H)yl)-1,3,4-thiadiazole Hydrochloride Salt;
2-(2-Chloro-4-(1H-pyrazol-4-yl)phenyl)-5-(2,7-diazaspiro[4.5]decan-2-yl)-1,3,4-thiadiazole Hydrochloride Salt;
(R)-(4-(5-(2-chloro-4-(1H-pyrazol-4-yl)phenyl)-1,3,4-thiadiazol-2-yl)piperazin-2-yl)methanol Hydrochloride Salt;
2-(5-(methyl(2,2,6,6-tetramethylpiperidin-4-yl)amino)-1,3,4-thiadiazol-2-yl)benzo[b]thiophene-5-carbonitrile; and
5-(3-chlorobenzo[b]thiophen-2-yl)-N-methyl-N-(2,2,6,6-tetramethylpiperidin-4-yl)-1,3,4-thiadiazol-2-amine;
or a pharmaceutically acceptable salt thereof;
for use in the treatment, prevention and/or delay of progression of cancer.

In a particular embodiment, the present invention relates to a FoxM1 gene splicing modifier selected from the group consisting of:
7-hydroxy-6-(6-(methyl(2,2,6,6-tetramethylpiperidin-4-yl)amino)pyridazin-3-yl)quinolin-2(1H)-one;
6-(6-((3aR,6aS)-5-methylhexahydropyrrolo[3,4-c]pyrrol-2(1H)-yl)pyridazin-3-yl)quinolin-7-ol;
7-hydroxy-1-methyl-6-(6-(methyl(2,2,6,6-tetramethylpiperidin-4-yl)amino)pyridazin-3-yl)quinolin-2(1H)-one;
6-(6-(methyl(1,2,2,6,6-pentamethylpiperidin-4-yl)amino)pyridazin-3-yl)quinolin-7-ol;
2-methyl-6-(6-(methyl(2,2,6,6-tetramethylpiperidin-4-yl)amino)pyridazin-3-yl)-4-morpholinoquinolin-7-ol;
4-chloro-2-methyl-6-(6-(methyl(2,2,6,6-tetramethylpiperidin-4-yl)amino)pyridazin-3-yl)quinolin-7-ol;
3-bromo-6-(6-(methyl(2,2,6,6-tetramethylpiperidin-4-yl)amino)pyridazin-3-yl)quinolin-7-ol;
3-ethyl-6-(6-(methyl(2,2,6,6-tetramethylpiperidin-4-yl)amino)pyridazin-3-yl)quinolin-7-ol;
3-(1H-imidazol-1-yl)-6-(6-(methyl(2,2,6,6-tetramethylpiperidin-4-yl)amino)pyridazin-3-yl)quinolin-7-ol;
6-(6-(methyl(2,2,6,6-tetramethylpiperidin-4-yl)amino)pyridazin-3-yl)-3-(1-methyl-1H-imidazol-4-yl)quinolin-7-ol;
3-isopropyl-6-(6-(methyl(2,2,6,6-tetramethylpiperidin-4-yl)amino)pyridazin-3-yl)quinolin-7-ol;
6-(6-(methyl(2,2,6,6-tetramethylpiperidin-4-yl)amino)pyridazin-3-yl)quinoline-3,7-diol;
7-hydroxy-6-(6-(methyl(2,2,6,6-tetramethylpiperidin-4-yl)amino)pyridazin-3-yl)quinoline-3-carbonitrile;
6-(6-(methyl(2,2,6,6-tetramethylpiperidin-4-yl)amino)pyridazin-3-yl)quinolin-7-ol;
4-(dimethylamino)-2-methyl-6-(6-(methyl(2,2,6,6-tetramethylpiperidin-4-yl)amino)pyridazin-3-yl)quinolin-7-ol;
3-chloro-6-(6-(methyl(2,2,6,6-tetramethylpiperidin-4-yl)amino)pyridazin-3-yl)quinolin-7-ol;
4-methoxy-2-methyl-6-(6-(methyl(2,2,6,6-tetramethylpiperidin-4-yl)amino)pyridazin-3-yl)quinolin-7-ol;
6-(3-(benzyloxy)isoquinolin-6-yi)-N-methyi-N-(2,2,6,6-tetramethylpiperidin-4-yl)pyridazin-3-amine;
8-(6-(methyl(2,2,6,6-tetramethylpiperidin-4-yl)amino)pyridazin-3-yl)quinolin-7-ol;
7-(6-(methyl(2,2,6,6-tetramethylpiperidin-4-yl)amino)pyridazin-3-yl)isoquinoline-1,6-diol;
7-(6-(methyl(1,2,2,6,6-pentamethylpiperidin-4-yl)amino)pyridazin-3-yl)isoquinolin-6-ol;
1-cyclopropyl-7-(6-(methyl(2,2,6,6-tetramethylpiperidin-4-yl)amino)pyridazin-3-yl)isoquinolin-6-ol;
7-(6-(methyl(2,2,6,6-tetramethylpiperidin-4-yl)amino)pyridazin-3-yl)isoquinolin-6-ol;
6-(1-(benzyloxy)isoquinolin-7-yi)-N-methyi-N-(2,2,6,6-tetramethylpiperidin-4-yl)pyridazin-3-amine;
7-(6-(methyl(2,2,6,6-tetramethylpiperidin-4-yl)amino)pyridazin-3-yl)quinolin-6-ol;
2-methyl-7-(6-(methyl(2,2,6,6-tetramethylpiperidin-4-yl)amino)pyridazin-3-yl)quinolin-6-ol;
2-methyl-6-(6-(methyl(2,2,6,6-tetramethylpiperidin-4-yl)amino)pyridazin-3-yl)-4-(1-methyl-1Hpyrazol-4-yl)quinolin-7-ol;
2-methyl-6-(6-(methyl(2,2,6,6-tetramethylpiperidin-4-yl)amino)pyridazin-3-yl)quinolin-7-ol;
4-ethoxy-2-methyl-6-(6-(methyl(2,2,6,6-tetramethylpiperidin-4-yl)amino)pyridazin-3-yl)quinolin-7-ol;
4-chloro-7-(6-(methyl(2,2,6,6-tetramethylpiperidin-4-yl)amino)pyridazin-3-yl)quinolin-6-ol;
6-(6-(methyl(2,2,6,6-tetramethylpiperidin-4-yl)amino)pyridazin-3-yl)-3-(tetrahydro-2H-pyran-4-yl)quinolin-7-ol;
3-chloro-7-(6-(methyl(2,2,6,6-tetramethylpiperidin-4-yl)amino)pyridazin-3-yl)quinolin-6-ol;
3-bromo-7-(6-(methyl(2,2,6,6-tetramethylpiperidin-4-yl)amino)pyridazin-3-yl)quinolin-6-ol;
3-methyl-7-(6-(methyl(2,2,6,6-tetramethylpiperidin-4-yl)amino)pyridazin-3-yl)quinolin-6-ol;
5-bromo-3-methyl-7-(6-(methyl(2,2,6,6-tetramethylpiperidin-4-yl)amino)pyridazin-3-yl)quinolin-6-ol;

6-hydroxy-1-methyl-7-(6-(methyl(2,2,6,6-tetramethylpiperidin-4-yl)amino)pyridazin-3-yl)quinolin-4(1H)-one;
2,3-di methyl-7-(6-(methyl(2,2,6,6-tetramethylpiperidin-4-yl)amino)pyridazin-3-yl)quinoxalin-6-ol;
2-methyl-7-(6-(methyl(2,2,6,6-tetramethylpiperidin-4-yl)amino)pyridazin-3-yl)quinoxalin-6-ol;
3-methyl-7-(6-(methyl(2,2,6,6-tetramethylpiperidin-4-yl)amino)pyridazin-3-yl)quinoxalin-6-ol;
4-methoxy-6-(6-(methyl(2,2,6,6-tetramethylpiperidin-4-yl)amino)pyridazin-3-yl)quinolin-7-ol;
4-(azetidin-1-yl)-2-methyl-6-(6-(methyl(2,2,6,6-tetramethylpiperidin-4-yl)amino)pyridazin-3-yl)quinolin-7-ol;
7-hydroxy-2-methyl-6-(6-(methyl(2,2,6,6-tetramethylpiperidin-4-yl)amino)pyridazin-3-yl)quinoline-4-carbonitrile;
4-cyclopropyl-2-methyl-6-(6-(methyl(2,2,6,6-tetramethylpiperidin-4-yl)amino)pyridazin-3-yl)quinolin-7-ol;
4-(3,6-dihydro-2H-pyran-4-yl)-2-methyl-6-(6-(methyl(2,2,6,6-tetramethylpiperidin-4-yl)amino)pyridazin-3-yl)quinolin-7-ol;
2-methyl-6-(6-(methyl(2,2,6,6-tetramethylpiperidin-4-yl)amino)pyridazin-3-yl)-4-(tetrahydro-2Hpyran-4-yl)quinolin-7-ol;
2-methyl-6-(6-(methyl(2,2,6,6-tetramethylpiperidin-4-yl)amino)pyridazin-3-yl)-4-(oxetan-3-yl)quinolin-7-ol;
4-(dimethylamino)-6-(6-(methyl(2,2,6,6-tetramethylpiperidin-4-yl)amino)pyridazin-3-yl)quinolin-7-ol;
7-hydroxy-6-(6-(methyl(2,2,6,6-tetramethylpiperidin-4-yl)amino)pyridazin-3-yl)quinazolin-4(1H)-one;
6-(6-(methyl(2,2,6,6-tetramethylpiperidin-4-yl)amino)pyridazin-3-yl)quinazolin-7-ol;
7-hydroxy-1-methyl-6-(6-(methyl(2,2,6,6-tetramethylpiperidin-4-yl)amino)pyridazin-3-yl)-3,4-dihydroquinolin-2(1H)-one;
7-hydroxy-1-methyl-6-(6-(methyl(2,2,6,6-tetramethylpiperidin-4-yl)amino)pyridazin-3-yl)-3,4-dihydroquinolin-2(1H)-one;
7-hydroxy-6-(6-(methyl(2,2,6,6-tetramethylpiperidin-4-yl)amino)pyridazin-3-yl)isoquinoline-1-carbonitrile;
7-hydroxy-6-(6-(methyl(2,2,6,6-tetramethylpiperidin-4-yl)amino)pyridazin-3-yl)quinoline-2-carbonitrile;
6-hydroxy-7-(6-(methyl(2,2,6,6-tetramethylpiperidin-4-yl)amino)pyridazin-3-yl)quinoline-2-carbonitrile;
6-hydroxy-7-(6-(methyl(2,2,6,6-tetramethylpiperidin-4-yl)amino)pyridazin-3-yl)quinoline-2-carbonitrile;
7-hydroxy-6-(6-(methyl(2,2,6,6-tetramethylpiperidin-4-yl)amino)pyridazin-3-yl)isoquinoline-1-carboxamide;
7-hydroxy-6-(6-(methyl(2,2,6,6-tetramethylpiperidin-4-yl)amino)pyridazin-3-yl)quinoline-2-carboxamide;
6-hydroxy-7-(6-(methyl(2,2,6,6-tetramethylpiperidin-4-yl)amino)pyridazin-3-yl)quinoline-2-carboxamide;
methyl6-hydroxy-7-(6-(methyl(2,2,6,6-tetramethylpiperidin-4-yl)amino)pyridazin-3-yl)quinoline-2-carboxylate;
6-hydroxy-7-(6-(piperazin-1-yl)pyridazin-3-yl)quinoline-2-carbonitrile;
7-hydroxy-6-(6-(piperazin-1-yl)pyridazin-3-yl)quinoline-2-carbonitrile;
7-(6-(piperazin-1-yl)pyridazin-3-yl)isoquinolin-6-ol;
7-(6-(1,2,3,6-tetrahydropyridin-4-yl)pyridazin-3-yl)quinolin-6-ol;
1-methyl-6-(6-(methyl(2,2,6,6-tetramethylpiperidin-4-yl)amino)pyridazin-3-yl)isoquinolin-7-ol;
1-methyl-7-(6-(methyl(2,2,6,6-tetramethylpiperidin-4-yl)amino)pyridazin-3-yl)isoquinolin-6-ol;
1,3-dimethyl-7-(6-(methyl(2,2,6,6-tetramethylpiperidin-4-yl)amino)pyridazin-3-yl)isoquinolin-6-ol;
7-hydroxy-3-methyl-6-(6-(methyl(2,2,6,6-tetramethylpiperidin-4-yl)amino)pyridazin-3-yl)isoquinoline-1-carbonitrile;
1-amino-7-(6-(methyl(2,2,6,6-tetramethylpiperidin-4-yl)amino)pyridazin-3-yl)isoquinolin-6-ol;
7-hydroxy-1,3-dimethyl-6-(6-(methyl(2,2,6,6-tetramethylpiperidin-4-yl)amino)pyridazin-3-yl)quinazoline-2,4(1H,3H)-dione;
6-hydroxy-5-(6-(methyl(2,2,6,6-tetramethylpiperidin-4-yl)amino)pyridazin-3-yl)benzo[d]oxazol-2(3H)-one;
2-methyl-5-(6-(methyl(2,2,6,6-tetramethylpiperidin-4-yl)amino)pyridazin-3-yl)-2H-indazol-6-ol;
1-methyl-5-(6-(methyl(2,2,6,6-tetramethylpiperidin-4-yl)amino)pyridazin-3-yl)-1H-indazol-6-ol;
6-hydroxy-2-methyl-7-(6-(methyl(2,2,6,6-tetramethylpiperidin-4-yl)amino)pyridazin-3-yl)isoquinolin-1(2H)-one;
2-ethyl-6-hydroxy-7-(64(2,2,6,6-tetramethylpiperidin-4-yl)oxy)pyridazin-3-yl)isoquinolin-1(2H)-one;
1-ethoxy-7-(6-(methyl(2,2,6,6-tetramethylpiperidin-4-yl)amino)pyridazin-3-yl)isoquinolin-6-ol;
7-(6-((2,2,6,6-tetramethylpiperidin-4-yl)oxy)pyridazin-3-yl)isoquinoline-1,6-diol;
7-(6-(methyl(2,2,6,6-tetramethyl-piperidin-4-yl)amino)-pyridazin-3-yl)-3-phenylisoquinoline-6-ol;
3-methyl-7-(6-(methyl(2,2,6,6-tetramethylpiperidin-4-yl)amino)pyridazin-3-yl)isoquinolin-6-ol;
3-cyclopropyl-7-(6-(methyl(2,2,6,6-tetramethyl-piperidin-4-yl)amino)pyridazin-3-yl)isoquinolin-6-ol;
3-isopropyl-7-(6-(methyl(2,2,6,6-tetramethyl-piperidin-4-yl)amino)pyridazin-3-yl)isoquinolin-6-ol;
3-propyl-7-(6-((2,2,6,6-tetramethylpiperidin-4-yl)oxy)-pyridazin-3-yl)isoquinolin-6-ol;
3-isopropyl-7-(6-(2,2,6,6-tetramethylpiperidin-4-yl)oxy)-pyridazin-3-yl)isoquinolin-6-ol; and
3-methyl-7-(6-(piperazin-1-yl)pyridazin-3-yl)isoquinolin-6-ol;

or a pharmaceutically acceptable salt thereof;

for use in the treatment, prevention and/or delay of progression of cancer.

In a particular embodiment, the present invention relates to a FoxM1 gene splicing modifier selected from the group consisting of:
3-(6-(methyl(2,2,6,6-tetramethylpiperidin-4-yl)amino)pyridazin-3-yl)naphthalen-2-ol;
3-hydroxy-4-(6-(methyl(2,2,6,6-tetramethylpiperidin-4-yl)amino)pyridazin-3-yl)benzonitrile;
5-(1H-pyrazol-4-yl)-2-(6-(methyl(2,2,6,6-tetramethylpiperidin-4-yl)amino)pyridazin-3-yl)phenol 2-(6-(methyl-(2,2,6,6-tetramethylpiperidin-4-yl)amino)pyridazin-3-yl)-5-(1-methyl-1H-pyrazol-4-yl)phenol;
5-pyrazol-1-yl-2-[6-((2,2,6,6-tetramethylpiperidin-4-yloxy)-pyridazin-3-yl]-phenol;
5-(1H-pyrazol-4-yl)-2-(6-(2,2,6,6-tetramethylpiperidin-4-yl)oxy)pyridazin-3-yl)phenol;
3-(6-((2,2,6,6-tetramethylpiperidin-4-yl)oxy)pyridazin-3-yl)naphthalene-2,7-diol;
3-(6-(methyl-(2,2,6,6-tetramethylpiperidin-4-yl)amino)pyridazin-3-yl)naphthalene-2,7-diol;
7-methoxy-3-(6-(methyl(2,2,6,6-tetramethylpiperidin-4-yl)amino)pyridazin-3-yl)naphthalen-2-ol;
5-(3-hydroxy-4-(6-(methyl-(2,2,6,6-tetramethylpiperidin-4-yl)amino)pyridazin-3-yl)phenyl)-1-methylpyridin-2(1H)-one;
4-(3-hydroxy-4-(6-(methyl-(2,2,6,6-tetramethylpiperidin-4-yl)amino)pyridazin-3-yl)phenyl)-1-methylpyridin-2(1H)-one;
4-(3-chloro-4-(5-(methyl(2,2,6,6-tetramethylpiperidin-4-yl)amino)-1,3,4-thiadiazol-2-yl)phenyl)-1-methylpyridin-2(1H)-one;

5-(2-Chloro-4-(1H-pyrazol-4-yl)phenyl)-N-methyl-N-(2,2,
 6,6-tetramethylpiperidin-4-yl)-1,3,4-thiadiazol-2-amine;
5-(2,5-difluoro-4-(1H-pyrazol-5-yl)phenyl)-N-methyl-N-(2,
 2,6,6-tetramethylpiperidin-4-yl)-1,3,4-thiadiazol-2-
 amine;
or a pharmaceutically acceptable salt thereof;
for use in the treatment, prevention and/or delay of progression of cancer.

In a particular embodiment, the present invention relates to the use of a FoxM1 gene splicing modifier as described herein for the preparation of a medicament for the treatment, prevention and/or delay of progression of cancer.

In a particular embodiment, the present invention relates to the use of a FoxM1 gene splicing modifier as described herein for the treatment, prevention and/or delay of progression of cancer.

In a particular embodiment, the present invention relates to a method for the treatment, prevention and/or delay of progression of cancer comprising administering an effective amount of a FoxM1 gene splicing modifier as described herein to a subject, in particular to a mammal.

In a particular embodiment, the present invention relates to a pharmaceutical composition comprising a FoxM1 gene splicing modifier as described herein for use in the treatment, prevention and/or delay of progression of cancer.

In a particular embodiment, the present invention relates to a combination comprising a therapeutically effective amount of a FoxM1 gene splicing modifier as described herein or a pharmaceutically acceptable salt thereof and one or more therapeutically active co-agents.

Manufacturing Processes

Compounds of formula (I) can be prepared according to methods as disclosed in WO 2014/028459 (A1) or WO 2015/017589 (A1), which are herewith incorporated by reference. General synthetic processes are described in WO 2014/028459 (A1) on pages 34 to 37 and specific preparations of working examples on pages 37 to 188.

Compounds of formula (VI) can be prepared according to methods as disclosed in WO 2014/116845 (A1), which is herewith incorporated by reference. General synthetic processes are described therein on pages 38 to 41 and specific preparations of working examples on pages 41 to 123.

Pharmaceutical Compositions, Administration and Uses

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized composition or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to modify FoxM1 gene splicing. For example, such amount may be below the amount that is toxic to normal cells, or the mammal as a whole.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical composition is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The compositions may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aidin the manufacturing of the pharmaceutical product (i.e., medicament).

An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol composition can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

In a particular embodiment, the present invention relates to a pharmaceutical composition comprising a FoxM1 gene splicing modifier as described herein or pharmaceutically acceptable salt thereof.

In a particular embodiment, the present invention relates to a pharmaceutical composition comprising a FoxM1 gene splicing modifier as described herein or pharmaceutically acceptable salt thereof together with one or more pharmaceutically acceptable excipients.

In a particular embodiment, the present invention relates to a pharmaceutical composition comprising a therapeutically effective amount of a FoxM1 gene splicing modifier as described herein or pharmaceutically acceptable salt thereof together with one or more pharmaceutically acceptable excipients.

In a particular embodiment, the present invention relates to a combination comprising a therapeutically effective amount of a FoxM1 gene splicing modifier as described herein or pharmaceutically acceptable salt thereof and one or more other therapeutically active pharmaceutical ingredients.

In specific embodiments, the cancer treated by the compounds of the present invention is leukemia, acute myeloid leukemia, colon cancer, gastric cancer, macular degeneration, acute monocytic leukemia, breast cancer, hepatocellular carcinoma, cone-rod dystrophy, alveolar soft part sarcoma, myeloma, skin melanoma, prostatitis, pancreatitis, pancreatic cancer, retinitis, adenocarcinoma, adenoiditis, adenoid cystic carcinoma, cataract, retinal degeneration, gastrointestinal stromal tumor, Wegener's granulomatosis, sarcoma, myopathy, prostate adenocarcinoma, Hodgkin's lymphoma, ovarian cancer, non-Hodgkin's lymphoma, multiple myeloma, chronic myeloid leukemia, acute lymphoblastic leukemia, renal cell carcinoma, transitional cell carcinoma, colorectal cancer, chronic lymphocytic leukemia, anaplastic large cell lymphoma, kidney cancer, breast cancer, cervical cancer.

In specific embodiments, the cancer prevented and/or treated in accordance with the present invention is basal cell carcinoma, goblet cell metaplasia, or a malignant glioma, cancer of the liver, breast, lung, prostate, cervix, uterus, colon, pancreas, kidney, stomach, bladder, ovary, or brain.

In specific embodiments, the cancer prevented and/or treated in accordance with the present invention include, but are not limited to, cancer of the head, neck, eye, mouth, throat, esophagus, esophagus, chest, bone, lung, kidney, colon, rectum or other gastrointestinal tract organs, stomach, spleen, skeletal muscle, subcutaneous tissue, prostate, breast, ovaries, testicles or other reproductive organs, skin, thyroid, blood, lymph nodes, kidney, liver, pancreas, and brain or central nervous system.

Specific examples of cancers that can be prevented and/or treated in accordance with present invention include, but are not limited to, the following: renal cancer, kidney cancer, glioblastoma multiforme, metastatic breast cancer; breast carcinoma; breast sarcoma; neurofibroma; neurofibromatosis; pediatric tumors; neuroblastoma; malignant melanoma; carcinomas of the epidermis; leukemias such as but not limited to, acute leukemia, acute lymphocytic leukemia, acute myelocytic leukemias such as myeloblastic, promyelocytic, myelomonocytic, monocytic, erythroleukemia leukemias and myclodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone cancer and connective tissue sarcomas such as but not limited to bone sarcoma, myeloma bone disease, multiple myeloma, cholesteatoma-induced bone osteosarcoma, Paget's disease of bone, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, and synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease) and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; cervical carcinoma; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; KRAS mutated colorectal cancer; colon carcinoma; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as KRAS-mutated non-small cell lung cancer, non-small cell lung cancer, squamous cell carcinoma (epidermoid carcinoma), adenocarcinoma, large-cell carcinoma and small-cell lung cancer; lung carcinoma; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, androgen-independent prostate cancer, androgen-dependent prostate cancer, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acrallentiginous melanoma; kidney cancers such as but not limited to renal cell cancer, adenocarcinoma, hypernephroma, fibrosarcoma, transitional cell cancer (renal pelvis and/or uterer); renal carcinoma; Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

In certain embodiments cancers that can be prevented and/or treated in accordance with the present invention include, the following: pediatric solid tumor, Ewing's sarcoma, Wilms tumor, neuroblastoma, neurofibroma, carcinoma of the epidermis, malignant melanoma, cervical carcinoma, colon carcinoma, lung carcinoma, renal carcinoma, breast carcinoma, breast sarcoma, metastatic breast cancer, HIV-related Kaposi's sarcoma, prostate cancer, androgen-independent prostate cancer, androgen-dependent prostate cancer, neurofibromatosis, lung cancer, non-small cell lung cancer, KRAS-mutated non-small cell lung cancer, malignant melanoma, melanoma, colon cancer, KRAS-mutated colorectal cancer, glioblastoma multiforme, renal cancer, kidney cancer, bladder cancer, ovarian cancer, hepatocellular carcinoma, thyroid carcinoma, rhabdomyosarcoma, acute myeloid leukemia, and multiple myeloma.

In certain embodiments, cancers and conditions associated therewith that are prevented and/or treated in accordance with the present invention are breast carcinomas, lung carcinomas, gastric carcinomas, esophageal carcinomas, colorectal carcinomas, liver carcinomas, ovarian carcinomas, thecomas, arrhenoblastomas, cervical carcinomas, endometrial carcinoma, endometrial hyperplasia, endometriosis, fibrosarcomas, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as that associated with brain tumors), or Meigs' syndrome. In specific embodiment, the cancer an astrocytoma, an oligodendroglioma, a mixture of oligodendroglioma and an astrocytoma elements, an ependymoma, a meningioma, a pituitary adenoma, a primitive neuroectodermal tumor, a medullblastoma, a primary central nervous system (CNS) lymphoma, or a CNS germ cell tumor.

In specific embodiments, the cancer treated in accordance with the present invention is an acoustic neuroma, an anaplastic astrocytoma, a glioblastoma multiforme, or a meningioma.

In other specific embodiments, the cancer treated in accordance with the present invention is a brain stem glioma, a craniopharyngioma, an ependyoma, a juvenile pilocytic astrocytoma, a medulloblastoma, an optic nerve glioma, primitive neuroectodermal tumor, or a rhabdoid tumor.

EXAMPLES

All compounds being the subject matter of the present application are disclosed and characterized in WO 2014/028459 (A1), WO 2014/116845 (A1) or WO 2015/017589 (A1). WO2014/028459 (A1), WO 2014/116845 (A1) and WO 2015/017589 (A1) disclose methods for the preparation of the compounds being the subject matter of the present application. WO2014/028459 (A1), WO 2014/116845 (A1) and WO 2015/017589 (A1) are hereby incorporated by reference.

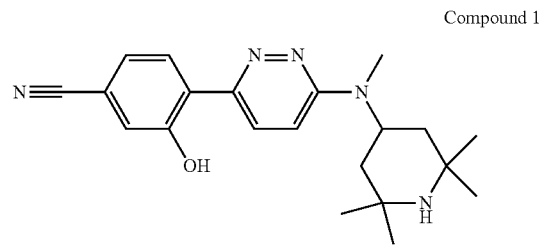 [SMILES: CN(c1ccc(-c2ccc(C#N)cc2O)nn1)C1CC(C)(C)NC(C)(C)C1]

Compound 1

3-hydroxy-4-(6-(methyl(2,2,6,6-tetramethylpiperidin-4-yl)amino)pyridazin-3-yl)benzonitrile was prepared as described in WO2014/028459 (A1) on pages 59-60 for Example 5-1.

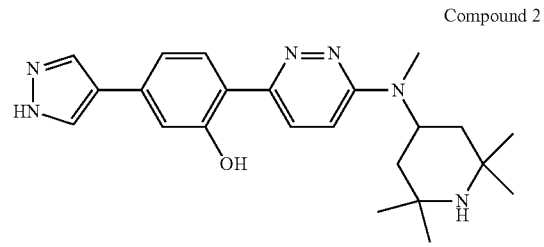 [SMILES: CN(c1ccc(-c2ccc(-c3cn[nH]c3)cc2O)nn1)C1CC(C)(C)NC(C)(C)C1]

Compound 2

5-(1H-pyrazol-4-yl)-2-(6-(methyl(2,2,6,6-tetramethylpiperidin-4-yl)amino)pyridazin-3-yl)phenol was prepared as described in WO2014/028459 (A1) on pages 69-71 for Example 14-1.

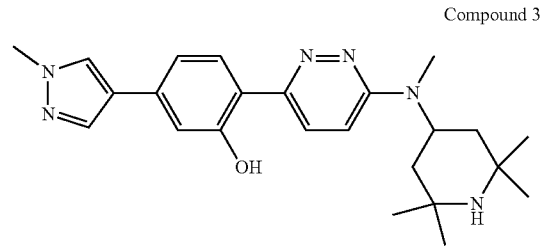

Compound 3

2-(6-(methyl-(2,2,6,6-tetramethylpiperidin-4-yl)amino) pyridazin-3-yl)-5-(1-methyl-1H-pyrazol-4-yl)phenol was prepared as described in WO2014/028459 (A1) on page 74 for Example 16-2.

Compound 4

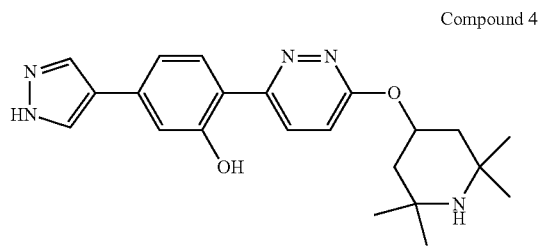 [SMILES: CC1(C)CC(Oc2ccc(-c3ccc(-c4cn[nH]c4)cc3O)nn2)CC(C)(C)N1]

5-(1H-pyrazol-4-yl)-2-(6-(2,2,6,6-tetramethylpiperidin-4-yl)oxy)pyridazin-3-yl)phenol was prepared as described in WO2014/028459 (A1) on pages 81-83 for Example 17-13.

Compound 5

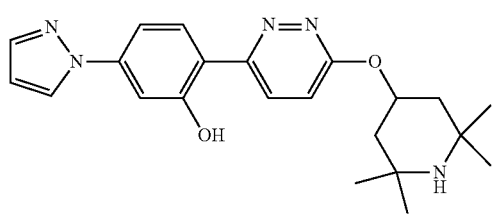

5-pyrazol-1-yl-2-[6-(2,2,6,6-tetramethylpiperidin-4-yl)oxy)-pyridazin-3-yl]-phenol was prepared as described in WO2014/028459 (A1) on page 81 for Example 17-12.

Compound 6

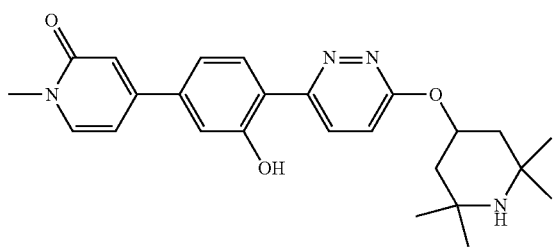

4-(3-hydroxy-4-(6-(methyl-(2,2,6,6-tetramethylpiperidin-4-yl)amino)pyridazin-3-yl)phenyl)-1-methylpyridin-2(1H)-one was prepared as described in WO2014/028459 (A1) on pages 168-169 for Example 41-7.

Compound 7

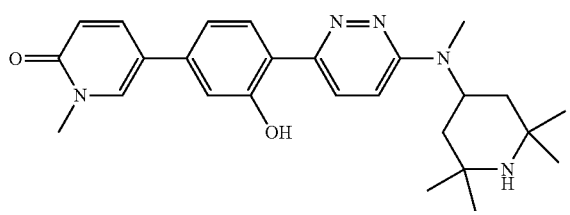

5-(3-hydroxy-4-(6-(methyl-(2,2,6,6-tetramethylpiperidin-4-yl)amino)pyridazin-3-yl)phenyl)-1-methylpyridin-2(1H)-one was prepared as described in WO2014/028459 (A1) on page 168 for Example 14-6.

Compound 8

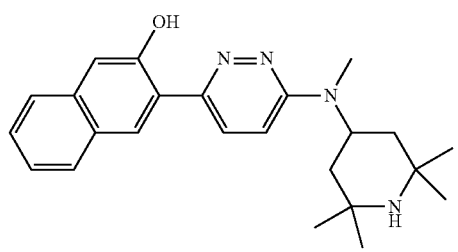

3-(6-(methyl(2,2,6,6-tetramethylpiperidin-4-yl)amino)pyridazin-3-yl)naphthalen-2-ol was prepared as described in WO2014/028459 (A1) on page 55 for Example 3-1.

Compound 9

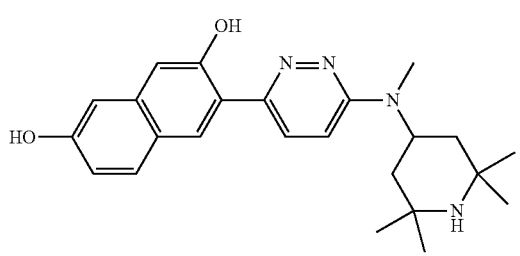

3-(6-(methyl-(2,2,6,6-tetramethylpiperidin-4-yl)amino)pyridazin-3-yl)naphthalene-2,7-diol was prepared as described in WO2014/028459 (A1) on pages 92-93 for Example 20-2.

Compound 10

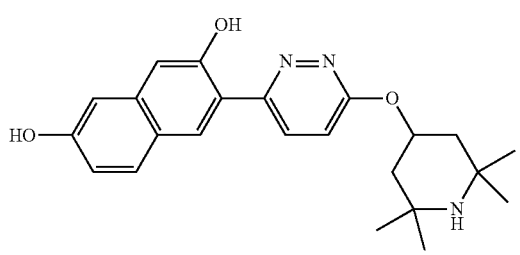

3-(6-((2,2,6,6-tetramethylpiperidin-4-yl)oxy)pyridazin-3-yl)naphthalene-2,7-diol was prepared as described in WO2014/028459 (A1) on page 92 for Example 20-1.

Compound 11

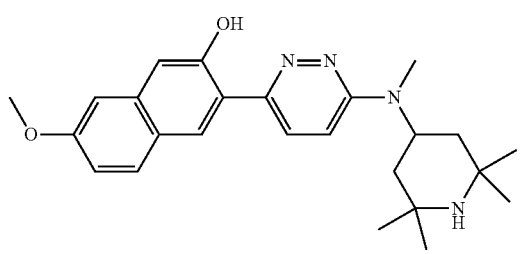

7-methoxy-3-(6-(methyl(2,2,6,6-tetramethylpiperidin-4-yl)amino)pyridazin-3-yl)naphthalen-2-ol was prepared as described in WO2014/028459 (A1) on page 118 for Example 24-6.

Compound 12

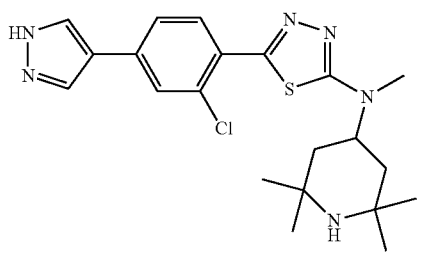

5-(2-Chloro-4-(1H-pyrazol-4-yl)phenyl)-N-methyl-N-(2,2,6,6-tetramethylpiperidin-4-yl)-1,3,4-thiadiazol-2-amine was prepared as described in WO2014/116845 (A1) on page 74 for Example 40.

Compound 13

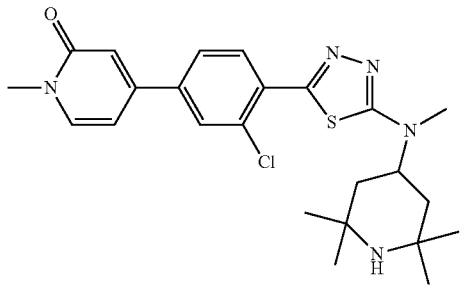

4-(3-chloro-4-(5-(methyl(2,2,6,6-tetramethylpiperidin-4-yl)amino)-1,3,4-thiadiazol-2-yl)phenyl)-1-methylpyridin-2(1H)-one was prepared as described in WO2014/116845 (A1) on page 74 for Example 39.

Compound 14

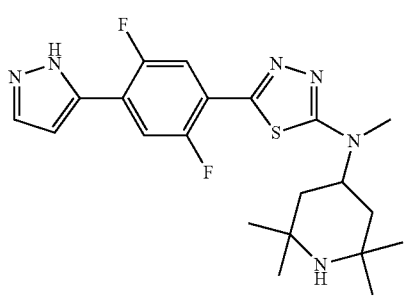

5-(2,5-difluoro-4-(1H-pyrazol-5-yl)phenyl)-N-methyl-N-(2,2,6,6-tetramethylpiperidin-4-yl)-1,3,4-thiadiazol-2-amine was prepared as described in WO2014/116845 (A1) on page 78 for Example 51.

Example 1

Monitoring Expression Levels of FoxM1 Splice Variants using Real-time Quantitative PCR Human fibroblasts were plated at 10,000 cells/well in 200 µl DMEM with GlutaMAX and 10% FBS in 96-well plates in a cell culture incubator (37° C., 5% CO2, 100% relative humidity). Cells were then treated with compounds at different concentrations (0.1-300 nM, each in 0.5% DMSO) in triplicate for 24 hours. RNA extraction was performed as per instructions mentioned in the Ambion® Cells-to-CT™ Kits from Applied Biosystems®. RNA samples were frozen at −20° C. until further analysis. Relative expression levels of full-length FoxM1 (FoxM1_FL) or FoxM1 lacking exon VIIa (FoxM1_ΔVIIa) with GAPDH for internal control, was measured using one-step multiplex reverse transcription-polymerase chain reaction (RT-PCR). TaqMan® FAM probes were used for relative quantitation of FoxM1_FL or FoxM1_ΔVIIa expression levels and TaqMan® VIC probes were used for relative quantitation of human GAPDH levels. The fidelity of the amplification methods was determined using the ΔΔCt relative quantification method for quantitative PCR.

Compounds Induce Alternative Splicing of FoxM1 Towards Full-length FoxM1

To investigate an effect on splicing of FoxM1, human fibroblasts were treated for 24 hours with compounds of the present invention in dose response, and analysed by RT-qPCR for presence of mRNA including (FoxM1_FL) or excluding the exon VIIa (FoxM1_ΔVIIa). FIG. 1 shows that all compounds increased expression of the FoxM1_FL mRNA. Correspondingly, the mRNAs for FoxM1_ΔVIIa declined. The data demonstrate that upregulation of FoxM1_FL with downregulation of FoxM1_ΔVIIa by treatment with compounds of present invention are directly correlated, indicating an effect of the compounds on alternative splicing of FoxM1. The resulting concentration dependence curves of the FoxM1_ΔVIIa splice variant were fitted to a Hill binding equation to yield IC50 values that are described in Table 1. The data demonstrate that all compounds affect FoxM1 splicing with various potencies, ranging from IC50 values from 0.7 to 345 nM. Taken together, the data underline a splicing modifying activity in the FoxM1 gene. This may result in arrest of cell cycle and induction of apoptosis, as the FoxM1_FL variant created by compound treatment is functionally inactive, and therefore will antagonize the pro-proliferating effect of functional FoxM1 (H. Ye, T. F. Kelly, U. Samadani, L. Lim, S. Rubio, D.b G. Overdier, K. A. Roebuck, R. H. Costa, Mol. Cell Biol. 17 (1997) 1626-1641).

TABLE 1

Half-maximal effects for the FoxM1_ΔVIIa splice variant and for the SMN protein. FoxM1_ΔVIIa IC50 values were calculated from concentration dependence curves in FIG. 1 using a Hill binding equation. SMN protein EC50 values were taken from Activity Tables on pages 189 to 192 of WO 2014/028459 (A1) on pages 124 to 141 of WO 2014/116845 (A1) and on pages 131 to 139 of WO 2015/017589 (A1).

| Compound | FoxM1_ΔVIIa IC50 | SMN Protein EC50 |
|---|---|---|
| 1 | 41 nM | 54 nM |
| 2 | 0.9 nM | 4 nM |

TABLE 1-continued

Half-maximal effects for the FoxM1_ΔVIIa splice variant and for the SMN protein. FoxM1_ΔVIIa IC50 values were calculated from concentration dependence curves in FIG. 1 using a Hill binding equation. SMN protein EC50 values were taken from Activity Tables on pages 189 to 192 of WO 2014/028459 (A1) on pages 124 to 141 of WO 2014/116845 (A1) and on pages 131 to 139 of WO 2015/017589 (A1).

| Compound | FoxM1_ΔVIIa IC50 | SMN Protein EC50 |
| --- | --- | --- |
| 3 | 9.8 nM | 15 nM |
| 4 | 17 nM | 17 nM |
| 5 | 278 nM | 31 nM |
| 6 | 1.5 nM | 7 nM |
| 7 | 167 nM | 10 nM |
| 8 | 3.7 nM | 10 nM |
| 9 | 0.7 nM | 4 nM |
| 10 | — | 18 nM |
| 11 | 0.8 nM | 6 nM |
| 12 | 265 nM | 34 nM |
| 13 | 345 nM | 50 nM |
| 14 | 144 nM | 85 nM |

Example 2

Monitoring Expression Levels of SMN Splice Variants using Real-time Quantitative PCR Spinal muscular atrophy (SMA) is a neuromuscular disorder due to mutations in the Survival of Motor Neuron (SMN) gene. Loss of SMN is deleterious to motor neurons and results in neuromuscular insufficiency, a hallmark of the disease. From a genetic point of view, SMA is an autosomal recessive condition, caused by disruption of SMN1 gene, located in 5q13 (Lefebvre S. et al. (1995) Cell 80: 155-165). More than 98% of patients with spinal muscular atrophy have a homozygous disruption of SMN1 by deletion, rearrangement, or mutation. All these patients, however, retain at least one copy of the related SMN2 gene.

Compounds of present invention have been described in WO 2014/028459 (A1), WO 2014/116845 (A1) and in WO 2015/017589 (A1) as being effective splicing modifiers of the SMN2 gene and thus suitable for upregulation of SMN protein and thus for the treatment of SMA.

The potency of the compounds of present invention regarding SMN2 splicing modulation as assessed by the half-maximal effects (EC50) of SMN protein is evident from Activity Table on pages 189 to 192 of WO2014028459A1 and from Activity Table on pages 124 to 141 of WO2014116845A1.

The method of cellular SMN ELISA to measure the effects of compounds on SMN protein elevation is described on page 189 of WO2014028459A1 and on page 123 of WO2014116845A1.

Potency for Splicing Modulation of FoxM1 Gene is Linearly Correlated to Potency of Splicing Modulation of SMN2 Gene It has surprisingly been found that the potency of all compounds investigated to modulate splicing of SMN2 gene is linearly related to the potency to modulate splicing of FoxM1 gene.

Figure 2:
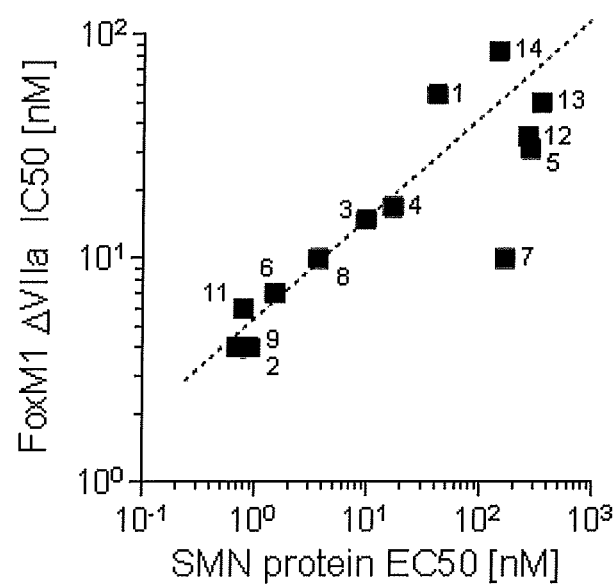
FIG. 2. Correlation of in vitro potency of the compounds of the invention for modulation of the FoxM1 splicing vs. splicing of the survival of motoneuron 2 (SMN2) gene. Half-maximal effects for the FoxM1_ΔVIIa splice variant and for the SMN protein are shown. Data was obtained as described in Example 2.

FIG. 2 shows a graph wherein the half-maximal effects for the FoxM1_ΔVIIa splice variant (IC50) have been plotted versus the half-maximal effects for the SMN protein (EC50).

A regression analysis of the values has resulted in a linear correlation according to the Equation 1:

$$Y = 0.102 * X + 15.2 \quad \text{(Equation 1)}$$

With Y=log(FoxM1_ΔVIIa IC50) and X=log(SMN protein EC50), this linear correlation allows the calculation of FoxM1_ΔVIIa IC50 values from SMN protein EC50 values according to Equation 2:

$$\text{FoxM1\_}\Delta\text{VIIa } IC50 = 10^{(0.102 * log(SMN\ protein\ EC50) + 15.2)} \quad \text{(Equation 2)}$$

The slope of the linear correlation of Equation 1 is 0.102. Thereby the slope of the linear correlation suggests that on average, a 10-fold higher concentration (1/0.102=9.8) of each compound is needed to achieve 50% of splicing correction in the FoxM1 gene as compared to the SMN2 gene.

The invention claimed is:

1. A method for treating cancer comprising administering to a subject in need thereof an effective amount of a FoxM1 gene splicing modifier, wherein the FoxM1 gene splicing modifier is a compound of formula (IV), (V) or (VIII):

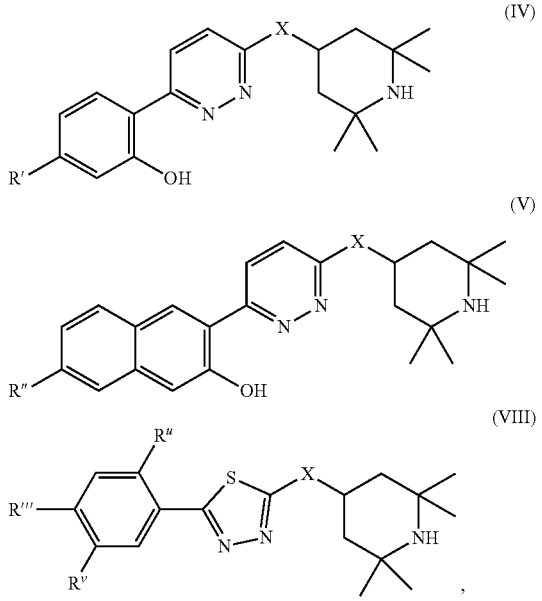

wherein X is —O— or —N(CH$_3$)—; R' is cyano, pyrazolyl optionally substituted with methyl, or pyridinyl substituted with methyl and hydroxy; R" is hydrogen, methyl or methoxy; R''' is pyrazolyl optionally substituted with methyl, or pyridinyl substituted with methyl and hydroxy; R$^u$ is hydrogen, chloro or fluoro; and R$^v$ is hydrogen, chloro or fluoro;
or a pharmaceutically acceptable salt thereof.

2. The method of claim 1, wherein the FoxM1 gene splicing modifier is a compound selected from the group consisting of:
   3-(6-(methyl(2,2,6,6-tetramethylpiperidin-4-yl)amino)pyridazin-3-yl)naphthalen-2-ol;
   3-hydroxy-4-(6-(methyl(2,2,6,6-tetramethylpiperidin-4-yl)amino)pyridazin-3-yl)benzonitrile;
   5-(1H-pyrazol-4-yl)-2-(6-(methyl(2,2,6,6-tetramethylpiperidin-4-yl)amino)pyridazin-3-yl)phenol 2-(6-(methyl-(2,2,6,6-tetramethylpiperidin-4-yl)amino)pyridazin-3-yl)-5-(1-methyl-1H-pyrazol-4-yl)phenol;
   5-pyrazol-1-yl-2-[6-((2,2,6,6-tetramethylpiperidin-4-yloxy)-pyridazin-3-yl]-phenol;
   5-(1H-pyrazol-4-yl)-2-(6-((2,2,6,6-tetramethylpiperidin-4-yl)oxy)pyridazin-3-yl)phenol;
   3-(6-((2,2,6,6-tetramethylpiperidin-4-yl)oxy)pyridazin-3-yl)naphthalene-2,7-diol;
   3-(6-(methyl-(2,2,6,6-tetramethylpiperidin-4-yl)amino)pyridazin-3-yl)naphthalene-2,7-diol;
   7-methoxy-3-(6-(methyl(2,2,6,6-tetramethylpiperidin-4-yl)amino)pyridazin-3-yl)naphthalen-2-ol;
   5-(3-hydroxy-4-(6-(methyl-(2,2,6,6-tetramethylpiperidin-4-yl)amino)pyridazin-3-yl)phenyl)-1-methylpyridin-2(1H)-one;
   4-(3-hydroxy-4-(6-(methyl-(2,2,6,6-tetramethylpiperidin-4-yl)amino)pyridazin-3-yl)phenyl)-1-methylpyridin-2(1H)-one;
   4-(3-chloro-4-(5-(methyl(2,2,6,6-tetramethylpiperidin-4-yl)amino)-1,3,4-thiadiazol-2-yl)phenyl)-1-methylpyridin-2(1H)-one;
   5-(2-Chloro-4-(1H-pyrazol-4-yl)phenyl)-N-methyl-N-(2,2,6,6-tetramethylpiperidin-4-yl)-1,3,4-thiadiazol-2-amine; and
   5-(2,5-difluoro-4-(1H-pyrazol-5-yl)phenyl)-N-methyl-N-(2,2,6,6-tetramethylpiperidin-4-yl)-1,3,4-thiadiazol-2-amine;
or a pharmaceutically acceptable salt thereof.

3. The method of claim 2, wherein the FoxM1 gene splicing modifier induces a transcriptionally inactive FoxM1 variant, and wherein the FoxM1 gene is the human FoxM1 gene.

4. The method of claim 3, wherein the FoxM1 gene splicing modifier induces the transcriptionally inactive FoxM1 variant FoxM1A.

5. The method of claim 2, wherein the cancer is selected from the group consisting of leukemia, acute myeloid leukemia, colon cancer, gastric cancer, macular degeneration, acute monocytic leukemia, breast cancer, hepatocellular carcinoma, cone-rod dystrophy, alveolar soft part sarcoma, myeloma, skin melanoma, prostatitis, pancreatitis, pancreatic cancer, retinitis, adenocarcinoma, adenoiditis, adenoid cystic carcinoma, cataract, retinal degeneration, gastrointestinal stromal tumor, Wegener's granulomatosis, sarcoma, myopathy, prostate adenocarcinoma, Hodgkin's lymphoma, ovarian cancer, non-Hodgkin's lymphoma, multiple myeloma, chronic myeloid leukemia, acute lymphoblastic leukemia, renal cell carcinoma, transitional cell carcinoma, colorectal cancer, chronic lymphocytic leukemia, anaplastic large cell lymphoma, kidney cancer, and cervical cancer.

6. A method for treating cancer comprising administering to a subject in need thereof a pharmaceutical composition comprising a FoxM1 gene splicing modifier according to claim 2.

7. A method for treating cancer comprising administering to a subject in need thereof a FoxM1 gene splicing modifier according to claim 2 and one or more therapeutically active co-agents.

8. The method of claim 1, wherein the FoxM1 gene splicing modifier induces a transcriptionally inactive FoxM1 variant.

9. The method of claim 1, wherein the FoxM1 gene splicing modifier induces the transcriptionally inactive FoxM1 variant FoxM1A.

10. The method of claim 1, wherein the FoxM1 gene is the human FoxM1 gene.

11. The method of claim 1, wherein the cancer is selected from the group consisting of cancer of the liver, prostate, brain, breast, lung, colon, pancreas, skin, cervix, ovary, mouth, blood and nervous system.

12. The method of claim 1, wherein the cancer is selected from the group consisting of leukemia, acute myeloid leukemia, colon cancer, gastric cancer, macular degeneration, acute monocytic leukemia, breast cancer, hepatocellular carcinoma, cone-rod dystrophy, alveolar soft part sarcoma, myeloma, skin melanoma, prostatitis, pancreatitis, pancreatic cancer, retinitis, adenocarcinoma, adenoiditis, adenoid cystic carcinoma, cataract, retinal degeneration, gastrointestinal stromal tumor, Wegener's granulomatosis, sarcoma, myopathy, prostate adenocarcinoma, Hodgkin's lymphoma, ovarian cancer, non-Hodgkin's lymphoma, multiple myeloma, chronic myeloid leukemia, acute lymphoblastic leukemia, renal cell carcinoma, transitional cell carcinoma, colorectal cancer, chronic lymphocytic leukemia, anaplastic large cell lymphoma, kidney cancer, and cervical cancer.

13. A method for treating cancer comprising administering to a subject in need thereof a pharmaceutical composition comprising a FoxM1 gene splicing modifier according to claim 1.

14. A method for treating cancer comprising administering to a subject in need thereof a FoxM1 gene splicing modifier according to claim 1 and one or more therapeutically active co-agents.

15. A method for treating cancer comprising administering to a subject in need thereof an effective amount of a FoxM1 gene splicing modifier, wherein the FoxM1 gene splicing modifier is a compound selected from the group consisting of:
- 6-(naphthalen-2-yl)-N-(2,2,6,6-tetramethylpiperidin-4-yl)pyridazin-3-amine;
- 6-(benzo[b]thio-phen-2-yl)-N-methyl-N-(2,2,6,6-tetramethylpiperidin-4-yl)pyridazin-3-amine;
- 2-(6-(2,2,6,6-tetra methylpiperidin-4-ylamino)-pyridazin-3-yl)phenol;
- 2-(6-(methyl-(2,2,6,6-tetra-methylpiperidin-4-yl)amino) pyridazin-3-yl)benzo[b]-thiophene-5-carbonitrile;
- 6-(quinolin-3-yl)-N-(2,2,6,6-tetramethyl-piperidin-4-yl)pyridazin-3-amine;
- 3-(benzo[b]-thiophen-2-yl)-6-(2,2,6,6-tetra-methylpiperidin-4-yloxy)pyridazine;
- 2-(6-(methyl-(2,2,6,6-tetra-methylpiperidin-4-yl)amino)-pyridazin-3-yl)phenol;
- 6-(6-(methyl-(2,2,6,6-tetra-methylpiperidin-4-yl)amino)-pyridazin-3-yl)naphthalen-2-ol;
- 6-(benzo[b]-thiophen-2-yl)-N-(2,2,6,6-tetra-methylpiperidin-4-yl)pyridazin-3-amine;
- 7-(6-((2,2,6,6-tetramethylpiperidin-4-yl)oxy)pyridazin-3-yl)isoquinoline;
- 6-(6-((2,2,6,6-tetramethylpiperidin-4-yl)oxy)pyridazin-3-yl)isoquinoline;
- N-methyl-6-(quinolin-7-yl)-N-(2,2,6,6-tetramethyl-piperidin-4-yl)pyridazin-3-amine;
- N-methyl-6-(quinolin-6-yl)-N-(2,2,6,6-tetramethylpiperidin-4-yl)pyridazin-3-amine;
- 6-(isoquinolin-7-yl)-N-methyl-N-(2,2,6,6-tetramethylpiperidin-4-yl)pyridazin-3-amine;
- 6-(isoquinolin-6-yl)-N-methyl-N-(2,2,6,6-tetramethylpiperidin-4-yl)pyridazin-3-amine;
- 6-(imidazo[1,2-a]pyridin-6-yl-pyridazin-3-yl)-methyl-(2,2,6,6-tetramethyl-piperidin-4-yl)-amine
- methyl-[6-(6-phenyl-pyridin-3-yl)-pyridazin-3-yl]-(2,2,6,6-tetramethyl-piperidin-4-yl)-amine;
- methyl-[6-(6-pyrrol-1-yl-pyridin-3-yl)-pyridazin-3-yl]-(2,2,6,6-tetra methyl-piperidin-4-yl)-amine;
- methyl-(6-quinoxalin-2-yl-pyridazin-3-yl)-(2,2,6,6-tetramethyl-piperidin-4-yl)-amine;
- methyl-(6-quinolin-3-yl-pyridazin-3-yl)-(2,2,6,6-tetramethyl-piperidin-4-yl)-amine;
- N-methyl-6-(phthalazin-6-yl)-N-(2,2,6,6-tetramethylpiperidin-4-yl)pyridazin-3-amine;
- 6-(benzo[c][1,2,5]oxa-diazol-5-yl)-N-(2,2,6,6-tetramethyl-piperidin-4-yl)pyridazin-3-amine;
- 6-(benzo[d]thiazol-5-yl)-N-(2,2,6,6-tetramethyl-piperidin-4-yl)pyridazin-3-amine;
- 6-(2-methylbenzo-[d]oxazol-6-yl)-N-(2,2,6,6-tetramethyl-piperidin-4-yl)pyridazin-3-amine;
- 3-(6-(methyl(2,2,6,6-tetramethylpiperidin-4-yl)amino) pyridazin-3-yl)naphthalen-2-ol;
- 5-chloro-2-(6-(methyl(1,2,2,6,6-pentamethylpiperidin-4-yl)amino)pyridazin-3-yl)phenol;
- 3-(6-(2,2,6,6-tetramethylpiperidin-4-ylamino)pyridazin-3-yl)naphthalen-2-ol;
- 5-chloro-2-(6-(1,2,2,6,6-pentamethylpiperidin-4-ylamino)pyridazin-3-yl)phenol;
- 4-hydroxy-3-(6-(methyl(2,2,6,6-tetramethylpiperidin-4-yl)amino)pyridazin-3-yl)benzonitrile;
- 3-[6-(2,2,6,6-tetramethyl-piperidin-4-yloxy)-pyridazin-3-yl]-naphthalen-2-ol;
- 2-{6-[methyl-(2,2,6,6-tetramethyl-piperidin-4-yl)-amino]-pyridazin-3-yl}-4-trifluoromethylphenol;
- 2-fluoro-6-{6-[methyl-(2,2,6,6-tetramethyl-piperidin-4-yl)-amino]-pyridazin-3-yl}-phenol;
- 3,5-dimethoxy-2-{6-[methyl-(2,2,6,6-tetramethyl-piperidin-4-yl)-amino]-pyridazin-3-yl}-phenol;
- 4,5-dimethoxy-2-{6-[methyl-(2,2,6,6-tetramethyl-piperidin-4-yl)-amino]-pyridazin-3-yl}-phenol;
- 5-methoxy-2-{6-[methyl-(2,2,6,6-tetramethyl-piperidin-4-yl)-amino]-pyridazin-3-yl}-phenol;
- 4,5-difluoro-2-{6-[methyl-(2,2,6,6-tetramethyl-piperidin-4-yl)-amino]-pyridazin-3-yl}-phenol;
- 5-fluoro-2-{6-[methyl-(2,2,6,6-tetramethyl-piperidin-4-yl)-amino]-pyridazin-3-yl}-phenol;
- 3-hydroxy-4-(6-(methyl(2,2,6,6-tetramethylpiperidin-4-yl)amino)pyridazin-3-yl)benzonitrile;
- 1-allyl-6-(6-(methyl(2,2,6,6-tetramethylpiperidin-4-yl)amino)pyridazin-3-yl)naphthalen-2-ol;
- 6-(benzo[b]thiophen-2-yl)-N-(1,2,2,6,6-pentamethylpiperidin-4-yl)pyridazin-3-amine;
- N-allyl-3-hydroxy-4-(6-(methyl(2,2,6,6-tetramethylpiperidin-4-yl)amino)pyridazin-3-yl)benzamide;
- 2-(6-(methyl(2,2,6,6-tetramethylpiperidin-4-yl)amino) pyridazin-3-yl)-5-(1H-pyrazol-1-yl)phenol;
- 5-(5-methyl-oxazol-2-yl)-2-{6-[methyl-(2,2,6,6-tetramethyl-piperidin-4-yl)-amino]-pyridazin-3-yl}-phenol;
- 5-(4-hydroxymethyl)-1H-pyrazole-1-yl)-2-(6-(methyl(2,2,6,6-tetramethylpiperidin-4-yl) amino)pyridazin-3-yl) phenol;
- 5-(1H-imidazole-1-yl)-2-(6-(methyl(2,2,6,6-tetramethyl-piperidin-4-yl)amino)pyridazin-3-yl)phenol;
- 5-(4-amino-1H-pyrazole-1-yl)-2-(6-(methyl(2,2,6,6-tetramethylpiperidin-4-yl)amino)pyridazin-3-yl)phenol;
- 5-(4-amino-1H-pyrazol-1-yl)-2-(6-(methyl(2,2,6,6-tetramethylpiperidin-4-yl)amino)pyridazin-3-yl)phenol;
- 5-(3-amino-pyrazol-1-yl)-2-{6-[methyl-(2,2,6,6-tetra methyl-piperidin-4-yl)-amino]-pyridazin-3-yl}-phenol;
- 2-(6-(methyl-(2,2,6,6-tetramethylpiperidin-4-yl)amino) pyridazin-3-yl)-5-(1-(2-morpholinoethyl)-1H-pyrazol-4-yl)phenol;
- 2-(6-(methyl-(2,2,6,6-tetramethylpiperidin-4-yl)amino) pyridazin-3-yl)-5-(1-methyl-1H-pyrazol-4-yl)phenol;
- 5-(5-amino-1H-pyrazol-1-yl)-2-(6-(methyl-(2,2,6,6-tetramethyl-piperidin-4-yl)amino)pyridazin-3-yl)phenol;
- 2-(6-(methyl-(2,2,6,6-tetramethylpiperidin-4-yl)amino) pyridazin-3-yl)-4-(1H-pyrazol-1-yl)phenol;
- 2-{6-[(2-hydroxy-ethyl)-(2,2,6,6-tetra methyl-piperidin-4-yl)-amino]-pyridazin-3-yl}-5-pyrazol-1-yl-phenol;
- 2-(6-(piperidin-4-yloxy)pyridazin-3-yl)-5-(1H-pyrazol-1-yl)phenol;
- 2-(6-(((2S,4R,6R)-2,6-dimethylpiperidin-4-yl)oxy) pyridazin-3-yl)-5-(1H-pyrazol-1-yl)phenol;
- 5 2-(6-((2,6-di-methylpiperidin-4-yl)oxy)pyridazin-3-yl)-5-(1H-pyrazol-1-yl)phenol;
- 2-(6-((2,6-di-methylpiperidin-4-yl)oxy)pyridazin-3-yl)-5-(1H-pyrazol-1-yl)phenol;
- 5-(1H-pyrazol-1-yl)-2-(6-(pyrrolidin-3-yloxy)pyridazin-3-yl)phenol;
- 2-(6-((-2-methylpiperidin-4-yl)oxy)pyridazin-3-yl)-5-(1H-pyrazol-1-yl)phenol;

(S)-5-(1H-pyrazol-1-yl)-2-(6-(pyrrolidin-3-ylmethoxy) pyridazin-3-yl)phenol;

(R)-5-(1H-pyrazol-1-yl)-2-(6-(pyrrolidin-3-yl methoxy) pyridazin-3-yl)phenol;

2-(6-((3-fluoropiperidin-4-yl)oxy)pyridazin-3-yl)-5-(1H-pyrazol-1-yl)-phenol;

2-[6-(1,2,2,6,6-pentamethyl-piperidin-4-yloxy)-pyridazin-3-yl]-5-pyrazol-1-yl-phenol;

5-pyrazol-1-yl-2-[6-((2,2,6,6-tetramethylpiperidin-4-yloxy)-pyridazin-3-yl]-phenol;

5-(1H-pyrazol-4-yl)-2-(6-((2,2,6,6-tetramethylpiperidin-4-yl)oxy)pyridazin-3-yl)phenol;

2-(6-piperazin-1-yl-pyridazin-3-yl)-5-pyrazol-1-yl-phenol;

3-[6-(azetidin-3-yl-amino)-pyridazin-3-yl]-naphthalen-2-ol;

2-[6-(azetidin-3-ylamino)-pyridazin-3-yl]-5-pyrazol-1-yl-phenol;

2-[6-(3,5-di methyl-piperazin-1-yl)-pyridazin-3-yl]-5-pyrazol-1-yl-phenol;

2-[6-(7-methyl-2,7-diaza-spiro[4.4]non-2-yl)-pyridazin-3-yl]-5-pyrazol-1-yl-phenol;

2-(6-[1,4]diazepan-1-yl-pyridazin-3-yl)-5-pyrazol-1-yl-phenol;

2-{6-[4-(2-hydroxy-ethyl)-piperazin-1-yl]-pyridazin-3-yl}-5-pyrazol-1-yl-phenol;

2-[6-(3,6-diaza-bicyclo[3.2.1]oct-3-yl)-pyridazin-3-yl]-5-pyrazol-1-yl-phenol;

2-[6-(2,7-diaza-spiro[3.5]non-7-yl)-pyridazin-3-yl]-5-pyrazol-1-yl-phenol;

2-[6-(3-hydroxy-methyl-piperazin-1-yl)-pyridazin-3-yl]-5-pyrazol-1-yl-phenol;

2-[6-(1,7-diaza-spiro[4.4]non-7-yl)-pyridazin-3-yl]-5-pyrazol-1-yl-phenol;

2-[6-(4-amino-4-methyl-piperidin-1-yl)-pyridazin-3-yl]-5-pyrazol-1-yl-phenol;

2-[6-(3-dimethyl-amino-piperidin-1-yl)-pyridazin-3-yl]-5-pyrazol-1-yl-phenol;

2-[6-(1,2,2,6,6-pentamethyl-piperidin-4-ylamino)-pyridazin-3-yl]-5-pyrazol-1-yl-phenol;

2-[6-(3,3-di methyl-piperazin-1-yl)-pyridazin-3-yl]-5-pyrazol-1-yl-phenol;

2-(6-(7-(2-hydroxyethyl)-2,7-diazaspiro[4.4]-nonan-2-yl) pyridazin-3-yl)-5-(1H-pyrazol-1-yl)phenol;

2-(6-((3aR,6aS)-hexahydropyrrolo[3,4-c]pyrrol-2(1H)-yl)pyridazin-3-yl)-5-(1H-pyrazol-1-yl)phenol;

3-(6-(piperazin-1-yl)pyridazin-3-yl)naphthalene-2,7-diol;

5-pyrazol-1-yl-2[6-(1,2,3,6-tetrahydro-pyridin-4-yl)-pyridazin-3-yl]-phenol;

2-(6-piperidin-4-yl-pyridazin-3-yl)-5-pyrazol-1-yl-phenol;

3-(6-(1,2,3,6-tetra-hydropyridin-4-yl)pyridazin-3-yl) naphthalen-2-ol;

3-(6-(1,2,3,6-tetrahydropyridin-4-yl)pyridazin-3-yl) naphthalene-2,7-diol;

3-(6-(2,2,6,6-tetramethyl-1,2,3,6-tetrahydropyridin-4-yl) pyridazin-3-yl)naphthalene-2,7-diol;

3-(6-(1-methyl-1,2,3,6-tetrahydropyridin-4-yl)pyridazin-3-yl)naphthalene-2,7-diol;

3-(6-(piperidin-4-yl)pyridazin-3-yl)naphthalene-2,7-diol;

3-(6-((2,2,6,6-tetramethylpiperidin-4-yl)oxy)pyridazin-3-yl)naphthalene-2,7-diol;

3-(6-(methyl-(2,2,6,6-tetramethylpiperidin-4-yl)amino) pyridazin-3-yl)naphthalene-2,7-diol;

3-(6-((2,2,6,6-tetramethylpiperidin-4-yl)amino) pyridazin-3-yl)naphthalene-2,7-diol;

[3-(7-hydroxy-6-{6-[methyl-(2,2,6,6-tetra methyl-piperidin-4-yl)-amino]-pyridazin-3-yl}-naphthalen-2-yloxy)-propyl]-carbamic acid tert-butyl ester;

7-(3-amino-propoxy)-3-{6-[methyl-(2,2,6,6-tetramethyl-piperidin-4-yl)-amino]-pyridazin-3-yl}naphthalen-2-ol;

N-[3-(7-hydroxy-6-{6-[methyl-(2,2,6,6-tetra methyl-piperidin-4-yl)-amino]-pyridazin-3-yl}naphthalen-2-yloxy)-propyl]-acetamide;

7-(3-hydroxypropoxy)-3-(6-(methyl(2,2,6,6-tetramethylpiperidin-4-yl)amino)pyridazin-3-yl)naphthalen-2-ol;

7-(3-methoxypropoxy)-3-(6-(methyl(2,2,6,6-tetramethylpiperidin-4-yl)amino)pyridazin-3-yl)naphthalen-2-ol;

7-(2-morpholinoethoxy)-3-(6-((2,2,6,6-tetramethylpiperidin-4-yl)oxy)pyridazin-3-yl)naphthalen-2-ol;

3-(6-(piperidin-4-ylmethyl)pyridazin-3-yl)naphthalen-2-ol;

5-(1H-pyrazol-1-yl)-2-(6-((2,2,6,6-tetramethylpiperidin-4-yl)methyl)pyridazin-3-yl)phenol;

3-methoxy-2-(6-(methyl(2,2,6-trimethylpiperidin-4-yl) amino)pyridazin-3-yl)-5-(5-methyloxazol-2-yl)phenol;

2-(6-((6S)-6-((S)-1-hydroxyethyl)-2,2-dimethylpiperidin-4-yloxy)pyridazin-3-yl)-5-(1H pyrazol-1-yl)phenol;

7-hydroxy-6-(6-(methyl(2,2,6,6-tetramethylpiperidin-4-yl)amino)pyridazin-3-yl)-2-naphthonitrile;

3-(6-(methyl(2,2,6,6-tetramethylpiperidin-4-yl)amino) pyridazin-3-yl)-7-(piperidin-1-ylmethyl)naphthalen-2-ol;

3-(6-(methyl(2,2,6,6-tetramethylpiperidin-4-yl)amino) pyridazin-3-yl)-7-(pyrrolidin-1-ylmethyl)naphthalen-2-ol;

1-bromo-6-(6-(methyl(2,2,6,6-tetramethylpiperidin-4-yl) amino)pyridazin-3-yl)naphthalene-2,7-diol;

1-chloro-6-(6-(methyl(2,2,6,6-tetramethylpiperidin-4-yl) amino)pyridazin-3-yl)naphthalene-2,7-diol;

7-methoxy-3-(6-(methyl(2,2,6,6-tetramethylpiperidin-4-yl)amino)pyridazin-3-yl)naphthalen-2-ol;

7-methoxy-3-(6-(methyl(1,2,2,6,6-pentamethylpiperidin-4-yl)amino)pyridazin-3-yl)naphthalen-2-ol;

7-(3,6-dihydro-2H-pyran-4-yl)-3-(6-(methyl(2,2,6,6-tetramethylpiperidin-4-yl)amino)pyridazin-3-yl)naphthalen-2-ol;

3-(6-(methyl-(2,2,6,6-tetramethylpiperidin-4-yl)amino) pyridazin-3-yl)-7-(tetrahydro-2H-pyran-4-yl)naphthalen-2-ol;

7-(difluoromethyl)-3-(6-(methyl-(2,2,6,6-tetramethylpiperidin-4-yl)amino)pyridazin-3-yl)naphthalen-2-ol;

7-((4-hydroxy-2-methyl butan-2-yl)oxy)-3-(6-(methyl(2,2,6,6-tetramethylpiperidin-4-yl)amino)pyridazin-3-yl) naphthalen-2-ol;

7-(3-hydroxy-3-methylbutoxy)-3-(6-(methyl-(2,2,6,6-tetramethylpiperidin-4-yl)amino)pyridazin-3-yl)naphthalen-2-ol;

2-(6-(methyl(2,2,6,6-tetramethylpiperidin-4-yl)amino) pyridazin-3-yl)-5-(1H-pyrazol-4-yl)benzene-1,3-diol;

3-methoxy-2-(6-(methyl-(2,2,6,6-tetramethylpiperidin-4-yl)amino)pyridazin-3-yl)-5-(1H pyrazol-4-yl)phenol;

5-(1H-pyrazol-4-yl)-2-(6-((2,2,6,6-tetramethylpiperidin-4-yl)amino)pyridazin-3-yl)-3-(trifluoromethoxy)phenol;

2-(6-(methyl(2,2,6,6-tetramethylpiperidin-4-yl)amino) pyridazin-3-yl)-5-(1-methyl-1H-pyrazol-4-yl)-3-(trifluoromethoxy)phenol;

2-(6-(methyl(2,2,6,6-tetramethylpiperidin-4-yl)amino) pyridazin-3-yl)-5-(1H-pyrazol-4-yl)-3-(trifluoromethoxy)phenol;

4-(3-hydroxy-4-(6-(methyl-(2,2,6,6-tetramethylpiperidin-4-yl)amino)pyridazin-3-yl)-5-(trifluoromethoxy) phenyl)-1-methylpyridin-2(1H)-one;

3-methoxy-2-(6-(methyl-(2,2,6,6-tetramethylpiperidin-4-yl)amino)pyridazin-3-yl)-5-(1-methyl-1H-pyrazol-4-yl)phenol;

3-methoxy-2-(6-(methyl-(2,2,6,6-tetramethylpiperidin-4-yl)amino)pyridazin-3-yl)-5-(5,6,7,8-tetrahydroimidazo[1,2-a]pyridin-3-yl)phenol;

3-methoxy-2-(6-(methyl-(2,2,6,6-tetramethylpiperidin-4-yl)amino)pyridazin-3-yl)-5-(pyridin-3-yl)phenol;

5-(1-cyclopentyl-1H-pyrazol-4-yl)-3-methoxy-2-(6-(methyl(2,2,6,6-tetra methylpiperidin-4-yl)amino) pyridazin-3-yl)phenol;

3' 5-dimethoxy-4-(6-(methyl-(2,2,6,6-tetramethylpiperidin-4-yl)amino)pyridazin-3-yl)-[1,1'-biphenyl]-3-ol;

3-(benzyloxy)-2-(6-(methyl-(2,2,6,6-tetramethylpiperidin-4-yl)amino)pyridazin-3-yl)-5-(5-methyloxazol-2-yl)phenol;

3-ethoxy-2-(6-(methyl-(2,2,6,6-tetramethylpiperidin-4-yl)amino)pyridazin-3-yl)-5-(5-methyloxazol-2-yl)phenol;

5 3-(cyclopropylmethoxy)-2-(6-(methyl-(2,2,6,6-tetramethylpiperidin-4-yl)amino)-pyridazin-3-yl)-5-(5-methyloxazol-2-yl)phenol;

2-methyl-5-(6-(methyl-(2,2,6,6-tetramethylpiperidin-4-yl)amino)pyridazin-3-yl)-1H benzo[d]imidazol-6-ol;

5-chloro-2-(6-(methyl-(2,2,6,6-tetramethylpiperidin-4-yl)amino)pyridazin-3-yl)phenol;

5-(1H-pyrazol-1-yl)-2-(6-((2,2,6,6-tetramethylpiperidin-4-yl)amino)pyridazin-3-yl)phenol;

3-hydroxy-4-(6-((2,2,6,6-tetramethylpiperidin-4-yl) amino)pyridazin-3-yl)benzonitrile;

2-(6-((2,2-dimethylpiperidin-4-yl)oxy)pyridazin-3-yl)-5-(1H-pyrazol-4-yl)phenol;

2-(6-(methyl-(2,2,6,6-tetramethylpiperidin-4-yl)amino) pyridazin-3-yl)-4-(1H-pyrazol-4-yl)phenol;

2-(6-(methyl-(2,2,6,6-tetramethylpiperidin-4-yl)amino) pyridazin-3-yl)-4-(4,5,6,7-tetrahydropyrazolo[1,5-a] pyri din-3-yl)phenol;

2-(6-(methyl-(2,2,6,6-tetramethylpiperidin-4-yl)amino) pyridazin-3-yl)-4-(4,5,6,7-tetrahydropyrazolo[1,5-a] pyrazin-3-yl)phenol;

4-(1H-indol-2-yl)-2-(6-(methyl-(2,2,6,6-tetramethylpiperidin-4-yl)amino)pyridazin-3-yl)phenol;

4-(cyclopent-1-en-1-yl)-2-(6-(methyl(2,2,6,6-tetramethylpiperidin-4-yl)amino)pyridazin-3-yl)phenol;

2-(6-(methyl-(2,2,6,6-tetramethylpiperidin-4-yl)amino) pyridazin-3-yl)-4-(1H-pyrazol-3-yl)phenol;

4-(4-hydroxy-3-(6-(methyl-(2,2,6,6-tetramethylpiperidin-4-yl)amino)pyridazin-3-yl)phenyl)pyridin-2-ol;

4-(4-hydroxy-3-(6-((2,2,6,6-tetra methylpiperidin-4-yl) oxy)pyridazin-3-yl)phenyl)-1-methylpyridin-2-(1H)-one;

4-(4-hydroxy-3-(6-((2,2,6,6-tetramethylpiperidin-4-yl) oxy)pyridazin-3-yl)phenyl)pyridin-2-ol;

5-(1H-indazol-7-yl)-2-(6-(methyl-(2,2,6,6-tetramethylpiperidin-4-yl)amino)pyridazin-3-yl)phenol;

4-chloro-2-(6-(methyl-(2,2,6,6-tetramethylpiperidin-4-yl)amino)pyridazin-3-yl)-5-(1H-pyrazol-4-yl)phenol;

4-fluoro-2-(6-(methyl-(2,2,6,6-tetramethylpiperidin-4-yl) amino)pyridazin-3-yl)-5-(1H-pyrazol-4-yl)phenol;

5-fluoro-4-(1H-imidazol-4-yl)-2-(6-(methyl-(2,2,6,6-tetramethylpiperidin-4-yl)amino)pyridazin-3-yl)phenol;

5-fluoro-2-(6-(methyl-(2,2,6,6-tetramethylpiperidin-4-yl) amino)pyridazin-3-yl)-4-(1H-pyrazol-4-yl)phenol;

5-fluoro-2-(6-(methyl-(2,2,6,6-tetramethylpiperidin-4-yl) amino)pyridazin-3-yl)-4-(1H-pyrazol-5-yl)phenol;

5,6-hydroxy-5-(6-(methyl-(2,2,6,6-tetramethylpiperidin-4-yl)amino)pyridazin-3-yl)-2,3-dihydro-1H-inden-1-one;

6-(6-(methyl-(2,2,6,6-tetramethylpiperidin-4-yl)amino) pyridazin-3-yl)-1,4-dihydroindeno[1,2-c]pyrazol-7-ol;

6-hydroxy-5-(6-(methyl-(2,2,6,6-tetramethylpiperidin-4-yl)amino)pyridazin-3-yl)-2,3-dihydro-1H-inden-1-one oxime hydrochloride salt;

5-(6-(methyl-(2,2,6,6-tetramethylpiperidin-4-yl)amino) pyridazin-3-yl)-2,3-dihydro-1H-indene-1,6-diol;

2-amino-6-(6-(methyl-(2,2,6,6-tetramethylpiperidin-4-yl) amino)pyridazin-3-yl)-8H-indeno[1,2-d]thiazol-5-ol hydrochloride salt;

15   9-(6-(methyl-(2,2,6,6-tetramethylpiperidin-4-yl) amino)pyridazin-3-yl)-5,6-dihydroimidazo[5,1-a]isoquinolin-8-ol hydrochloride salt;

4-hydroxy-3-(6-(methyl-(2,2,6,6-tetramethylpiperidin-4-yl)amino)pyridazin-3-yl)-N-((1-methyl-1H-pyrazol-4-yl)methyl)benzamide;

4-(4-(hydroxymethyl)-1H-pyrazol-1-yl)-2-(6-(methyl(2, 2,6,6-tetramethylpiperidin-4-yl)amino)pyridazin-3-yl) phenol;

5-(1H-pyrazol-4-yl)-2-(6-((2,2,6,6-tetramethylpiperidin-4-yl)methyl)pyridazin-3-yl)phenol;

6-(3-(benzyloxy)isoquinolin-6-yl)-N-methyl-N-(2,2,6,6-tetramethylpiperidin-4-yl)pyridazin-3-amine;

6-(1-(benzyl oxy)isoquinolin-7-yl)-N-methyl-N-(2,2,6,6-tetramethylpiperidin-4-yl)pyridazin-3-amine;

3-fluoro-5-(2-methoxypyridin-4-yl)-2-(6-(methyl-(2,2,6, 6-tetramethylpiperidin-4-yl)amino)pyridazin-3-yl)phenol hydrochloride salt;

4-(3-fluoro-5-hydroxy-4-(6-(methyl-(2,2,6,6-tetramethylpiperidin-4-yl)amino)pyridazin-3-yl)phenyl)pyridin-2(1H)-one hydrochloride salt;

4-(3-fluoro-5-hydroxy-4-(6-(methyl-(2,2,6,6-tetramethylpiperidin-4-yl)amino)pyridazin-3-yl)phenyl)-1-methylpyridin-2(1H)-one hydrochloride salt;

5-(3-fluoro-5-hydroxy-4-(6-(methyl-(2,2,6,6-tetramethylpiperidin-4-yl)amino)pyridazin-3-yl)phenyl)-1-methylpyridin-2(1H)-one hydrochloride salt;

3-fluoro-5-(1H-pyrazol-4-yl)-2-(6-((2,2,6,6-tetramethylpiperidin-4-yl)oxy)pyridazin-3-yl)phenol hydrochloride salt;

5-chloro-3-fluoro-2-(6-(methyl-(2,2,6,6-tetramethylpiperidin-4-yl)amino)pyridazin-3-yl)phenol hydrochloride salt;

3-fluoro-2-(6-(methyl-(2,2,6,6-tetramethylpiperidin-4-yl) amino)pyridazin-3-yl)-5-(1H-pyrazol-4-yl)phenol hydrochloride salt;

3-fluoro-2-(6-(methyl-(2,2,6,6-tetramethylpiperidin-4-yl) amino)pyridazin-3-yl)-5-(1-methyl-1H pyrazol-4-yl) phenol hydrochloride salt;

5-(5-methoxypyridin-3-yl)-2-(6-(methyl-(2,2,6,6-tetramethylpiperidin-4-yl)amino)pyridazin-3-yl)phenol;

5-(3-hydroxy-4-(6-methyl-(2,2,6,6-tetramethylpiperidin-4-yl)amino)pyridazin-3-yl)phenyl)pyridin-2-ol;

4-(3-hydroxy-4-(6-methyl-(2,2,6,6-tetramethylpiperidin-4-yl)amino)pyridazin-3-yl)phenyl)pyridin-2-ol;

5-(6-methoxypyridin-3-yl)-2-(6-(methyl-(2,2,6,6-tetramethylpiperidin-4-yl)amino)pyridazin-3-yl)phenol;

15 5-(3-hydroxy-4-(6-(methyl-(2,2,6,6-tetramethylpiperidin-4-yl)amino)pyridazin-3-yl)phenyl)-3-(trifluoromethyl)pyridin-2-ol;

5-(3-hydroxy-4-(6-(methyl-(2,2,6,6-tetramethylpiperidin-4-yl)amino)pyridazin-3-yl)phenyl)-1-methylpyridin-2(1H)-one;

4-(3-hydroxy-4-(6-(methyl-(2,2,6,6-tetramethylpiperidin-4-yl)amino)pyridazin-3-yl)phenyl)-1-methylpyridin-2(1H)-one;

5-(2-methoxypyridin-4-yl)-2-(6-(methyl-(2,2,6,6-tetramethylpiperidin-4-yl)amino)pyridazin-3-yl)phenol;

4-(3-hydroxy-4-(6-((2,2,6,6-tetramethylpiperidin-4-yl)oxy)pyridazin-3-yl)phenyl)pyridin-2-ol;

5-(6-(dimethylamino)pyridin-3-yl)-2-(6-(methyl(2,2,6,6-tetramethylpiperidin-4-yl)amino)pyridazin-3-yl)phenol;

4-(3-hydroxy-4-(6-((2,2,6,6-tetra methylpiperidin-4-yl)oxy)pyridazin-3-yl)phenyl)-1-methylpyridin-2(1H)-one;

2-(6-(methyl-(2,2,6,6-tetramethylpiperidin-4-yl)amino)pyridazin-3-yl)-5-(pyrimidin-5-yl)phenol;

5-(3-hydroxy-4-(6-(methyl-(2,2,6,6-tetramethylpiperidin-4-yl)amino)pyridazin-3-yl)phenyl)pyridin-3-ol;

1-cyclopropyl-4-(3-hydroxy-4-(6-(methyl(2,2,6,6-tetra methylpiperidin-4-yl)amino)pyridazin-3-yl)phenyl)pyridin-2(1H)-one;

2-(6-(methyl-(2,2,6,6-tetramethylpiperidin-4-yl)amino)pyridazin-3-yl)-5-(1,2,3,6-tetrahydropyridin-4-yl)phenol;

5-(cyclopent-1-en-1-yl)-2-(6-(methyl(2,2,6,6-tetramethylpiperidin-4-yl)amino)pyridazin-3-yl)phenol;

5-(3,6-dihydro-2H-pyran-4-yl)-2-(6-(methyl(2,2,6,6-tetramethylpiperidin-4-yl)amino)pyridazin-3-yl)phenol;

5-(imidazo[1,5-a]pyridin-7-yl)-2-(6-(methyl(2,2,6,6-tetramethylpiperidin-4-yl)amino)pyridazin-3-yl)phenol;

5-(imidazo[1,2-a]pyridin-7-yl)-2-(6-(methyl(2,2,6,6-tetramethylpiperidin-4-yl)amino)pyridazin-3-yl)phenol;

2-(6-(methyl(2,2,6,6-tetramethylpiperidin-4-yl)amino)pyridazin-3-yl)-5-(2-methylpyridin-4-yl)phenol;

5-(1H-imidazol-2-yl)-2-(6-(methyl-(2,2,6,6-tetramethylpiperidin-4-yl)amino)pyridazin-3-yl)phenol;

5-(1H-imidazol-4-yl)-2-(6-(methyl-(2,2,6,6-tetramethylpiperidin-4-yl)amino)pyridazin-3-yl)phenol;

5-(imidazo[1,2-a]pyrazin-3-yl)-2-(6-(methyl(2,2,6,6-tetramethylpiperidin-4-yl)amino)pyridazin-3-yl)phenol;

2-(6-(methyl-(2,2,6,6-tetramethylpiperidin-4-yl)amino)pyridazin-3-yl)-5-(5,6,7,8-tetrahydroimidazo[1,2-a]pyrazin-3-yl)phenol;

2-(6-(methyl-(2,2,6,6-tetramethylpiperidin-4-yl)amino)pyridazin-3-yl)-5-(4-methyl-1H-imidazol-2-yl)phenol;

2-(6-(methyl-(2,2,6,6-tetramethylpiperidin-4-yl)amino)pyridazin-3-yl)-5-(1-methyl-1H-imidazol-4-yl)phenol;

2-(6-(methyl-(2,2,6,6-tetramethylpiperidin-4-yl)amino)pyridazin-3-yl)-5-(1-methyl-1H imidazol-5-yl)phenol;

2-(6-(methyl-(2,2,6,6-tetramethylpiperidin-4-yl)amino)pyridazin-3-yl)-5-(4-nitro-1H-imidazol-2-yl)phenol;

25 2-(6-(methyl-(2,2,6,6-tetramethylpiperidin-4-yl)amino)pyridazin-3-yl)-5-(2-methyl-1H imidazol-4-yl)phenol;

5-(1,2-dimethyl-1H-imidazol-4-yl)-2-(6-(methyl(2,2,6,6-tetramethylpiperidin-4-yl)amino)pyridazin-3-yl)phenol;

1-(3-hydroxy-4-(6-(methyl-(2,2,6,6-tetramethylpiperidin-4-yl)amino)pyridazin-3-yl)phenyl)-1H-pyrazole-4-carboxamide;

2-(6-((3aR,6aS)-5-(2-hydroxyethyl)hexahydropyrrolo[3,4-c]pyrrol-2 (1H)-yl)pyridazin-3-yl)-5-(1H-pyrazol-4-yl)phenol;

2-(6-((3aR,6aS)-hexahydropyrrolo[3,4-c]pyrrol-2(1H)-yl)pyridazin-3-yl)-5-(1H-pyrazol-4-yl)phenol;

2-(6-((3aR,6aS)-5-methylhexahydropyrrolo[3,4-c]pyrrol-2(1H)-yl)pyridazin-3-yl)-5-(1 Hpyrazol-4-yl)phenol;

4-(3-hydroxy-4-(6-(5-methylhexahydropyrrolo[3,4-c]pyrrol-2(1H)-yl)pyridazin-3-yl)phenyl)-1-methylpyridin-2(1H)-one;

4-(3-hydroxy-4-(6-((3aR,6aR)-1-methylhexahydropyrrolo[3,4-b]pyrrol-5(1H)-yl)pyridazin-3-yl)phenyl)-1-methylpyridin-2(1H)-one;

2-(6-(2,7-diazaspiro[4.5]decan-2-yl)pyridazin-3-yl)-5-(1H-pyrazol-4-yl)phenol; and 4-(4-(6-(2,7-diazaspiro[4.5]decan-2-yl)pyridazin-3-yl)-3-hydroxyphenyl)-1-methylpyridin-2(1H)-one;

5-(2-Methoxy-4-(1H-pyrazol-1-yl)phenyl)-N-methyl-N-(2,2,6,6-tetramethylpiperidin-4-yl)-1,3,4-thiadiazol-2-amine;

6-(5-(Methyl(2,2,6,6-tetramethylpiperidin-4-yl)amino)-1,3,4-thiadiazol-2-yl)naphthalen-2-ol;

5-(2-Methoxyquinolin-3-yl)-N-methyl-N-(2,2,6,6-tetramethylpiperidin-4-yl)-1,3,4-thiadiazol-2-amine;

5-(3-Methoxynaphthalen-2-yl)-N-methyl-N-(2,2,6,6-tetramethylpiperidin-4-yl)-1,3,4-thiadiazol-2-amine;

5-(2-Methoxy-4-(1H-pyrazol-1-yl)phenyl)-N-(1,2,2,6,6-pentamethylpiperidin-4-yl)-1,3,4-thiadiazol-2-amine;

5-(2-Methoxy-4-(1-methyl-1H-pyrazol-4-yl)phenyl)-N-methyl-N-(2,2,6,6-tetramethylpiperidin-4-yl)-1,3,4-thiadiazol-2-amine;

5-(2-Methoxy-4-(1H-pyrazol-4-yl)phenyl)-N-methyl-N-(2,2,6,6-tetramethylpiperidin-4-yl)-1,3,4-thiadiazol-2-amine;

4-(3-Methoxy-4-(5-(methyl(2,2,6,6-tetramethylpiperidin-4-yl)amino)-1,3,4-thiadiazol-2-yl)phenyl)-1-methylpyridin-2(1H)-one;

5-(3-Methoxy-4-(5-(methyl(2,2,6,6-tetramethylpiperidin-4-yl)amino)-1,3,4-thiadiazol-2-yl)phenyl)pyridin-2-ol;

5-(3-Methoxy-4-(5-(methyl(2,2,6,6-tetramethylpiperidin-4-yl)amino)-1,3,4-thiadiazol-2-yl)phenyl)-1-methylpyridin-2(1H)-one;

N-Methyl-5-(2-methyl-4-(1-methyl-1H-pyrazol-4-yl)phenyl)-N-(2,2,6,6-tetramethylpiperidin-4-yl)-1,3,4-thiadiazol-2-amine;

1-Methyl-4-(4-(5-(methyl(2,2,6,6-tetramethylpiperidin-4-yl)amino)-1,3,4-thiadiazol-2-yl)-3-(trifluoromethoxy)phenyl)pyridin-2(1H)-one;

5-(4-(3,5-Dimethyl-1H-pyrazol-4-yl)-2-methoxyphenyl)-N-methyl-N-(2,2,6,6-tetramethylpiperidin-4-yl)-1,3,4-thiadiazol-2-amine;

5-(2-Methoxy-4-(1-methyl-1H-pyrazol-4-yl)phenyl)-N-methyl-N-(2,2,6,6-tetramethylpiperidin-4-yl)-1,3,4-thiadiazol-2-amine;

2-(5-(Methyl(2,2,6,6-tetramethylpiperidin-4-yl)amino)-1,3,4-thiadiazol-2-yl)-5-(1-methyl-1H-pyrazol-4-yl)phenol;

2-(5-(Methyl(2,2,6,6-tetramethylpiperidin-4-yl)amino)-1,3,4-thiadiazol-2-yl)-5-(1H-pyrazol-1-yl)phenol;

5-(3-Hydroxy-4-(5-(methyl(2,2,6,6-tetramethylpiperidin-4-yl)amino)-1,3,4-thiadiazol-2-yl)phenyl)-1-methylpyridin-2(1H)-one;

4-(3-Hydroxy-4-(5-(methyl(2,2,6,6-tetramethylpiperidin-4-yl)amino)-1,3,4-thiadiazol-2-yl)phenyl)-1-methylpyridin-2(1H)-one;

5-(3-Hydroxy-4-(5-(methyl(2,2,6,6-tetramethylpiperidin-4-yl)amino)-1,3,4-thiadiazol-2-yl)phenyl)pyridin-2-ol;

3-(5-(Methyl(2,2,6,6-tetramethylpiperidin-4-yl)amino)-1,3,4-thiadiazol-2-yl)naphthalene-2,7-diol;

3-(5-((3 aR,6aS)-Hexahydropyrrolo[3,4-c]pyrrol-2(1H)-yl)-1,3,4-thiadiazol-2-yl)naphthalene-2,7-diol;

3-(5-(Methyl(2,2,6,6-tetramethylpiperidin-4-yl)amino)-1,3,4-thiadiazol-2-yl)naphthalen-2-ol hydrobromide salt;

3-(5-(Methyl(2,2,6,6-tetramethylpiperidin-4-yl)amino)-1,3,4-thiadiazol-2-yl)quinolin-2-ol;

2-(5-(Methyl(2,2,6,6-tetramethylpiperidin-4-yl)amino)-1,3,4-thiadiazol-2-yl)-4-(1H-pyrazol-1-yl)phenol;

5-(2-Chloro-4-(1-methyl-1H-pyrazol-4-yl)phenyl)-N-methyl-N-(2,2,6,6-tetramethylpiperidin-4-yl)-1,3,4-thiadiazol-2-amine;

3-Chloro-2-(5-(methyl(2,2,6,6-tetramethylpiperidin-4-yl)amino)-1,3,4-thiadiazol-2-yl)-5-(1-methyl-1H-pyrazol-4-yl)phenol;

5-(2-Chloro-4-(1-methyl-1H-pyrazol-4-yl)phenyl)-N-(2,2,6,6-tetramethylpiperidin-4-yl)-1,3,4-thiadiazol-2-amine;

3-Methoxy-2-(5-(methyl(2,2,6,6-tetramethylpiperidin-4-yl)amino)-1,3,4-thiadiazol-2-yl)-5-(5-methyloxazol-2-yl)phenol;

2-(2-Methoxy-4-(1H-pyrazol-1-yl)phenyl)-5-(1,2,3,6-tetrahydropyridin-4-yl)-1,3,4-thiadiazole;

2-(5-(piperazin-1-yl)-1,3,4-thiadiazol-2-yl)-5-(1H-pyrazol-1-yl)phenol;

5-(7-Methoxyquinolin-6-yl)-N-methyl-N-(2,2,6,6-tetramethylpiperidin-4-yl)-1,3,4-thiadiazol-2-amine;

6-(5-(Methyl(2,2,6,6-tetramethylpiperidin-4-yl)amino)-1,3,4-thiadiazol-2-yl)quinolin-7-ol;

3-methoxy-4-(5-(methyl(2,2,6,6-tetramethylpiperidin-4-yl)amino)-1,3,4-thiadiazol-2-yl)benzonitrile;

3-fluoro-4-(5-(methyl(2,2,6,6-tetramethylpiperidin-4-yl)amino)-1,3,4-thiadiazol-2-yl)benzonitrile;

methyl 3-fluoro-4-(5-(methyl(2,2,6,6-tetramethylpiperidin-4-yl)amino)-1,3,4-thiadiazol-2-yl)benzoate;

5-(2-methoxy-4-(3-(methyl amino)-1H-pyrazol-1-yl)phenyl)-N-methyl-N-(2,2,6,6-tetramethylpiperidin-4-yl)-1,3,4-thiadiazol-2-amine;

7-methoxy-6-(5-(methyl(2,2,6,6-tetramethylpiperidin-4-yl)amino)-1,3,4-thiadiazol-2-yl)quinoline-2-carbonitrile;

4-(3-methoxy-4-(5-((2,2,6,6-tetramethylpiperidin-4-yl)oxy)-1,3,4-thiadiazol-2-yl)phenyl)-1-methylpyridin-2(1H)-one;

4-(3-chloro-4-(5-(methyl(2,2,6,6-tetramethylpiperidin-4-yl)amino)-1,3,4-thiadiazol-2-yl)phenyl)-1-methylpyridin-2(1H)-one;

5-(2-Chloro-4-(1H-pyrazol-4-yl)phenyl)-N-methyl-N-(2,2,6,6-tetramethylpiperidin-4-yl)-3,4-thiadiazol-2-amine;

5-(2-Chloro-4-(4,5,6,7-tetrahydropyrazolo[1,5-a]pyridin-3-yl)phenyl)-N-methyl-N-(2,2,6,6-tetramethylpiperidin-4-yl)-1,3,4-thiadiazol-2-amine;

N-methyl-5-(5-methyl-1H-pyrazol-4-yl)pyridin-2-yl)-N-(2,2,6,6-tetramethylpiperidin-4-yl)-1,3,4-thiadiazol-2-amine Hydrochloride salt;

2-(2-chloro-4-(1-methyl-1H-pyrazol-4-yl)phenyl)-5-((2,2,6,6-tetramethylpiperidin-4-yl)oxy)-1,3,4-thiadiazole;

5-(2-chloro-4-(6-methoxypyridin-3-yl)phenyl)-N-methyl-N-(2,2,6,6-tetramethylpiperidin-4-yl)-1,3,4-thiadiazol-2-amine;

5-(4-(6-aminopyridin-3-yl)-2-fluorophenyl)-N-methyl-N-(2,2,6,6-tetramethylpiperidin-4-yl)-1,3,4-thiadiazol-2-amine;

5-(2-fluoro-4-(3-methyl-1H-pyrazol-5-yl)phenyl)-N-methyl-N-(2,2,6,6-tetramethylpiperidin-4-yl)-1,3,4-thiadiazol-2-amine;

5-(2-fluoro-4-(1H-pyrazol-5-yl)phenyl)-N-methyl-N-(2,2,6,6-tetramethylpiperidin-4-yl)-1,3,4-thiadiazol-2-amine;

5-(2,3-difluoro-4-(1H-pyrazol-4-yl)phenyl)-N-methyl-N-(2,2,6,6-tetramethylpiperidin-4-yl)-1,3,4-thiadiazol-2-amine;

5-(2,3-difluoro-4-(1H-pyrazol-5-yl)phenyl)-N-methyl-N-(2,2,6,6-tetramethylpiperidin-4-yl)-1,3,4-thiadiazol-2-amine;

5-(2,5-difluoro-4-(1H-pyrazol-4-yl)phenyl)-N-methyl-N-(2,2,6,6-tetramethylpiperidin-4-yl)-1,3,4-thiadiazol-2-amine;

5-(2,5-difluoro-4-(1H-pyrazol-5-yl)phenyl)-N-methyl-N-(2,2,6,6-tetramethylpiperidin-4-yl)-1,3,4-thiadiazol-2-amine;

5-(2,6-difluoro-4-(1H-pyrazol-4-yl)phenyl)-N-methyl-N-(2,2,6,6-tetramethylpiperidin-4-yl)-1,3,4-thiadiazol-2-amine;

2-(2,5-difluoro-4-(1H-pyrazol-4-yl)phenyl)-5-((3aR,6aS)-hexahydropyrrolo[3,4-c]pyrrol-2(1H)-yl)-1,3,4-thiadiazole;

5-(2-chloro-5-fluoro-4-(1H-pyrazol-4-yl)phenyl)-N-methyl-N-(2,2,6,6-tetramethylpiperidin-4-yl)-1,3,4-thiadiazol-2-amine;

5-(3-fluoro-5-(1H-pyrazol-4-yl)pyridin-2-yl)-N-methyl-N-(2,2,6,6-tetramethylpiperidin-4-yl)-1,3,4-thiadiazol-2-amine;

5-(4-(2-aminopyrimidin-4-yl)-2-chlorophenyl)-N-methyl-N-(2,2,6,6-tetramethylpiperidin-4-yl)-1,3,4-thiadiazol-2-amine;

5-(5-(2-aminopyrimidin-4-yl)-2-chlorophenyl)-N-methyl-N-(2,2,6,6-tetramethylpiperidin-4-yl)-1,3,4-thiadiazol-2-amine;

5-(4-(2,4-dimethylthiazol-5-yl)-2,5-difluorophenyl)-N-methyl-N-(2,2,6,6-tetramethylpiperidin-4-yl)-1,3,4-thiadiazol-2-amine;

5-(4-(2,4-dimethylthiazol-5-yl)-2,3-difluorophenyl)-N-methyl-N-(2,2,6,6-tetramethylpiperidin-4-yl)-1,3,4-thiadiazol-2-amine;

4-(3-hydroxy-4-(5-(methyl(2,2,6,6-tetramethylpiperidin-4-yl)amino)-1,3,4-thiadiazol-2-yl)-5-(trifluoromethoxy)phenyl)-1-methylpyridin-2(1H)-one;

5-(2-fluoro-6-methoxy-4-(1H-pyrazol-4-yl)phenyl)-N-methyl-N-(2,2,6,6-tetramethylpiperidin-4-yl)-1,3,4-thiadiazol-2-amine;

2-(2-fluoro-6-methoxy-4-(1H-pyrazol-4-yl)phenyl)-5-((3aR,6aS)-5-methylhexahydropyrrolo[3,4-c]pyrrol-2(1H)-yl)-1,3,4-thiadiazole;

5-(2,3-difluoro-6-methoxy-4-(1H-pyrazol-4-yl)phenyl)-N-methyl-N-(2,2,6,6-tetramethylpiperidin-4-yl)-1,3,4-thiadiazol-2-amine;

6-methoxy-2-(5-(methyl(2,2,6,6-tetramethylpiperidin-4-yl)amino)-1,3,4-thiadiazol-2-yl)-3,4-dihydroisoquinolin-1(2H)-one;

5-(2-Chloro-4-(1H-pyrazol-1-yl)phenyl)-N-methyl-N-(2,2,6,6-tetramethylpiperidin-4-yl)-1,3,4-thiadiazol-2-amine;

5-(2-Chloro-4-(1H-1,2,3-triazol-1-yl)phenyl)-N-methyl-N-(2,2,6,6-tetramethylpiperidin-4-yl)-1,3,4-thiadiazol-2-amine;

5-(2-chloro-4-(2H-1,2,3-triazol-2-yl)phenyl)-N-methyl-N-(2,2,6,6-tetramethylpiperidin-4-yl)-1,3,4-thiadiazol-2-amine;

5-(2-chloro-4-(1H-1,2,4-triazol-1-yl)phenyl)-N-methyl-N-(2,2,6,6-tetramethylpiperidin-4-yl)-1,3,4-thiadiazol-2-amine;

5-(4-(3-amino-1H-pyrazol-1-yl)-2-chlorophenyl)-N-methyl-N-(2,2,6,6-tetramethylpiperidin-4-yl)-1,3,4-thiadiazol-2-amine;

2-(2-chloro-4-(1H-imidazol-1-yl)phenyl)-5-((3 aR,6aS)-5-methylhexahydropyrrolo[3,4-c]pyrrol-2(1H)-yl)-1,3,4-thiadiazole;

5-(2-Chloro-4-(1H-imidazol-1-yl)phenyl)-N-methyl-N-(2,2,6,6-tetramethylpiperidin-4-yl)-1,3,4-thiadiazol-2-amine;

5-(2-fluoro-4-(1H-imidazol-1-yl)phenyl)-N-methyl-N-(2,2,6,6-tetramethylpiperidin-4-yl)-1,3,4-thiadiazol-2-amine;

5-(2-methoxy-4-(1H-pyrazol-5-yl)phenyl)-N-methyl-N-(2,2,6,6-tetramethylpiperidin-4-yl)-1,3,4-thiadiazol-2-amine;

5-(4-(2,4-dimethylthiazol-5-yl)-2-methoxyphenyl)-N-methyl-N-(2,2,6,6-tetramethylpiperidin-4-yl)-1,3,4-thiadiazol-2-amine;

5-(2-methoxy-4-(pyridin-3-yl)phenyl)-N-methyl-N-(2,2,6,6-tetramethylpiperidin-4-yl)-1,3,4-thiadiazol-2-amine;

5-(2-fluoro-4-(1H-pyrazol-4-yl)phenyl)-N-methyl-N-(2,2,6,6-tetramethylpiperidin-4-yl)-1,3,4-thiadiazol-2-amine;

5-(2-methoxy-4-(2-methoxypyridin-4-yl)phenyl)-N-methyl-N-(2,2,6,6-tetramethylpiperidin-4-yl)-1,3,4-thiadiazol-2-amine;

5-(2-methoxy-4-(6-methoxypyridin-3-yl)phenyl)-N-methyl-N-(2,2,6,6-tetramethylpiperidin-4-yl)-1,3,4-thiadiazol-2-amine;

2-(2-Chloro-4-(1-methyl-1H-pyrazol-4-yl)phenyl)-5-((3 aR,6aS)-5-methylhexahydropyrrolo[3,4-c]pyrrol-2(1H)-yl)-1,3,4-thiadiazole;

2-(2-chloro-4-(1H-pyrazol-4-yl)phenyl)-5-((3aR,6aS)-5-methylhexahydropyrrolo[3,4-c]pyrrol-2(1H)-yl)-1,3,4-thiadiazole;

2-(2-Chloro-4-(1H-pyrazol-4-yl)phenyl)-5-((3aR,6aR)-1-methylhexahydropyrrolo[3,4-b]pyrrol-5(1H)-yl)-1,3,4-thiadiazole;

1-(4-(5-(2-chloro-4-(1H-pyrazol-4-yl)phenyl)-1,3,4-thiadiazol-2-yl)morpholin-2-yl)-N,N-dimethylmethanamine;

2-(2-chloro-4-(1H-pyrazol-4-yl)phenyl)-5-(2-methyl-2,7-diazaspiro[4.5]decan-7-yl)-1,3,4-thiadiazole;

2-(2-fluoro-4-(1H-pyrazol-4-yl)phenyl)-5-((3 aR, 6aS)-5-methylhexahydropyrrolo[3,4-c]pyrrol-2(1H)-yl)-1,3,4-thiadiazole;

2-(2-methoxy-4-(1-methyl-1H-pyrazol-4-yl)phenyl)-5-(2,6-diazaspiro[3.5]nonan-2-yl)-1,3,4-thiadiazole;

2-(2-methoxy-4-(1-methyl-1H-pyrazol-4-yl)phenyl)-5-(2,7-diazaspiro[3.5]nonan-2-yl)-1,3,4-thiadiazole;

2-(5-(Methyl(2,2,6,6-tetramethylpiperidin-4-yl)amino)-1,3,4-thiadiazol-2-yl)-5-(1H-pyrazol-1-yl)phenol;

5-(3-chloro-4-(5-(methyl(2,2,6,6-tetramethylpiperidin-4-yl)amino)-1,3,4-thiadiazol-2-yl)phenyl)pyridin-2(1H)-one;

2-(5-(methyl(2,2,6,6-tetramethylpiperidin-4-yl)amino)-1,3,4-thiadiazol-2-yl)-5-(3-(methylamino)-1H-pyrazol-1-yl)phenol;

3-fluoro-2-(5-(methyl(2,2,6,6-tetramethylpiperidin-4-yl)amino)-1,3,4-thiadiazol-2-yl)-5-(1H-pyrazol-4-yl)phenol;

3,4-difluoro-2-(5-(methyl(2,2,6,6-tetramethylpiperidin-4-yl)amino)-1,3,4-thiadiazol-2-yl)-5-(1H-pyrazol-4-yl)phenol;

6-hydroxy-5-(5-(methyl(2,2,6,6-tetramethylpiperidin-4-yl)amino)-1,3,4-thiadiazol-2-yl)-2,3-dihydro-1H-inden-1-one;

2-(5-(methyl(2,2,6,6-tetramethylpiperidin-4-yl)amino)-1,3,4-thiadiazol-2-yl)-5-(1H-pyrazol-4-yl)phenol;

2-(5-(2,6-diazaspiro[3.5]nonan-2-yl)-1,3,4-thiadiazol-2-yl)-5-(1-methyl-1H-pyrazol-4-yl)phenol;

2-(5-(2,7-diazaspiro[3.5]nonan-2-yl)-1,3,4-thiadiazol-2-yl)-5-(1-methyl-1H-pyrazol-4-yl)phenol;

3-fluoro-2-(5-((3 aR,6aS)-hexahydropyrrolo[3,4-c]pyrrol-2(1H)-yl)-1,3,4-thiadiazol-2-yl)-5-(1H-pyrazol-4-yl)phenol Di-hydrochloride salt;

3-Chloro-2-(5-(methyl(2,2,6,6-tetramethylpiperidin-4-yl)amino)-1,3,4-thiadiazol-2-yl)-5-(1H-pyrazol-4-yl)phenol;

2-(2-methoxy-4-(1H-pyrazol-1-yl)phenyl)-5-((2,2,6,6-tetramethylpiperidin-4-yl)methyl)-1,3,4-thiadiazole;

2-(2,3-difluoro-4-(1H-pyrazol-4-yl)phenyl)-5-(2,7-diazaspiro[3.5]nonan-2-yl)-1,3,4-thiadiazole;

2-(5-(2,7-diazaspiro[3.5]nonan-2-yl)-1,3,4-thiadiazol-2-yl)-3-fluoro-5-(1H-pyrazol-4-yl)phenol;

4-methoxy-1-methyl-3-(5-(methyl(2,2,6,6-tetramethylpiperidin-4-yl)amino)-1,3,4-thiadiazol-2-yl)quinolin-2(1H)-one;

4-hydroxy-1-methyl-3-(5-(methyl(2,2,6,6-tetramethylpiperidin-4-yl)amino)-1,3,4-thiadiazol-2-yl)quinolin-2(1H)-one;

3-(5-(methyl(2,2,6,6-tetramethylpiperidin-4-yl)amino)-1,3,4-thiadiazol-2-yl)quinolin-2(1H)-one;

1-methyl-3-(5-(methyl(2,2,6,6-tetramethylpiperidin-4-yl)amino)-1,3,4-thiadiazol-2-yl)quinolin-2(1H)-one;

2-(2-Chloro-4-(1H-pyrazol-4-yl)phenyl)-5-((3aR,6aS)-hexahydropyrrolo[3,4-c]pyrrol-2(1H)yl)-1,3,4-thiadiazole Hydrochloride Salt;

2-(2-Chloro-4-(1H-pyrazol-4-yl)phenyl)-5-(2,7-diazaspiro[4.5]decan-2-yl)-1,3,4-thiadiazole Hydrochloride Salt;

(R)-(4-(5-(2-chloro-4-(1H-pyrazol-4-yl)phenyl)-1,3,4-thiadiazol-2-yl)piperazin-2-yl)methanol Hydrochloride Salt;

2-(5-(methyl(2,2,6,6-tetramethylpiperidin-4-yl)amino)-1,3,4-thiadiazol-2-yl)benzo[b]thiophene-5-carbonitrile; and 5-(3-chlorobenzo[b]thiophen-2-yl)-N-methyl-N-(2,2,6,6-tetramethylpiperidin-4-yl)-1,3,4-thiadiazol-2-amine;

7-hydroxy-6-(6-(methyl(2,2,6,6-tetramethylpiperidin-4-yl)amino)pyridazin-3-yl)quinolin-2(1H)-one;

6-(6-((3aR,6aS)-5-methylhexahydropyrrolo[3,4-c]pyrrol-2(1H)-yl)pyridazin-3-yl)quinolin-7-ol;

7-hydroxy-1-methyl-6-(6-(methyl(2,2,6,6-tetramethylpiperidin-4-yl)amino)pyridazin-3-yl)quinolin-2(1H)-one;

6-(6-(methyl(1,2,2,6,6-pentamethylpiperidin-4-yl)amino)pyridazin-3-yl)quinolin-7-ol;

2-methyl-6-(6-(methyl(2,2,6,6-tetramethylpiperidin-4-yl)amino)pyridazin-3-yl)-4-morpholinoquinoline-7-ol;

4-chloro-2-methyl-6-(6-(methyl(2,2,6,6-tetramethylpiperidin-4-yl)amino)pyridazin-3-yl)quinolin-7-ol;

3-bromo-6-(6-(methyl(2,2,6,6-tetramethylpiperidin-4-yl)amino)pyridazin-3-yl)quinolin-7-ol;

3-ethyl-6-(6-(methyl(2,2,6,6-tetramethylpiperidin-4-yl)amino)pyridazin-3-yl)quinolin-7-ol;

3-(1H-imidazol-1-yl)-6-(6-(methyl(2,2,6,6-tetramethylpiperidin-4-yl)amino)pyridazin-3-yl)quinolin-7-ol;

6-(6-(methyl(2,2,6,6-tetramethylpiperidin-4-yl)amino)pyridazin-3-yl)-3-(1-methyl-1H-imidazol-4-yl)quinolin-7-ol;

3-isopropyl-6-(6-(methyl(2,2,6,6-tetramethylpiperidin-4-yl)amino)pyridazin-3-yl)quinolin-7-ol;

6-(6-(methyl(2,2,6,6-tetramethylpiperidin-4-yl)amino)pyridazin-3-yl)quinoline-3,7-diol;

7-hydroxy-6-(6-(methyl(2,2,6,6-tetramethylpiperidin-4-yl)amino)pyridazin-3-yl)quinoline-3-carbonitrile;
6-(6-(methyl(2,2,6,6-tetramethylpiperidin-4-yl)amino)pyridazin-3-yl)quinolin-7-ol;
4-(dimethylamino)-2-methyl-6-(6-(methyl(2,2,6,6-tetramethylpiperidin-4-yl)amino)pyridazin-3-yl)quinolin-7-ol;
3-chloro-6-(6-(methyl(2,2,6,6-tetramethylpiperidin-4-yl)amino)pyridazin-3-yl)quinolin-7-ol;
4-methoxy-2-methyl-6-(6-(methyl(2,2,6,6-tetramethylpiperidin-4-yl)amino)pyridazin-3-yl)quinolin-7-ol;
6-(3-(benzyloxy)isoquinolin-6-yl)-N-methyl-N-(2,2,6,6-tetramethylpiperidin-4-yl)pyridazin-3-amine;
8-(6-(methyl(2,2,6,6-tetramethylpiperidin-4-yl)amino)pyridazin-3-yl)quinolin-7-ol;
7-(6-(methyl(2,2,6,6-tetramethylpiperidin-4-yl)amino)pyridazin-3-yl)isoquinoline-1,6-diol;
7-(6-(methyl(1,2,2,6,6-pentamethylpiperidin-4-yl)amino)pyridazin-3-yl)isoquinolin-6-ol;
1-cyclopropyl-7-(6-(methyl(2,2,6,6-tetramethylpiperidin-4-yl)amino)pyridazin-3-yl)isoquinolin-6-ol;
7-(6-(methyl(2,2,6,6-tetramethylpiperidin-4-yl)amino)pyridazin-3-yl)isoquinolin-6-ol;
6-(1-(benzyloxy)isoquinolin-7-yi)-N-methyi-N-(2,2,6,6-tetramethylpiperidin-4-yl)pyridazin-3-amine;
7-(6-(methyl(2,2,6,6-tetramethylpiperidin-4-yl)amino)pyridazin-3-yl)quinolin-6-ol;
2-methyl-7-(6-(methyl(2,2,6,6-tetramethylpiperidin-4-yl)amino)pyridazin-3-yl)quinolin-6-ol;
2-methyl-6-(6-(methyl(2,2,6,6-tetramethylpiperidin-4-yl)amino)pyridazin-3-yl)-4-(1-methyl-1Hpyrazol-4-yl)quinolin-7-ol;
2-methyl-6-(6-(methyl(2,2,6,6-tetramethylpiperidin-4-yl)amino)pyridazin-3-yl)quinolin-7-ol;
4-ethoxy-2-methyl-6-(6-(methyl(2,2,6,6-tetramethylpiperidin-4-yl)amino)pyridazin-3-yl)quinolin-7-ol;
4-chloro-7-(6-(methyl(2,2,6,6-tetramethylpiperidin-4-yl)amino)pyridazin-3-yl)quinolin-6-ol;
6-(6-(methyl(2,2,6,6-tetramethylpiperidin-4-yl)amino)pyridazin-3-yl)-3-(tetrahydro-2H-pyran-4-yl)quinolin-7-ol;
3-chloro-7-(6-(methyl(2,2,6,6-tetramethylpiperidin-4-yl)amino)pyridazin-3-yl)quinolin-6-ol;
3-bromo-7-(6-(methyl(2,2,6,6-tetramethylpiperidin-4-yl)amino)pyridazin-3-yl)quinolin-6-ol;
3-methyl-7-(6-(methyl(2,2,6,6-tetramethylpiperidin-4-yl)amino)pyridazin-3-yl)quinolin-6-ol;
5-bromo-3-methyl-7-(6-(methyl(2,2,6,6-tetramethylpiperidin-4-yl)amino)pyridazin-3-yl)quinolin-6-ol;
6-hydroxy-1-methyl-7-(6-(methyl(2,2,6,6-tetramethylpiperidin-4-yl)amino)pyridazin-3-yl)quinolin-4(1H)-one;
2,3-dimethyl-7-(6-(methyl(2,2,6,6-tetramethylpiperidin-4-yl)amino)pyridazin-3-yl)quinoxalin-6-ol;
2-methyl-7-(6-(methyl(2,2,6,6-tetramethylpiperidin-4-yl)amino)pyridazin-3-yl)quinoxalin-6-ol;
3-methyl-7-(6-(methyl(2,2,6,6-tetramethylpiperidin-4-yl)amino)pyridazin-3-yl)quinoxalin-6-ol;
4-methoxy-6-(6-(methyl(2,2,6,6-tetramethylpiperidin-4-yl)amino)pyridazin-3-yl)quinolin-7-ol;
4-(azetidin-1-yl)-2-methyl-6-(6-(methyl(2,2,6,6-tetramethylpiperidin-4-yl)amino)pyridazin-3-yl)quinolin-7-ol;
7-hydroxy-2-methyl-6-(6-(methyl(2,2,6,6-tetramethylpiperidin-4-yl)amino)pyridazin-3-yl)quinoline-4-carbonitrile;
4-cyclopropyl-2-methyl-6-(6-(methyl(2,2,6,6-tetramethylpiperidin-4-yl)amino)pyridazin-3-yl)quinolin-7-ol;
4-(3,6-dihydro-2H-pyran-4-yl)-2-methyl-6-(6-(methyl(2,2,6,6-tetramethylpiperidin-4-yl)amino)pyridazin-3-yl)quinolin-7-ol;
2-methyl-6-(6-(methyl(2,2,6,6-tetramethylpiperidin-4-yl)amino)pyridazin-3-yl)-4-(tetrahydro-2Hpyran-4-yl)quinolin-7-ol;
2-methyl-6-(6-(methyl(2,2,6,6-tetramethylpiperidin-4-yl)amino)pyridazin-3-yl)-4-(oxetan-3-yl)quinolin-7-ol;
4-(dimethylamino)-6-(6-(methyl(2,2,6,6-tetramethylpiperidin-4-yl)amino)pyridazin-3-yl)quinolin-7-ol;
7-hydroxy-6-(6-(methyl(2,2,6,6-tetramethylpiperidin-4-yl)amino)pyridazin-3-yl)quinazolin-4(1H)-one;
6-(6-(methyl(2,2,6,6-tetramethylpiperidin-4-yl)amino)pyridazin-3-yl)quinazolin-7-ol;
7-hydroxy-1-methyl-6-(6-(methyl(2,2,6,6-tetramethylpiperidin-4-yl)amino)pyridazin-3-yl)-3,4-dihydroquinolin-2(1H)-one;
7-hydroxy-1-methyl-6-(6-(methyl(2,2,6,6-tetramethylpiperidin-4-yl)amino)pyridazin-3-yl)-3,4-dihydroquinolin-2(1H)-one;
7-hydroxy-6-(6-(methyl(2,2,6,6-tetramethylpiperidin-4-yl)amino)pyridazin-3-yl)isoquinoline-1-carbonitrile;
7-hydroxy-6-(6-(methyl(2,2,6,6-tetramethylpiperidin-4-yl)amino)pyridazin-3-yl)quinoline-2-carbonitrile;
6-hydroxy-7-(6-(methyl(2,2,6,6-tetramethylpiperidin-4-yl)amino)pyridazin-3-yl)quinoline-2-carbonitrile;
6-hydroxy-7-(6-(methyl(2,2,6,6-tetramethylpiperidin-4-yl)amino)pyridazin-3-yl)isoquinoline-1-carboxamide;
7-hydroxy-6-(6-(methyl(2,2,6,6-tetramethylpiperidin-4-yl)amino)pyridazin-3-yl)quinoline-2-carboxamide;
6-hydroxy-7-(6-(methyl(2,2,6,6-tetramethylpiperidin-4-yl)amino)pyridazin-3-yl)quinoline-2-carboxamide;
methyl 6-hydroxy-7-(6-(methyl(2,2,6,6-tetramethylpiperidin-4-yl)amino)pyridazin-3-yl)quinoline-2-carboxylate;
6-hydroxy-7-(6-(piperazin-1-yl)pyridazin-3-yl)quinoline-2-carbonitrile;
7-hydroxy-6-(6-(piperazin-1-yl)pyridazin-3-yl)quinoline-2-carbonitrile;
7-(6-(piperazin-1-yl)pyridazin-3-yl)isoquinolin-6-ol;
7-(6-(1,2,3,6-tetrahydropyridin-4-yl)pyridazin-3-yl)quinolin-6-ol;
1-methyl-6-(6-(methyl(2,2,6,6-tetramethylpiperidin-4-yl)amino)pyridazin-3-yl)isoquinolin-7-ol;
1-methyl-7-(6-(methyl(2,2,6,6-tetramethylpiperidin-4-yl)amino)pyridazin-3-yl)isoquinolin-6-ol;
1,3-dimethyl-7-(6-(methyl(2,2,6,6-tetramethylpiperidin-4-yl)amino)pyridazin-3-yl)isoquinolin-6-ol;
7-hydroxy-3-methyl-6-(6-(methyl(2,2,6,6-tetramethylpiperidin-4-yl)amino)pyridazin-3-yl)isoquinoline-1-carbonitrile;
1-amino-7-(6-(methyl(2,2,6,6-tetramethylpiperidin-4-yl)amino)pyridazin-3-yl)isoquinolin-6-ol;
7-hydroxy-1,3-dimethyl-6-(6-(methyl(2,2,6,6-tetramethylpiperidin-4-yl)amino)pyridazin-3-yl)quinazoline-2,4(1H,3H)-dione;
6-hydroxy-5-(6-(methyl(2,2,6,6-tetramethylpiperidin-4-yl)amino)pyridazin-3-yl)benzo[d]oxazoi-2(3H)-one;
2-methyl-5-(6-(methyl(2,2,6,6-tetramethylpiperidin-4-yl)amino)pyridazin-3-yl)-2H-indazol-6-ol;
1-methyl-5-(6-(methyl(2,2,6,6-tetramethylpiperidin-4-yl)amino)pyridazin-3-yl)-1H-indazol-6-ol;
6-hydroxy-2-methyl-7-(6-(methyl(2,2,6,6-tetramethylpiperidin-4-yl)amino)pyridazin-3-yl)isoquinolin-1(2H)-one;

2-ethyl-6-hydroxy-7-(6-(2,2,6,6-tetramethylpiperidin-4-yl)oxy)pyridazin-3-yl)isoquinolin-1(2H)-one;
1-ethoxy-7-(6-(methyl(2,2,6,6-tetramethylpiperidin-4-yl)amino)pyridazin-3-yl)isoquinolin-6-ol;
7-(6-((2,2,6,6-tetramethylpiperidin-4-yl)oxy)pyridazin-3-yl)isoquinoline-1,6-diol;
7-(6-(methyl(2,2,6,6-tetramethyl-piperidin-4-yl)amino)-pyridazin-3-yl)-3-phenylisoquinoline-6-ol;
3-methyl-7-(6-(methyl(2,2,6,6-tetramethylpiperidin-4-yl)amino)pyridazin-3-yl)isoquinolin-6-ol;
3-cyclopropyl-7-(6-(methyl(2,2,6,6-tetramethyl-piperidin-4-yl)amino)pyridazin-3-yl)isoquinolin-6-ol;
3-isopropyl-7-(6-(methyl(2,2,6,6-tetramethyl-piperidin-4-yl)amino)pyridazin-3-yl)isoquinolin-6-ol;
3-propyl-7-(6-((2,2,6,6-tetramethylpiperidin-4-yl)oxy)pyridazin-3-yl)isoquinolin-6-ol;
3-isopropyl-7-(6-(2,2,6,6-tetramethylpiperidin-4-yl)oxy)-pyridazin-3-yl)isoquinolin-6-ol; and
3-methyl-7-(6-(piperazin-1-yl)pyridazin-3-yl)isoquinolin-6-ol;
or a pharmaceutically acceptable salt thereof.

16. The method of claim 15, wherein the FoxM1 gene splicing modifier induces a transcriptionally inactive FoxM1 variant, and wherein the FoxM1 gene is the human FoxM1 gene.

17. The method of claim 16, wherein the FoxM1 gene splicing modifier induces the transcriptionally inactive FoxM1 variant FoxM1A.

18. The method of claim 15, wherein the cancer is selected from the group consisting of cancer of the liver, prostate, brain, breast, lung, colon, pancreas, skin, cervix, ovary, mouth, blood and nervous system.

19. A method for treating cancer comprising administering to a subject in need thereof a pharmaceutical composition comprising a FoxM1 gene splicing modifier according to claim 15.

20. A method for treating cancer comprising administering to a subject in need thereof a FoxM1 gene splicing modifier according to claim 15 and one or more therapeutically active co-agents.

* * * * *